US011856850B2

(12) United States Patent
Kim et al.

(10) Patent No.: US 11,856,850 B2
(45) Date of Patent: Dec. 26, 2023

(54) PLURALITY OF HOST MATERIALS AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Bitnari Kim, Gyeonggi-do (KR); Su-Hyun Lee, Gyeonggi-do (KR); So-Young Jung, Gyeonggi-do (KR); Hyo-Soon Park, Gyeonggi-do (KR); Tae-Jun Han, Gyeonggi-do (KR); Young-Jun Cho, Gyeonggi-do (KR); Sang-Hee Cho, Gyeonggi-do (KR)

(73) Assignee: Rohm and Haas Electronic Materials Korea Ltd.

( * ) Notice: Subject to any disclaimer, the term of this patent is extended or adjusted under 35 U.S.C. 154(b) by 589 days.

(21) Appl. No.: 16/640,082

(22) PCT Filed: Sep. 21, 2018

(86) PCT No.: PCT/KR2018/011199
§ 371 (c)(1),
(2) Date: Feb. 19, 2020

(87) PCT Pub. No.: WO2019/059695
PCT Pub. Date: Mar. 28, 2019

(65) Prior Publication Data
US 2020/0212310 A1 Jul. 2, 2020

(30) Foreign Application Priority Data

Sep. 22, 2017 (KR) .................. 10-2017-0122681
Aug. 17, 2018 (KR) .................. 10-2018-0095843

(51) Int. Cl.
*H10K 85/60* (2023.01)
*C07D 239/74* (2006.01)
*C07D 241/42* (2006.01)
*C07D 251/24* (2006.01)
*C07D 487/04* (2006.01)
*C09K 11/02* (2006.01)
*C09K 11/06* (2006.01)
*H10K 50/11* (2023.01)
*H10K 101/10* (2023.01)
*H10K 101/00* (2023.01)

(52) U.S. Cl.
CPC ....... *H10K 85/6572* (2023.02); *C07D 239/74* (2013.01); *C07D 241/42* (2013.01); *C07D 251/24* (2013.01); *C07D 487/04* (2013.01); *C09K 11/025* (2013.01); *C09K 11/06* (2013.01); *H10K 85/654* (2023.02); *H10K 85/6574* (2023.02); *H10K 85/6576* (2023.02); *C09K 2211/1018* (2013.01); *H10K 50/11* (2023.02); *H10K 2101/10* (2023.02); *H10K 2101/90* (2023.02)

(58) Field of Classification Search
CPC ............. H01L 51/0072; H01L 51/0067; H01L 51/0073; H01L 51/0074; H01L 51/5016; H01L 2251/5384; H01L 51/0085; H01L 51/0052; H01L 51/0058; H01L 51/5024; H01L 51/00; C07D 239/74; C07D 241/42; C07D 251/24; C07D 487/04; C09K 11/025; C09K 11/06; C09K 2211/1018; H10K 85/6572; H10K 85/654; H10K 85/6574; H10K 85/6576; H10K 50/11; H10K 2101/10; H10K 2101/90; H10K 85/342; H10K 85/615; H10K 85/626; H10K 50/12
USPC .......................................................... 428/690
See application file for complete search history.

(56) References Cited

U.S. PATENT DOCUMENTS

| 10,547,010 | B2 | 1/2020 | Moon |
| 2011/0156013 | A1* | 6/2011 | Kim ................ C09B 57/00 257/40 |
| 2014/0299865 | A1 | 10/2014 | Nishimura et al. |
| 2016/0225992 | A1 | 8/2016 | Ito et al. |
| 2016/0351817 | A1 | 12/2016 | Kim et al. |
| 2017/0047527 | A1 | 2/2017 | Lee et al. |

(Continued)

FOREIGN PATENT DOCUMENTS

| CN | 103247761 A * | 8/2013 | ............ H01L 51/50 |
| EP | 2991128 A1 * | 3/2016 | ........... C09K 11/025 |

(Continued)

OTHER PUBLICATIONS

Supplementary Partial European Search Report, Application No. 18857740.7, Application dated Sep. 21, 2018.

(Continued)

*Primary Examiner* — Douglas J Mc Ginty
(74) *Attorney, Agent, or Firm* — G. Creston Campbell

(57) ABSTRACT

The present disclosure relates to a plurality of host materials and organic electroluminescent devices comprising the same. The present disclosure may provide a plurality of host materials having a composition favorable to thermal denaturation due to a low deposition temperature, while improving hole properties and electronic properties of HOMO and LUMO, by comprising separate compounds represented by formulas 1 and 2 into a light-emitting layer. By comprising the plurality of host materials of the present disclosure, it is possible to provide an organic electroluminescent device having a lower driving voltage, higher luminous efficiency and/or longer lifetime.

6 Claims, No Drawings

(56) References Cited

U.S. PATENT DOCUMENTS

| | | | |
|---|---|---|---|
| 2017/0062730 A1 | 3/2017 | Ahn et al. | |
| 2018/0208837 A1 | 7/2018 | Ahn | |
| 2021/0296595 A1* | 9/2021 | Cho | H01L 51/0071 |
| 2021/0359216 A1* | 11/2021 | Kim | H01L 51/0059 |
| 2022/0052271 A1* | 2/2022 | Kim | C07D 209/86 |
| 2022/0102645 A1* | 3/2022 | Kim | H01L 51/0072 |

FOREIGN PATENT DOCUMENTS

| | | | |
|---|---|---|---|
| KR | 101311934 B | 9/2013 | |
| KR | 2014-0122680 A | 10/2014 | |
| WO | 2015099486 A1 | 7/2015 | |
| WO | WO-2015167259 A1 * | 11/2015 | C09K 11/025 |
| WO | 2016148390 A1 | 9/2016 | |
| WO | 2017078403 A1 | 5/2017 | |

OTHER PUBLICATIONS

Partial European Search Report, Application No. 21206373.0, Application dated Nov. 4, 2021.
Search Report from JPO for Japanese application No. 2020-516610; Application dated Sep. 21, 2018.
Search Report from SIPO for Chinese application No. 201880061125.1; Application dated Sep. 21, 2018.

* cited by examiner

PLURALITY OF HOST MATERIALS AND ORGANIC ELECTROLUMINESCENT DEVICE COMPRISING THE SAME

TECHNICAL FIELD

The present disclosure relates to a plurality of host materials and an organic electroluminescent device comprising the same.

BACKGROUND ART

In 1987, Tang et al. of Eastman Kodak first developed a small molecule green organic electroluminescent device (OLED) of TPD/Alq3 bilayer consisting of a light-emitting layer and a charge transport layer. Since then, the research on an OLED has been rapidly carried out, and it has been commercialized. An OLED changes electric energy into light by applying electricity to an organic light-emitting material, and commonly comprises an anode, a cathode, and an organic layer formed between the two electrodes. The organic layer of the OLED may comprise a hole injection layer, a hole transport layer, a hole auxiliary layer, a light-emitting auxiliary layer, an electron blocking layer, a light-emitting layer, an electron buffer layer, a hole blocking layer, an electron transport layer, an electron injection layer, etc., if necessary. The materials used in the organic layer can be classified into a hole injection material, a hole transport material, a hole auxiliary material, a light-emitting auxiliary material, an electron blocking material, a light-emitting material layer (containing host and dopant materials), an electron buffer material, a hole blocking material, an electron transport material, an electron injection material, etc., depending on functions.

The most important factor determining luminous efficiency in an OLED is light-emitting materials. The light-emitting materials are required to have high quantum efficiency, high movement degree of an electron and a hole, and uniformity and stability of the formed light-emitting material layer. The light-emitting material is classified into blue, green, and red light-emitting materials according to the light-emitting color, and further includes yellow or orange light-emitting materials. Furthermore, the light-emitting material is classified into a host material and a dopant material in a functional aspect. Recently, an urgent task is the development of an OLED having high efficiency and long lifespan. In particular, the development of highly excellent light-emitting material over conventional materials is urgently required, considering the EL properties necessary for medium- and large-sized OLED panels. For this, preferably, as a solvent in a solid state and an energy transmitter, a host material should have high purity and a suitable molecular weight in order to be deposited under vacuum. Furthermore, a host material is required to have high glass transition temperature and pyrolysis temperature to achieve thermal stability, high electrochemical stability to achieve a long lifespan, easy formability of an amorphous thin film, good adhesion with adjacent layers, and no movement between layers.

Korean Patent No. 1311934 and Korean Patent Application Laid-Open No. 2015-124902 disclose an organic electroluminescent device comprising an indolocarbazole compound as one of a plurality of host materials. However, the development for improving the performance of an OLED is still required.

DISCLOSURE OF THE INVENTION

Problems to be Solved

A material having various residues in an organic electroluminescent device can exhibit excellent luminescent properties by improving hole and electron properties. However, the higher the molecular weight, the higher the temperature required for deposition, and a higher deposition temperature is required. When heat is applied at a high deposition temperature for a period of time, the material is denatured, thereby deteriorating the inherent properties of the material and deteriorating the luminescent properties.

The objective of the present disclosure is to provide a plurality of host materials having conditions for favorable thermal denaturation due to a low deposition temperature while improving hole and electronic properties. Another objective of the present disclosure is to provide an organic electroluminescent device having a lower driving voltage, higher luminous efficiency and/or longer lifetime.

Solution to Problems

The present inventors have found that the combination of a compound of formula 1 and a compound of formula 2 as a light-emitting material can exhibit excellent luminescent properties by improving hole and electron properties by separating a HOMO part responsible for the hole properties and a LUMO part responsible for the electron properties. In addition, they have found that the combination can have favorable conditions for thermal denaturation by having a low deposition temperature.

According to one embodiment of the present disclosure, a plurality of host materials can be deposited at a relatively low temperature, so that deterioration of luminescent properties can be reduced.

Also, according to another embodiment of the present disclosure, an organic electroluminescent device comprising the compounds represented by formula 1 and formula 2 may have a lower driving voltage, higher luminous efficiency and/or longer lifetime.

Specifically, the above objective can be achieved by a plurality of host materials comprising a first host material and a second host material, wherein the first host material comprises a compound represented by the following formula 1:

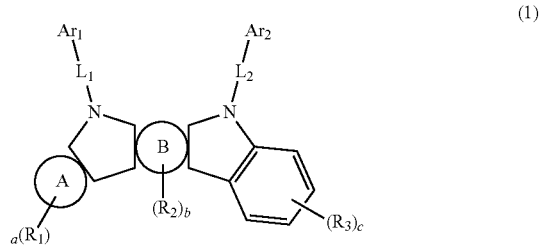

(1)

wherein $L_1$ and $L_2$, each independently, represent a single bond, a substituted or unsubstituted (C6-C30)arylene, or a substituted or unsubstituted (3- to 30-membered)heteroarylene;

$Ar_1$ and $Ar_2$, each independently, represent a substituted or unsubstituted (C6-C30)aryl, a substituted or unsubstituted (3- to 30-membered)heteroaryl, an amino, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino;

A and B, each independently, represent a benzene ring or a naphthalene ring, with the proviso that at least one of A and B represents a naphthalene ring;

$R_1$ to $R_3$, each independently, represent hydrogen, deuterium, a halogen, a cyano, a substituted or unsubstituted (C1-C30)alkyl, a substituted or unsubstituted (C2-C30)alkenyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or each of $R_1$ to $R_3$ may be linked to each other to form a substituted or unsubstituted (3- to 30-membered) mono- or polycyclic ring;

a represents an integer of 1 to 4, when A represents a benzene ring; or a represents an integer of 1 to 6, when A represents a naphthalene ring;

b represents 1 or 2, when B represents a benzene ring; or b represents an integer of 1 to 4, when B represents a naphthalene ring;

c represents an integer of 1 to 4; and where if a to c, each independently, are an integer of 2 or more, each of $R_1$ to $R_3$ may be the same or different; and the second host material comprises a compound represented by the following formula 2:

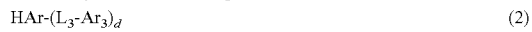

$$\text{HAr-(L}_3\text{-Ar}_3)_d \qquad (2)$$

wherein,

HAr represents a substituted or unsubstituted N-containing (3- to 10-membered) heteroaryl;

$L_3$ represents a single bond, or a substituted or unsubstituted (C6-C30)arylene;

$Ar_3$ represents a substituted or unsubstituted (C6-C30)aryl; and d represents an integer of 1 to 3, where if d is an integer of 2 or more, each ($L_3$-$Ar_3$) may be the same or different.

Effects of the Invention

By comprising the specific combination of compounds according to the present disclosure as a host material, an organic electroluminescent device having a lower driving voltage, higher luminous efficiency and/or longer lifetime may be provided. Also, the present disclosure may provide a plurality of host materials having a composition favorable to thermal denaturation due to a low deposition temperature, while improving hole properties and electronic properties of HOMO and LUMO, by comprising separate compounds represented by complementary formulas 1 and 2 in a light-emitting layer.

EMBODIMENTS OF THE INVENTION

Hereinafter, the present disclosure will be described in detail. However, the following description is intended to explain the disclosure, and is not meant in any way to restrict the scope of the disclosure.

The term "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material (containing host and dopant materials), an electron buffer material, a hole blocking material, an electron transport material, an electron injection material, etc.

The term "a plurality of organic electroluminescent materials" in the present disclosure means an organic electroluminescent material as a combination of at least two compounds, which may be comprised in any layer constituting an organic electroluminescent device. It may mean both a material before being comprised in an organic electroluminescent device (for example, before vapor deposition) and a material after being comprised in an organic electroluminescent device (for example, after vapor deposition). For example, a plurality of organic electroluminescent materials may be a combination of at least two compounds which may be comprised in at least one of a hole injection layer, a hole transport layer, a hole auxiliary layer, a light-emitting auxiliary layer, an electron blocking layer, a light-emitting layer, an electron buffer layer, a hole blocking layer, an electron transport layer, and an electron injection layer. At least two compounds may be comprised in the same layer or different layers by means of the methods used in the art, for example, may be mixture-evaporated or co-evaporated, or may be individually evaporated.

The term "a plurality of host materials" in the present disclosure means a host material as a combination of at least two compounds, which may be comprised in any light-emitting layer constituting an organic electroluminescent device. It may mean both a material before being comprised in an organic electroluminescent device (for example, before vapor deposition) and a material after being comprised in an organic electroluminescent device (for example, after vapor deposition). A plurality of host materials of the present disclosure may be a combination of at least two host materials, and may optionally conventional materials used in the organic electroluminescent material. At least two compounds comprised in a plurality of host materials may be comprised together in one light-emitting layer or may respectively be comprised in different light-emitting layers. If at least two host materials are comprised in one layer, for example, they may be mixture-evaporated to form a layer, or may be separately co-evaporated at the same time to form a layer.

Herein, the term "(C1-C30)alkyl" is meant to be a linear or branched alkyl having 1 to 30 carbon atoms constituting the chain, in which the number of carbon atoms is preferably 1 to 20, and more preferably 1 to 10. The above alkyl may include methyl, ethyl, n-propyl, iso-propyl, n-butyl, iso-butyl, tert-butyl, etc. The term "(C2-C30)alkenyl" is meant to be a linear or branched alkenyl having 2 to 30 carbon atoms constituting the chain, in which the number of carbon atoms is preferably 2 to 20, and more preferably 2 to 10. The above alkenyl may include vinyl, 1-propenyl, 2-propenyl, 1-butenyl, 2-butenyl, 3-butenyl, 2-methylbut-2-enyl, etc. The term "(C2-C30)alkynyl" is meant to be a linear or branched alkynyl having 2 to 30 carbon atoms constituting the chain, in which the number of carbon atoms is preferably 2 to 20, and more preferably 2 to 10. The above alkynyl may include ethynyl, 1-propynyl, 2-propynyl, 1-butynyl, 2-butynyl, 3-butynyl, 1-methylpent-2-ynyl, etc. The term "(C3-C30)cycloalkyl" is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, etc. The term "(3- to 7-membered)heterocycloalkyl" is meant to be a cycloalkyl having 3 to 7, preferably 5 to 7, ring backbone atoms, and including at least one heteroatom selected from the group consisting of B, N, O, S, Si, and P, and preferably the group consisting of O, S, and N. The above heterocycloalkyl may include tetrahydrofuran, pyrrolidine, thiolan, tetrahydropyran, etc. The term "(C6-C30)aryl(ene)" is meant to be a monocyclic or fused ring radical derived from an aromatic hydrocarbon having 6 to 30 ring backbone carbon atoms, in which the number of the ring backbone carbon atoms is preferably 6 to 25, more preferably 6 to 18. The above aryl(ene) may be partially saturated, and may comprise a spiro structure. The above aryl may include phenyl, biphenyl, terphenyl, naphthyl, binaphthyl, phenylnaphthyl, naphthylphenyl, phenylterphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, etc. The term "(3- to 30-membered)heteroaryl(ene)" is an aryl having 3 to 30 ring backbone atoms, and including at least one, preferably 1 to 4 heteroatoms selected from the group consisting of B, N, O, S, Si, and P. The above heteroaryl(ene) may be a monocyclic ring, or a fused ring condensed with at least one benzene ring; may be partially saturated; may be one formed by linking at least one heteroaryl or aryl group to a heteroaryl group via a single bond(s); and may comprise a spiro structure. The above heteroaryl may include a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, and pyridazinyl, and a fused ring-type heteroaryl such as benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, benzoquinazolinyl, quinoxalinyl, benzoquinoxalinyl, naphthyridinyl, carbazolyl, benzocarbazolyl, dibenzocarbazolyl, phenoxazinyl, phenothiazinyl, phenanthridinyl, benzodioxolyl, and dihydroacridinyl. Furthermore, "halogen" includes F, Cl, Br, and I.

Herein, "substituted" in the expression "substituted or unsubstituted" means that a hydrogen atom in a certain functional group is replaced with another atom or another functional group, i.e., a substituent. The substituents of the substituted aryl(ene), the substituted heteroaryl(ene), the substituted mono- or di-alkylamino, the substituted mono- or di-arylamino, the substituted alkylarylamino, the substituted alkyl, the substituted alkenyl, the substituted cycloalkyl, the substituted alkoxy, the substituted trialkylsilyl, the substituted dialkylarylsilyl, the substituted alkyldiarylsilyl, the substituted triarylsilyl, or the substituted mono- or polycyclic ring in the present disclosure, each independently, are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (5- to 30-membered)heteroaryl unsubstituted or substituted with a (C6-C30)aryl; a (C6-C30)aryl unsubstituted or substituted with a (5- to 30-membered) heteroaryl; a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino; a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl. According to one embodiment of the present disclosure, the substituents, each independently, are at least one of a (C1-C20)alkyl and a (C6-C25) aryl. According to another embodiment of the present disclosure, the substituents, each independently, are at least one of a (C1-C10)alkyl and a (C6-C18)aryl. For example, the substituents, each independently, are at least one of a methyl and a phenyl.

Herein, the heteroaryl(ene) and the heterocycloalkyl may contain at least one heteroatom selected from B, N, O, S, Si, and P. Also, the heteroatom may be bonded to at least one selected from the group consisting of hydrogen, deuterium, a halogen, a cyano, a substituted or unsubstituted (C1-C30) alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, and a substituted or unsubstituted (C1-C30)alkyl(C6-C30)arylamino.

In the formulas of the present disclosure, if a substituent is linked to an adjacent substituent to form a substituted or unsubstituted (3- to 30-membered) ring, the ring may be a mono- or polycyclic, alicyclic or aromatic ring, or the combination thereof, in which the formed ring may contain at least one heteroatom selected from nitrogen, oxygen, and sulfur.

In formula 1, $L_1$ and $L_2$, each independently, represent a single bond, a substituted or unsubstituted (C6-C30)arylene, or a substituted or unsubstituted (3- to 30-membered)heteroarylene. According to one embodiment of the present disclosure, $L_1$ and $L_2$, each independently, represent a single bond, a substituted or unsubstituted (C6-C25)arylene, or a substituted or unsubstituted (5- to 25-membered)heteroarylene. According to another embodiment of the present disclosure, $L_1$ and $L_2$, each independently, represent a single bond, an unsubstituted (C6-C18)arylene, or an unsubstituted (5- to 18-membered)heteroarylene. For example, $L_1$ and $L_2$, each independently, may represent a single bond, a phenylene, a naphthylene, a biphenylene, or a carbazolylene.

In formula 1, $Ar_1$ and $Ar_2$, each independently, represent a substituted or unsubstituted (C6-C30)aryl, a substituted or unsubstituted (3- to 30-membered)heteroaryl, an amino, a substituted or unsubstituted mono- or di-(C1-C30)alkylamino, a substituted or unsubstituted mono- or di-(C6-C30) arylamino, or a substituted or unsubstituted (C1-C30)alkyl (C6-C30)arylamino. According to one embodiment of the present disclosure, $Ar_1$ and $Ar_2$, each independently, represent a substituted or unsubstituted (C6-C25)aryl, a substituted or unsubstituted (3- to 25-membered)heteroaryl, or a substituted or unsubstituted mono- or di-(C6-C30)arylamino. According to another embodiment of the present disclosure, $Ar_1$ and $Ar_2$, each independently, represent a (C6-C18)aryl unsubstituted or substituted with at least one of (C1-C10)alkyl, an unsubstituted (5- to 18-membered) heteroaryl, or an unsubstituted di(C6-C18)arylamino. For example, $Ar_1$ and $Ar_2$, each independently, may represent a phenyl, a naphthyl, a biphenyl, a terphenyl, a phenanthrenyl, a dimethylfluorenyl, a dimethylbenzofluorenyl, a dibenzothiophenyl, a dibenzofuranyl, a diphenylamino, a phenylbiphenylamino, or a phenylnaphthylamino.

In formula 1, A and B, each independently, represent a benzene ring or a naphthalene ring, with the proviso that at least one of A and B represents a naphthalene ring. According to one embodiment of the present disclosure, A represents a naphthalene ring, and B represents a benzene ring or a naphthalene ring.

In formula 1, $R_1$ to $R_3$, each independently, represent hydrogen, deuterium, a halogen, a cyano, a substituted or unsubstituted (C1-C30)alkyl, a substituted or unsubstituted (C2-C30)alkenyl, a substituted or unsubstituted (C6-C30)aryl, a substituted or unsubstituted (3- to 30-membered) heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or each of $R_1$ to $R_3$ may be linked to each other to form a substituted or unsubstituted (3- to 30-membered) mono- or polycyclic ring. According to one embodiment of the present disclosure, $R_1$ to $R_3$, each independently, represent hydrogen, a substituted or unsubstituted (C1-C20)alkyl, a substituted or unsubstituted (C2-C20)alkenyl, a substituted or unsubstituted (C6-C25)aryl, or a substituted or unsubstituted (5- to 25-membered)heteroaryl; or each of $R_1$ to $R_3$ may be linked to each other to form a substituted or unsubstituted (3- to 25-membered) mono- or polycyclic ring. According to another embodiment of the present disclosure, $R_1$ to $R_3$, each independently, represent hydrogen, an unsubstituted (C1-C10)alkyl, an unsubstituted (C2-C10)alkenyl, or an unsubstituted (C6-C18)aryl; or two adjacent $R_3$'s may be linked to each other to form a substituted or unsubstituted (3- to 18-membered) mono- or polycyclic ring. For example, $R_1$ may be hydrogen or a phenyl; $R_2$ may be hydrogen; and $R_3$ may be hydrogen or a phenyl, or two adjacent $R_3$'s may be linked to each other to form a benzene ring.

In formula 1, a represents an integer of 1 to 4, when A represents a benzene ring; or a represents an integer of 1 to 6, when A represents a naphthalene ring; b represents 1 or 2, when B represents a benzene ring; or b represents an integer of 1 to 4, when B represents a naphthalene ring; and c represents an integer of 1 to 4. If a to c, each independently, are an integer of 2 or more, each of $R_1$ to $R_3$ may be the same or different. According to one embodiment of the present disclosure, a to c, each independently, represent 1 or 2.

The compound represented by formula 1 may be represented by at least one of the following formulas 3 and 4.

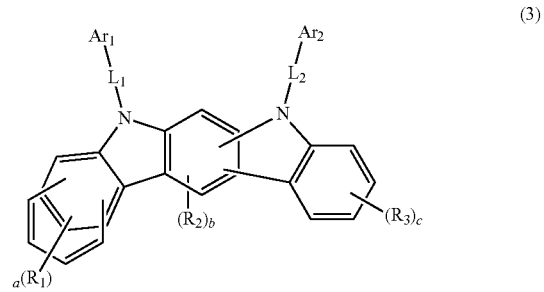

(3)

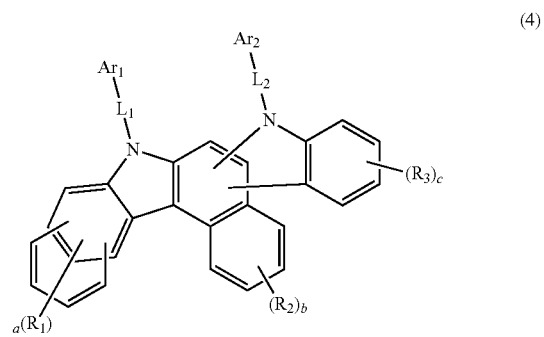

(4)

In formulas 3 and 4, $L_1$, $L_2$, $Ar_1$, $Ar_2$, $R_1$ to $R_3$, and a to c are as defined in formula 1.

In formula 2, HAr represents a substituted or unsubstituted N-containing (3- to 10-membered)heteroaryl. According to one embodiment of the present disclosure, HAr represents a substituted or unsubstituted N-containing (5- to 10-membered)heteroaryl. According to another embodiment of the present disclosure, HAr represents an unsubstituted N-containing (6- to 10-membered)heteroaryl. For example, HAr may represent a triazinyl, a pyrimidinyl, a quinoxalinyl, a quinazolinyl, or a quinolinyl.

In formula 2, $L_3$ represents a single bond, or a substituted or unsubstituted (C6-C30)arylene. According to one embodiment of the present disclosure, $L_3$ represents a single bond, or a substituted or unsubstituted (C6-C25)arylene. According to another embodiment of the present disclosure, $L_3$ represents a single bond, or an unsubstituted (C6-C20) arylene. For example, $L_3$ may represent a single bond, a phenylene, a naphthylene, a biphenylene, a naphthylphenylene, a phenylnaphthylene, or a phenylfluorenylene.

In formula 2, $Ar_3$ represents a substituted or unsubstituted (C6-C30)aryl. According to one embodiment of the present disclosure, $Ar_3$ represents a substituted or unsubstituted (C6-C25)aryl. According to another embodiment of the present disclosure, $Ar_3$ represents a (C6-C18)aryl unsubstituted or substituted with at least one of (C1-C6)alkyl and (C6-C18)aryl. For example, $Ar_3$ may represent a phenyl, a biphenyl, a naphthyl, a terphenyl, a triphenylenyl, a phenanthrenyl, a phenylfluorenyl, a diphenylfluorenyl, a dimethylfluorenyl, or a dimethylbenzofluorenyl.

In formula 2, d represents an integer of 1 to 3, where if d is an integer of 2 or more, each ($L_3$-$Ar_3$) may be the same or different. According to one embodiment of the present disclosure, d may represent 2 or 3.

The compound represented by formula 2 may be represented by at least one of the following formulas 5 and 6.

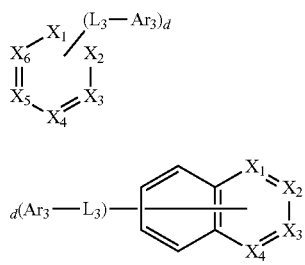

(5)

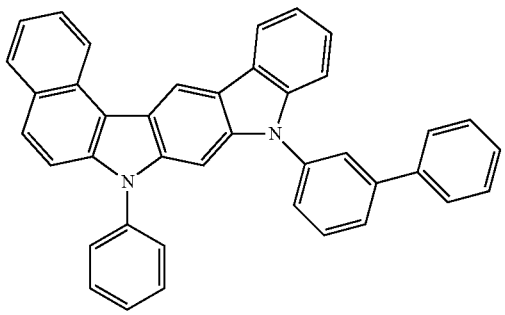

C-1-3

(6)

In formulas 5 and 6, $X_1$ to $X_6$, each independently, represent $CR_4$ or N. In formula 5, at least one of $X_1$ to $X_6$ may represent N. In formula 6, at least one of $X_1$ to $X_4$ may represent N.

$R_4$ represents hydrogen, a substituted or unsubstituted (C6-C30)aryl, a substituted or unsubstituted (C2-C30)alkenyl, or a substituted or unsubstituted (C1-C30)alkyl; or two adjacent $R_4$'s may be linked to each other to form a substituted or unsubstituted (3- to 30-membered) mono- or polycyclic ring. According to one embodiment of the present disclosure, $R_4$ represents hydrogen; or two adjacent $R_4$'s may be linked to each other to form an unsubstituted (3- to 18-membered) mono- or polycyclic ring. According to another embodiment of the present disclosure, $R_4$ represents hydrogen; or two adjacent $R_4$'s may be linked to each other to form an unsubstituted (3- to 10-membered) monocyclic ring. For example, $R_4$ may represent hydrogen; or two adjacent $R_4$'s may be linked to each other to form an unsubstituted benzene ring.

In formulas 5 and 6, $L_3$, $Ar_3$ and d are as defined in formula 2.

The compound represented by formula 1 includes the following compounds, but is not limited thereto.

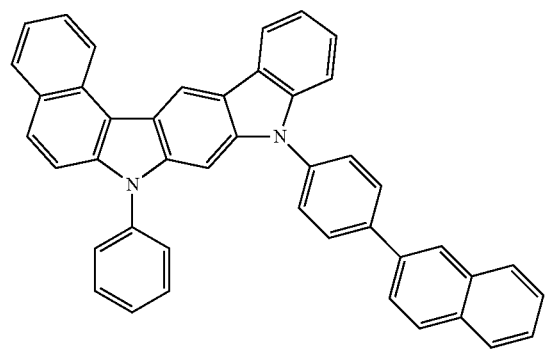

C-1-4

C-1-1

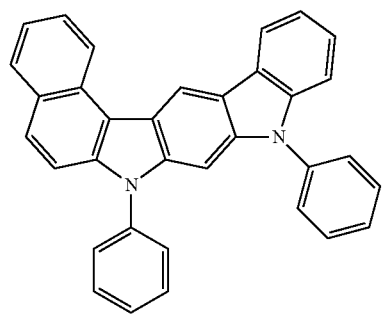

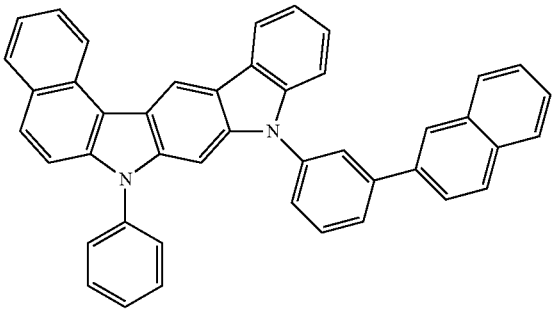

C-1-5

C-1-2

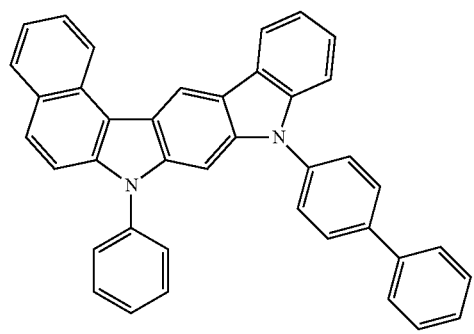

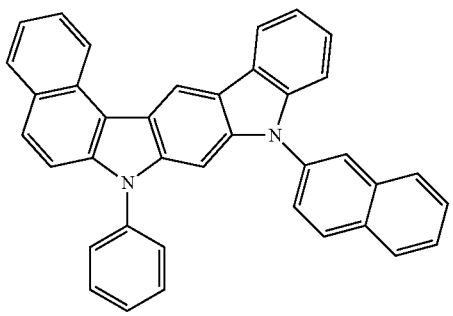

C-1-6

C-1-7
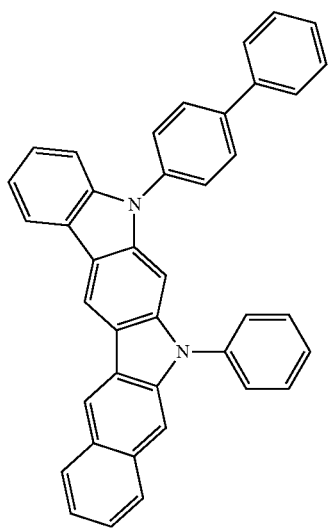
C-1-8
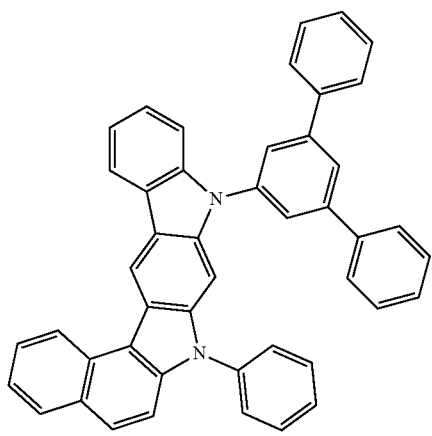
C-1-10
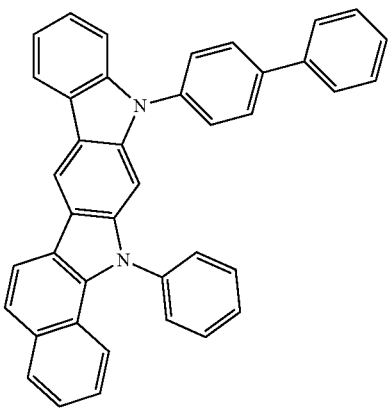
C-1-11
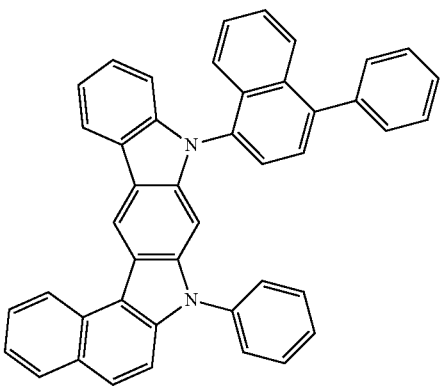
C-1-9
C-1-12

C-1-13
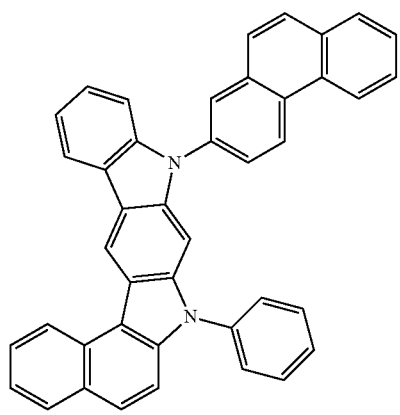
C-1-16
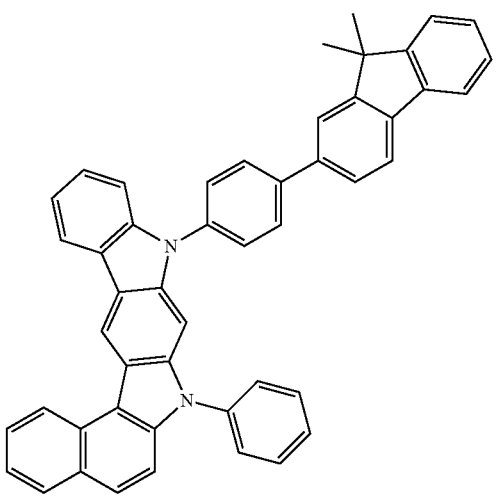
C-1-14
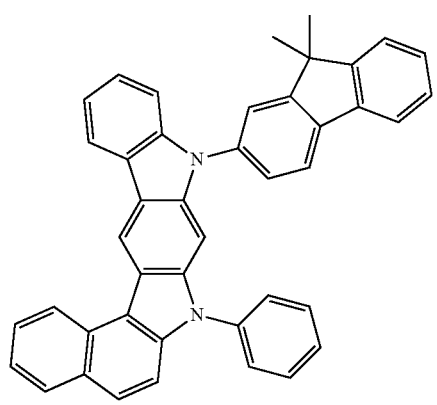
C-1-17
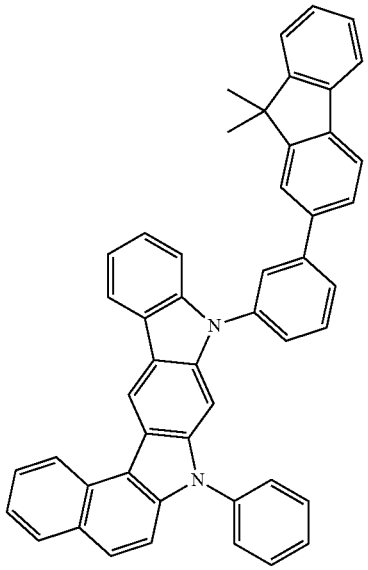
C-1-15
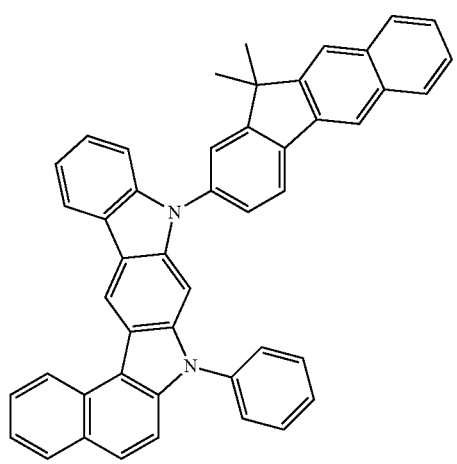
C-1-18
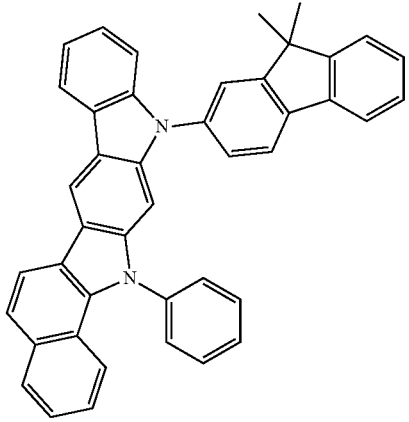

C-1-19
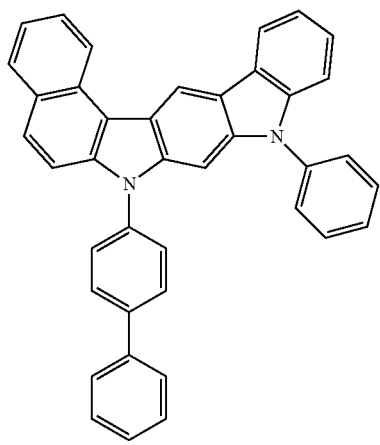
C-1-20
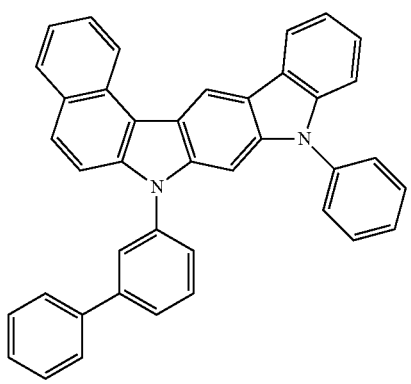
C-1-21
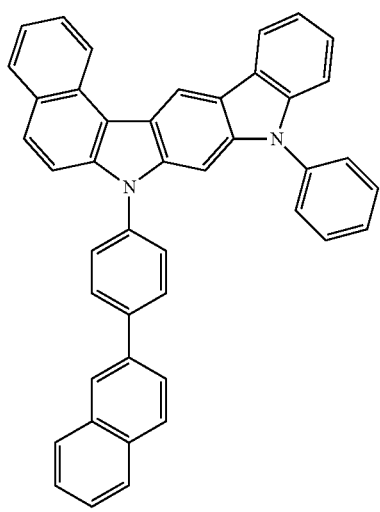
C-1-22
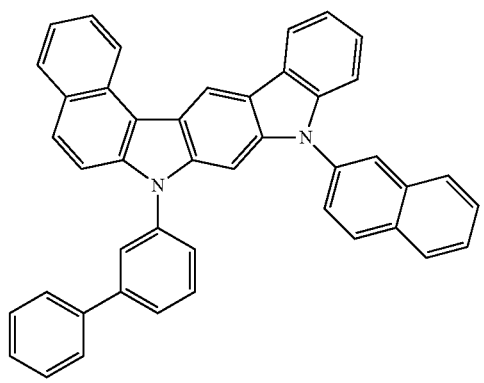
C-1-23
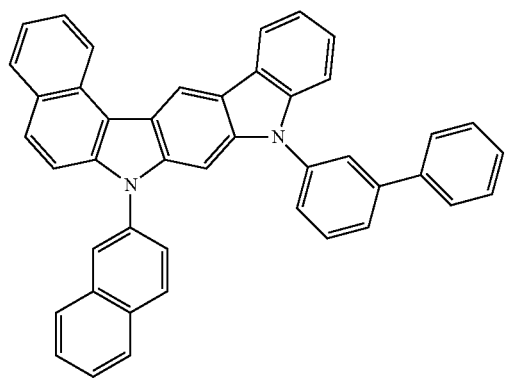
C-1-24
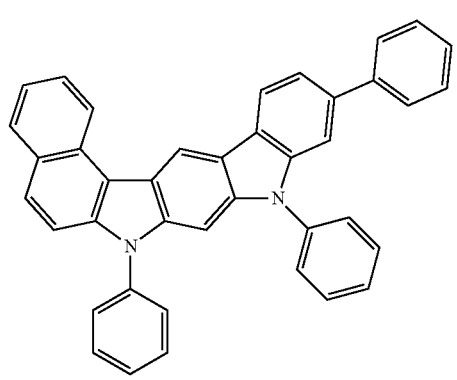
C-1-25
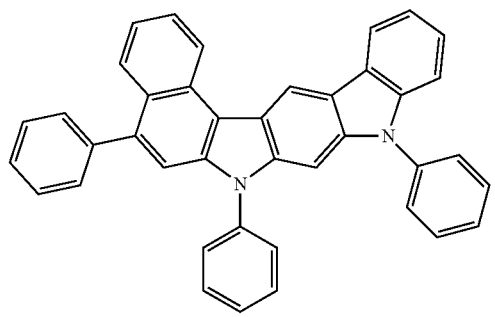

-continued
C-1-26
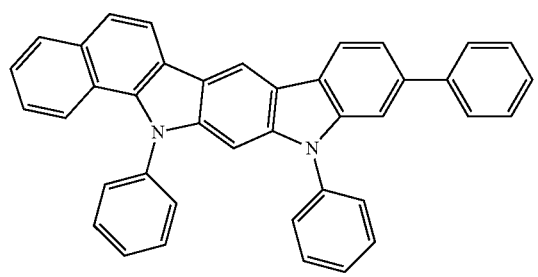
C-1-27
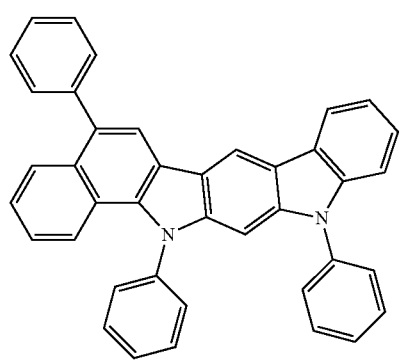
C-1-28
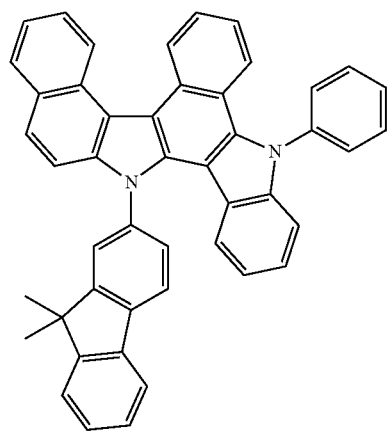
C-1-29
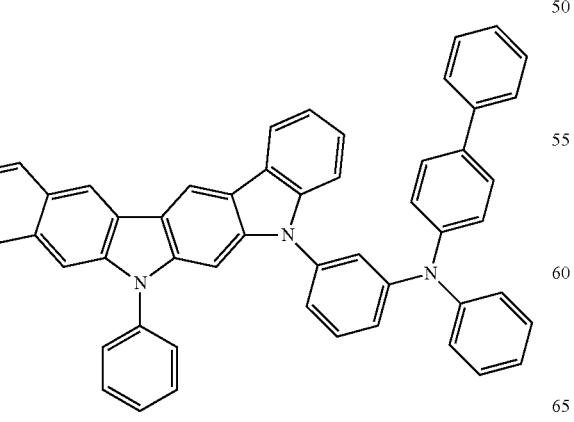
C-1-30
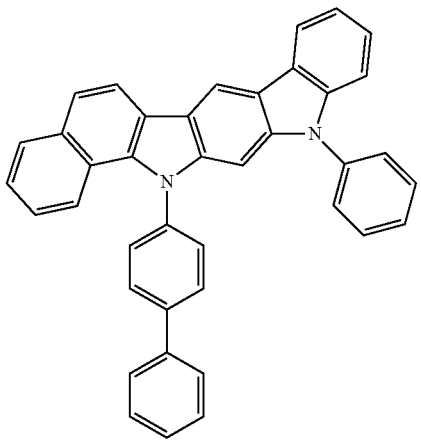
C-1-31
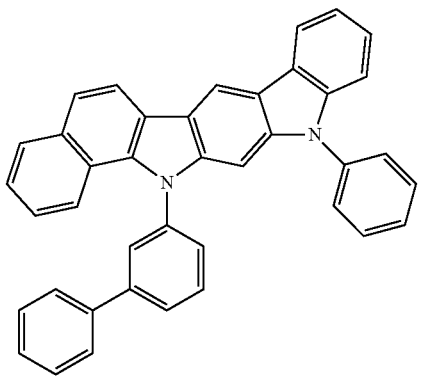
C-1-32
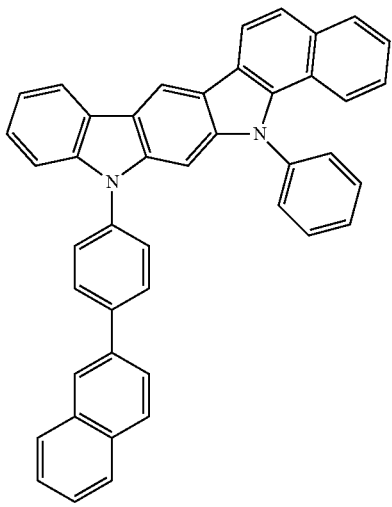

C-1-33
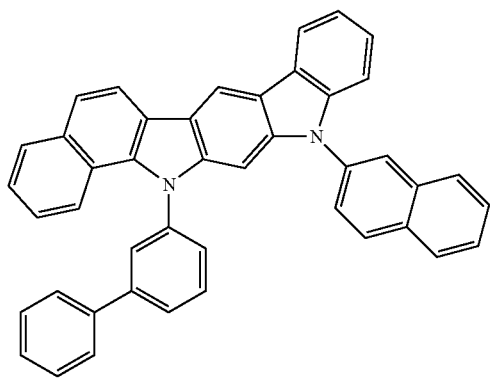
C-1-34
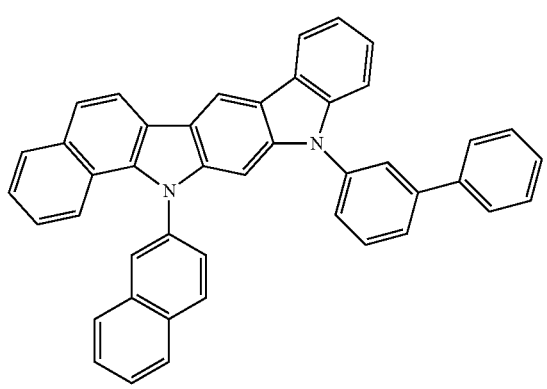
C-1-35
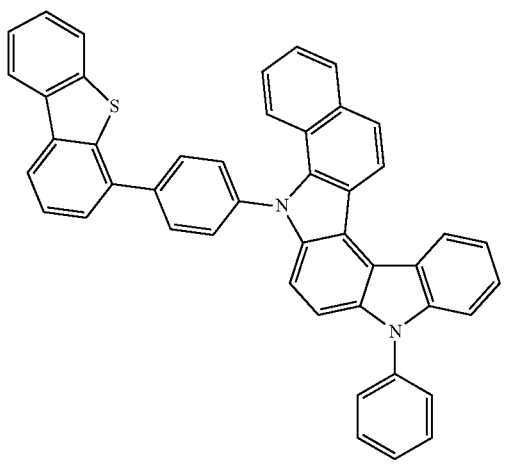
C-1-36
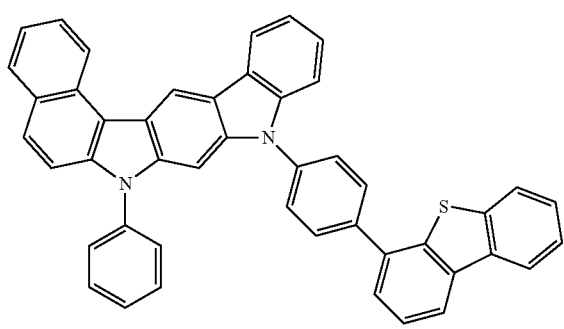
C-1-37
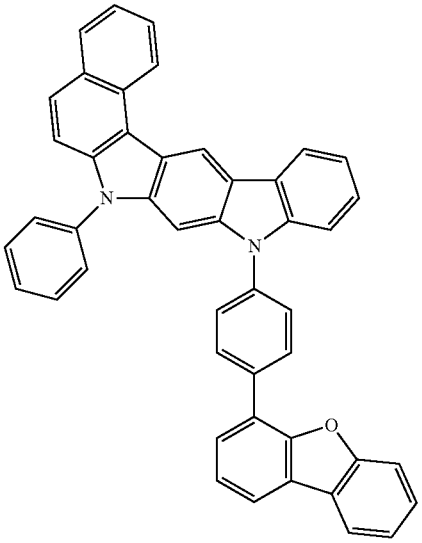
C-1-38
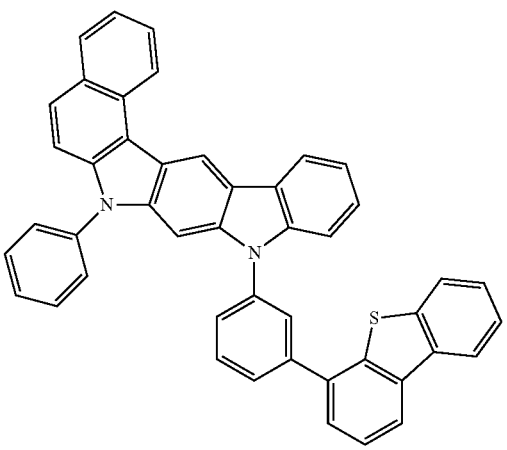
C-1-39
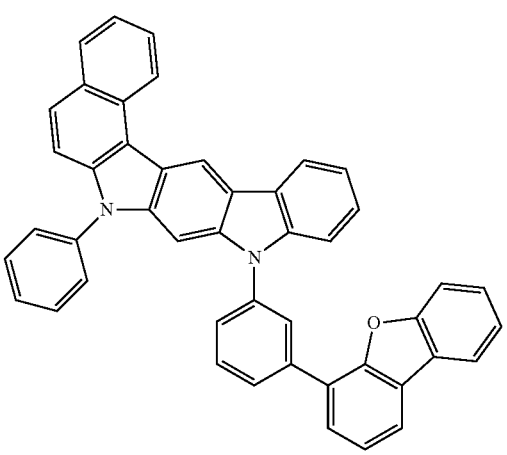

C-1-40
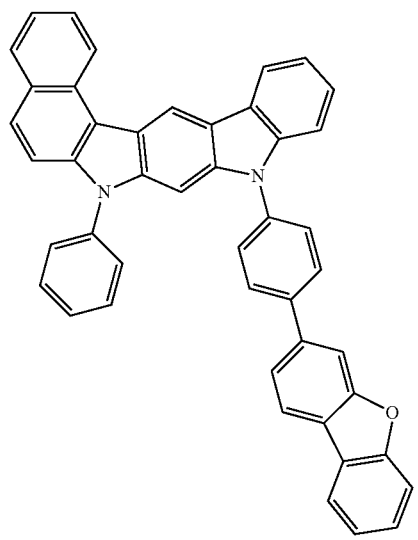
C-1-41
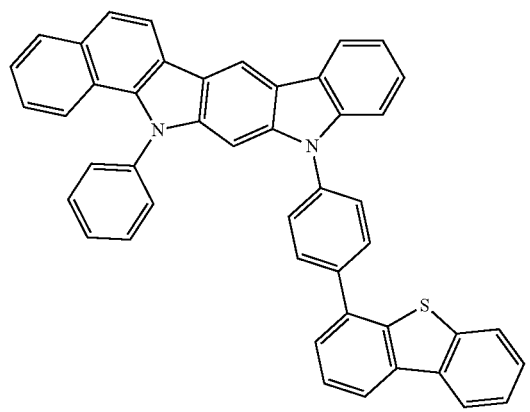
C-1-42
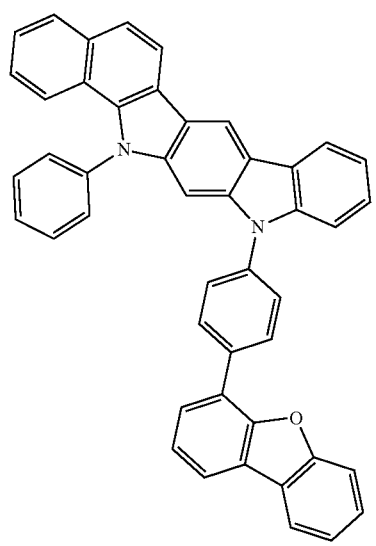
C-1-43
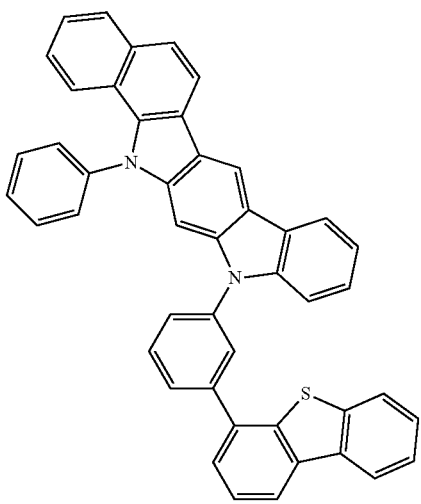
C-1-44
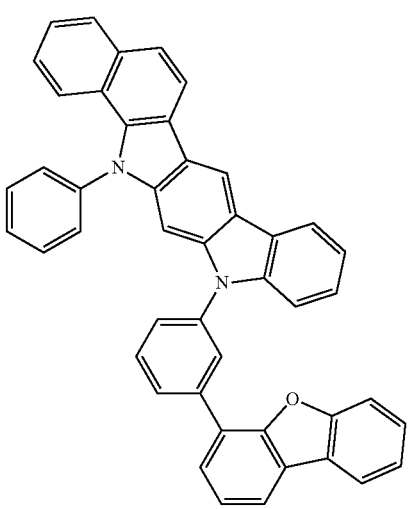
C-1-45
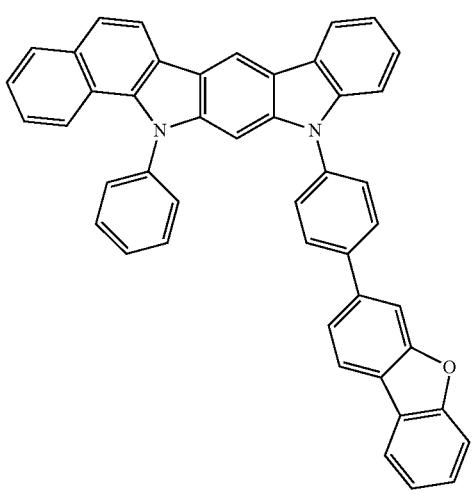

C-1-46
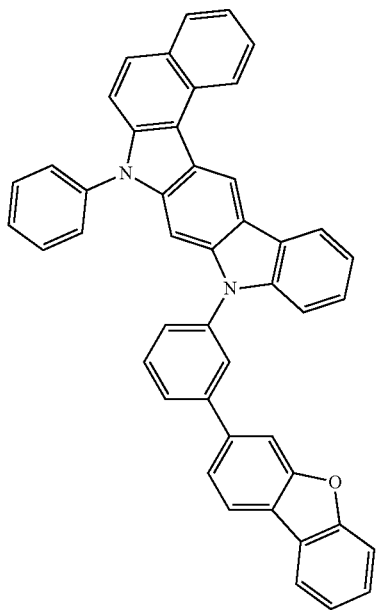
C-1-47
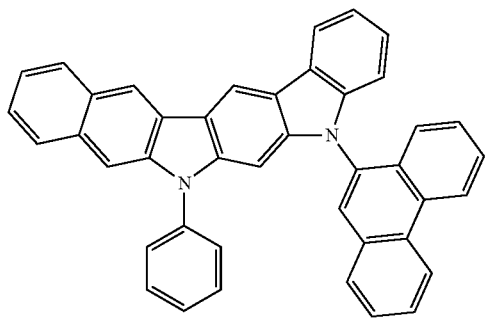
C-1-48
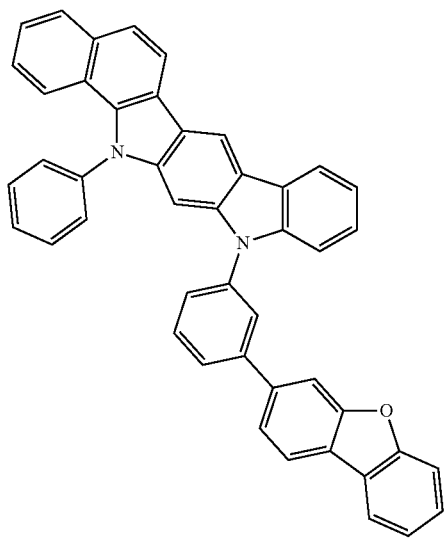
C-1-49
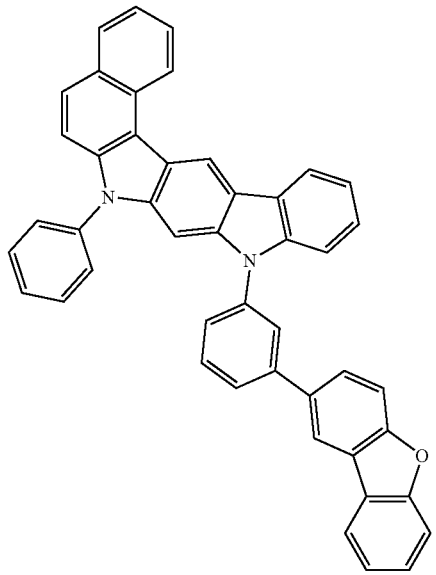
C-1-50
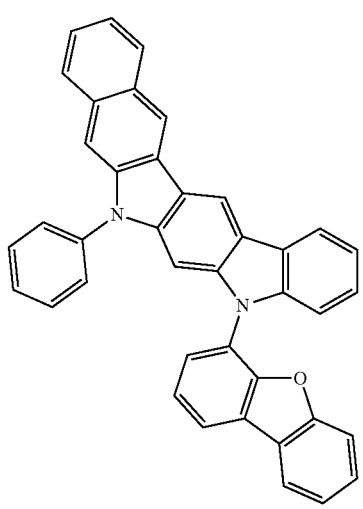
C-1-51
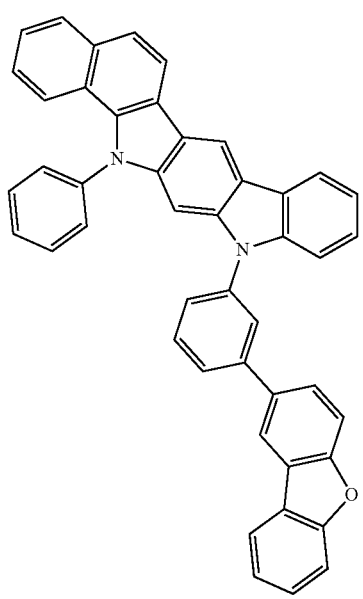

C-1-52
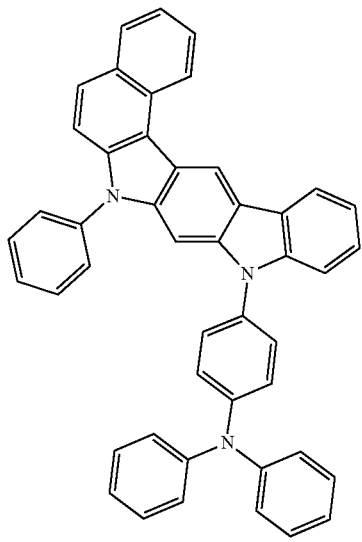
C-1-53
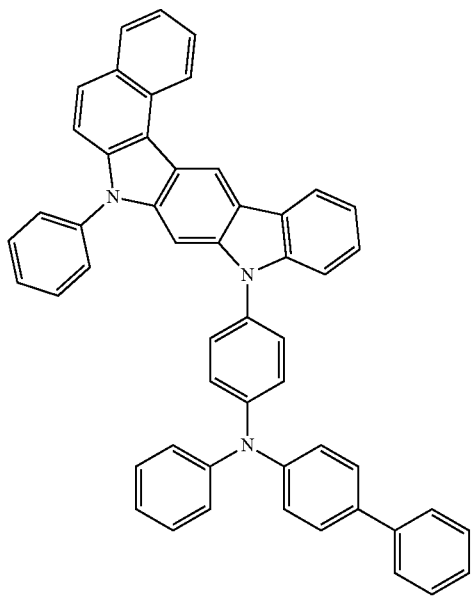
C-1-54
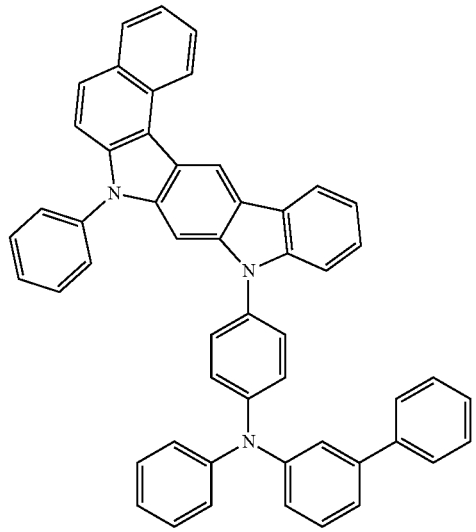
C-1-55
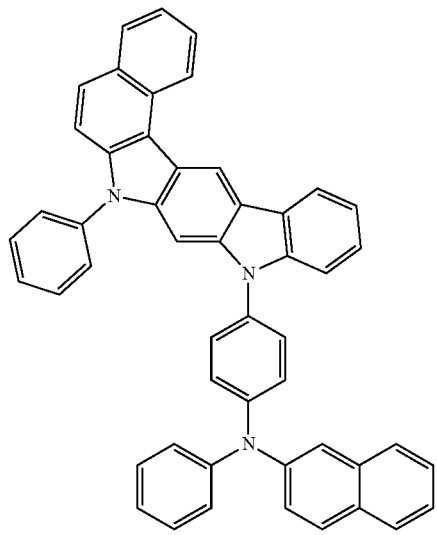
C-1-56
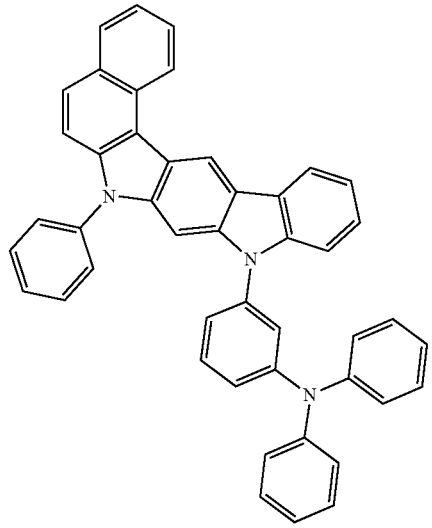

C-1-57
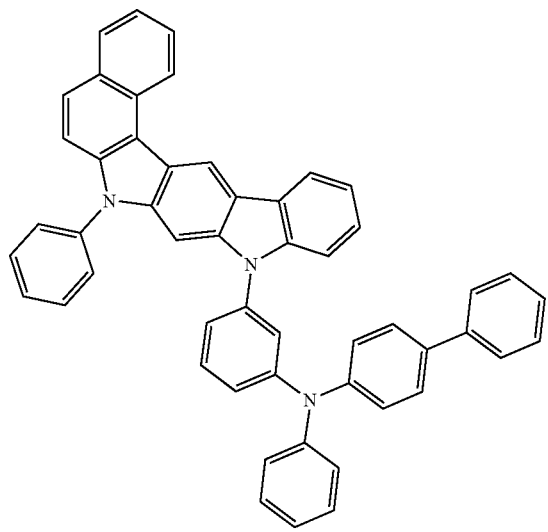
C-1-58
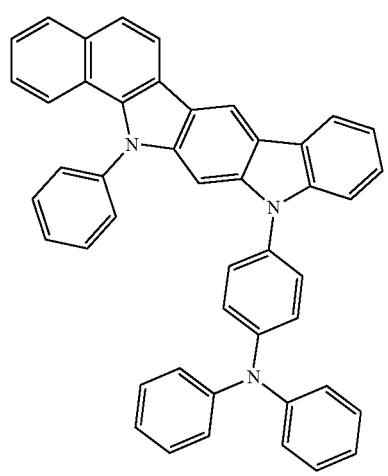
C-1-59
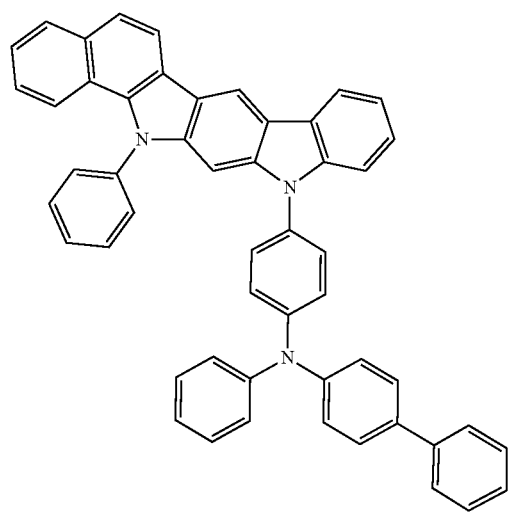
C-1-60
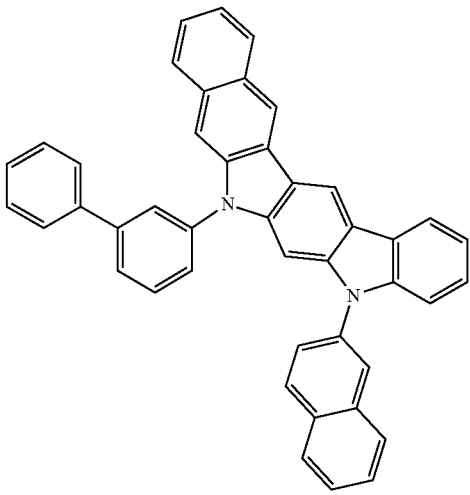
C-1-61
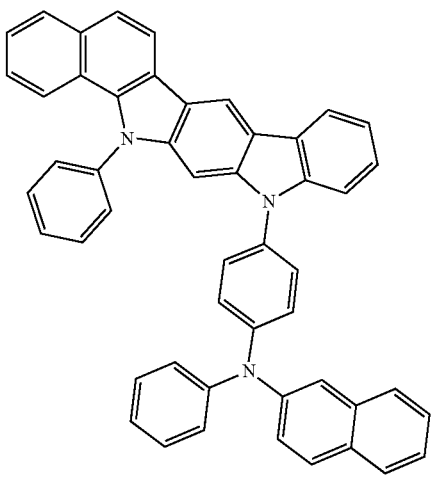
C-1-62
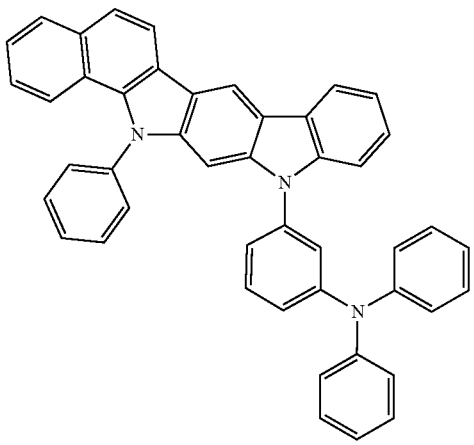

C-1-63
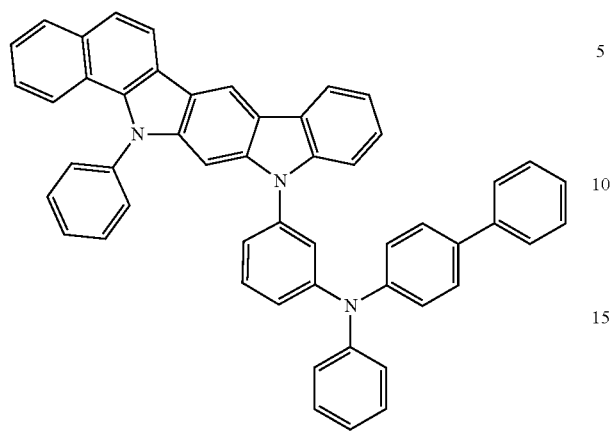
C-1-64
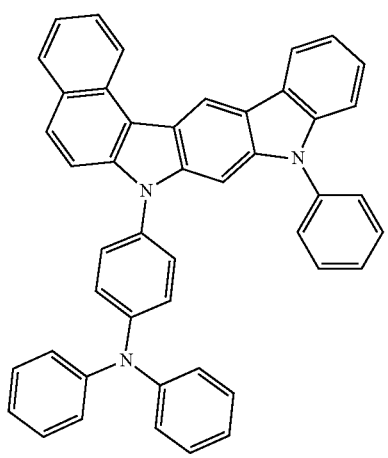
C-1-65
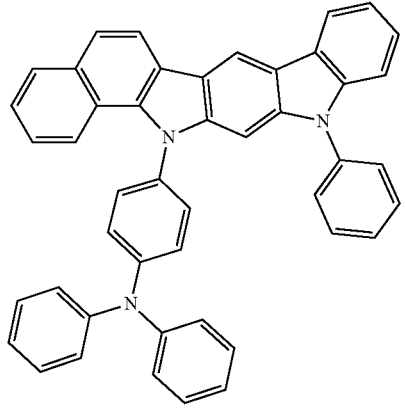
C-1-66
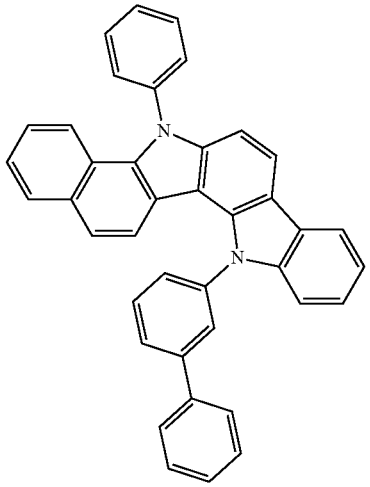
C-1-67
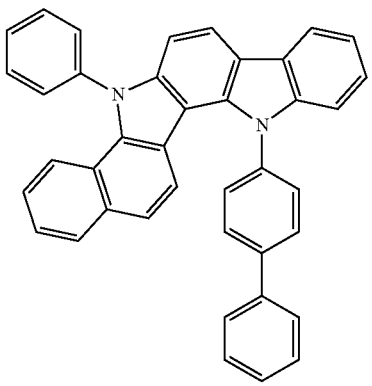
C-1-68
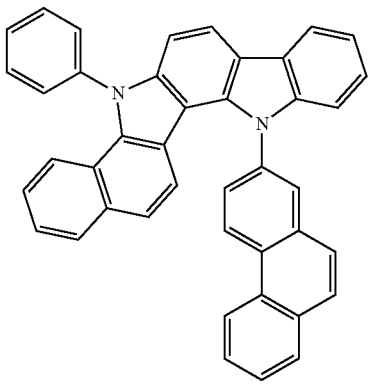
C-1-69
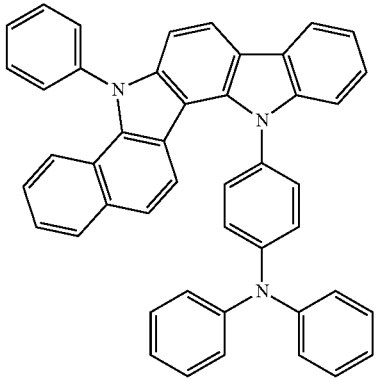

C-1-70
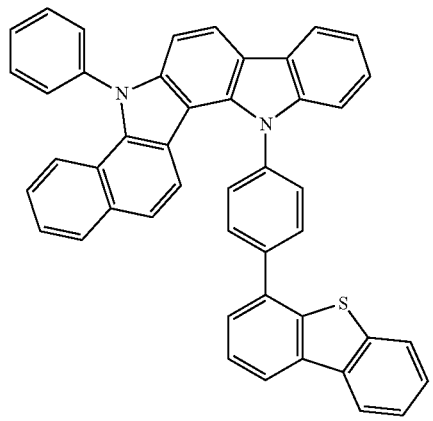
C-1-71
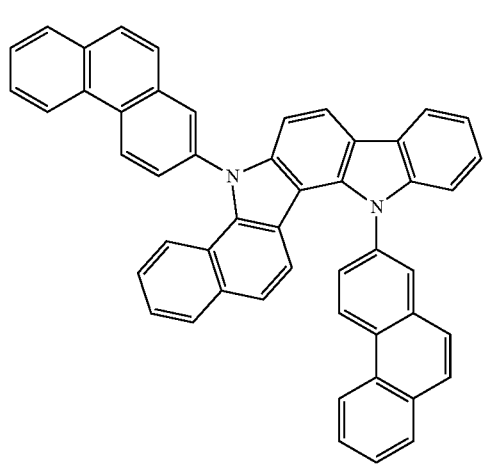
C-1-72
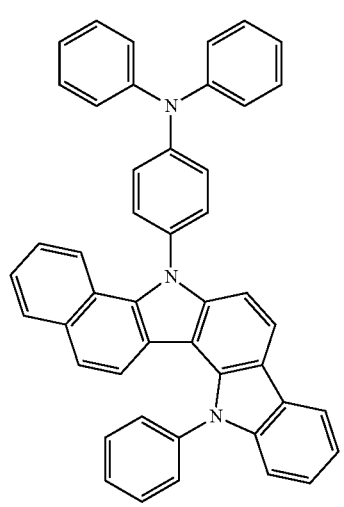
C-1-73
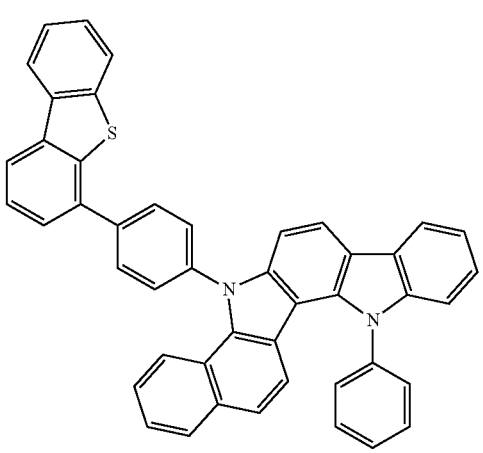
C-1-74
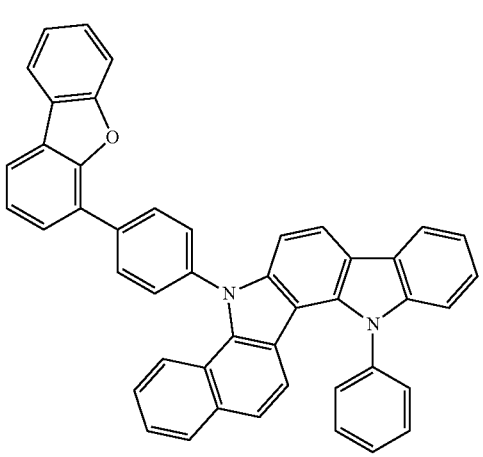
C-1-75
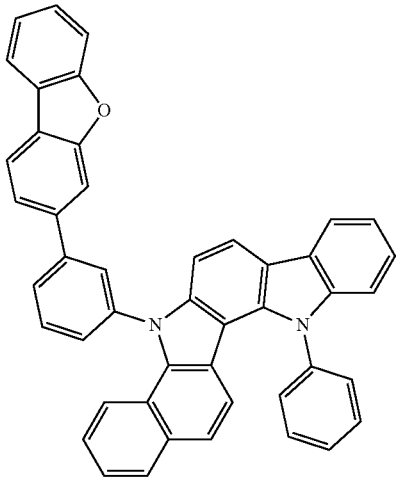

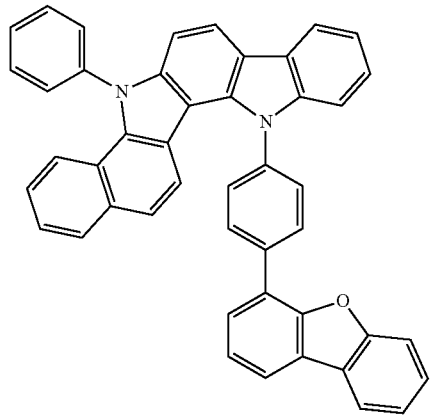
C-1-76
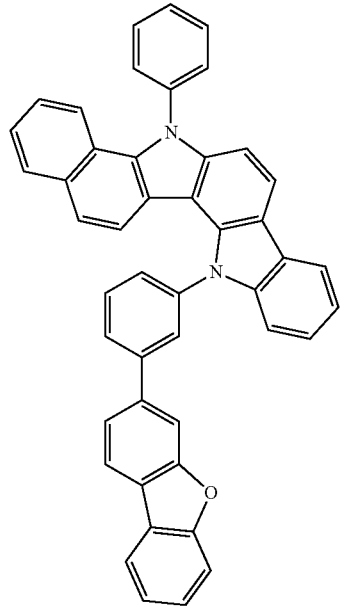
C-1-77
C-1-78
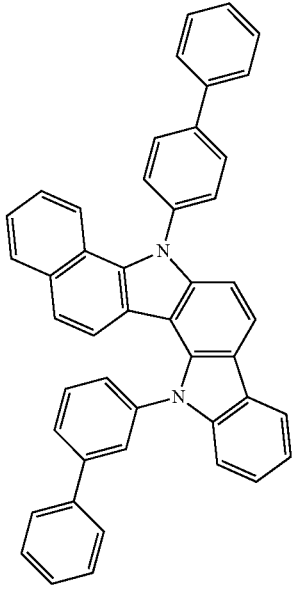
C-1-79
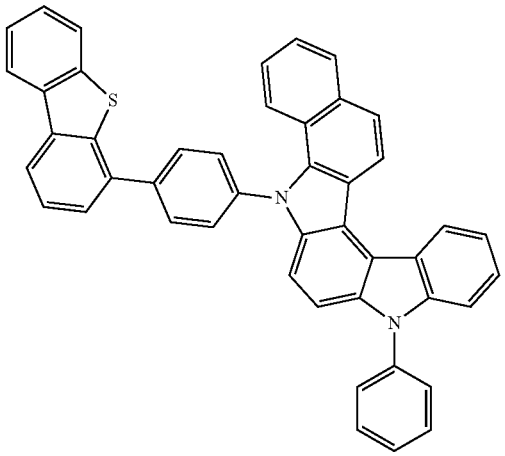
C-1-80
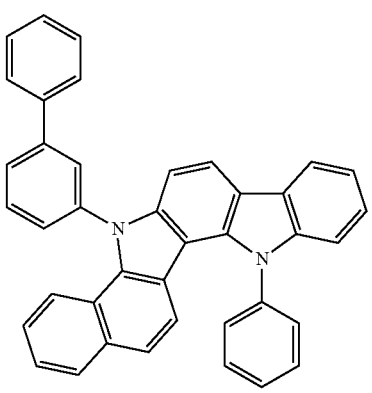
C-1-81

C-1-82
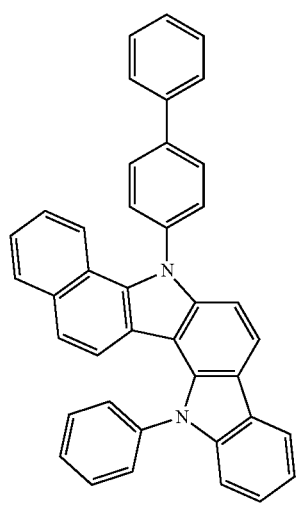
C-1-83
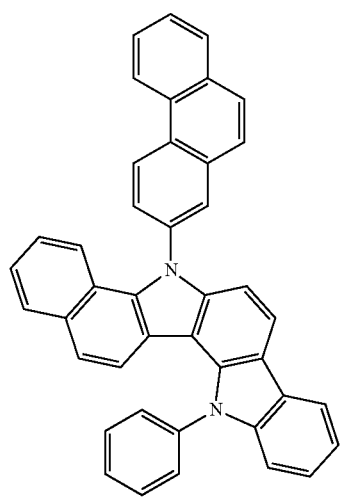
C-1-84
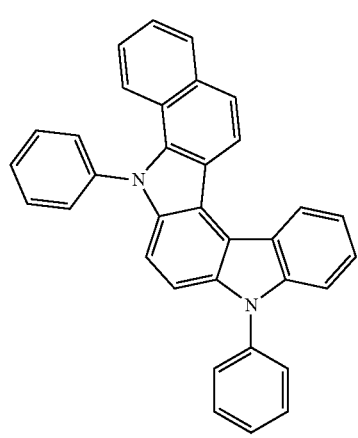
C-1-85
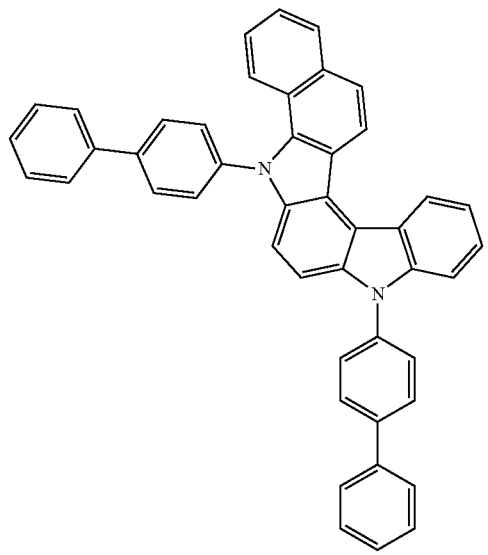
C-1-86
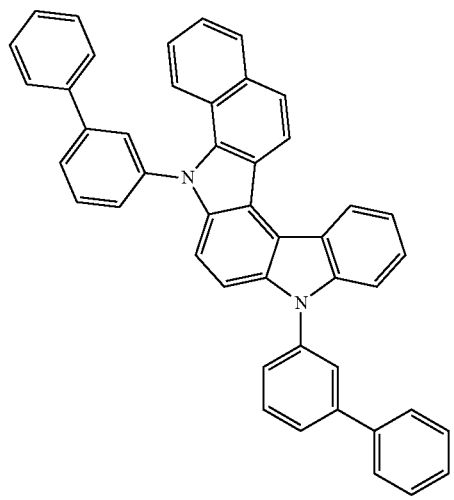
C-1-87
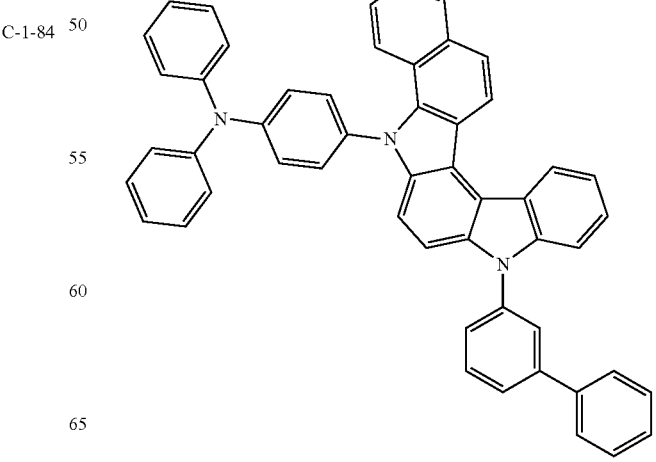

C-1-88
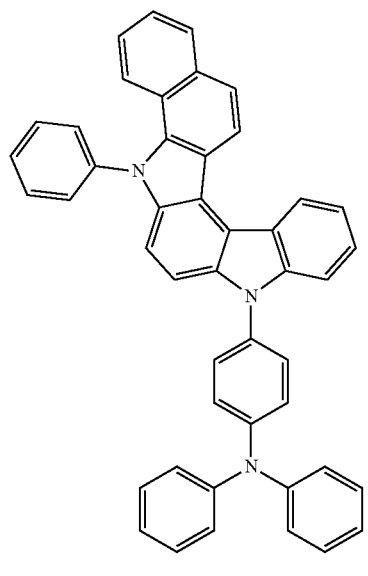
C-1-89
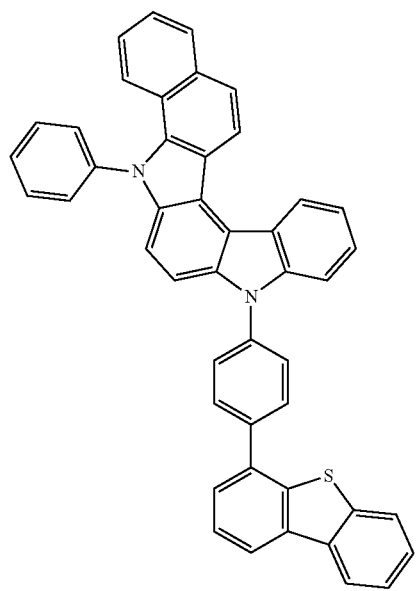
C-1-90
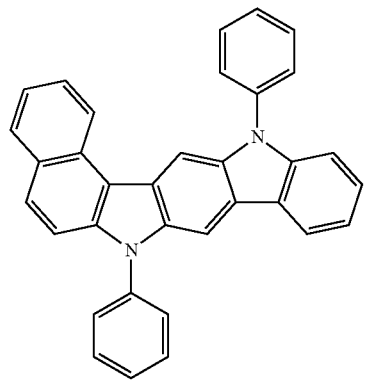
C-1-91
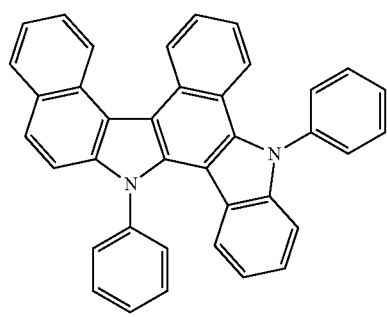
C-1-92
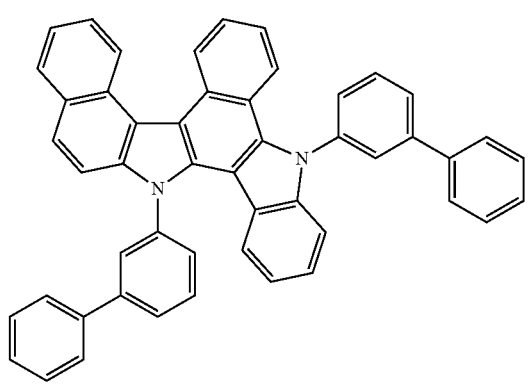
C-1-93
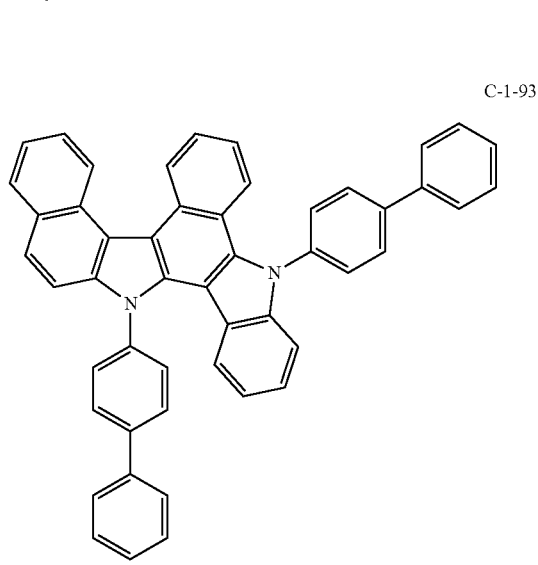
C-1-94
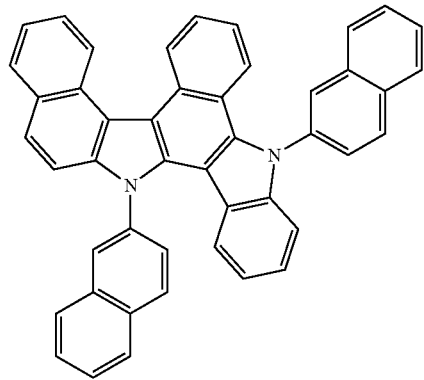

C-1-95
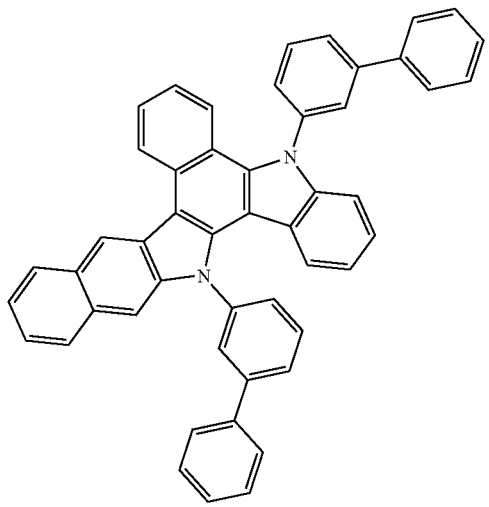
C-1-96
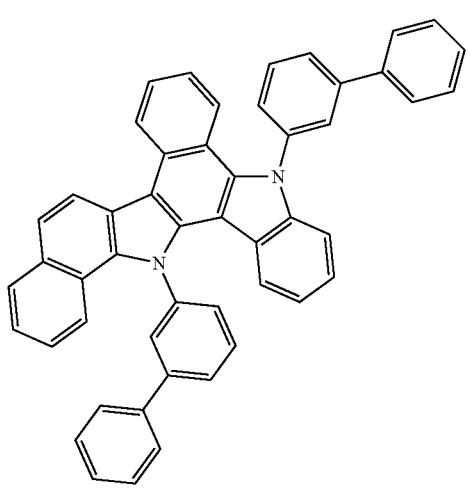
C-1-97
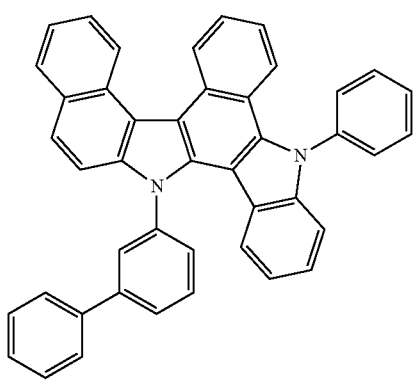
C-1-98
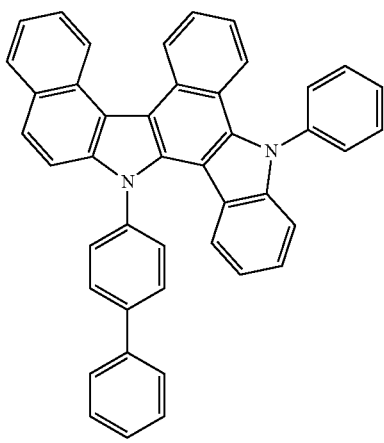
C-1-99
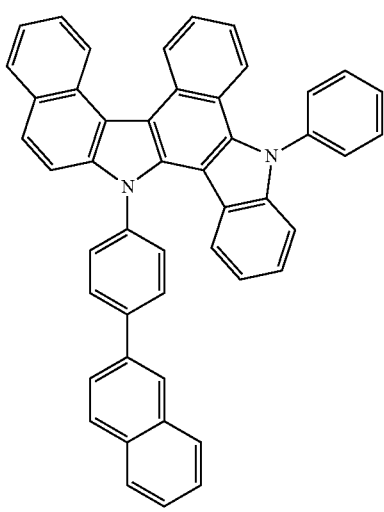
C-1-100
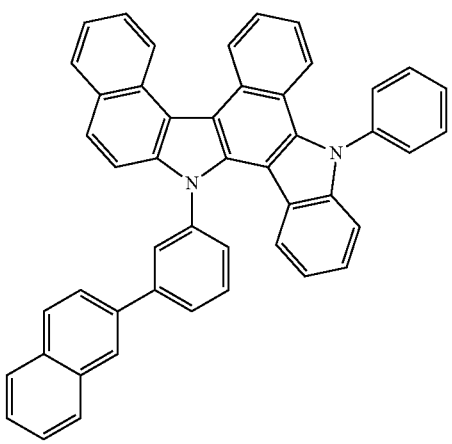

C-1-101
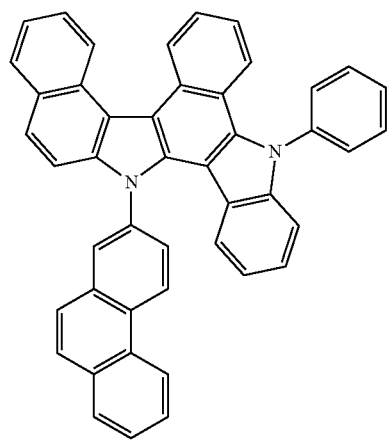
C-1-104
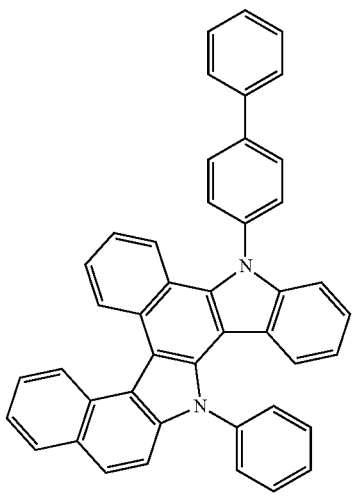
C-1-102
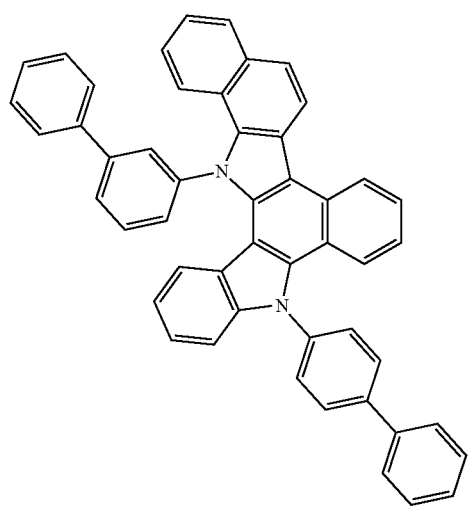
C-1-105
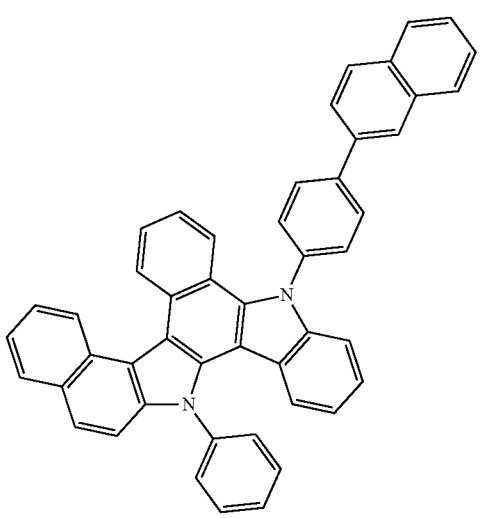
C-1-103
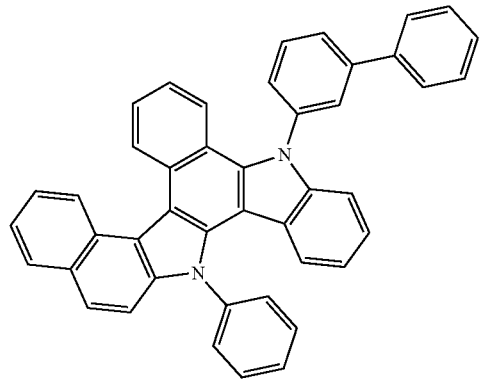
C-1-106
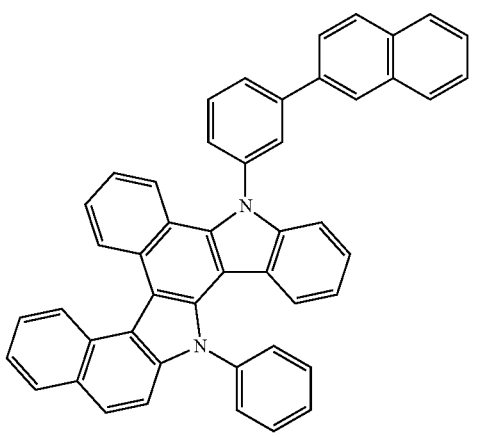

C-1-107
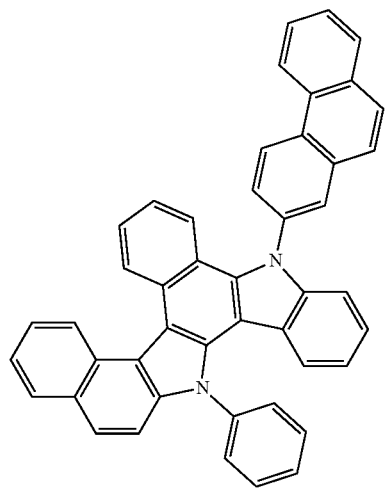
C-1-108
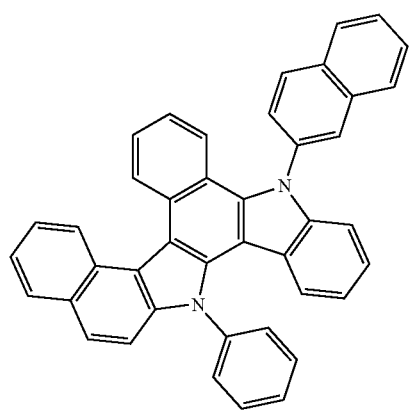
C-1-109
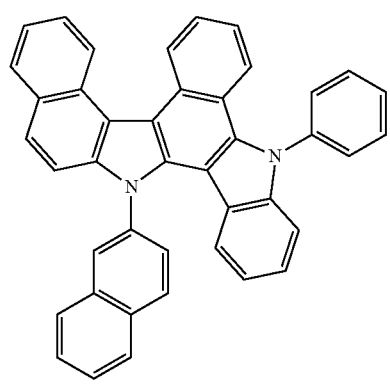
C-1-110
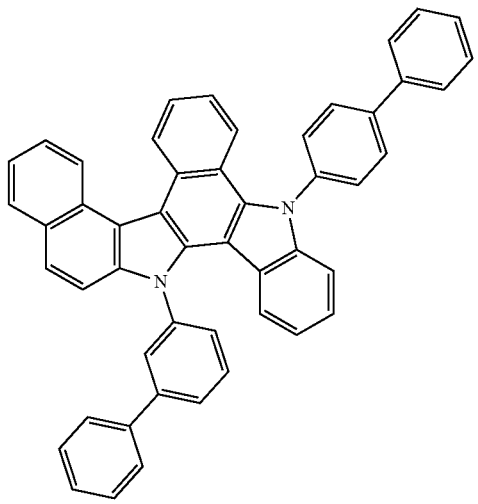
C-1-111
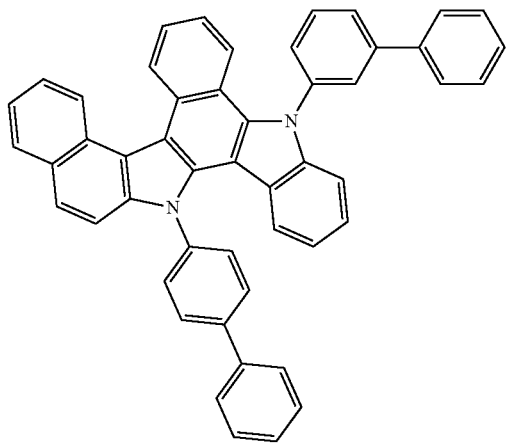
C-1-112
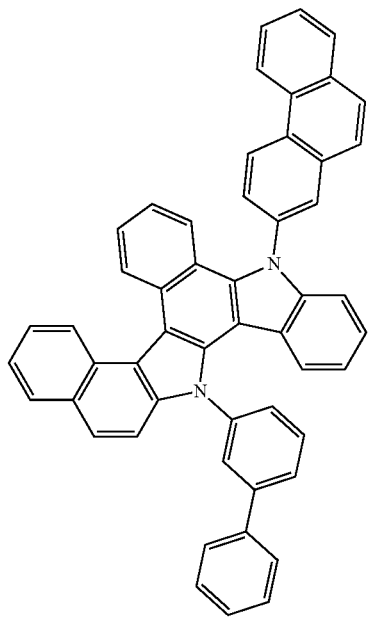

C-1-113
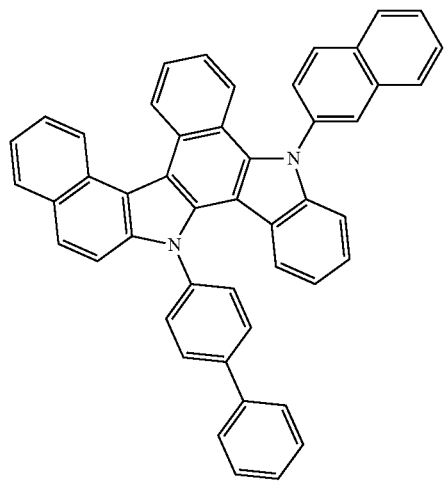
C-1-116
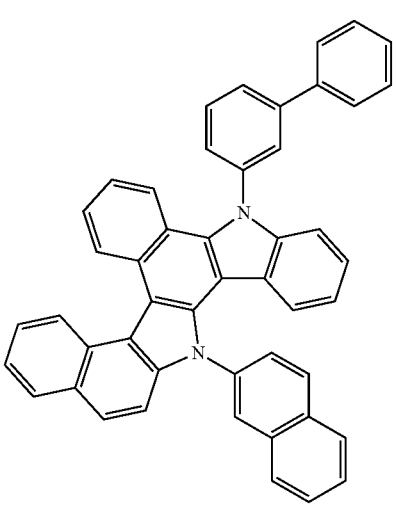
C-1-114
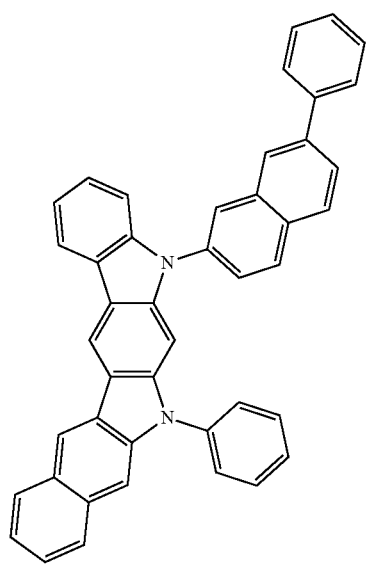
C-1-117
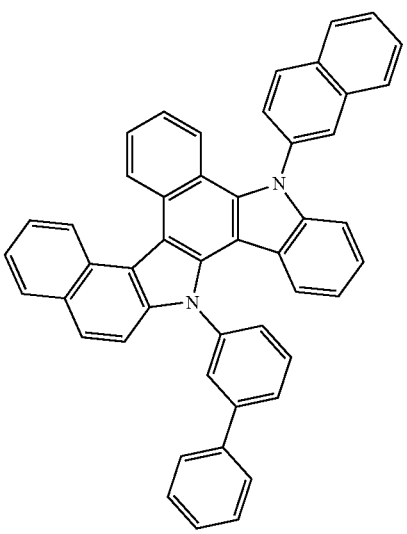
C-1-115
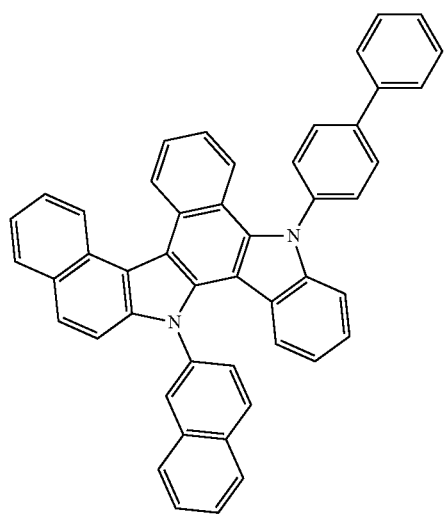
C-1-118
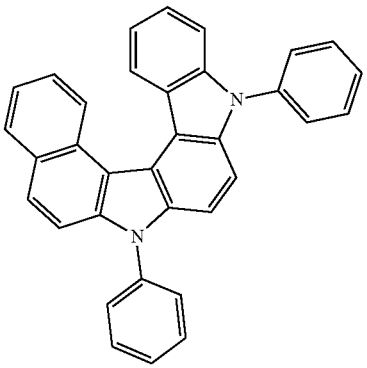

C-1-119
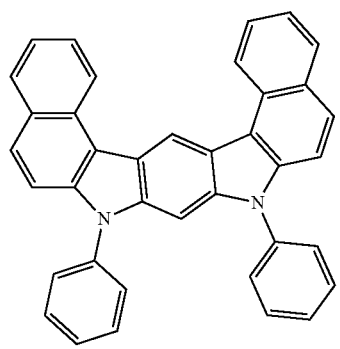
C-1-120
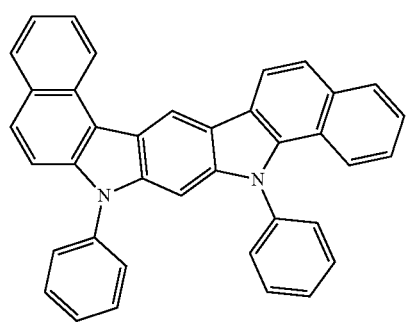
C-1-121
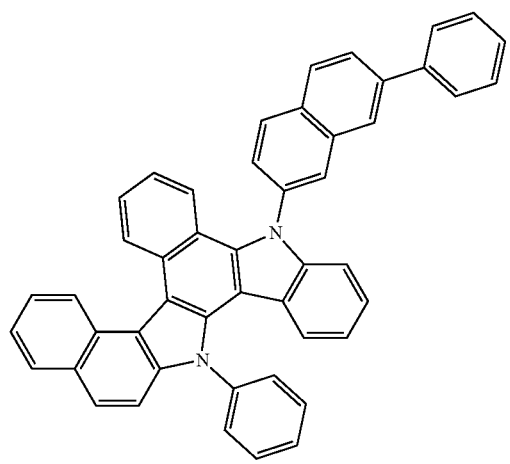
C-1-122
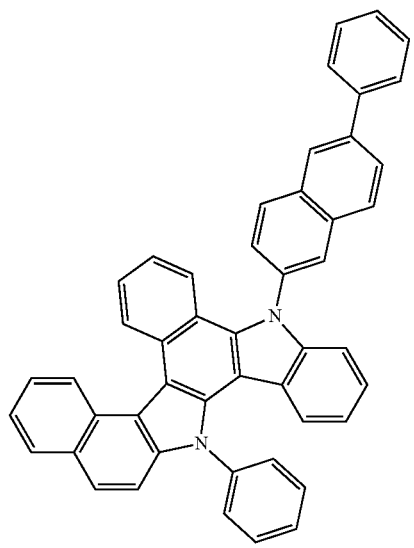
C-1-123
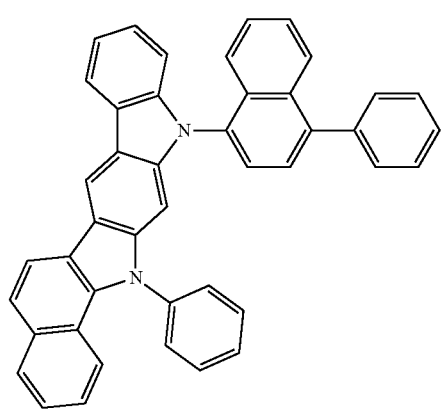
C-1-124
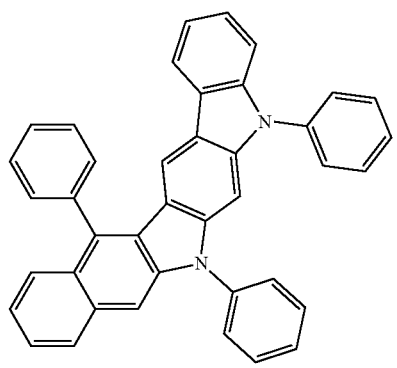

C-1-125
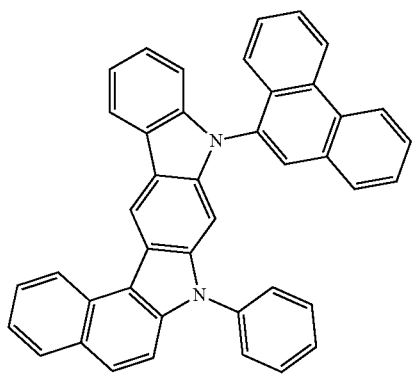
C-1-129
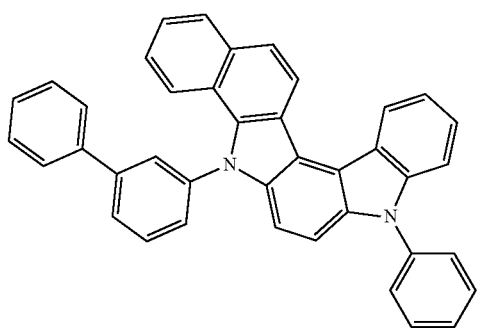
C-1-126
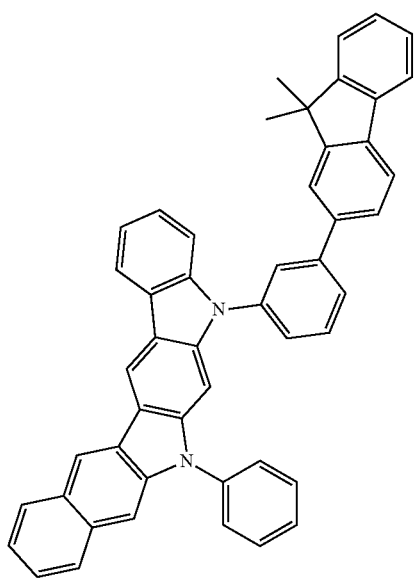
C-1-130
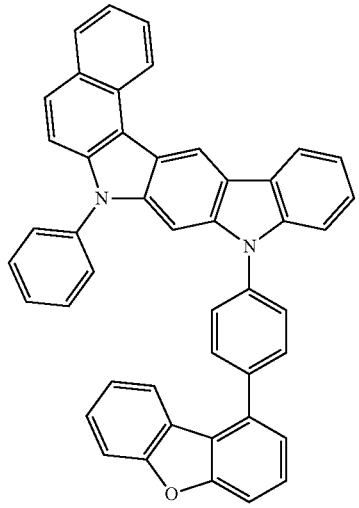
C-1-127
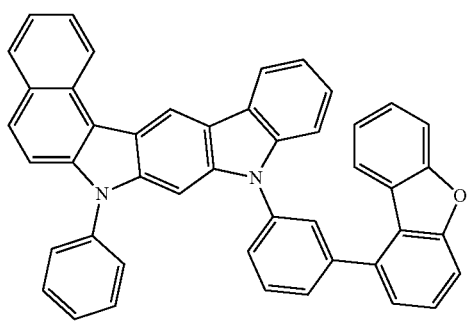
C-1-131
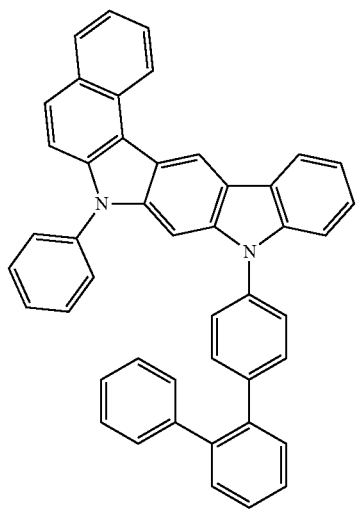
C-1-128

C-1-132
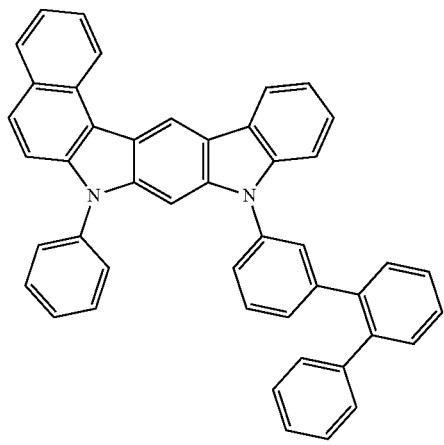
C-1-133
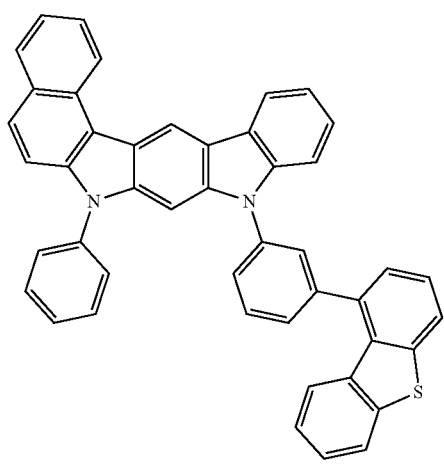
C-1-134
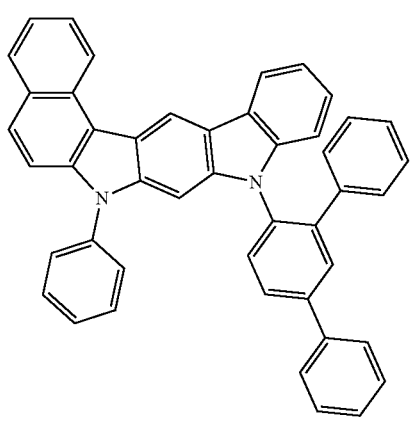
C-1-135
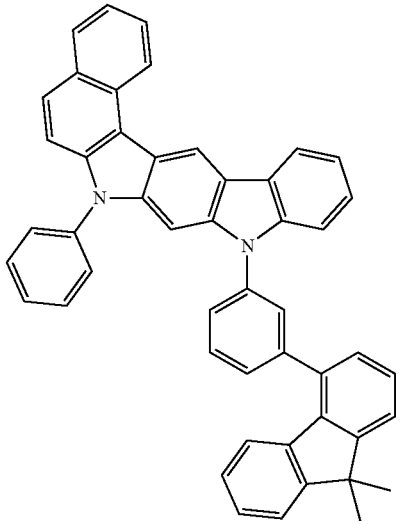
C-1-136
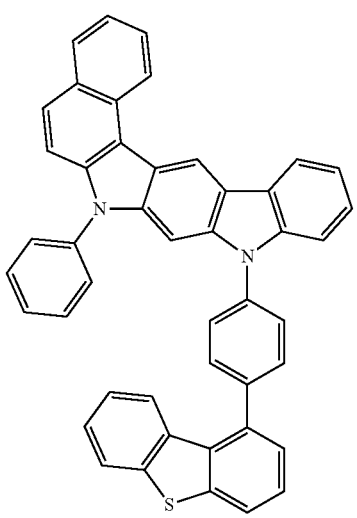
C-1-137
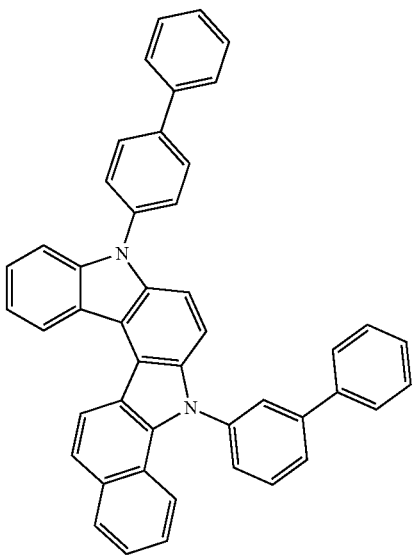

C-1-138
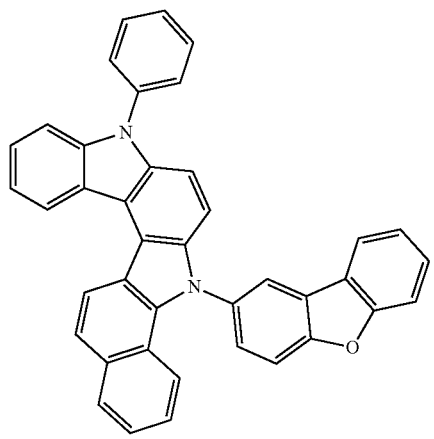
C-1-139
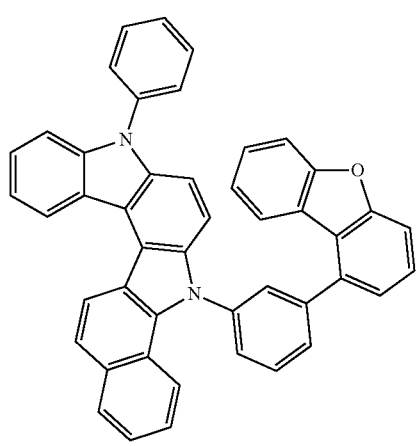
C-1-140
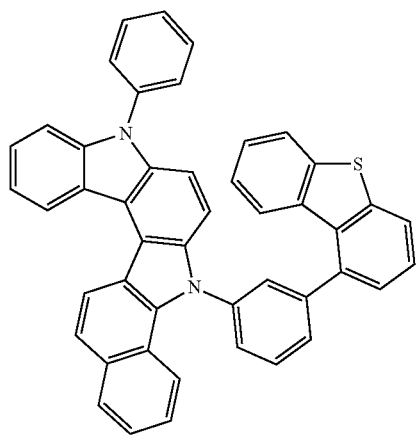
C-2-1
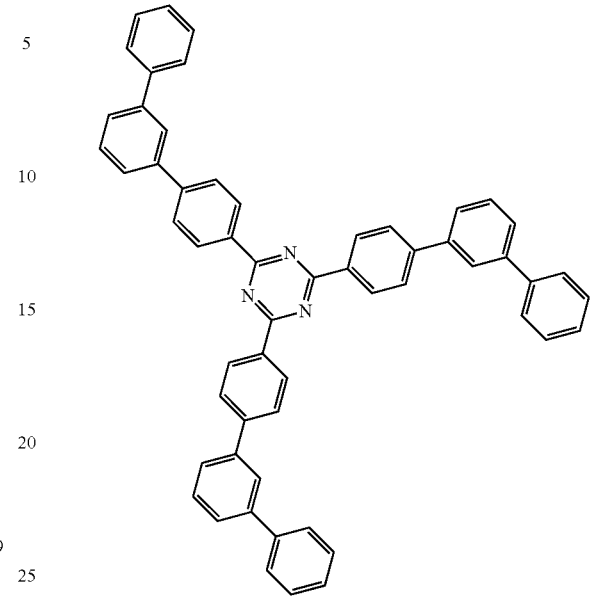
C-2-2
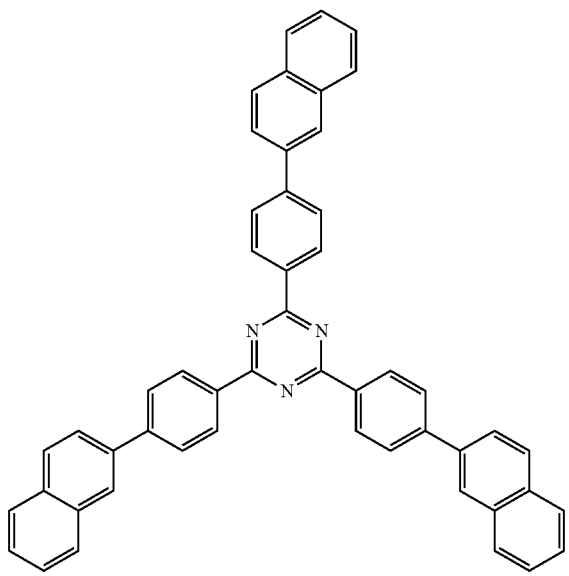
The compound represented by formula 2 includes the following compounds, but is not limited thereto.

C-2-3
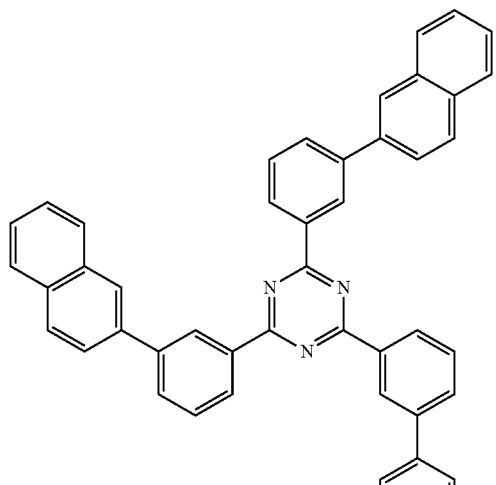
C-2-4
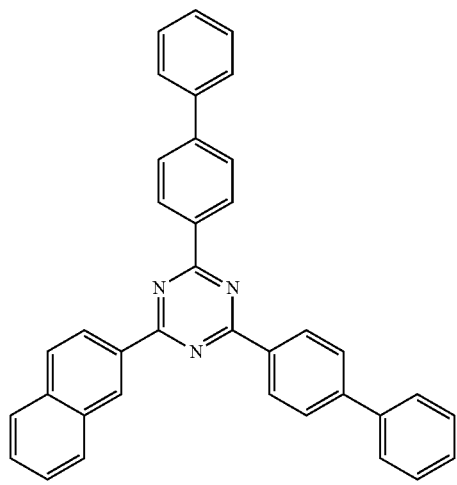
C-2-5
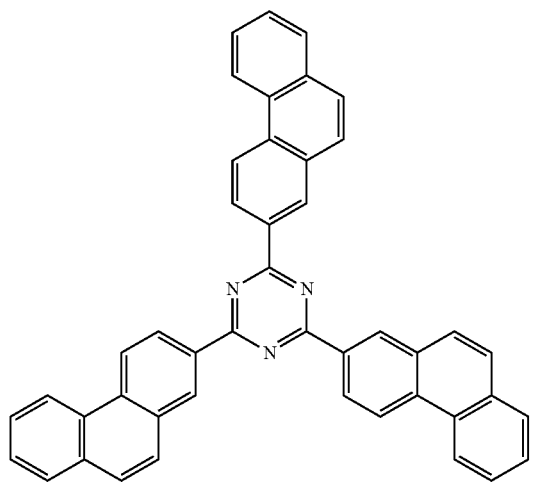
C-2-6
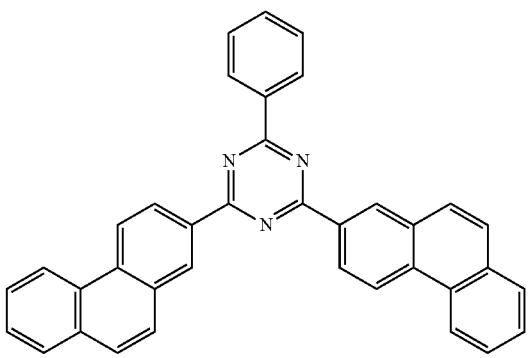
C-2-7
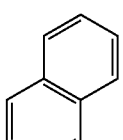
C-2-8
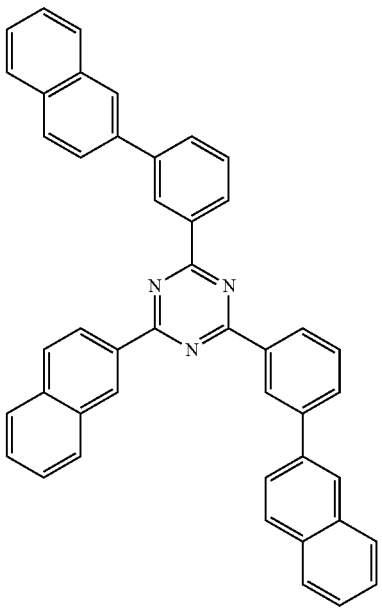

-continued
C-2-9
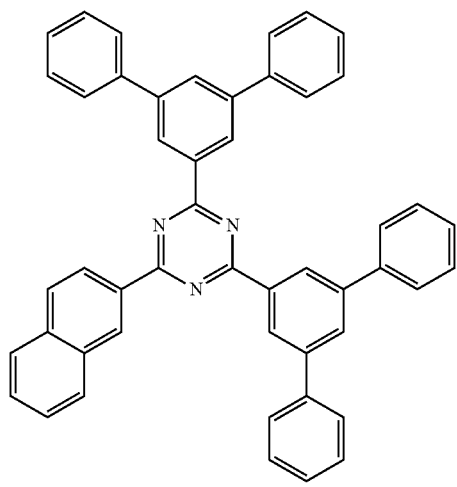
C-2-10
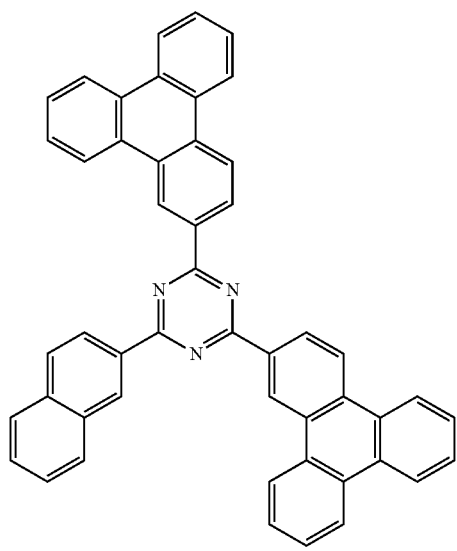
C-2-11
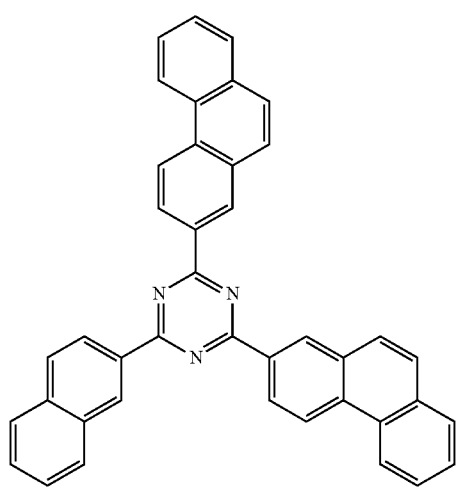
C-2-12
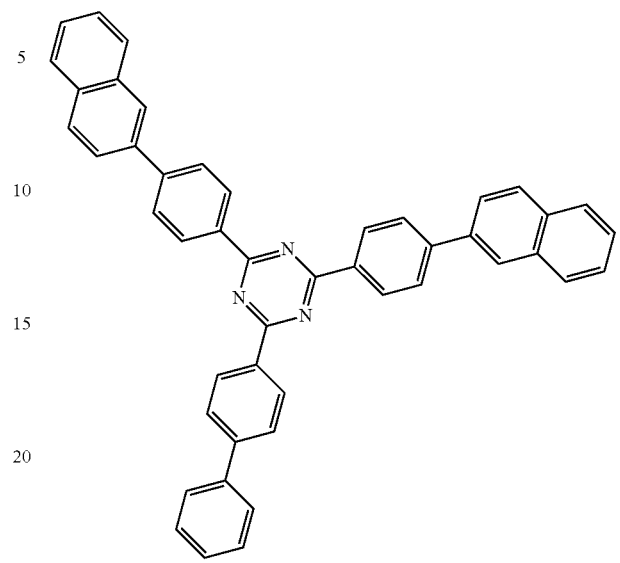
C-2-13
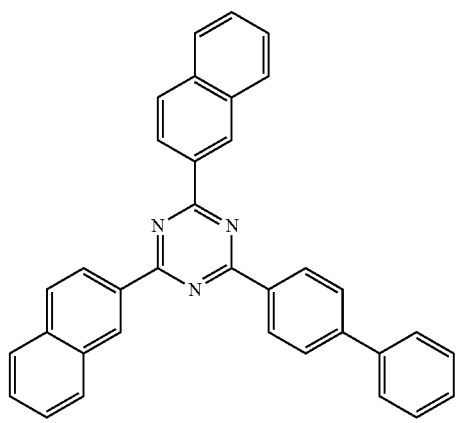
C-2-14
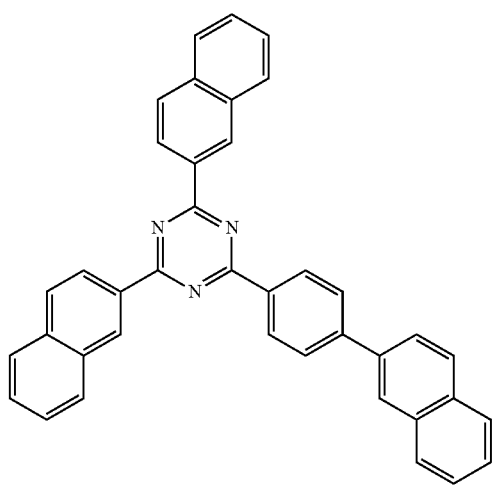

C-2-15
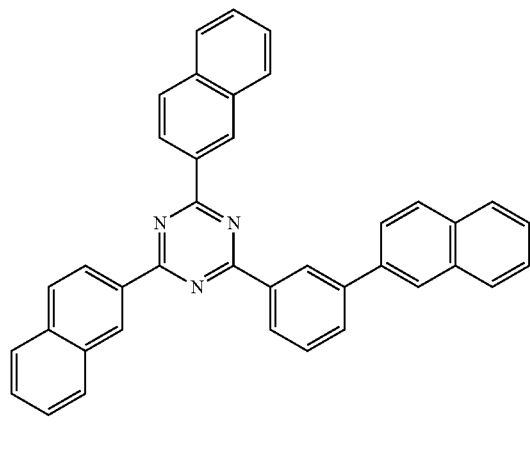
C-2-16
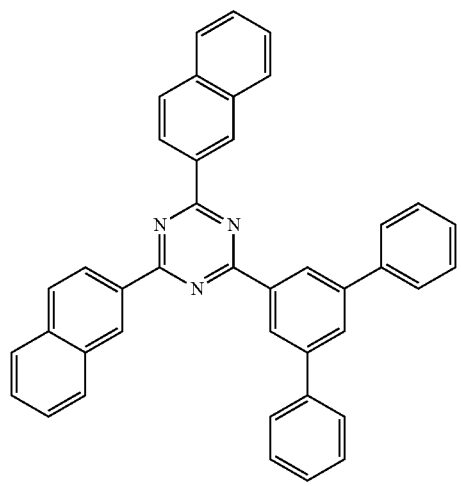
C-2-17
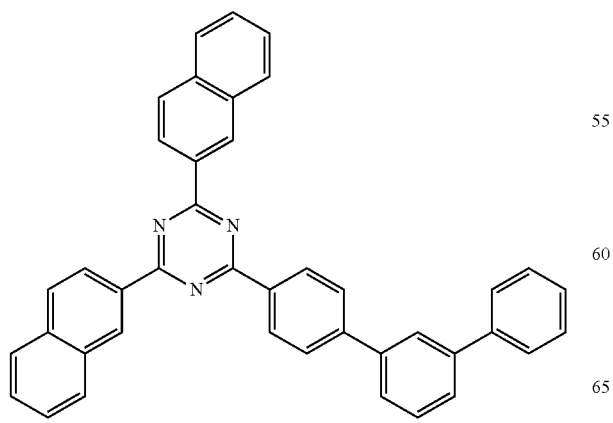
C-2-18
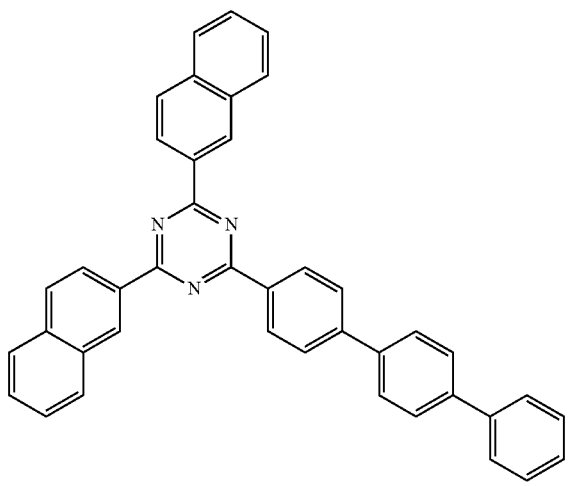
C-2-19
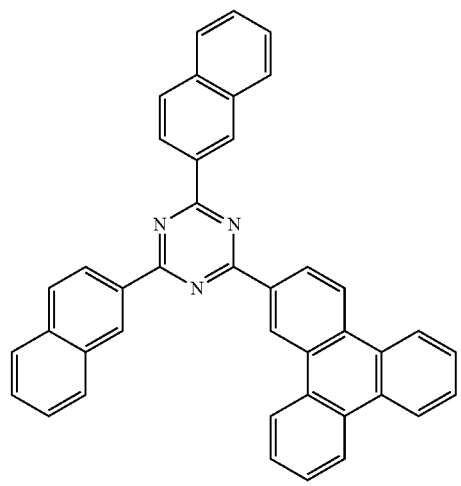
C-2-20
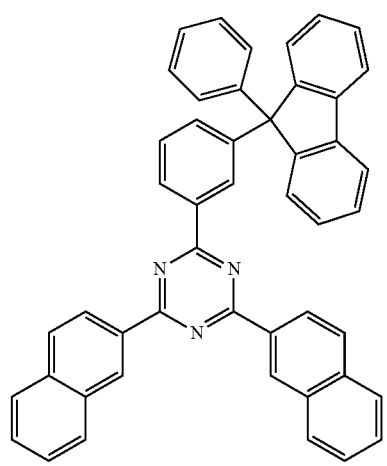

C-2-21
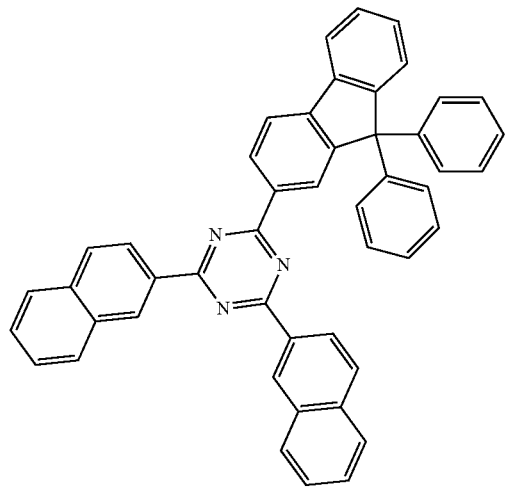
C-2-24
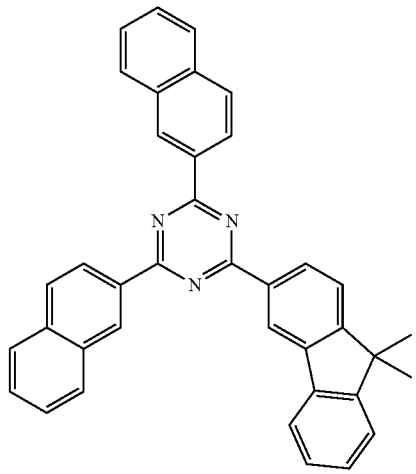
C-2-22
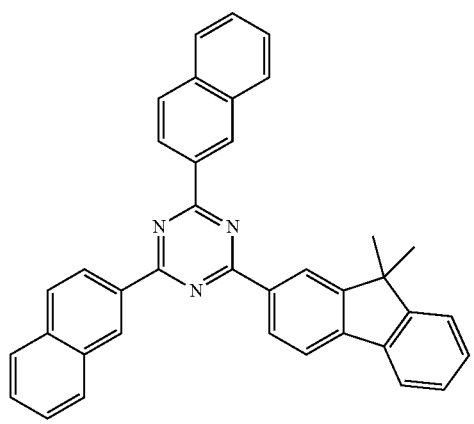
C-2-25
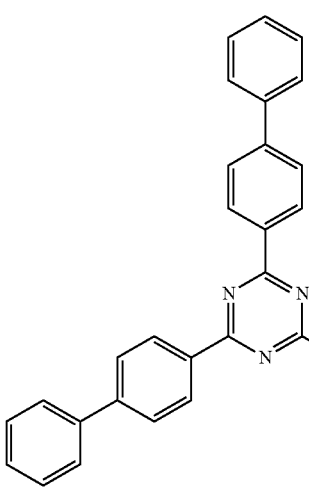
C-2-23
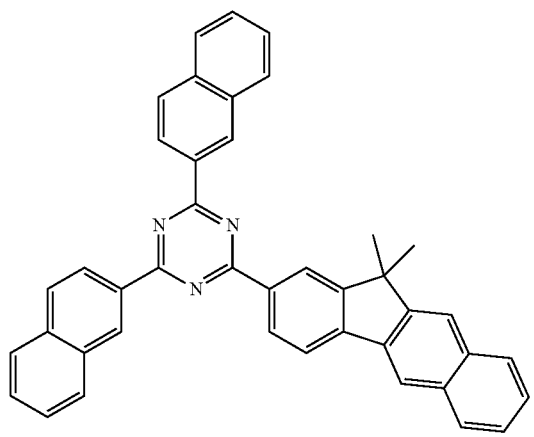
C-2-26
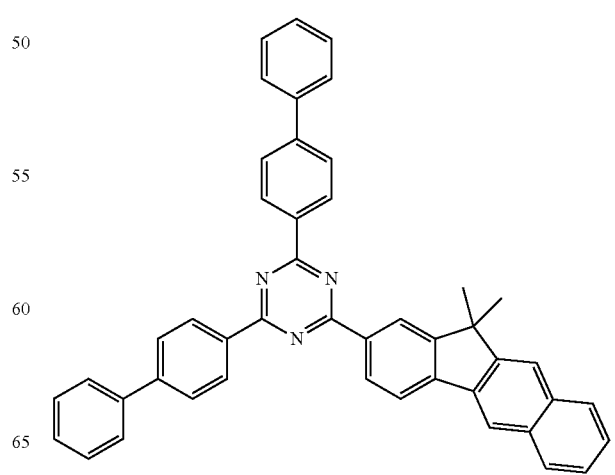

C-2-27
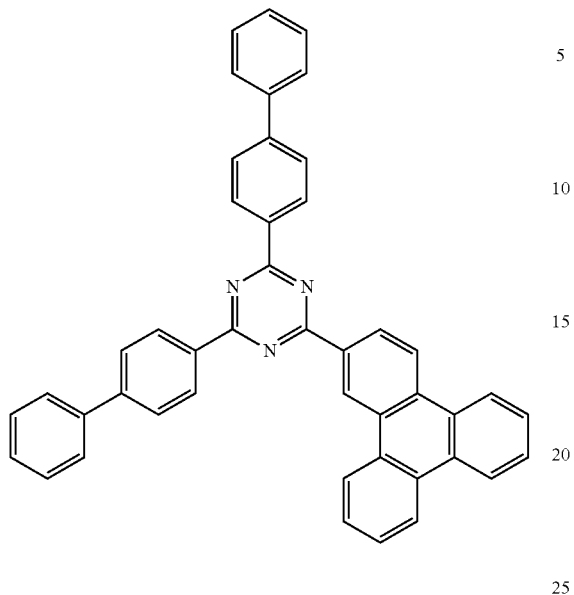
C-2-28
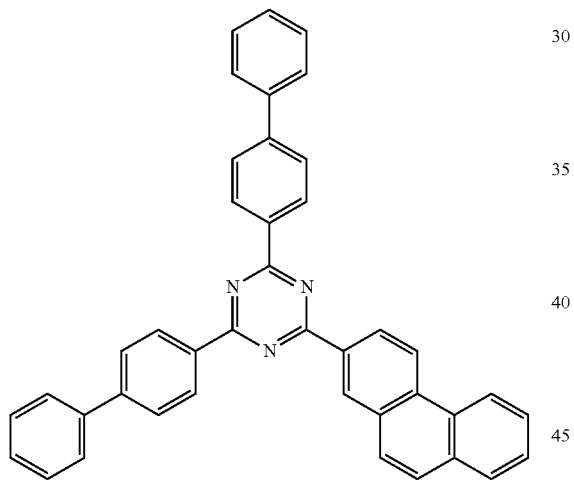
C-2-29
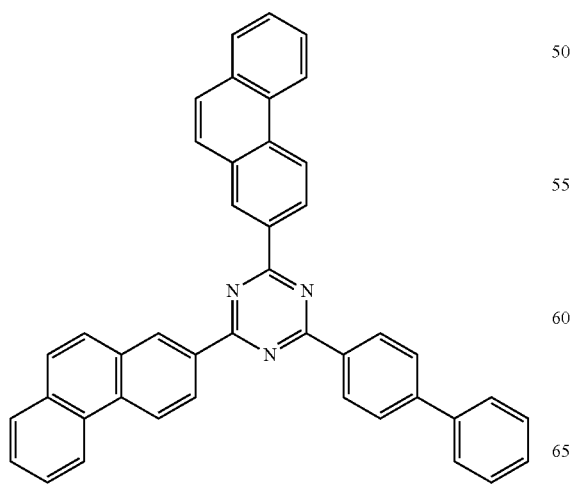
C-2-30
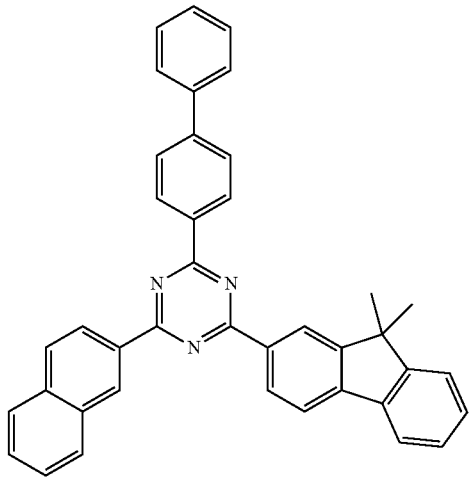
C-2-31
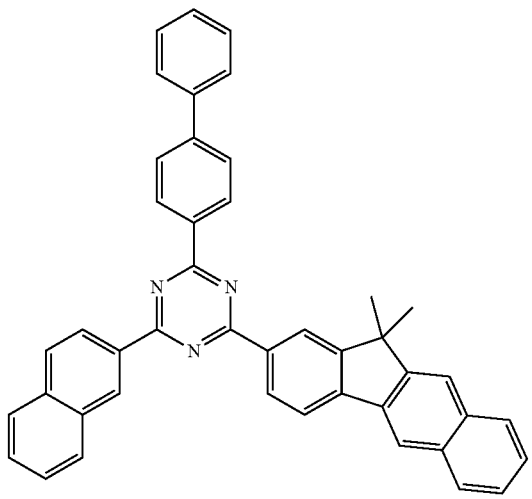
C-2-32
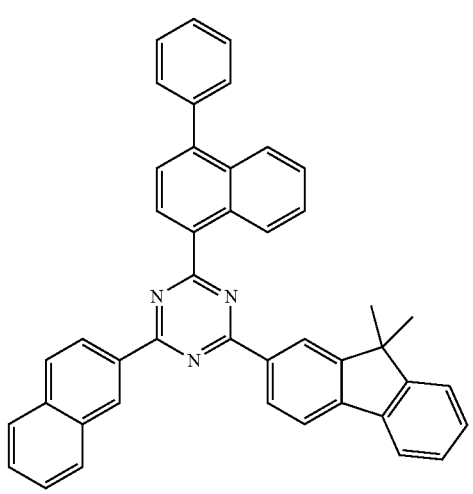

C-2-33
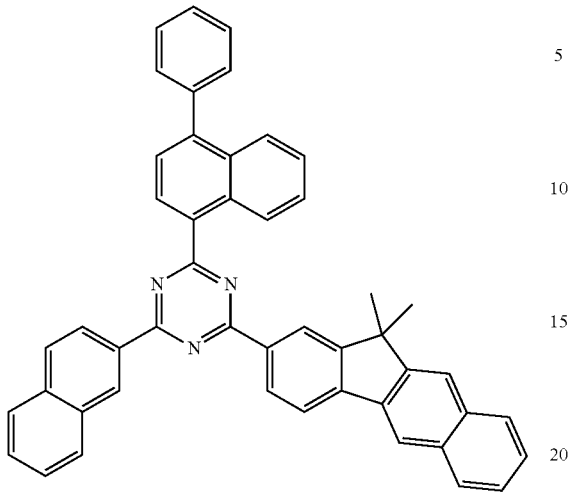
C-2-34
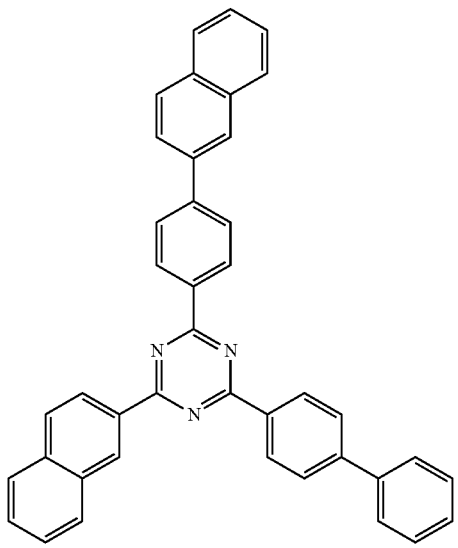
C-2-35
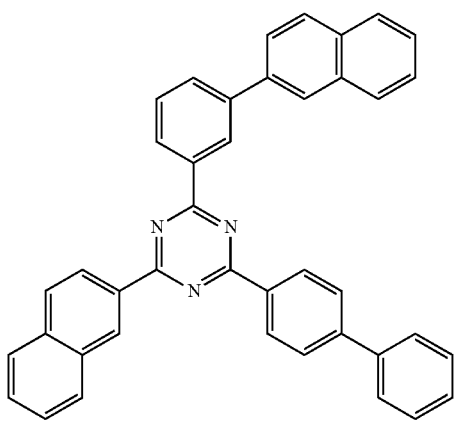
C-2-36
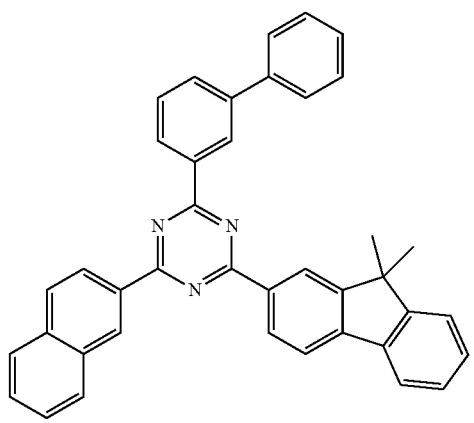
C-2-37
C-2-38

C-2-39
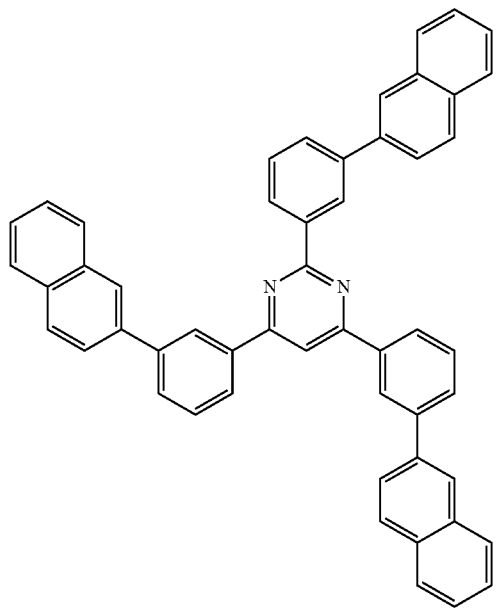
C-2-40
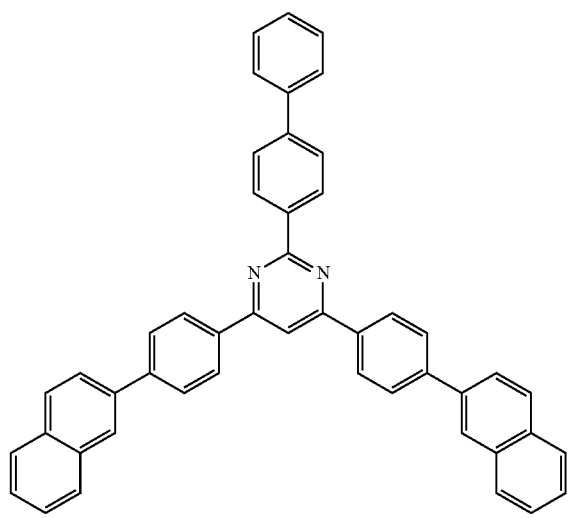
C-2-41
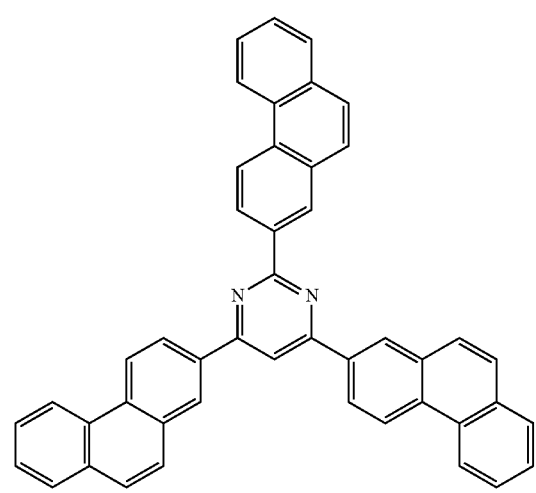
C-2-42
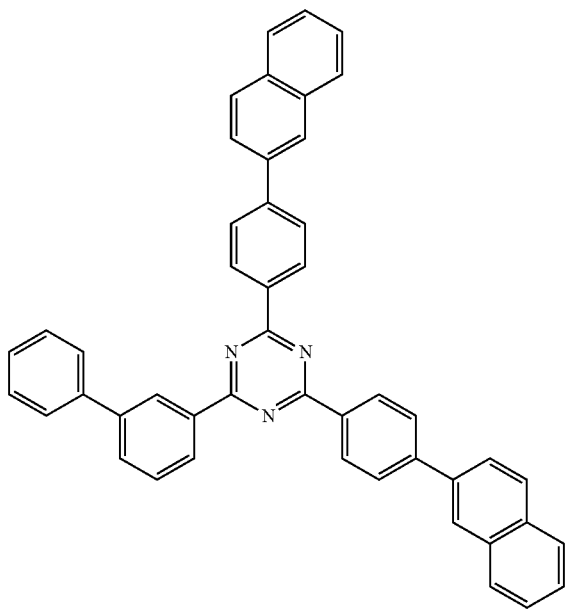
C-2-43
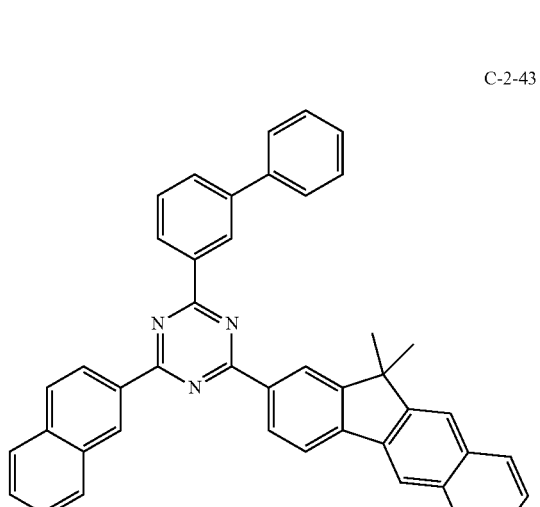
C-2-44
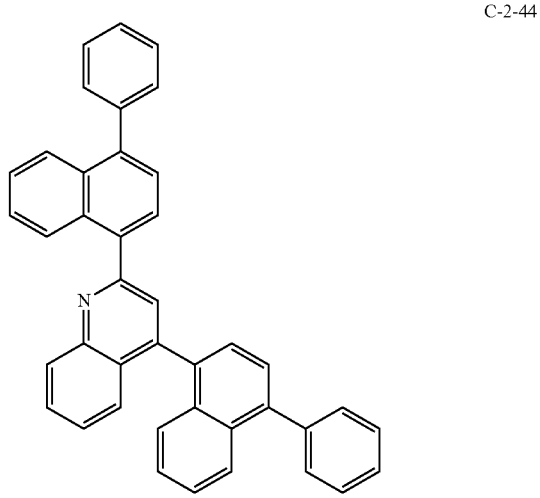

C-2-45
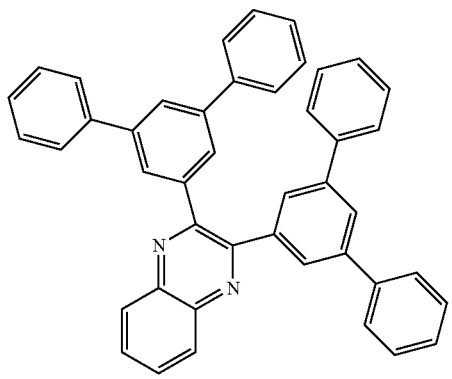
C-2-46
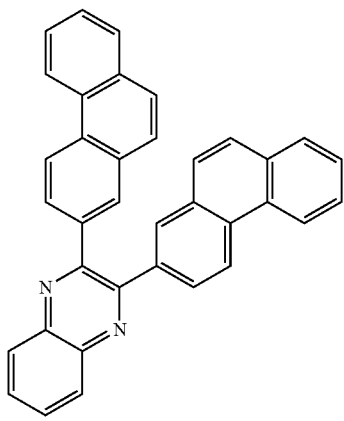
C-2-47
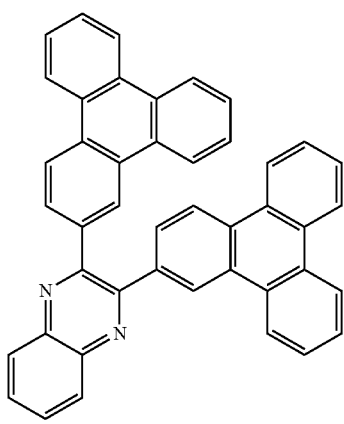
C-2-48
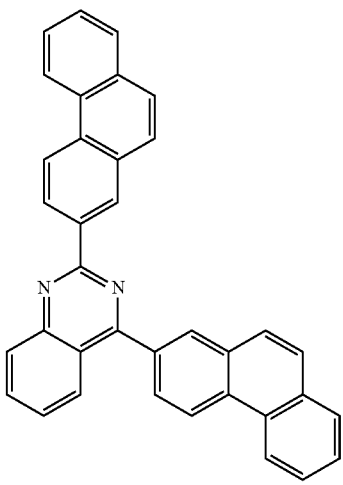
C-2-49
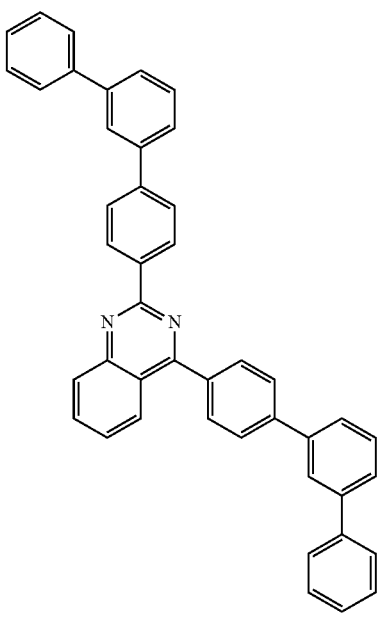
C-2-50
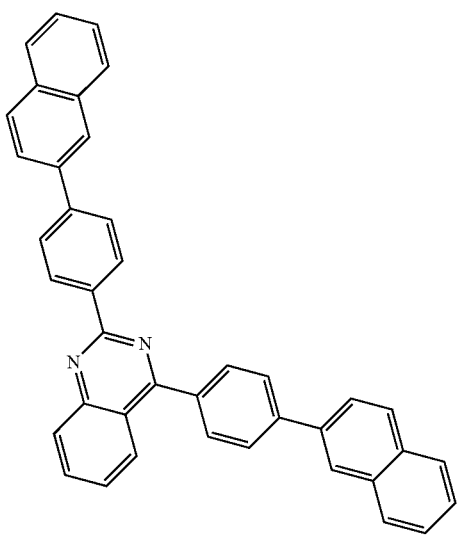

C-2-51
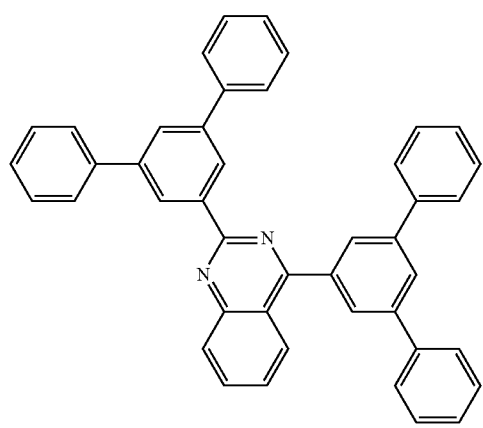
C-2-52
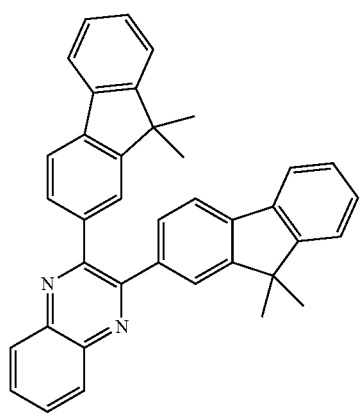
C-2-53
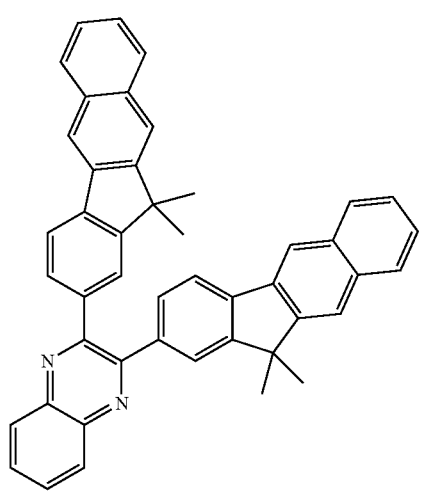
C-2-54
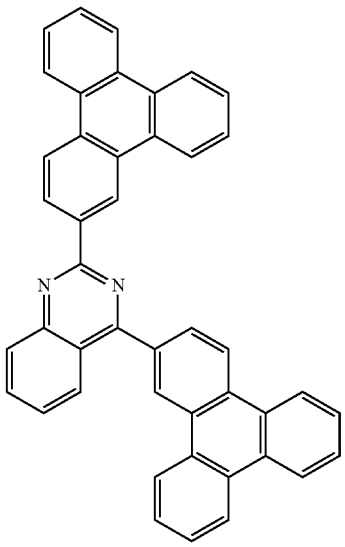
C-2-55
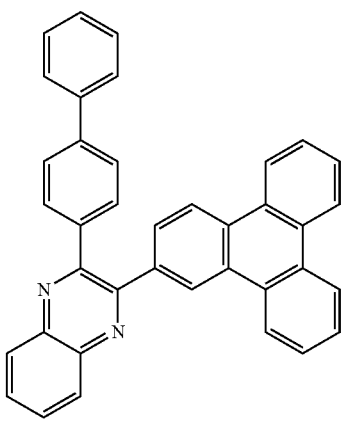
C-2-56
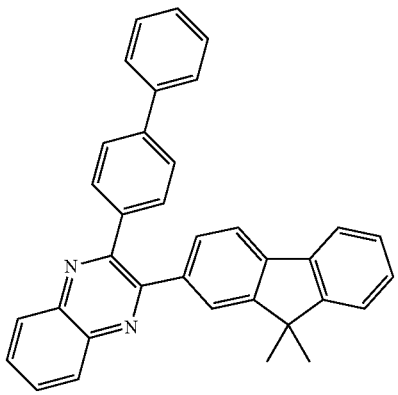

C-2-57
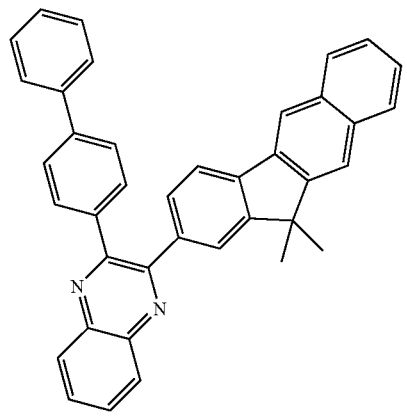
C-2-58
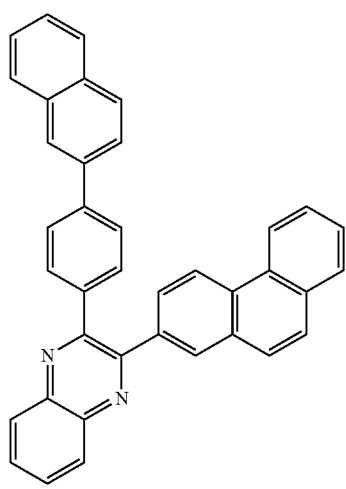
C-2-59
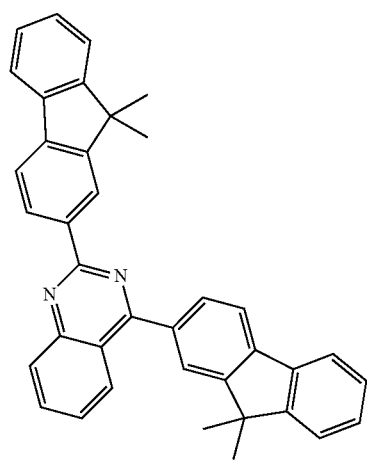
C-2-60
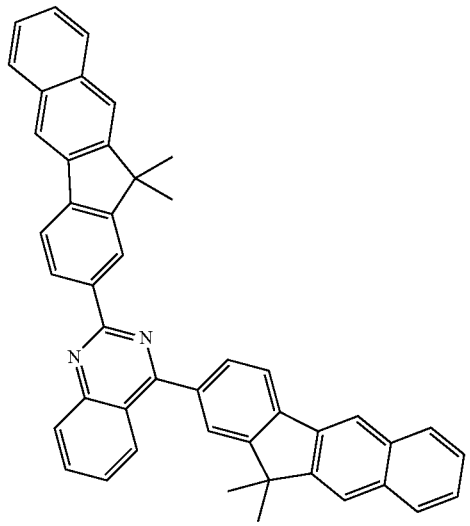
C-2-61
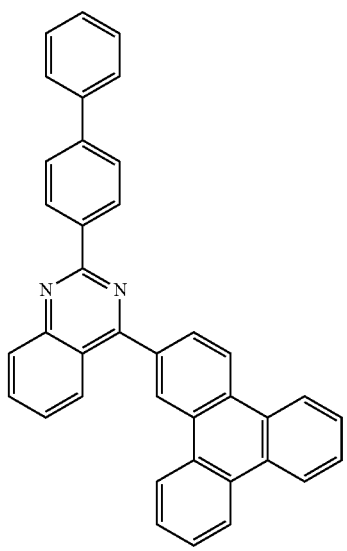
C-2-62
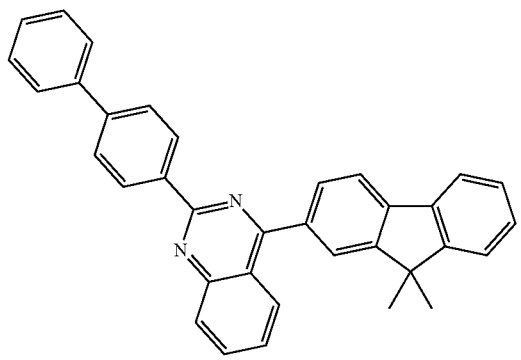

C-2-63
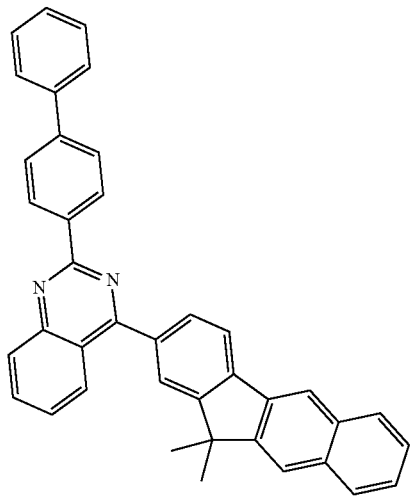
C-2-64
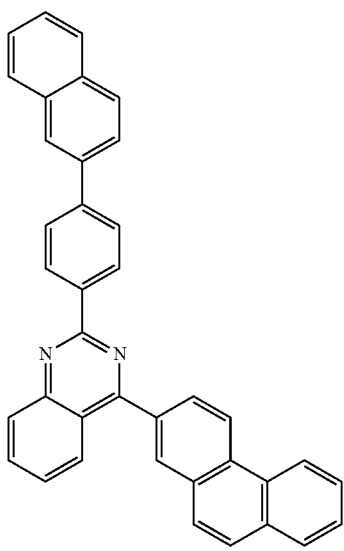
C-2-65
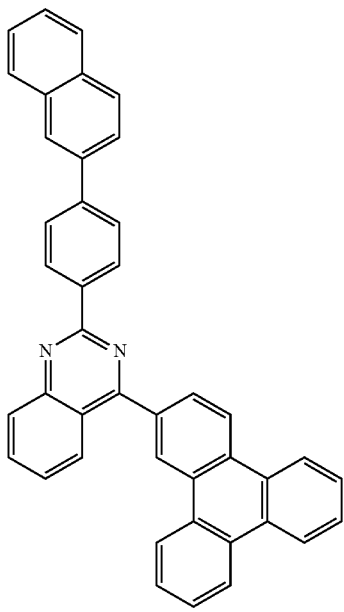
C-2-66
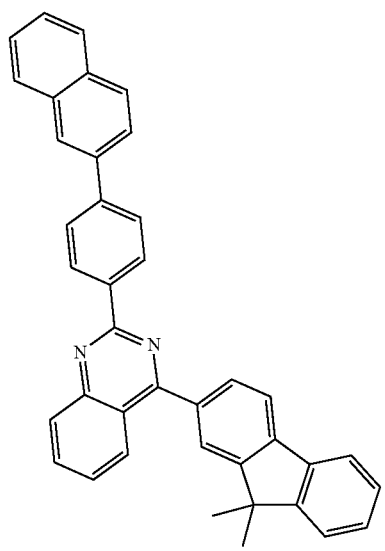
C-2-67
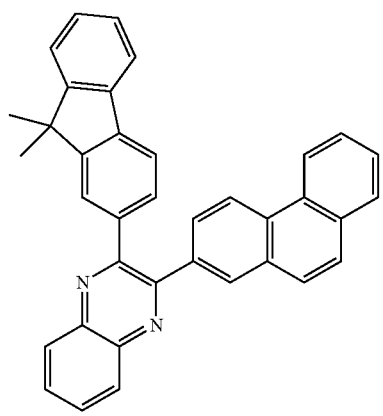
C-2-68
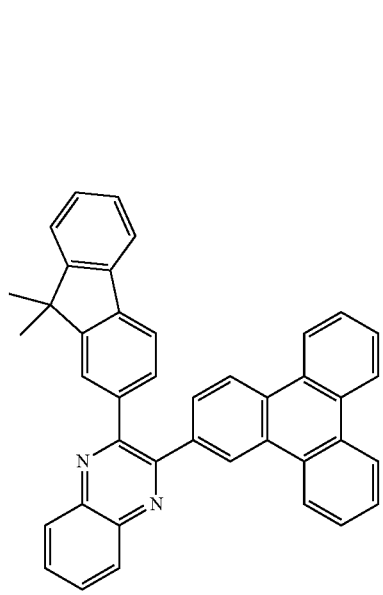

-continued
C-2-69
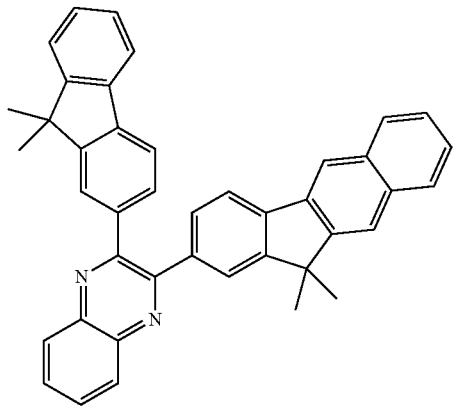
C-2-70
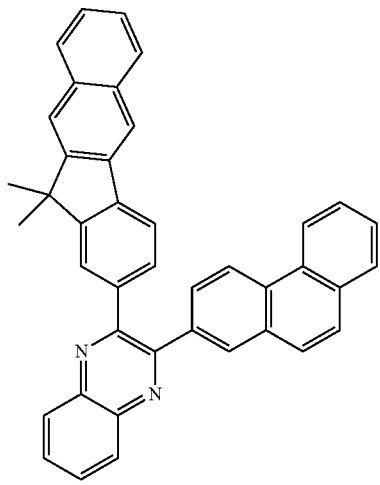
C-2-71
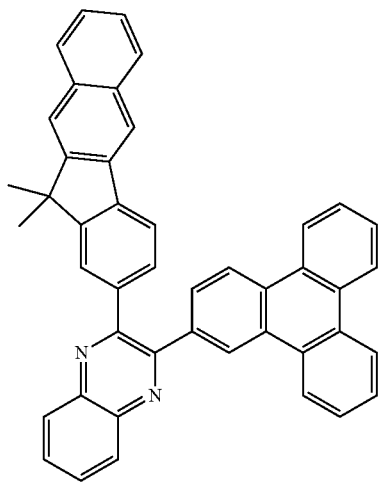
C-2-72
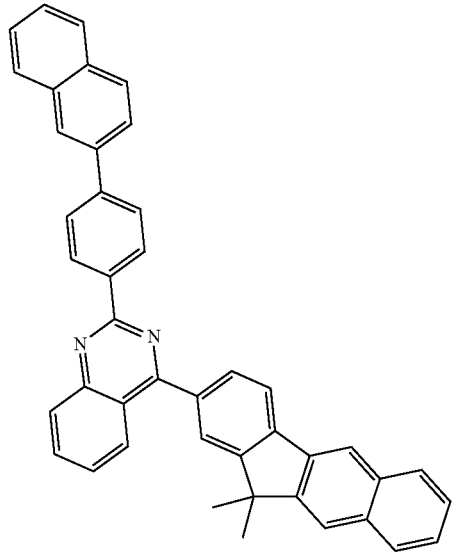
C-2-73
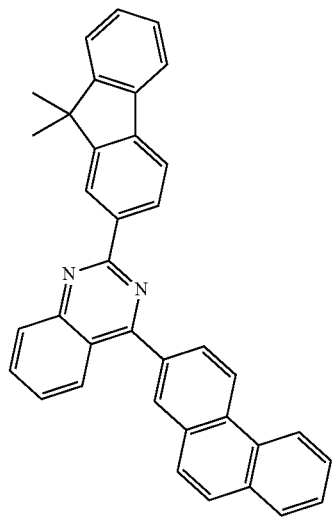
C-2-74
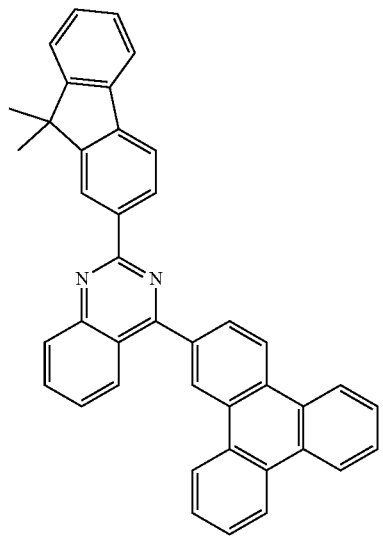

C-2-75
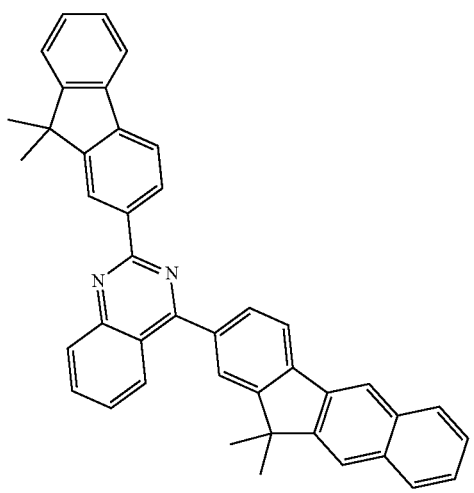
C-2-76
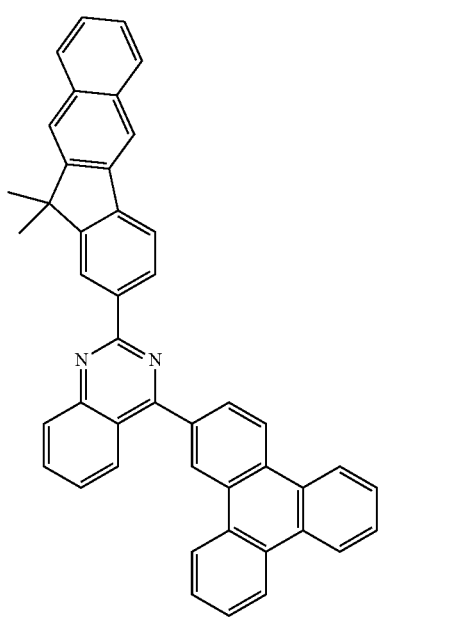
C-2-77
C-2-78
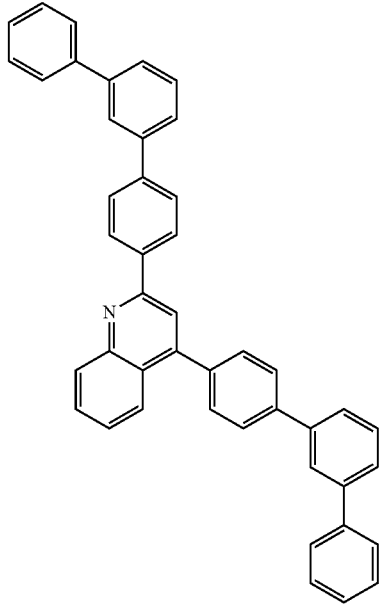
C-2-79
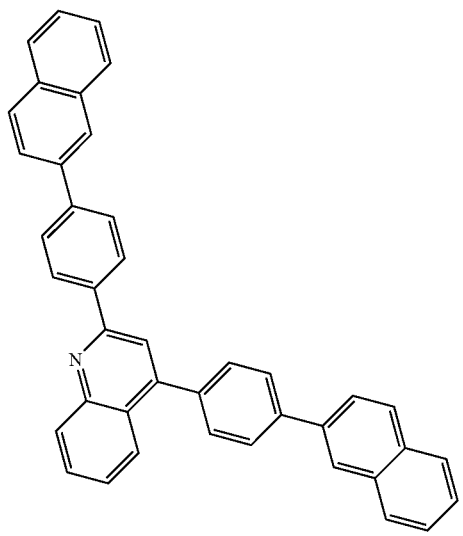

-continued
C-2-80
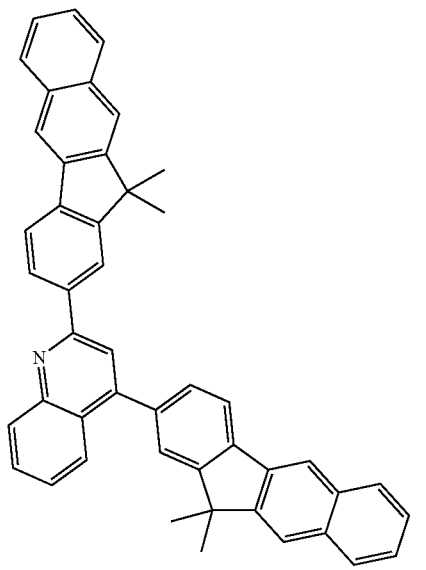
C-2-83
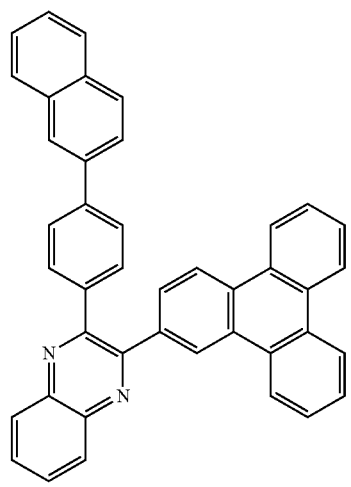
C-2-81
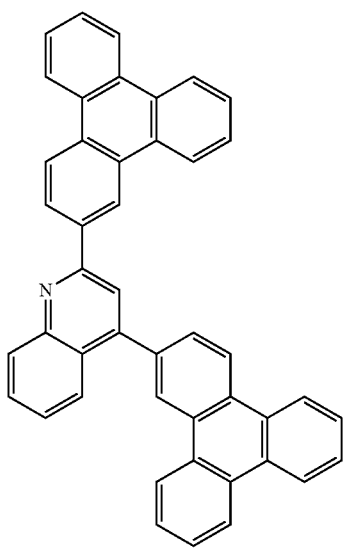
C-2-84
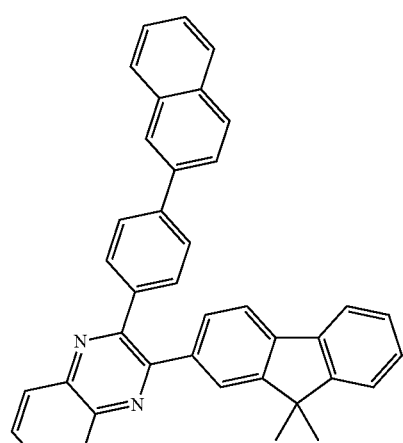
C-2-82
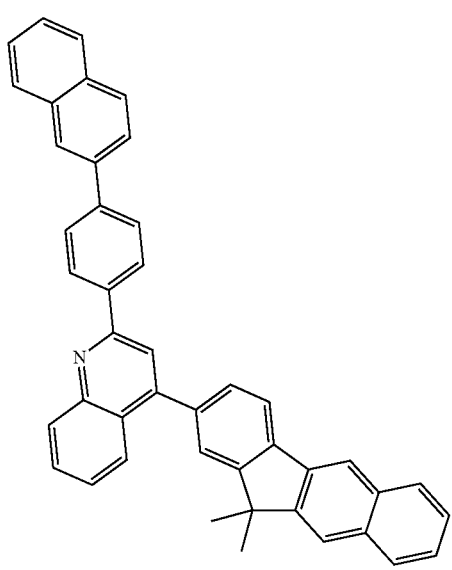
C-2-85
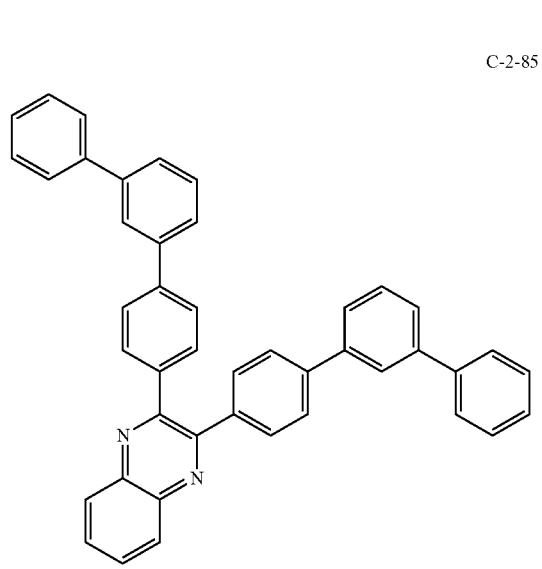

C-2-86
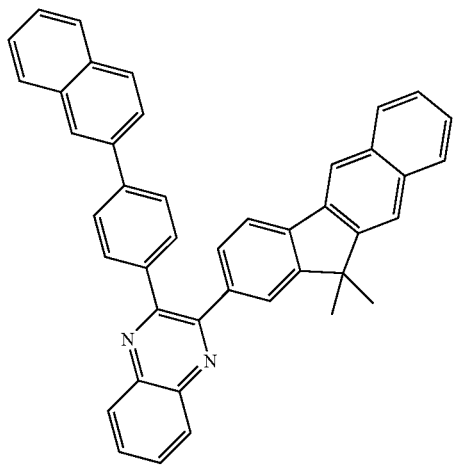
C-2-89
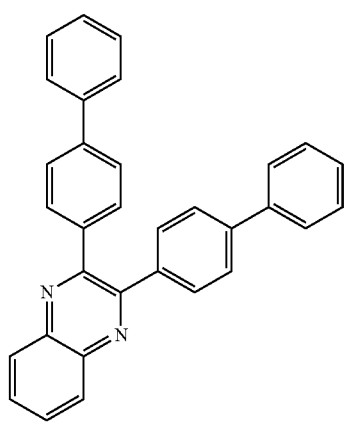
C-2-87
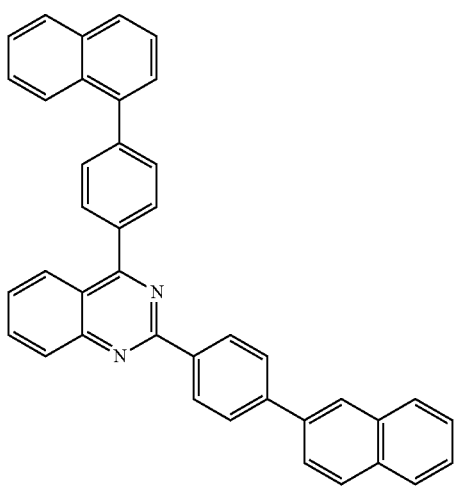
C-2-90
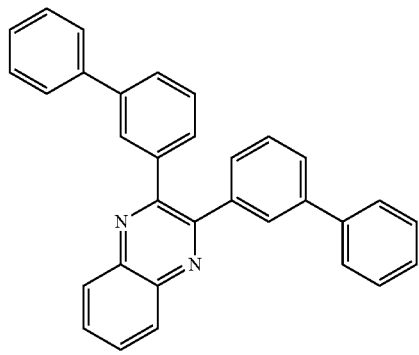
C-2-88
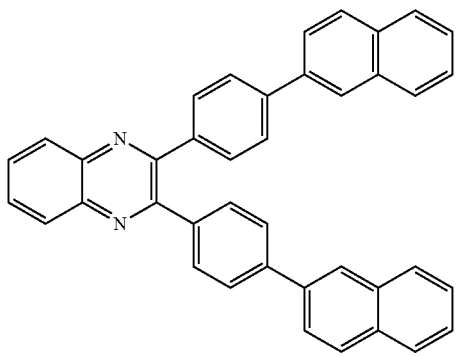
C-2-91
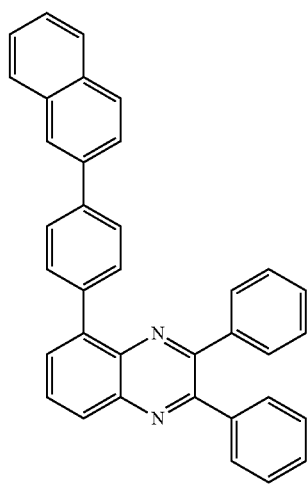

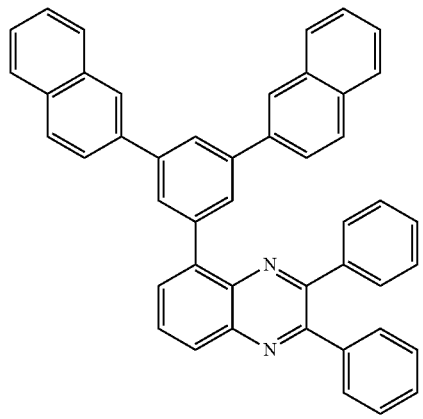
C-2-92
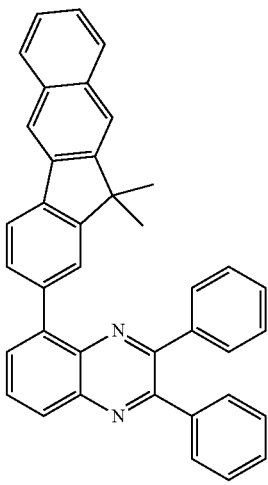
C-2-95
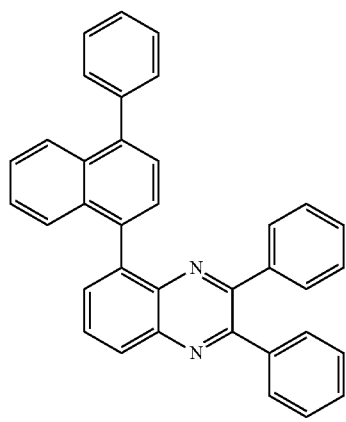
C-2-93
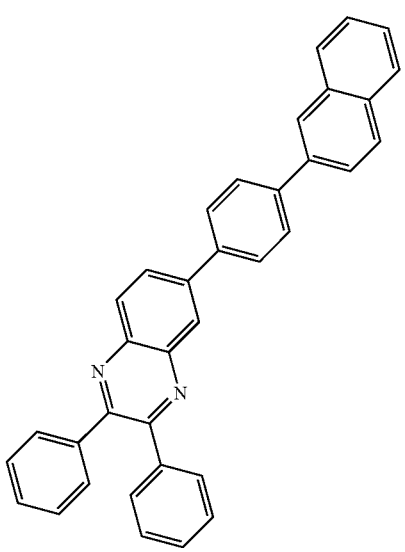
C-2-96
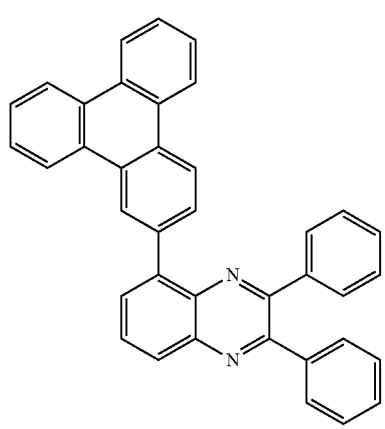
C-2-94
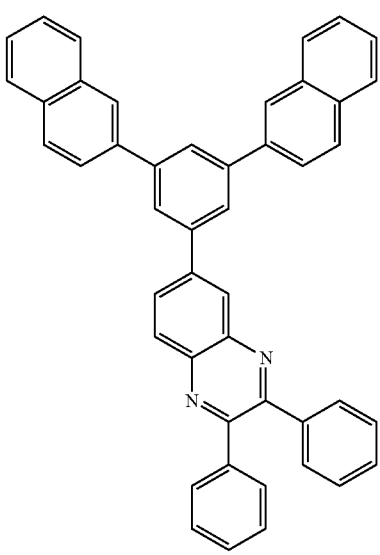
C-2-97

C-2-98
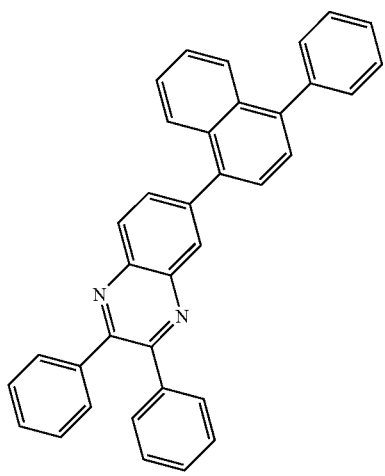
C-2-99
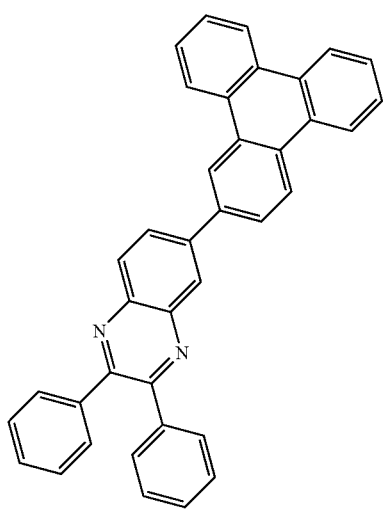
C-2-100
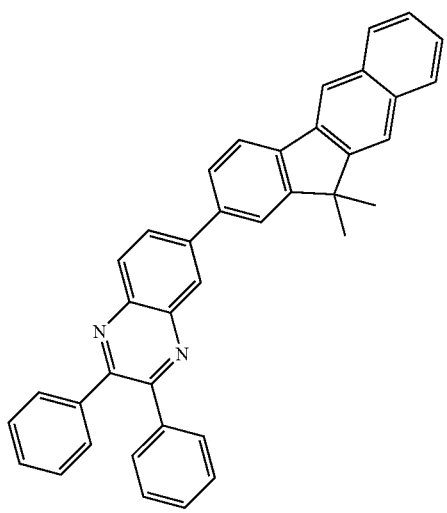
C-2-101
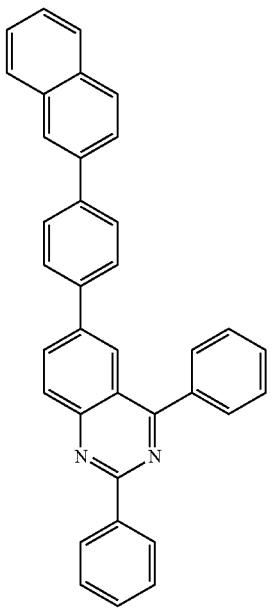
C-2-102
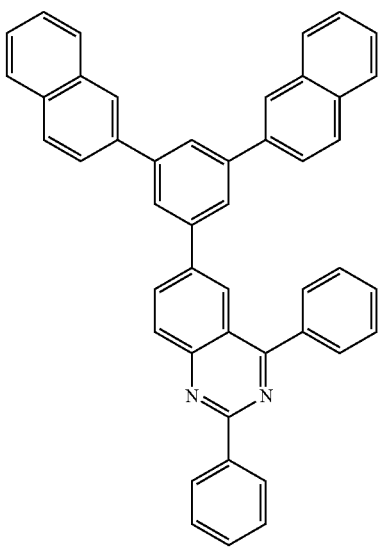

C-2-103
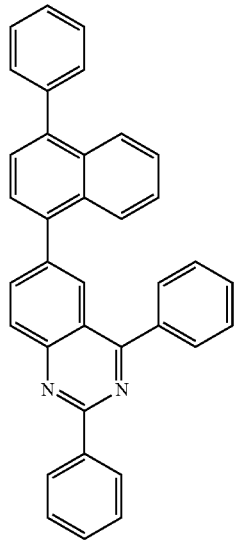
C-2-104
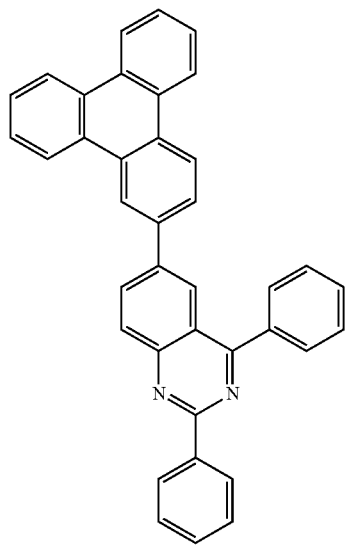
C-2-105
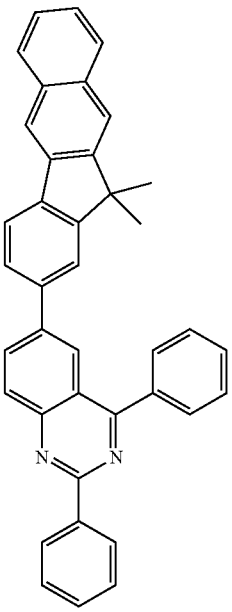
C-2-106
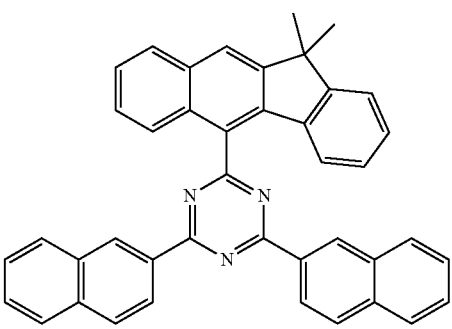
C-2-107

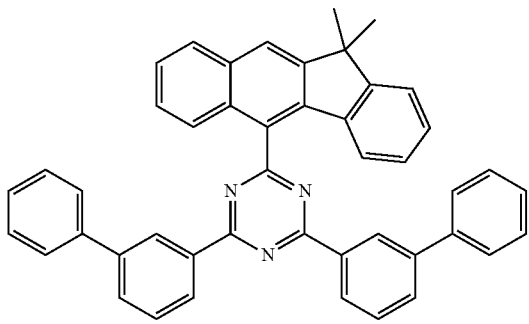
C-2-108

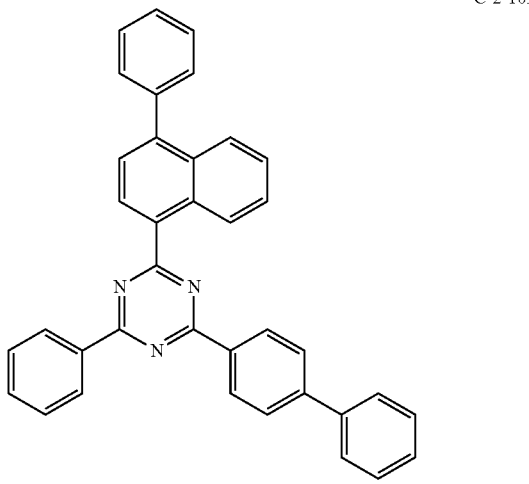
C-2-109

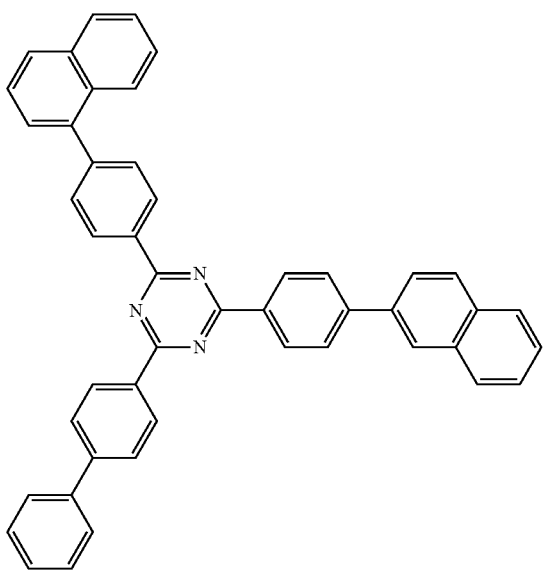
C-2-110

The combination of at least one of compounds C-1-1 to C-1-140 and at least one of compounds C-2-1 to C-2-110 may be used in an organic electroluminescent device.

According to one embodiment of the present disclosure, the compound represented by formula 2 may be specifically represented by the following formula 11. Also, the present disclosure may provide an organic electroluminescent compound represented by the following formula 11. According to another embodiment of the present disclosure, the present disclosure may provide a combination of the compound represented by formula 1 and the compound represented by the following formula 11. The present disclosure may also provide a combination of the compound represented by formula 2 and the compound represented by formula 11, or a combination of the compound represented by formula 1, the compound represented by formula 2, and the compound represented by formula 11. The organic electroluminescent device according to the present disclosure may include the above combinations. Also, the organic electroluminescent device according to the present disclosure may comprise a compound represented by the following formula 11, which may be used as a host material. According to another embodiment of the present disclosure, the present disclosure may provide a host material comprising a compound represented by the following formula 11. The host material may consist of only a single host, or may comprise a plurality of hosts.

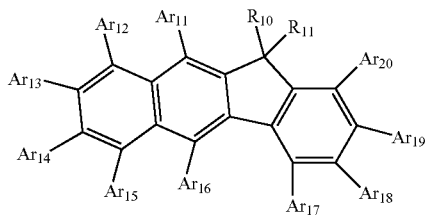
(11)

In formula 11, $Ar_{11}$ to $Ar_{20}$, each independently, represent hydrogen, deuterium, a substituted or unsubstituted (C1-C30)alkyl, a substituted or unsubstituted (C6-C30)aryl, a substituted or unsubstituted (5- to 30-membered)heteroaryl, a substituted or unsubstituted (3- to 7-membered)heterocycloalkyl, or a substituted or unsubstituted (C3-C30)cycloalkyl; with the proviso that at least one of $Ar_{11}$ to $Ar_{20}$ is represented by the following formula 11-1:

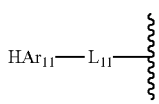
(11-1)

wherein
$HAr_{11}$ represents

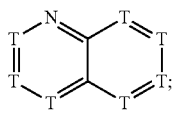

T, each independently, represents N or $CR_{31}$;

$L_{11}$ represents a single bond, a substituted or unsubstituted (C6-C30)arylene, or a substituted or unsubstituted (5- to 30-membered)heteroarylene;

$R_{10}$, $R_{11}$ and $R_{31}$, each independently, represent hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, a substituted or unsubstituted (3- to 25-membered)heteroaryl, —$NR_5R_6$, or —SiR$_7$R$_8$R$_9$; or R$_{10}$ and R$_{11}$, or the adjacent R$_{31}$'s may be linked to each other to form a ring; and R$_5$ to R$_9$, each independently, represent a substituted or unsubstituted (C1-C30)alkyl, a substituted or unsubstituted (C6-C30)aryl, or a substituted or unsubstituted (3- to 30-membered) heteroaryl.

According to one embodiment of the present disclosure, at least one of Ar$_{11}$ to Ar$_{20}$ is represented by formula 11-1, and the others of Ar$_{11}$ to Ar$_{20}$ represent hydrogen.

According to one embodiment of the present disclosure, L$_{11}$ represents a single bond, a substituted or unsubstituted (C6-C25)arylene, or a substituted or unsubstituted (5- to 25-membered)heteroarylene. According to another embodiment of the present disclosure, L$_{11}$ represents a single bond, an unsubstituted (C6-C18)arylene, or an unsubstituted (5- to 20-membered)heteroarylene. For example, L$_{11}$ may represent a single bond, a phenylene, a naphthylene, or a pyridylene.

According to one embodiment of the present disclosure, R$_{10}$ and R$_{11}$, each independently, represent a substituted or unsubstituted (C1-C20)alkyl, or a substituted or unsubstituted (C6-C25)aryl; or R$_{10}$ and R$_{11}$ may be linked to each other to form a ring. R$_{10}$ and R$_{11}$ may be the same as or different from each other. According to another embodiment of the present disclosure, R$_{10}$ and R$_{11}$, each independently, represent an unsubstituted (C1-C10)alkyl, or an unsubstituted (C6-C18)aryl; or R$_{10}$ and R$_{11}$ may be linked to each other to form a spiro ring. For example, R$_{10}$ and R$_{11}$, each independently, represent a methyl or a phenyl; or R$_{10}$ and R$_{11}$ may be linked to each other to form a spirofluorene ring.

According to one embodiment of the present disclosure, R$_{31}$, each independently, represent hydrogen, deuterium, a substituted or unsubstituted (C1-C20)alkyl, a substituted or unsubstituted (C6-C25)aryl, or a substituted or unsubstituted (5- to 25-membered)heteroaryl; or the adjacent R$_{31}$'s may be linked to each other to form a ring. According to one embodiment of the present disclosure, R$_{31}$, each independently, represent hydrogen, deuterium, or a (C6-C18)aryl unsubstituted or substituted with a (C1-C6)alkyl; or the adjacent R$_{31}$'s may be linked to each other to form an unsubstituted (5- to 25-membered) ring. For example, R$_{31}$, each independently, may represent hydrogen, a phenyl, a naphthyl, a biphenyl, a naphthylphenyl, a phenylnaphthyl, a phenanthrenyl, a triphenylenyl, a dimethylfluorenyl, or a dimethylbenzofluorenyl; or the adjacent R$_{31}$'s may be linked to each other to form a benzene ring.

In formula 11-1, HAr$_{11}$ may be represented by at least one of the following formulas 12-1 to 12-7.

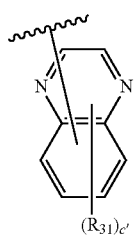
(12-1)

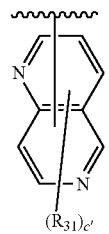
(12-2)

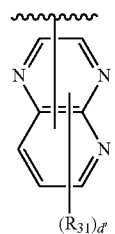
(12-3)

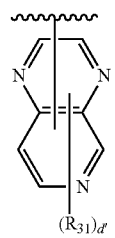
(12-4)

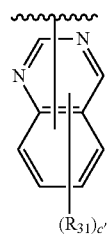
(12-5)

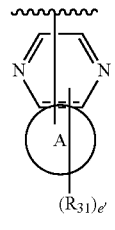
(12-6)

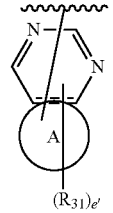
(12-7)

In formulas 12-1 to 12-7, A ring represents a naphthalene ring; R$_{31}$, each independently, is as defined in formula 11-1; c' represents an integer of 1 to 5; d' represents an integer of 1 to 4; and e' represents an integer of 1 to 7; where if c' to e', each independently, are an integer of 2 or more, each R$_{31}$ may be the same or different.

The compound represented by formula 11 includes the following compounds, but is not limited thereto.

C-2-53
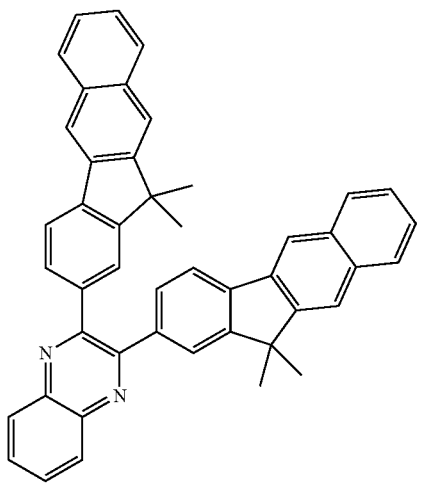
C-2-63
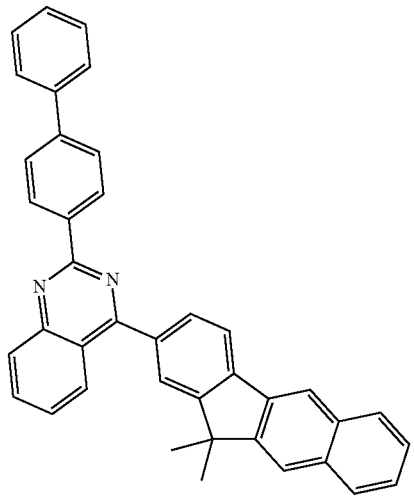
C-2-57
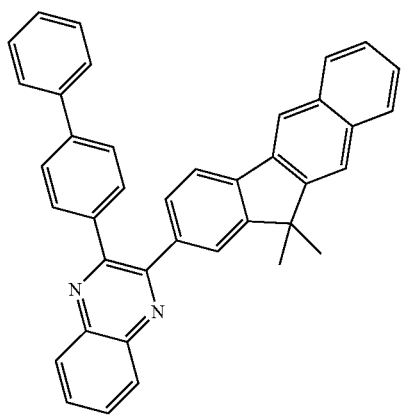
C-2-69
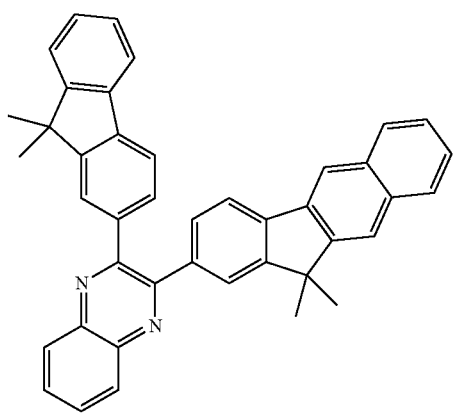
C-2-60
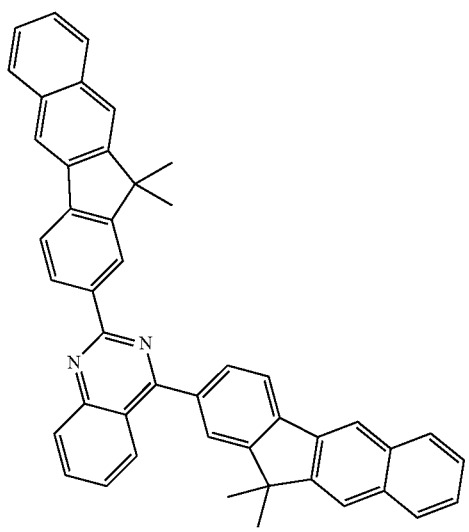
C-2-70
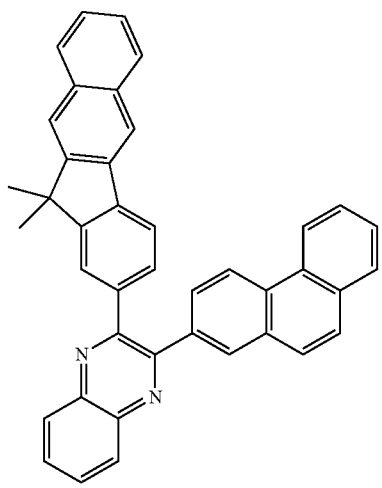

C-2-71
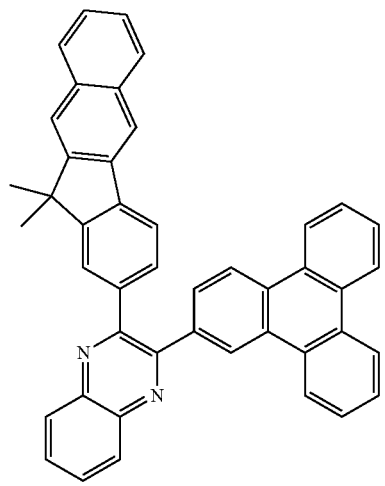
C-2-76
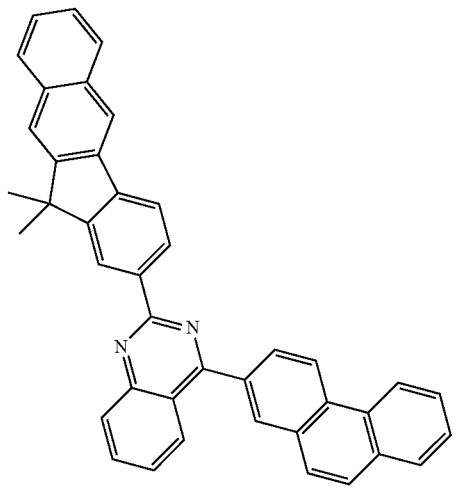
C-2-72
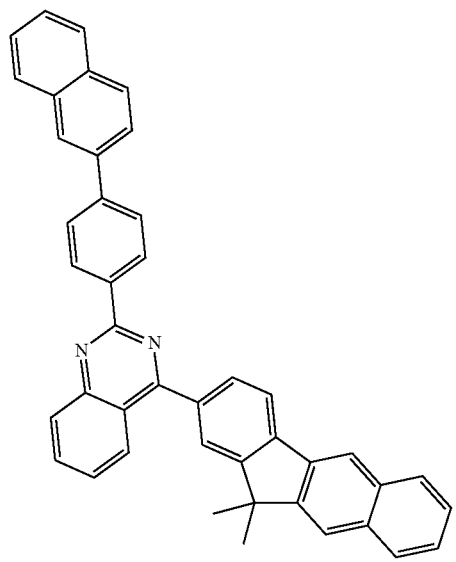
C-2-77
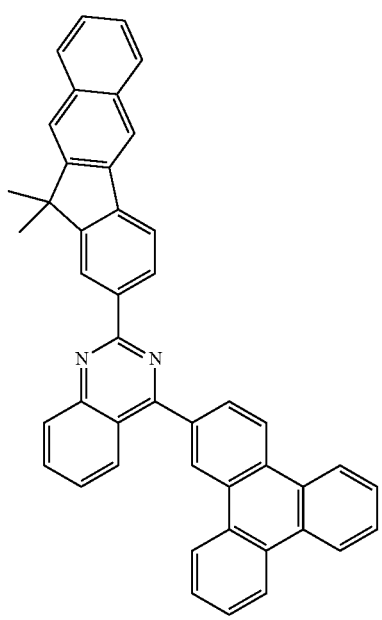
C-2-75
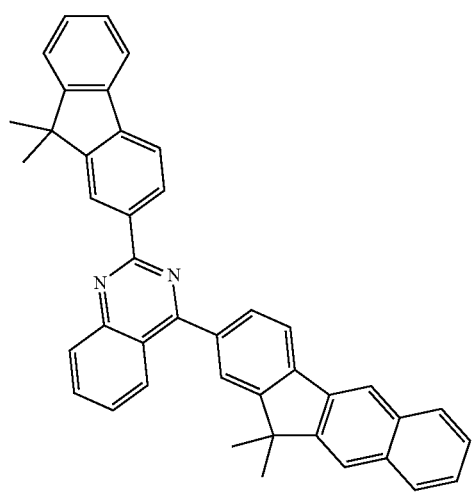
C-2-80
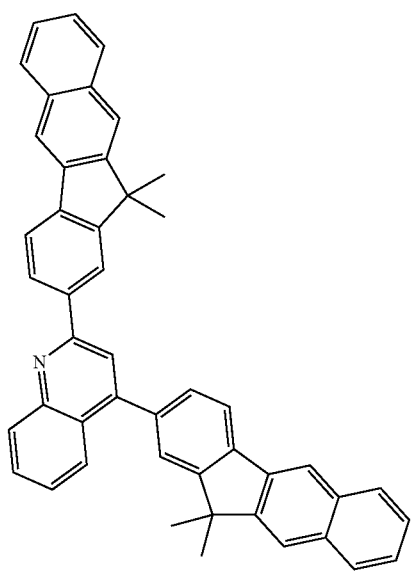

-continued
C-2-82
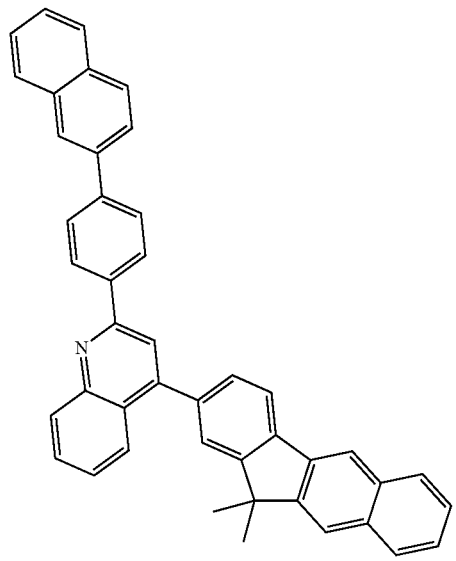
C-2-86
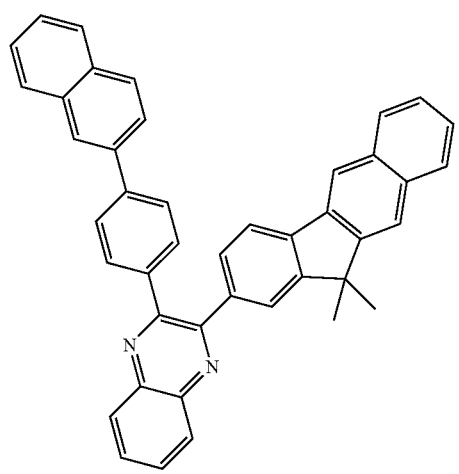
C-2-95
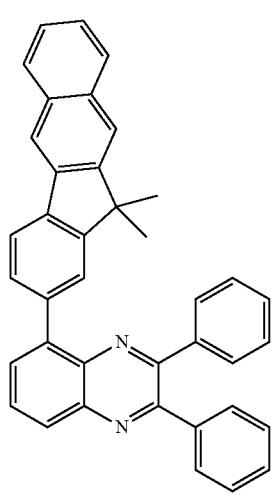
-continued
C-2-100
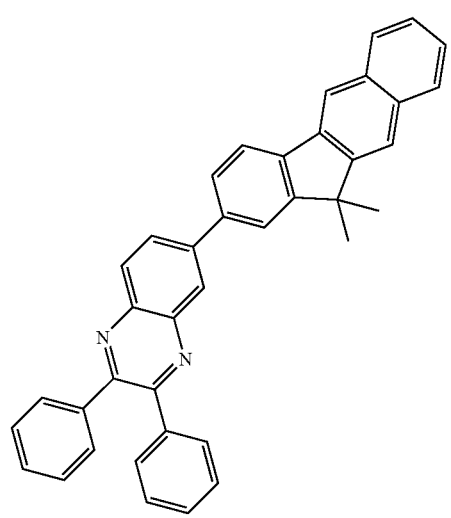
C-2-105
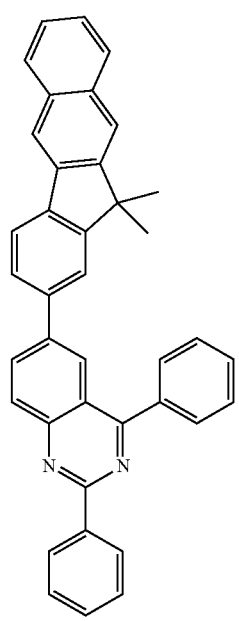
C-3-1
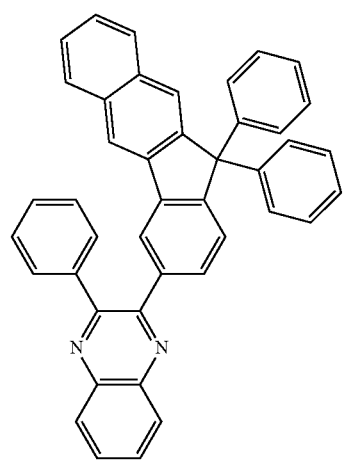

C-3-2
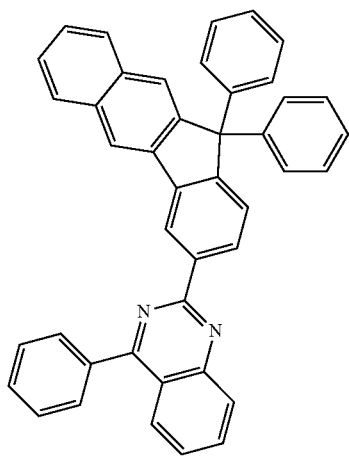
C-3-3
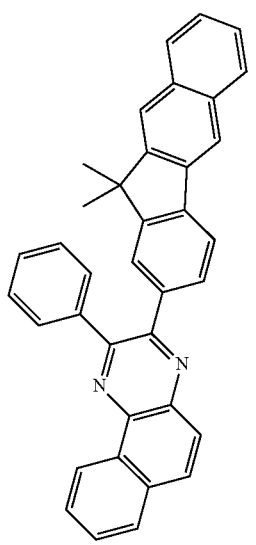
C-3-4
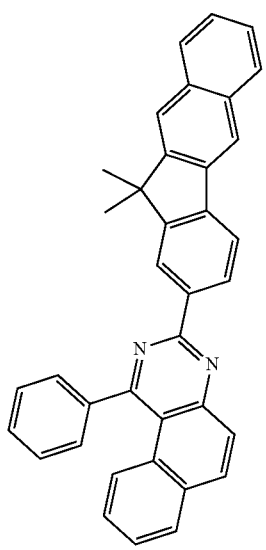
C-3-5
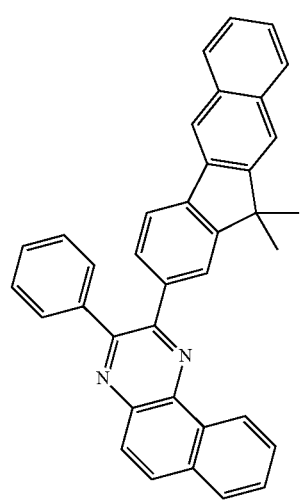
C-3-6
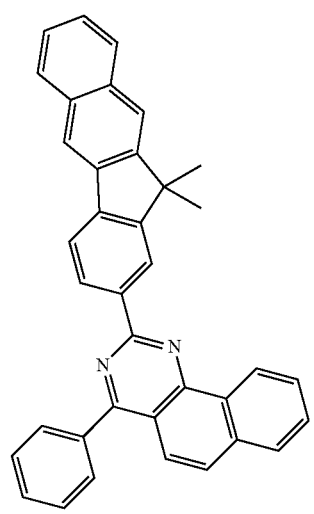
C-3-7
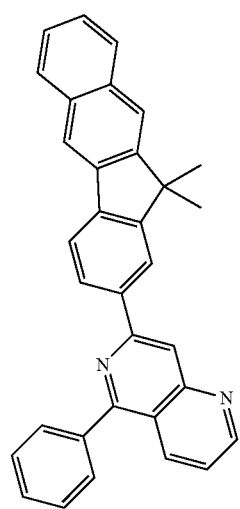

C-3-8
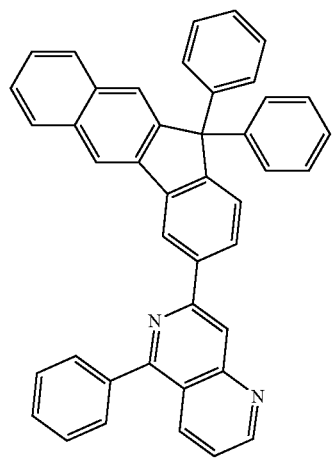
C-3-9
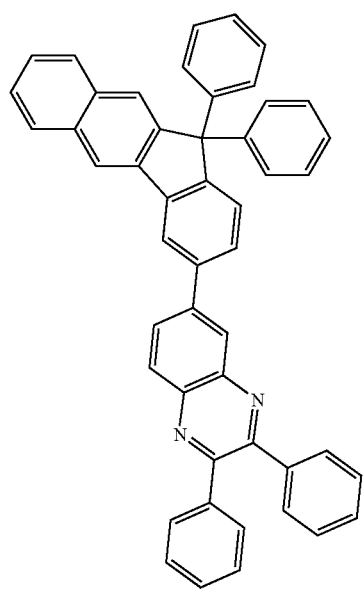
C-3-10
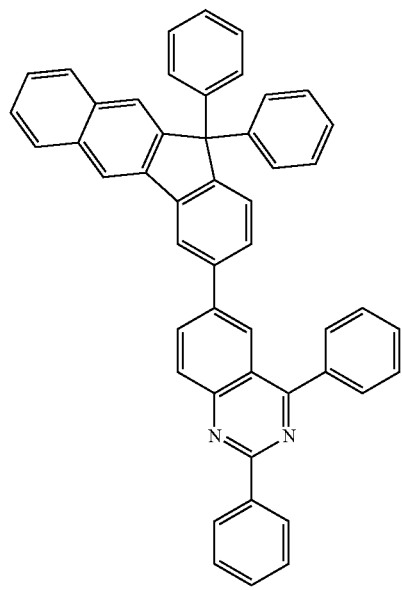
C-3-11
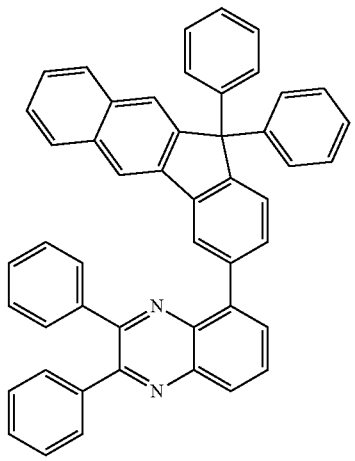
C-3-12
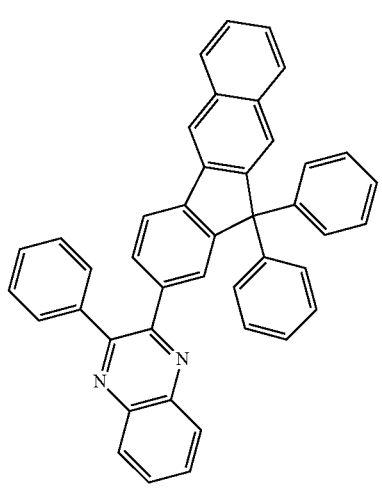
C-3-13
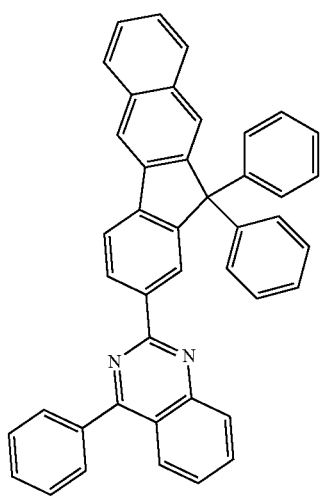

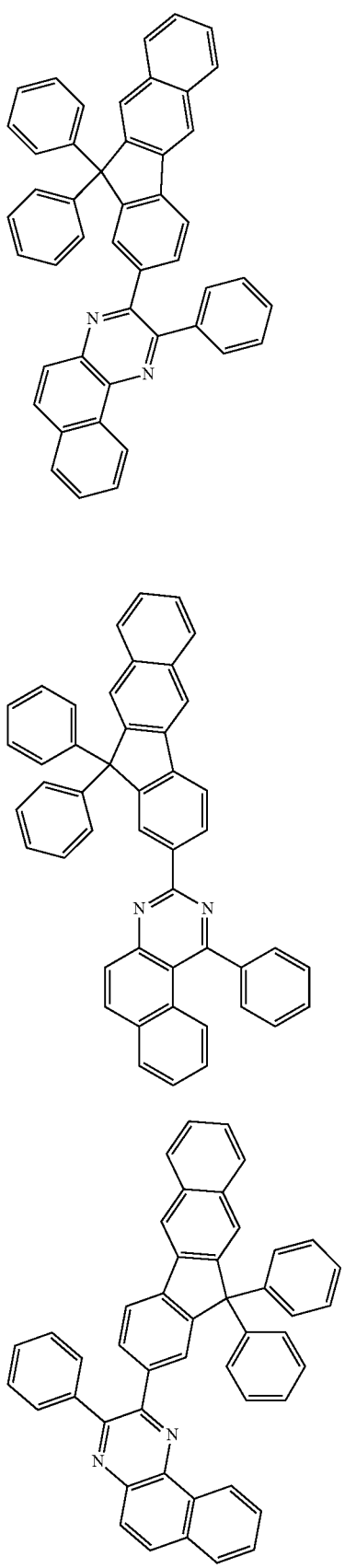
C-3-14
C-3-15
C-3-16
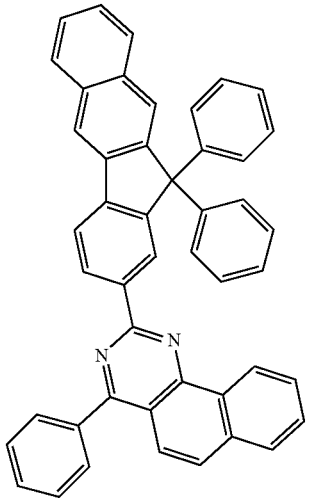
C-3-17
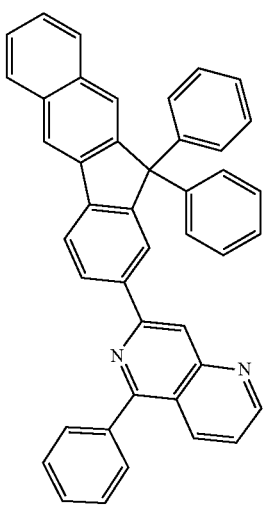
C-3-18
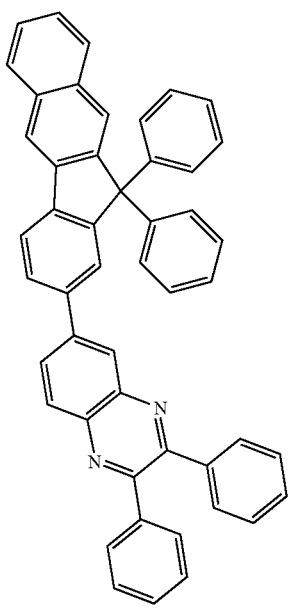
C-3-19

C-3-20
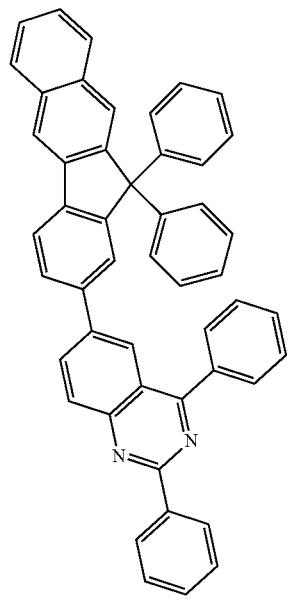
C-3-21
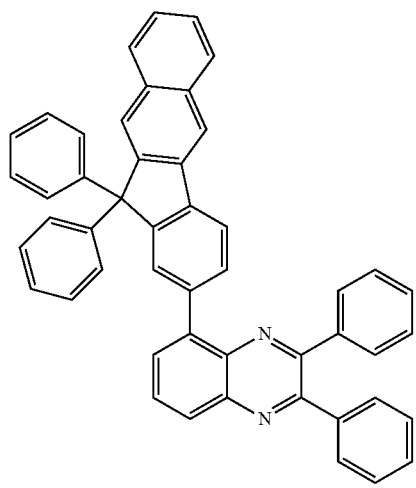
C-3-22
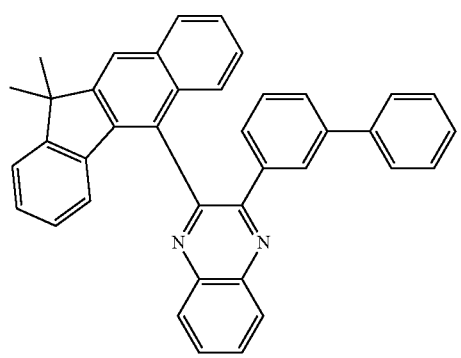
C-3-23
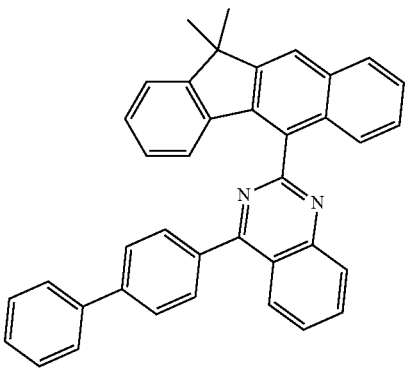
C-3-24
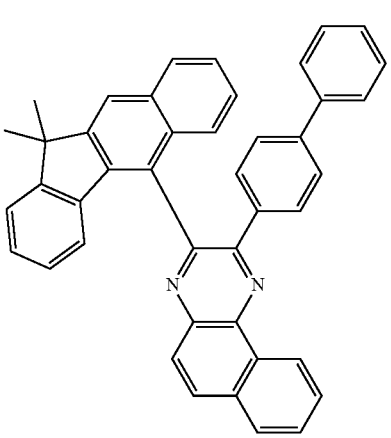
C-3-25
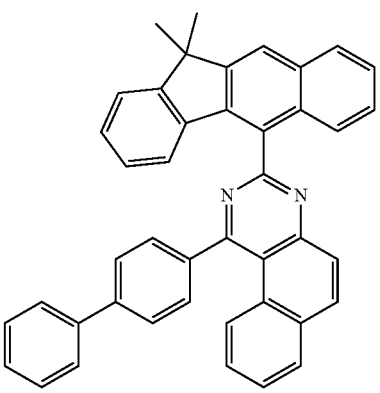
C-3-26
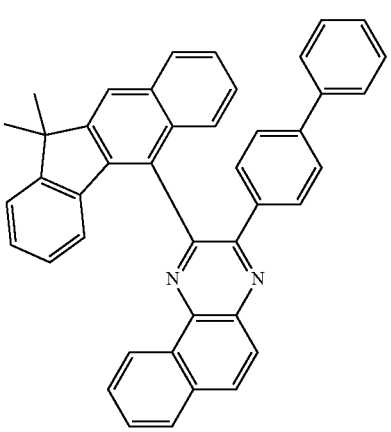

-continued
C-3-27
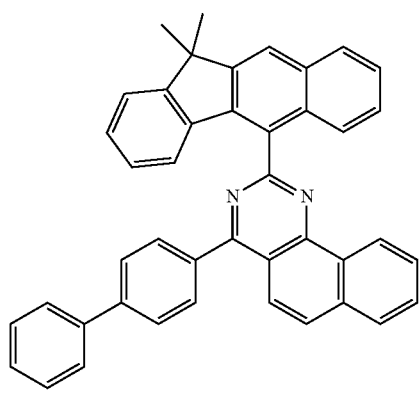
C-3-28
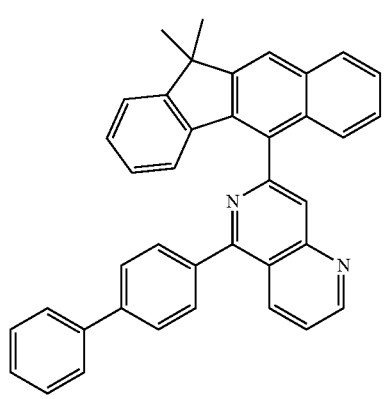
C-3-29
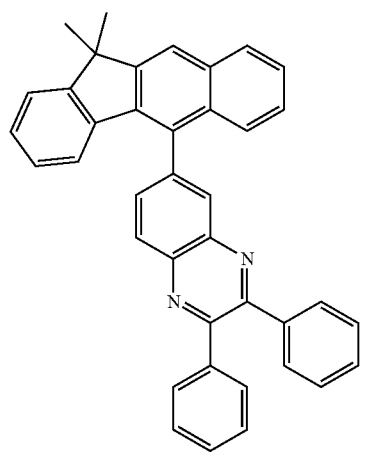
C-3-30
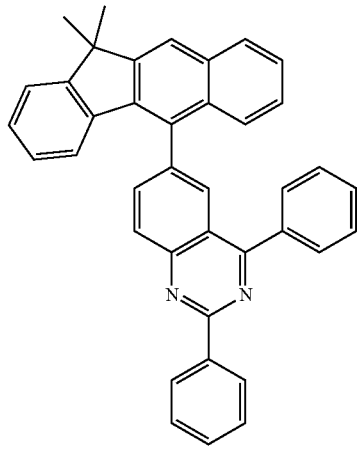
C-3-31
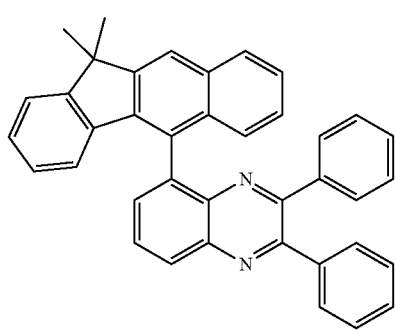
C-3-32
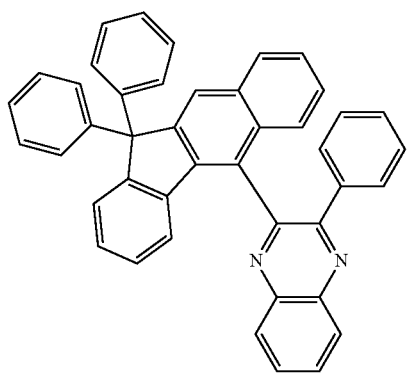
C-3-33
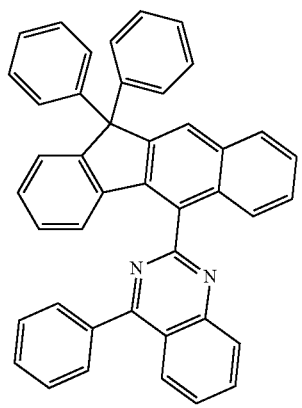

C-3-34
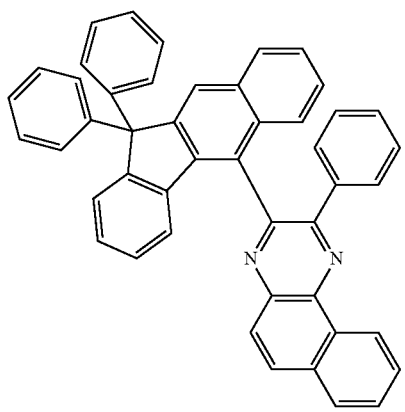
C-3-35
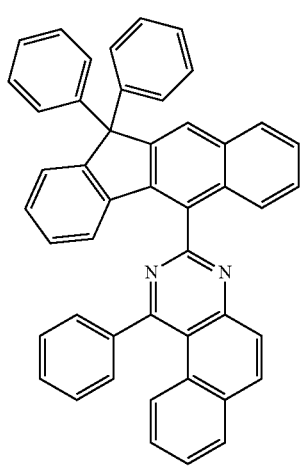
C-3-36
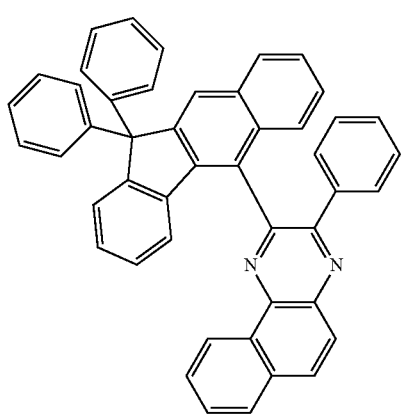
C-3-37
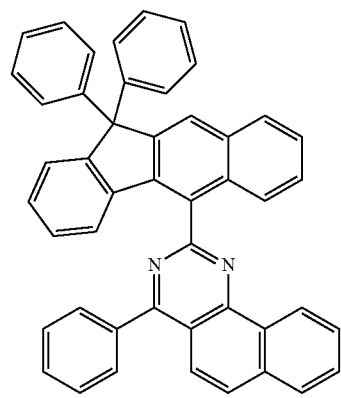
C-3-38
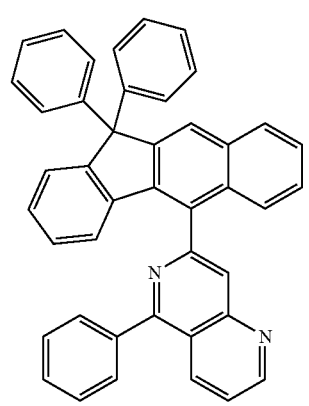
C-3-39
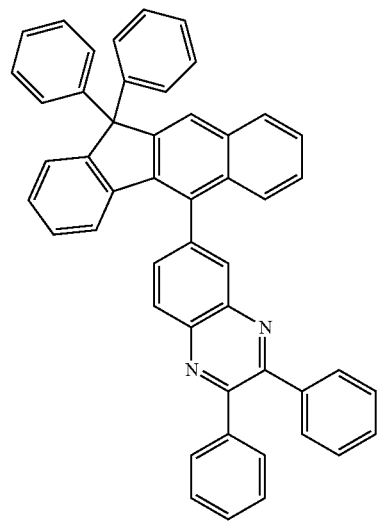

C-3-40
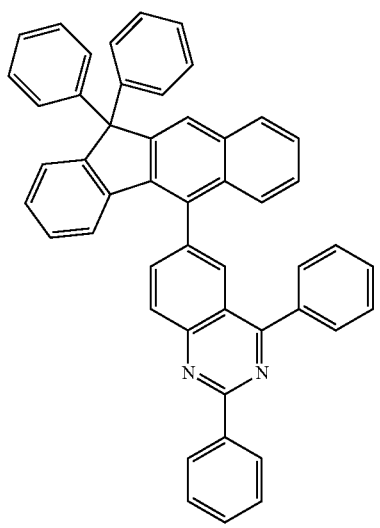
C-3-43
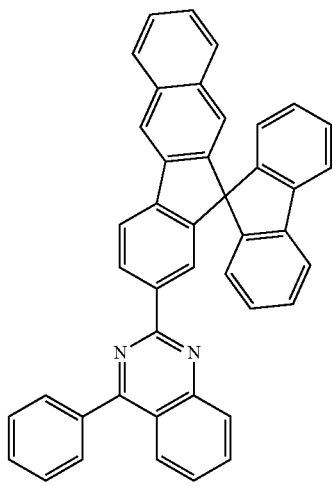
C-3-41
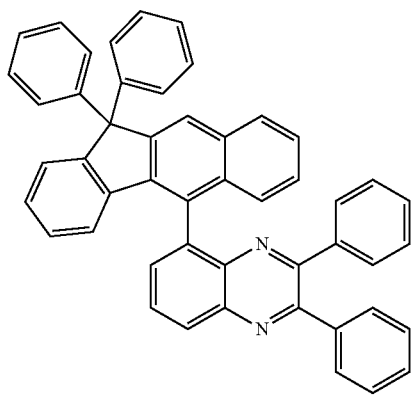
C-3-44
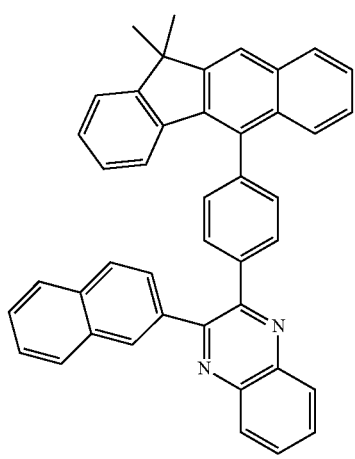
C-3-42
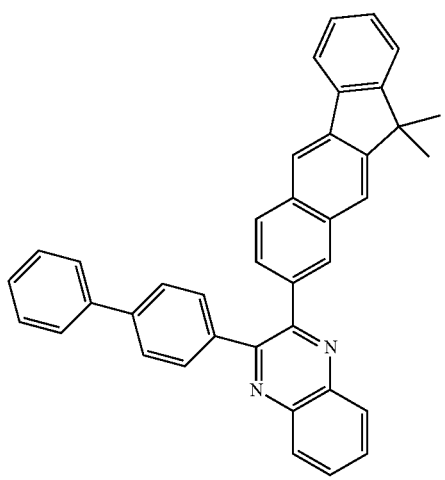
C-3-45
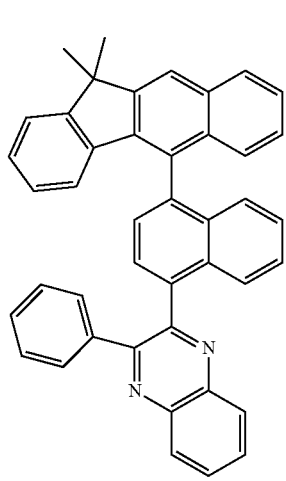

C-3-46

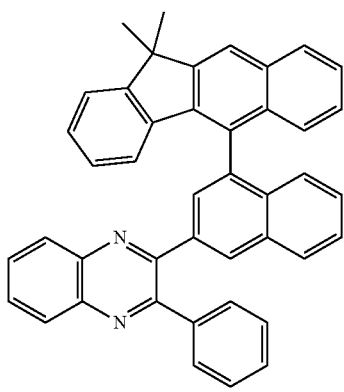

C-3-47

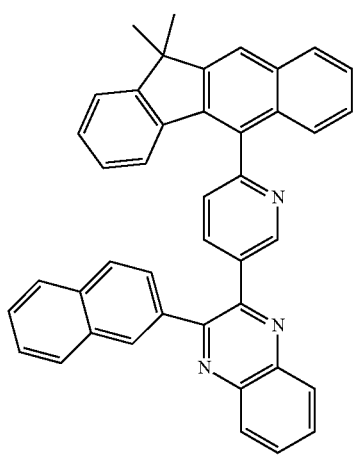

C-3-48

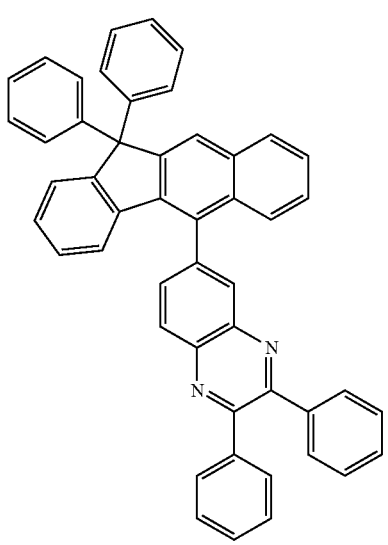

C-3-49

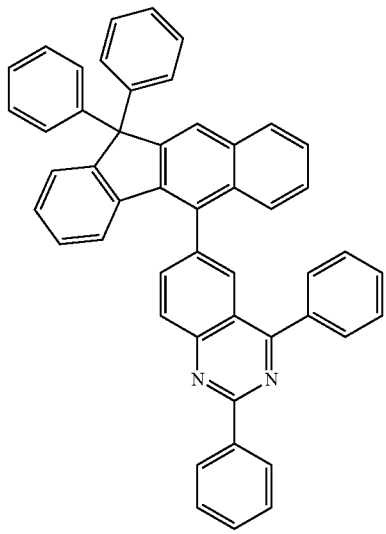

C-3-50

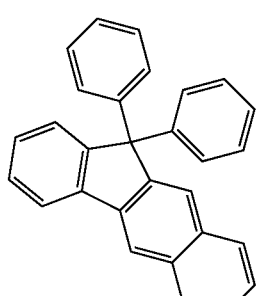

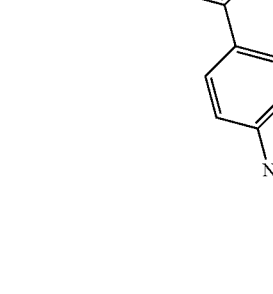

The combination of at least one of compounds C-1-1 to C-1-140, and/or at least one of compounds C-2-1 to C-2-110, and/or at least one of compounds C-3-1 to C-3-50 may be used in an organic electroluminescent device.

The compound of formula 1 according to the present disclosure may be prepared by a synthetic method known to one skilled in the art. For example, the compound represented by formula 3 or 4 can be prepared by referring to the following reaction scheme 1 or 2, but is not limited thereto.

[Reaction Scheme 1]

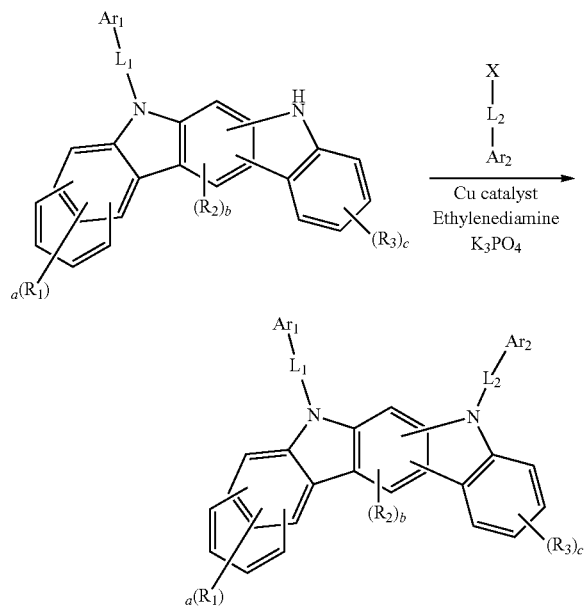

[Reaction Scheme 2]

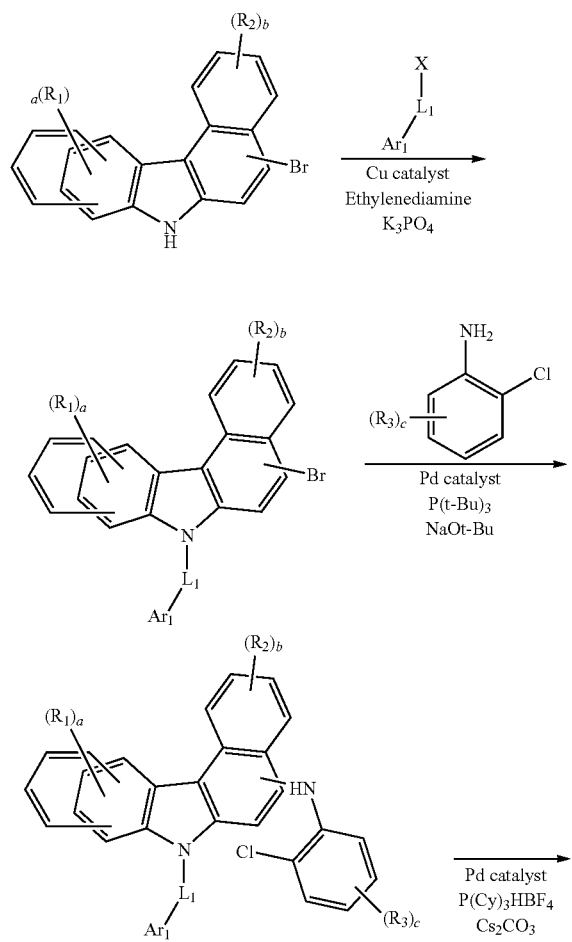

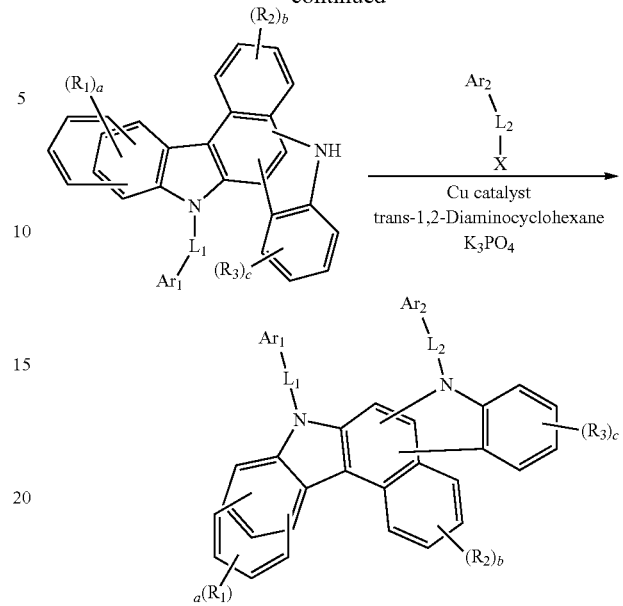

In reaction schemes 1 and 2, $L_1$, $L_2$, $Ar_1$, $Ar_2$, $R_1$ to $R_3$, and a to c are as defined in formula 1.

Also, the compound of formula 2 according to the present disclosure may be prepared by a synthetic method known to one skilled in the art. For example, the compound represented by formula 5 or 6 can be prepared by referring to the following reaction scheme 3 or 4, but is not limited thereto.

[Reaction Scheme 3]

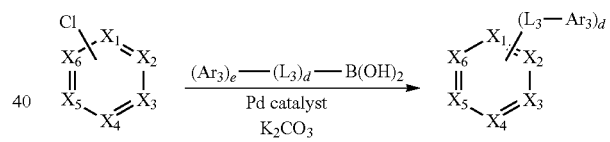

[Reation Scheme 4]

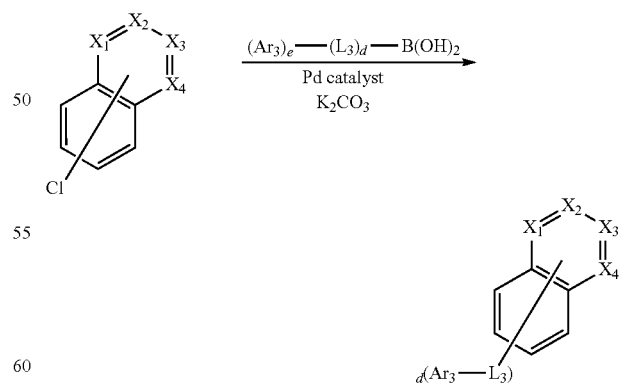

In reaction schemes 3 and 4, $L_3$, $Ar_3$ and d are as defined in formula 2, and $X_1$ to $X_6$ are as defined in formulas 5 and 6.

The compound of formula 11 according to the present disclosure may be prepared by a synthetic method known to one skilled in the art. For example, the compound represented by formula 11 can be prepared by referring to the following reaction scheme 5 or 6, but is not limited thereto.

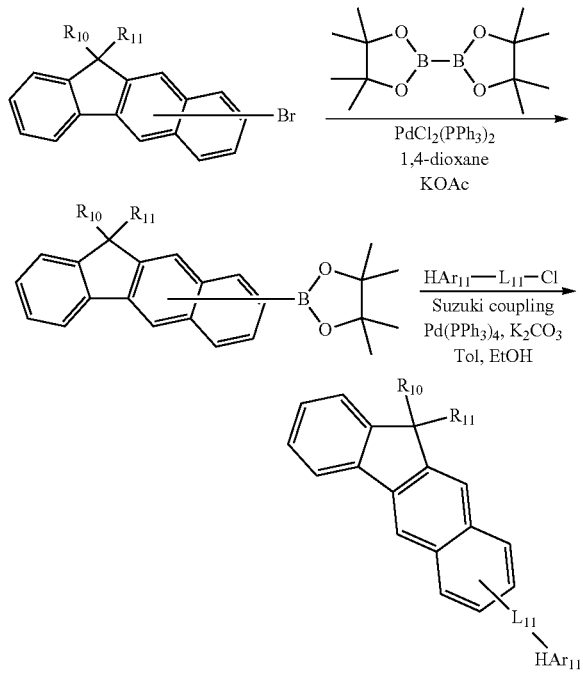

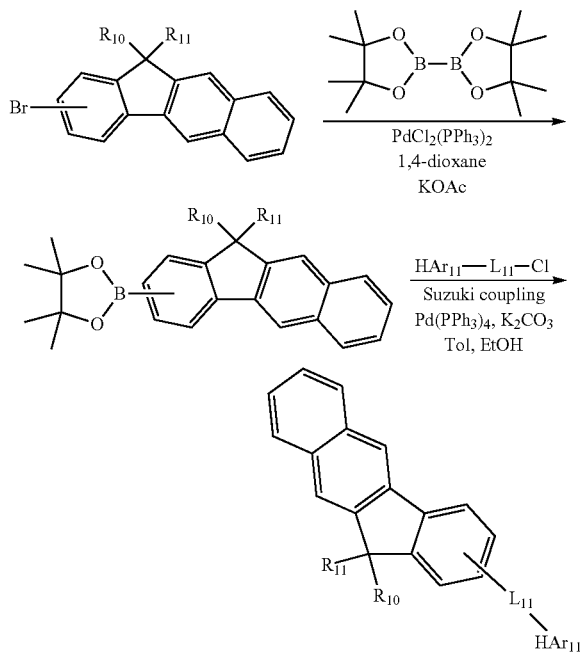

In reaction schemes 5 and 6, $R_{10}$, $R_{11}$, $L_{11}$, and $HAr_{11}$ are as defined in formula 11.

The organic electroluminescent device according to the present disclosure comprises an anode, a cathode, and at least one organic layer between the anode and the cathode. The organic layer may comprise a plurality of organic electroluminescent materials in which the compound represented by formula 1 is included as a first organic electroluminescent material, and the compound represented by formula 2 is included as a second organic electroluminescent material. According to one embodiment of the present disclosure, the organic electroluminescent device comprises an anode, a cathode, and at least one light-emitting layer between the anode and the cathode, and at least one layer of the light-emitting layer may comprise the compound represented by formula 1 and the compound represented by formula 2.

The light-emitting layer comprises a host and a dopant. The host comprises a plurality of host materials. The plurality of host materials comprises a first host material and a second host material. The first host material may consist of the compound represented by formula 1 alone, or may consist of at least one compound represented by the formula 1. The first host material may further comprise conventional materials included in the organic electroluminescent material. The second host material may consist of the compound represented by formula 2 alone, or may consist of at least one compound represented by the formula 2. The second host material may further comprise conventional materials included in the organic electroluminescent material. The weight ratio of the first host compound to the second host compound is in the range of about 1:99 to about 99:1, preferably about 10:90 to about 90:10, more preferably about 30:70 to about 70:30, even more preferably about 40:60 to 60:40, and still more preferably about 50:50.

The light-emitting layer is a layer from which light is emitted, and can be a single layer or a multi-layer in which two or more layers are stacked. In the plurality of host materials according to the present disclosure, the first and second host materials may both be comprised in one layer or may be respectively comprised in different light-emitting layers. In the light-emitting layer, it is preferable that the doping concentration of the dopant compound with respect to the host compound is less than 20 wt %.

The organic electroluminescent device of the present disclosure may further comprise at least one layer selected from a hole injection layer, a hole transport layer, a hole auxiliary layer, a light-emitting auxiliary layer, an electron transport layer, an electron injection layer, an interlayer, an electron buffer layer, a hole blocking layer, and an electron blocking layer. According to one embodiment of the present disclosure, the organic electroluminescent device may further comprise amine-based compounds in addition to a plurality of host materials of the present disclosure as at least one of a hole injection material, a hole transport material, a hole auxiliary material, a light-emitting material, a light-emitting auxiliary material and an electron blocking material. Also, according to one embodiment of the present disclosure, the organic electroluminescent device may further comprise azine-based compounds in addition to a plurality of host materials of the present disclosure as at least one of an electron transport material, an electron injection material, an electron buffer material and a hole blocking material.

The dopant compound, which can be used in combination with the host compound of the present disclosure, may comprise the compound represented by the following formula 101, but is not limited thereto.

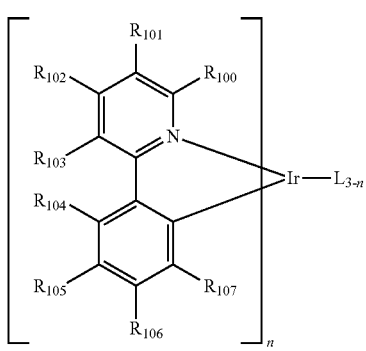

(101)

In formula 101, L₁ is selected from the following structures 1 and 2:

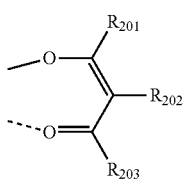

[Structure 1]

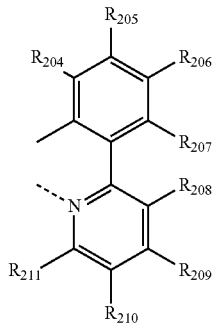

[Structure 2]

$R_{100}$ to $R_{103}$, each independently, represent hydrogen, deuterium, a halogen, a (C1-C30)alkyl unsubstituted or substituted with deuterium or a halogen, a substituted or unsubstituted (C3-C30)cycloalkyl, a substituted or unsubstituted (C6-C30)aryl, a cyano, a substituted or unsubstituted (3- to 30-membered)heteroaryl, or a substituted or unsubstituted (C1-C30)alkoxy; or may be linked to adjacent $R_{100}$ to $R_{103}$, to form a substituted or unsubstituted fused ring together with pyridine, e.g., a substituted or unsubstituted quinoline, a substituted or unsubstituted isoquinoline, a substituted or unsubstituted benzofuropyridine, a substituted or unsubstituted benzothienopyridine, a substituted or unsubstituted indenopyridine, a substituted or unsubstituted benzofuroquinoline, a substituted or unsubstituted benzothienoquinoline, or a substituted or unsubstituted indenoquinoline ring;

$R_{104}$ to $R_{107}$, each independently, represent hydrogen, deuterium, a halogen, a (C1-C30)alkyl unsubstituted or substituted with deuterium or a halogen, a substituted or unsubstituted (C3-C30)cycloalkyl, a substituted or unsubstituted (C6-C30)aryl, a substituted or unsubstituted (3- to 30-membered)heteroaryl, a cyano, or a substituted or unsubstituted (C1-C30)alkoxy; or may be linked to adjacent $R_{104}$ to $R_{107}$ to form a substituted or unsubstituted fused ring together with benzene, e.g., a substituted or unsubstituted naphthalene, a substituted or unsubstituted fluorene, a substituted or unsubstituted dibenzothiophene, a substituted or unsubstituted dibenzofuran, a substituted or unsubstituted indenopyridine, a substituted or unsubstituted benzofuropyridine, or a substituted or unsubstituted benzothienopyridine ring;

$R_{201}$ to $R_{211}$, each independently, represent hydrogen, deuterium, a halogen, a (C1-C30)alkyl unsubstituted or substituted with deuterium or a halogen, a substituted or unsubstituted (C3-C30)cycloalkyl, or a substituted or unsubstituted (C6-C30)aryl; or may be linked to adjacent $R_{201}$ to $R_{211}$ to form a substituted or unsubstituted fused ring; and n represents an integer of 1 to 3.

The specific examples of the dopant compound are as follows, but are not limited thereto.

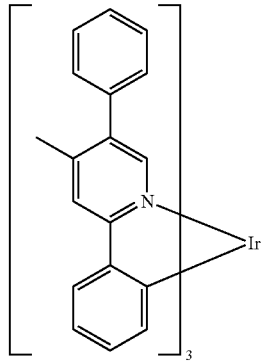

D-1

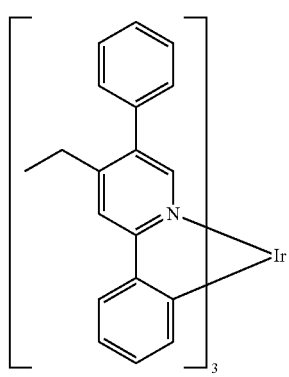

D-2

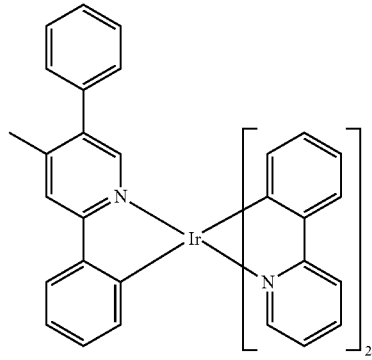

D-3

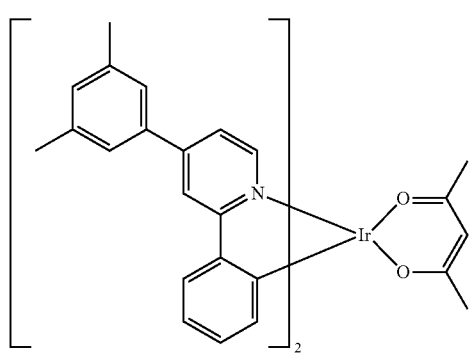
D-4
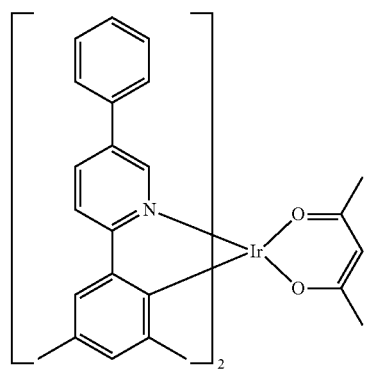
D-8
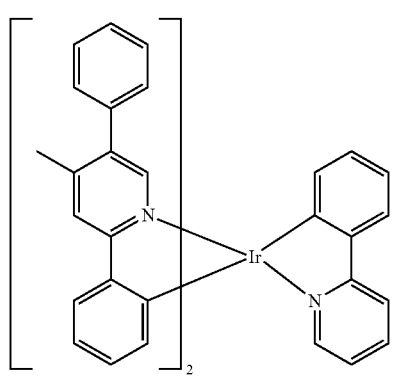
D-5
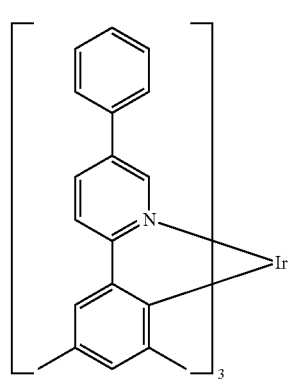
D-9
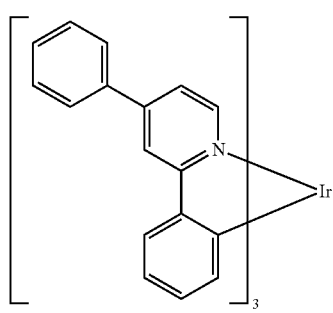
D-6
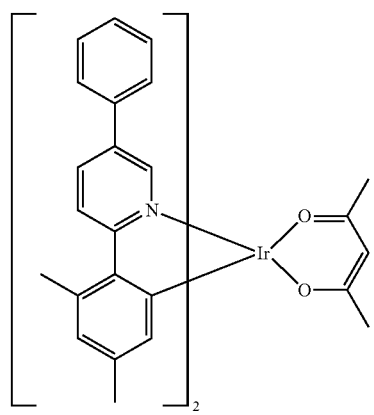
D-10
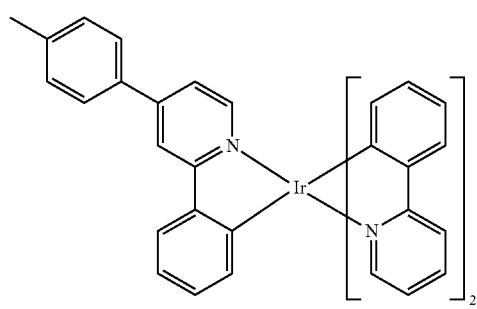
D-7
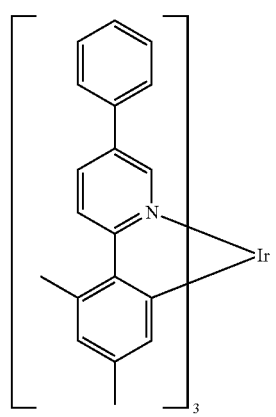
D-11

-continued
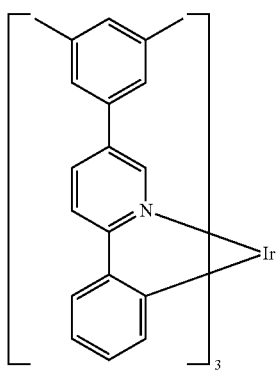
D-12
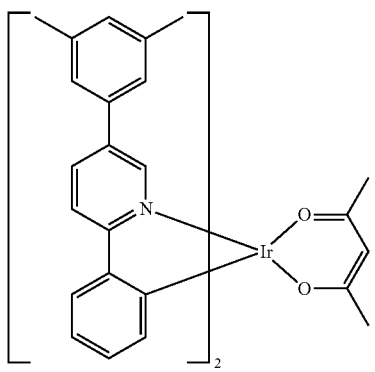
D-13
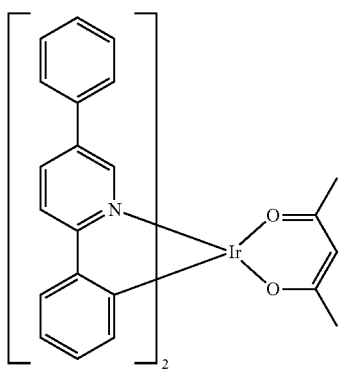
D-14
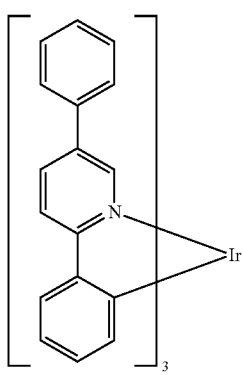
D-15
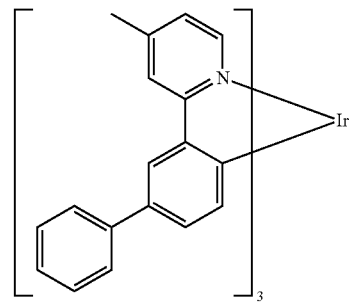
D-16
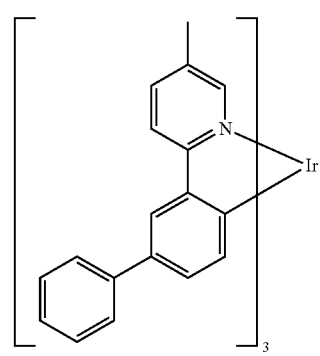
D-17
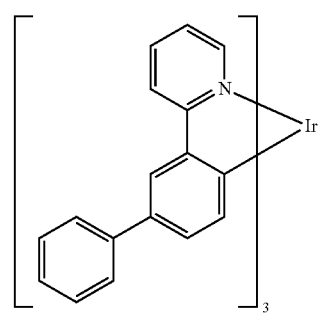
D-18
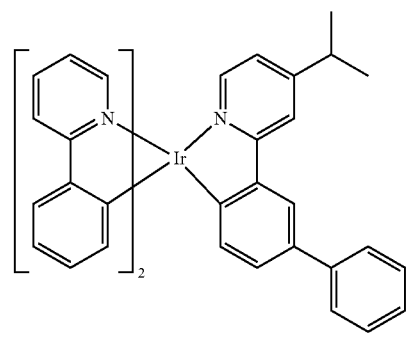
D-19
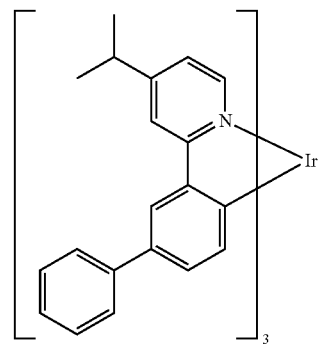
D-20

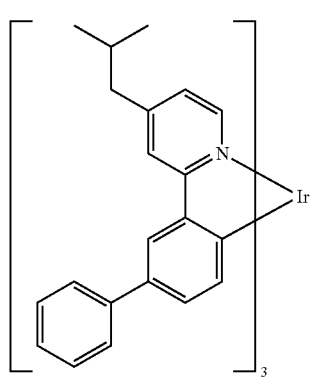 D-21
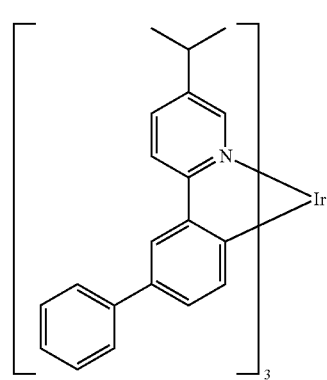 D-25
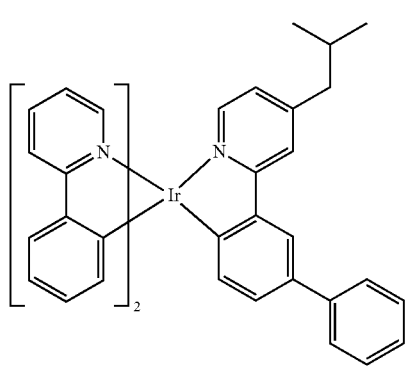 D-22
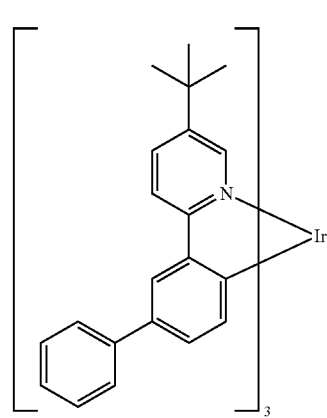 D-26
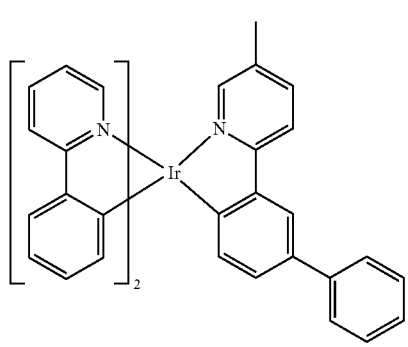 D-23
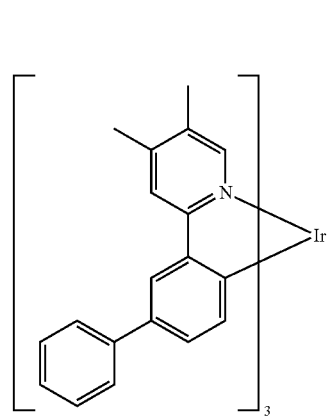 D-27
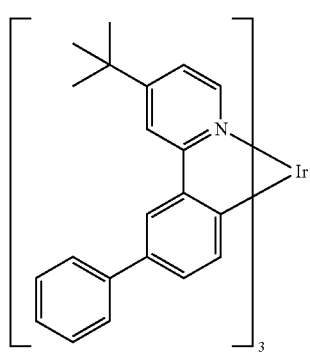 D-24
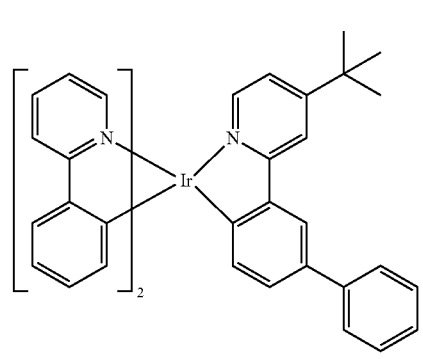 D-28

-continued
D-29
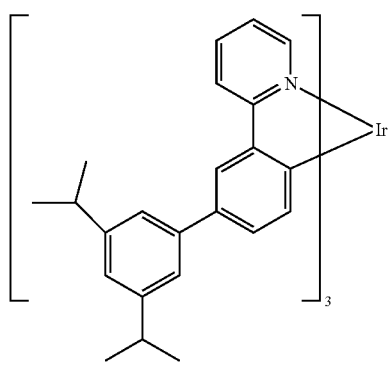
D-30
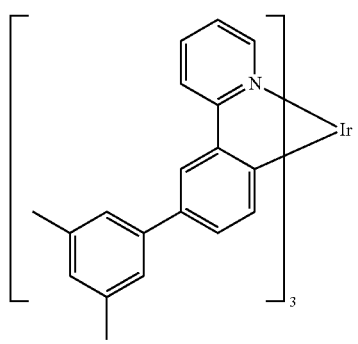
D-31
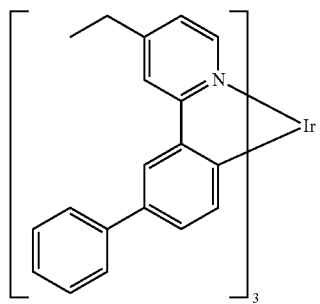
D-32
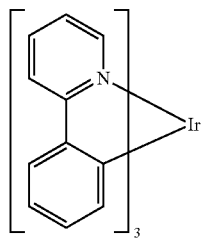
D-33
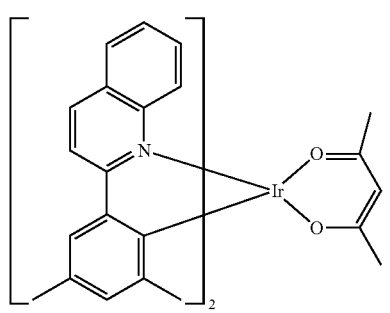
-continued
D-34
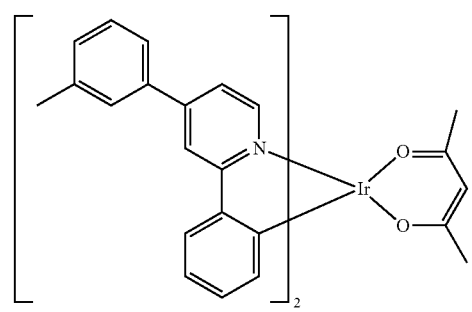
D-35
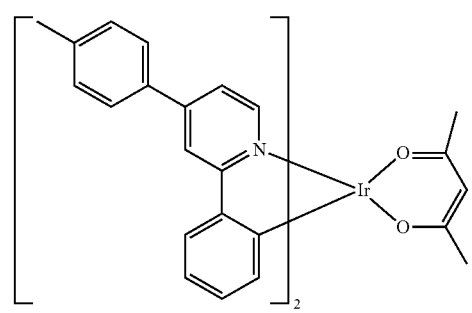
D-36
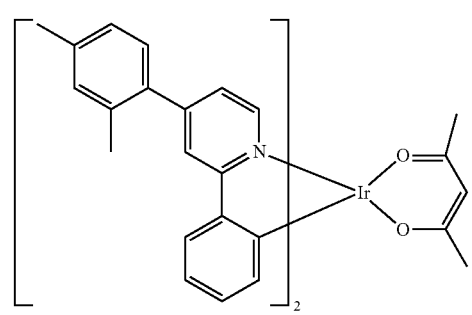
D-37
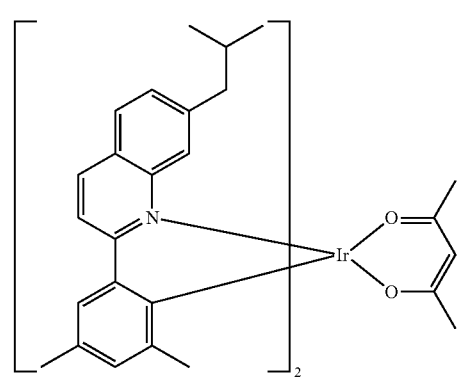
D-38
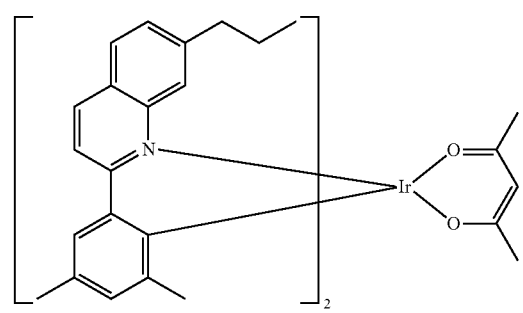

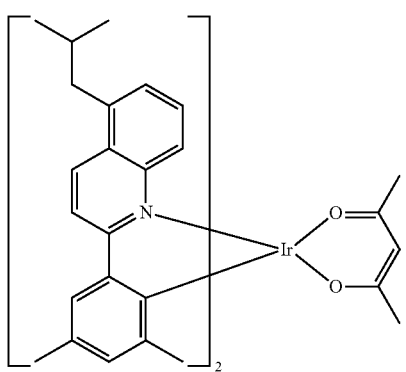
D-39
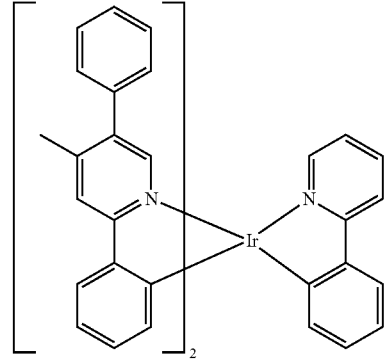
D-43
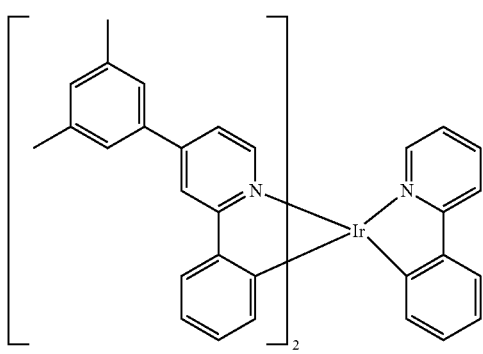
D-40
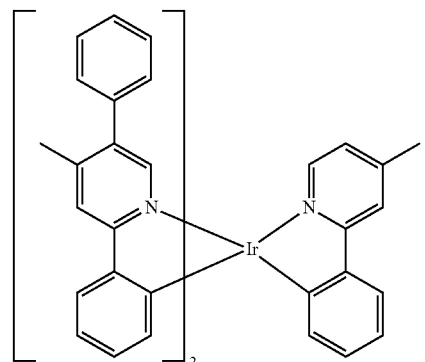
D-44
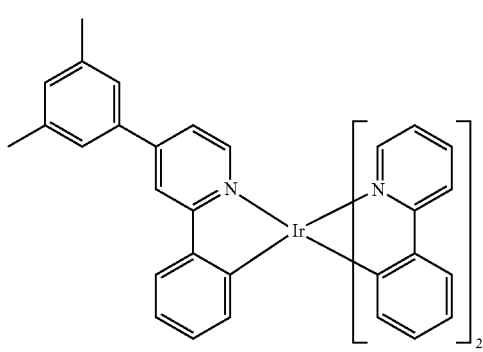
D-41
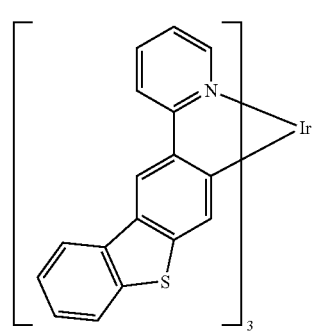
D-45
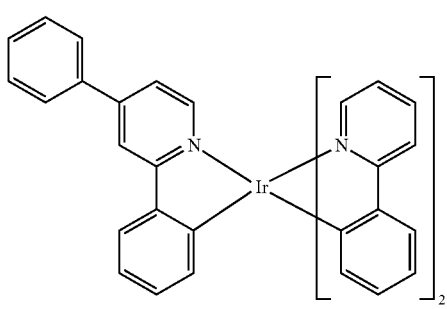
D-42
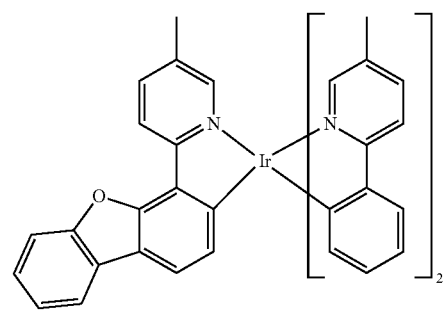
D-46

D-47
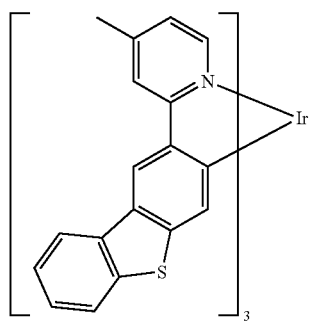
D-52
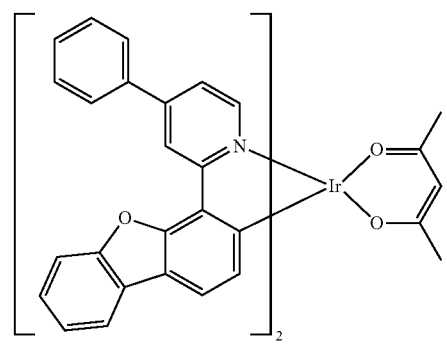
D-48
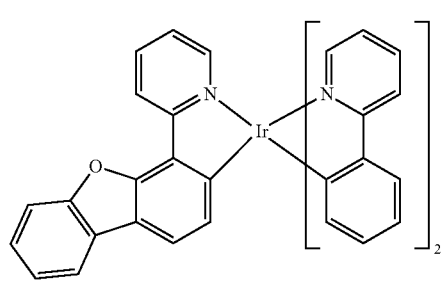
D-53
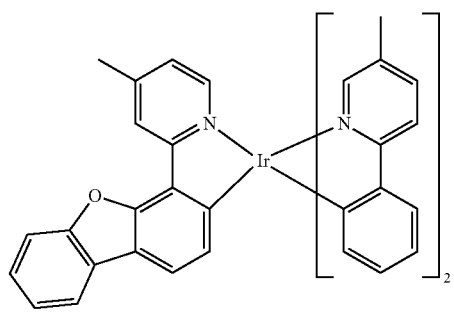
D-49
D-54
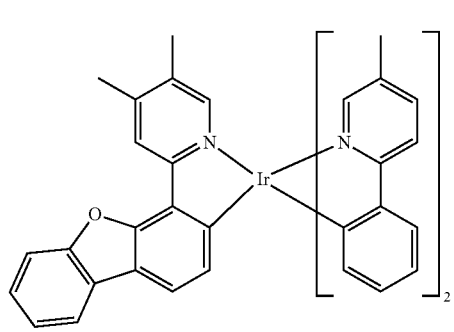
D-50
D-55
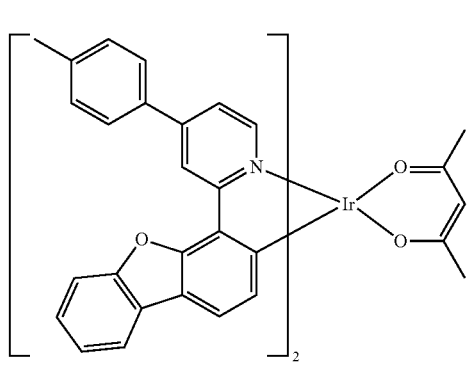
D-51
D-56
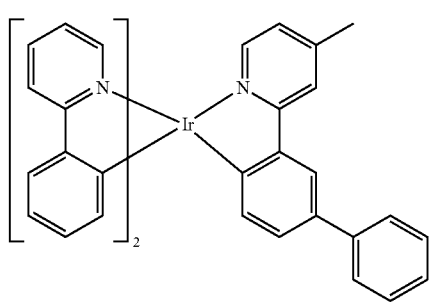

-continued
D-57
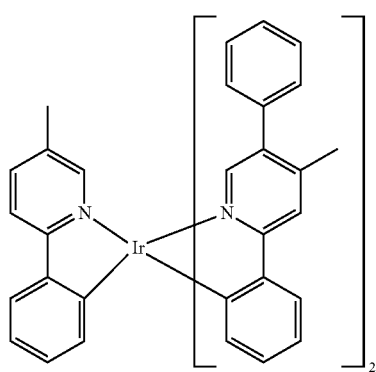
D-58
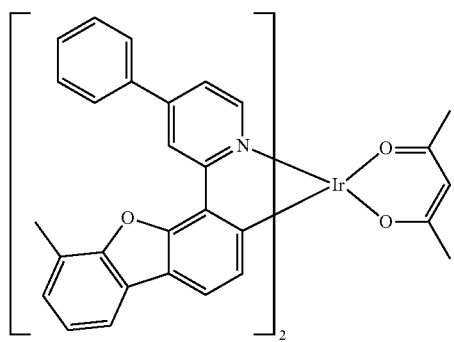
D-59
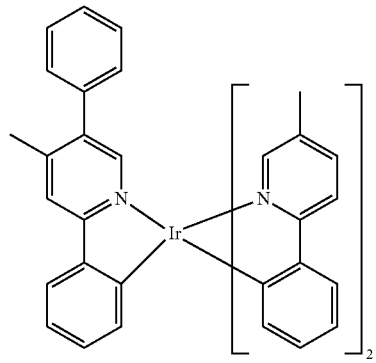
D-60
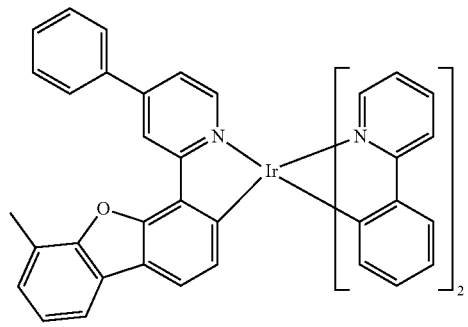
-continued
D-61
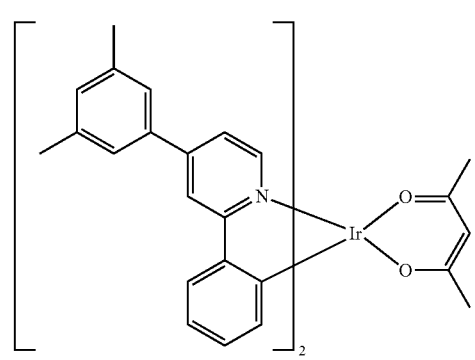
D-62
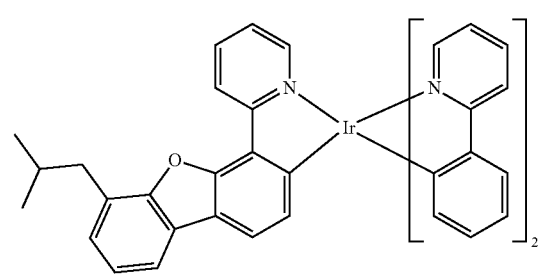
D-63
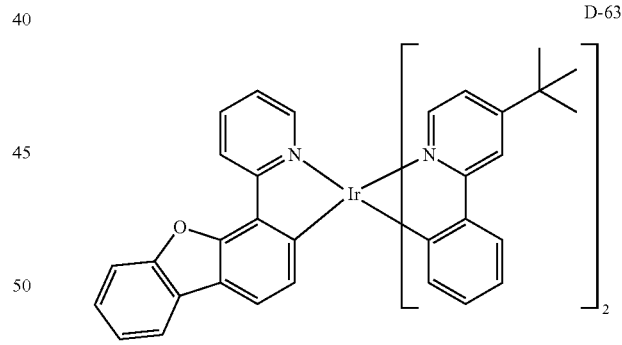
D-64
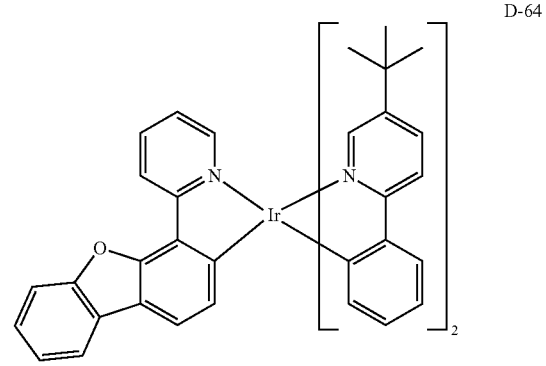

D-65
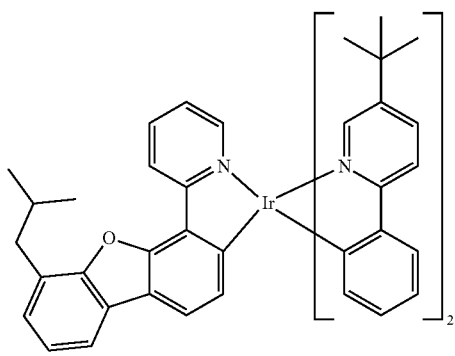
D-66
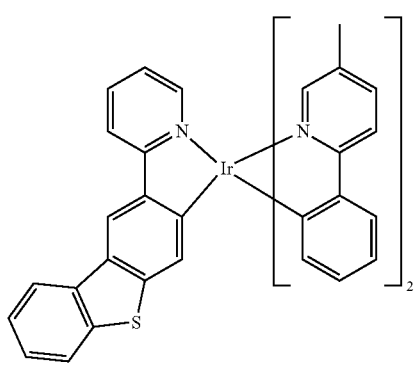
D-67
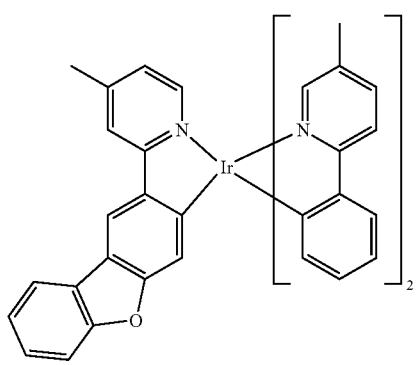
D-68
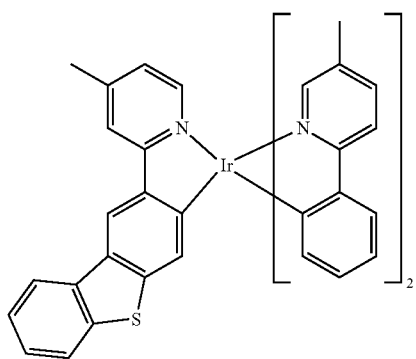
D-69
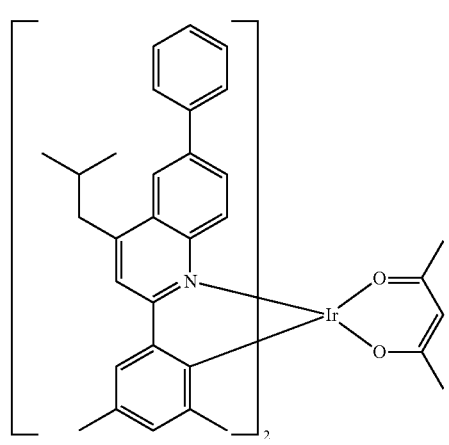
D-70
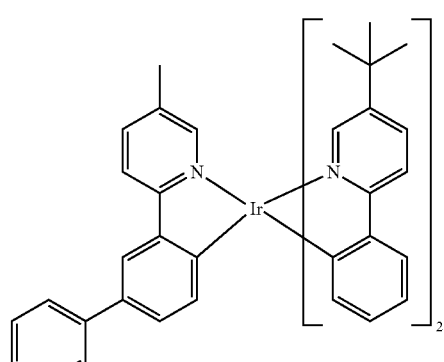
D-71
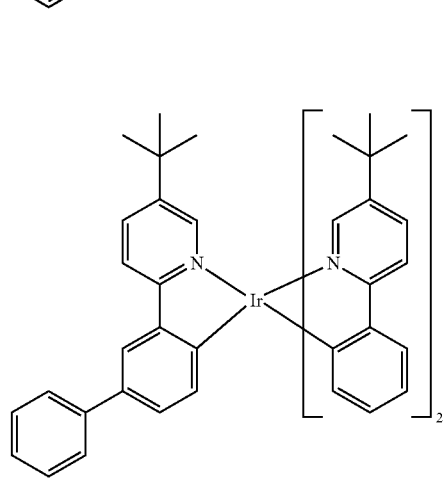
D-72
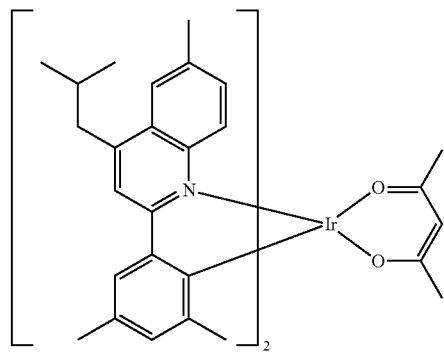

D-73
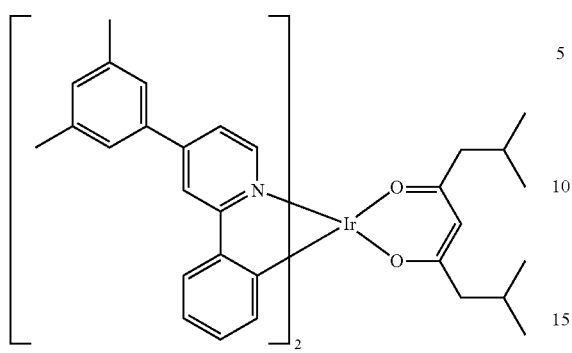
D-77
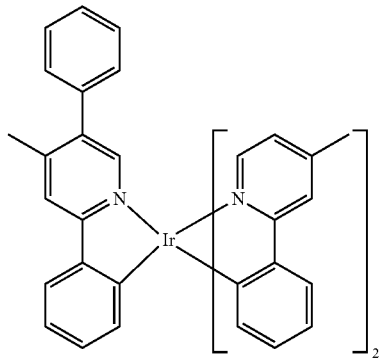
D-74
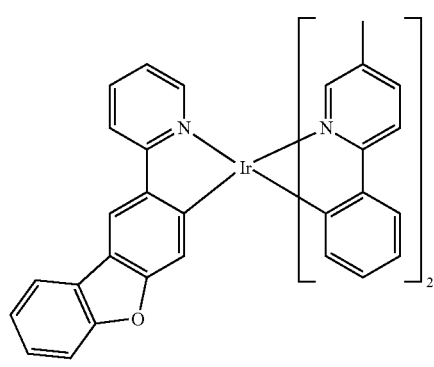
D-78
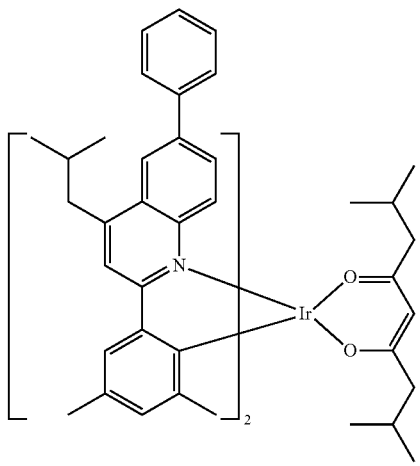
D-75
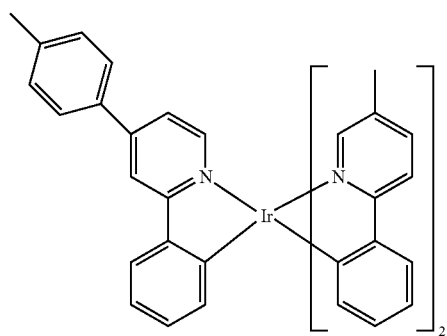
D-79
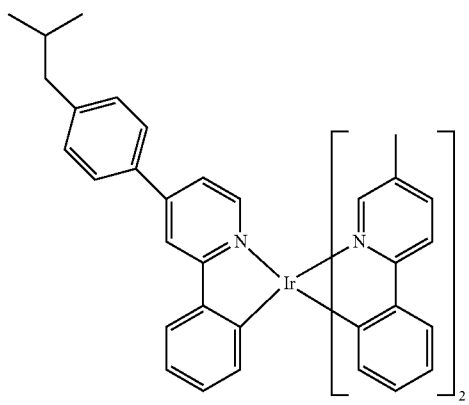
D-76
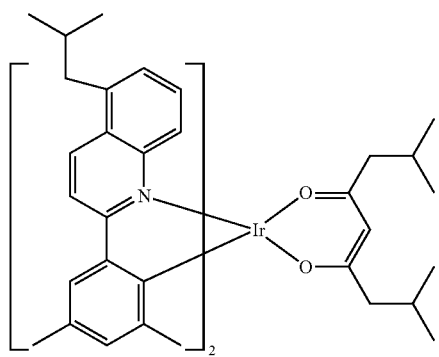
D-80
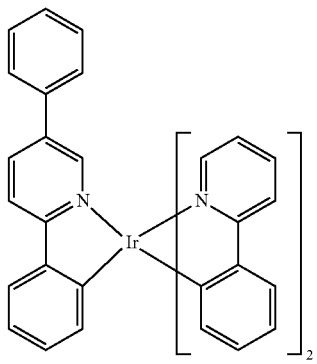

-continued
D-81
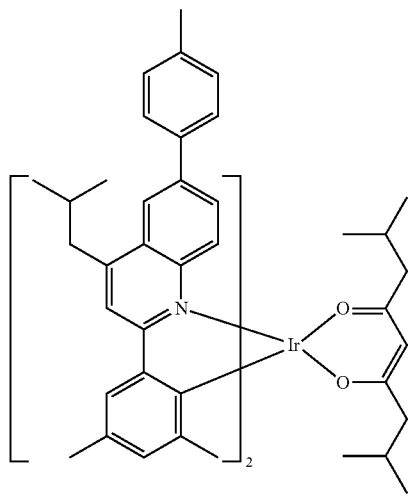
D-82
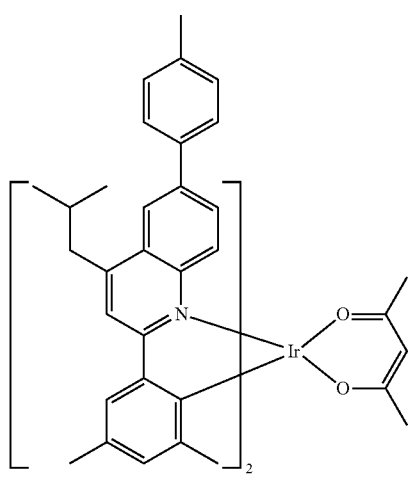
D-83
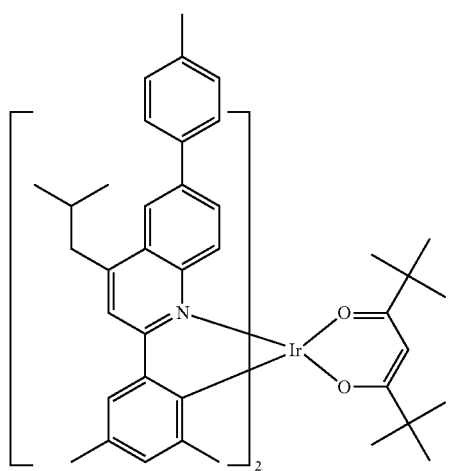
-continued
D-84
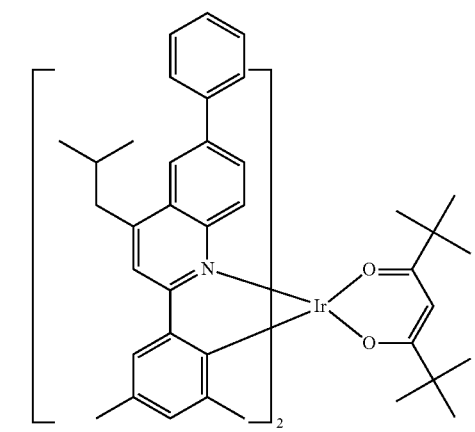
D-85
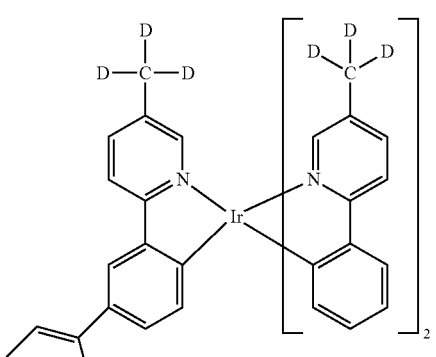
D-86
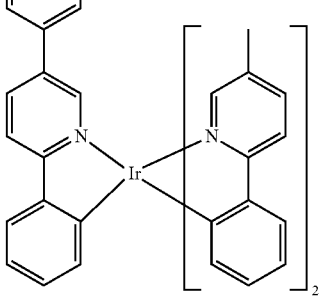
D-87
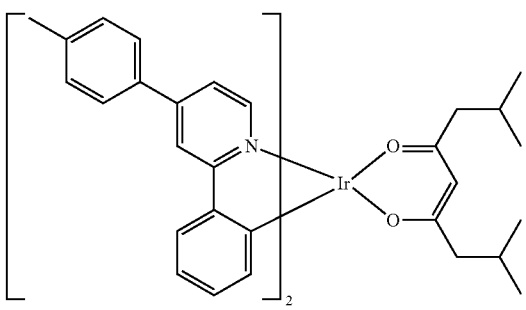

D-88
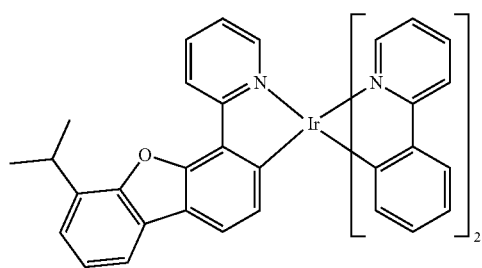
D-89
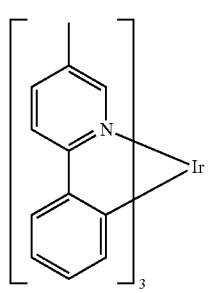
D-90
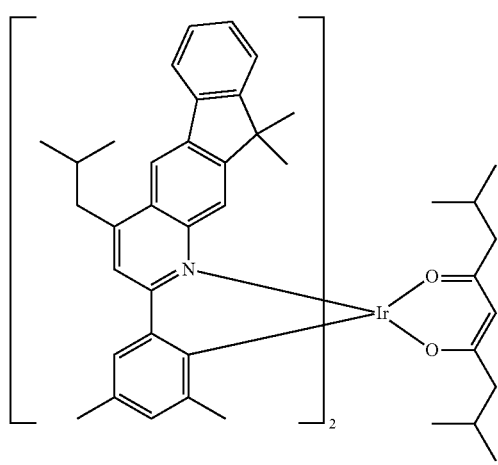
D-91
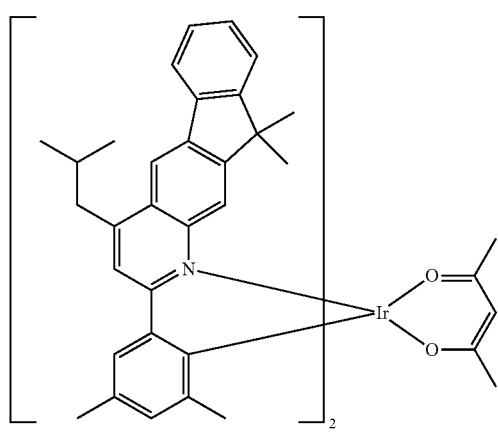
D-92
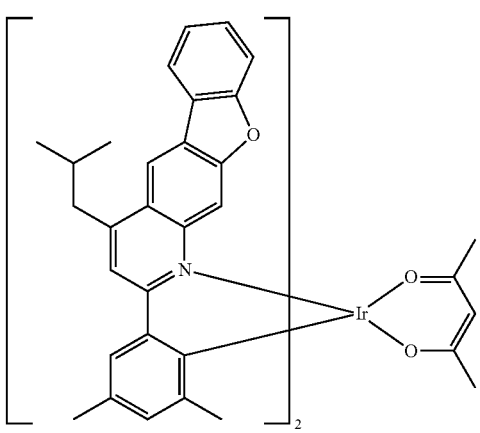
D-93
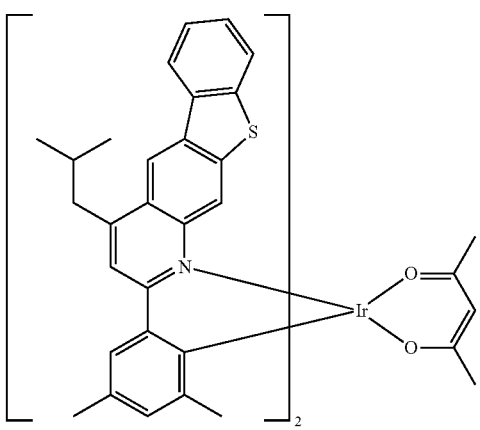
D-94
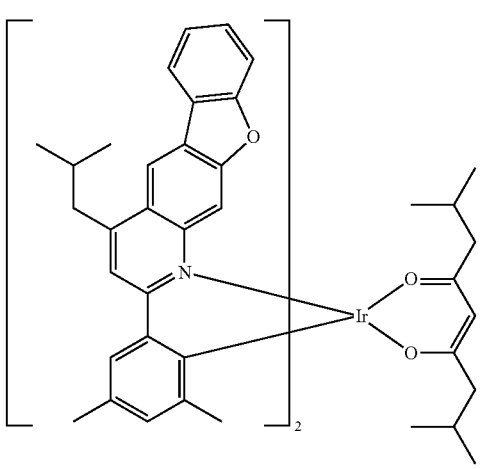

D-95
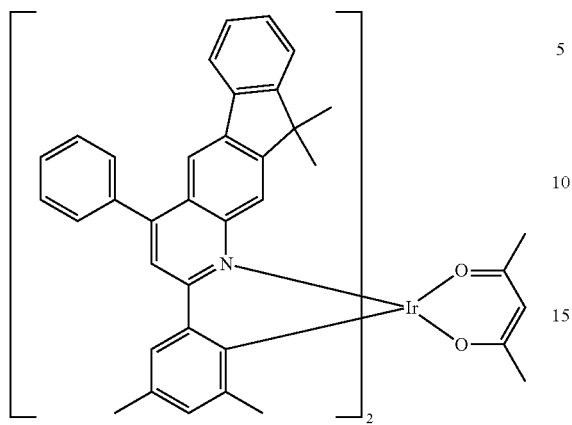
D-99
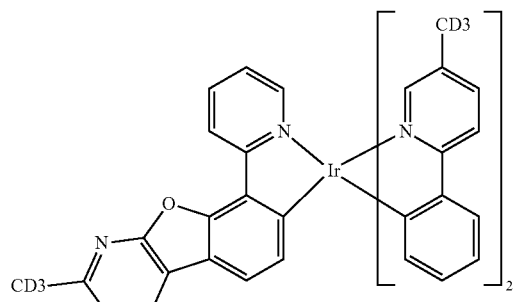
D-96
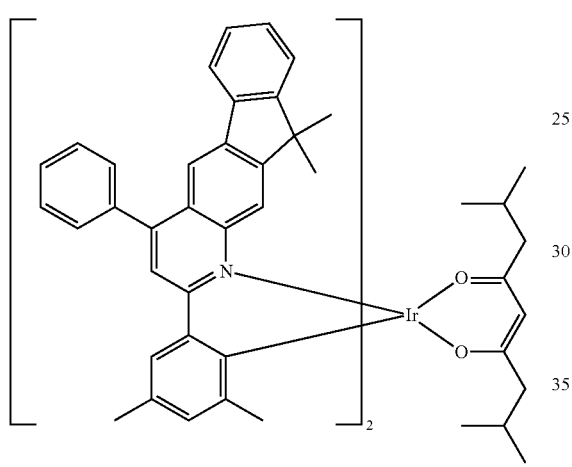
D-100
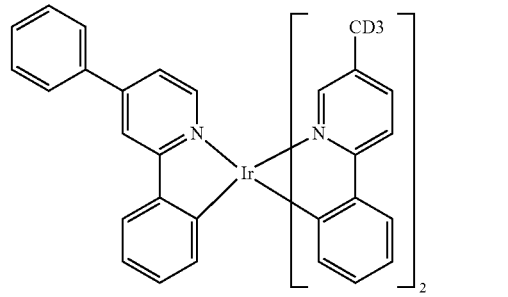
D-97
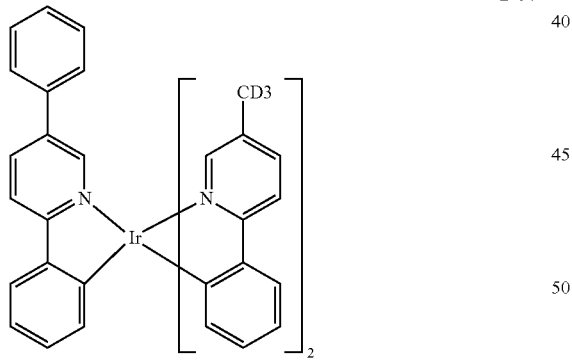
D-101
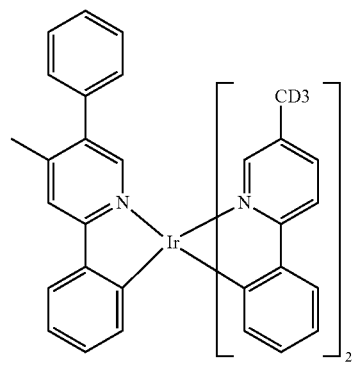
D-98
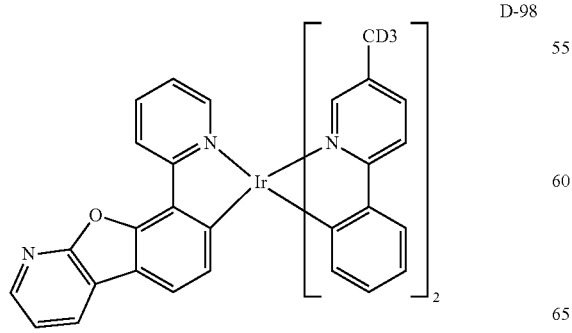
D-102
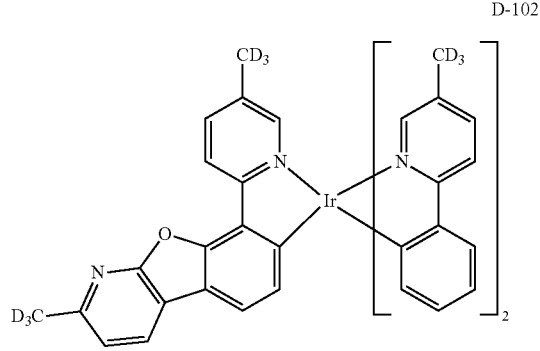

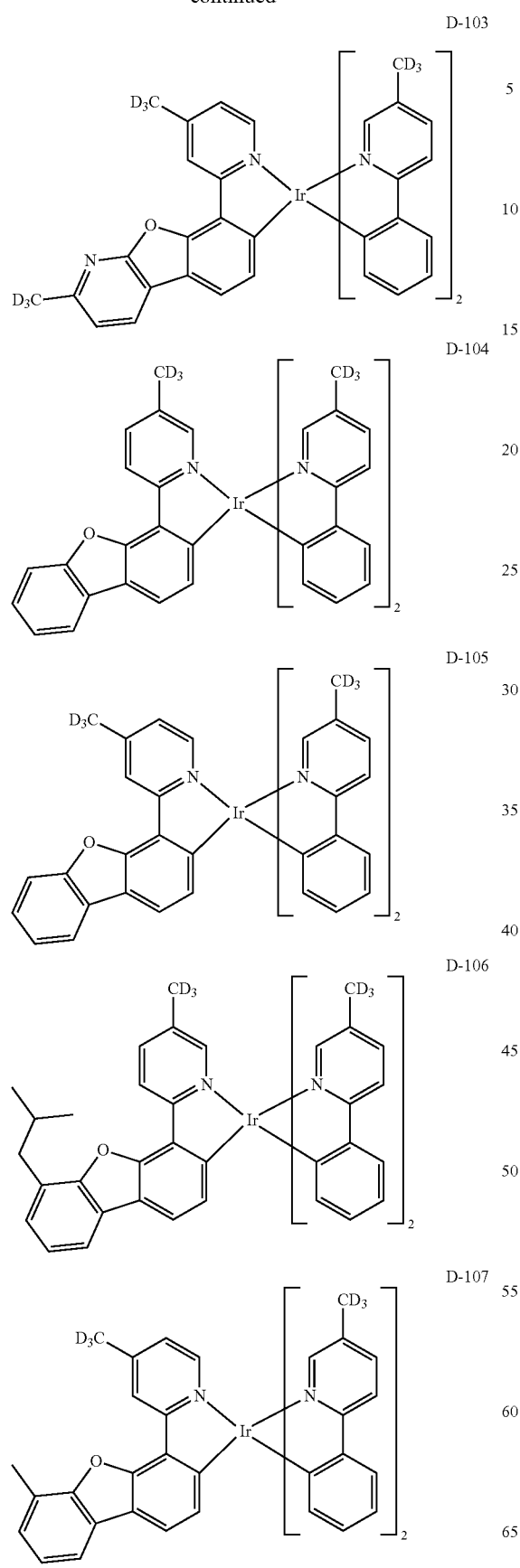
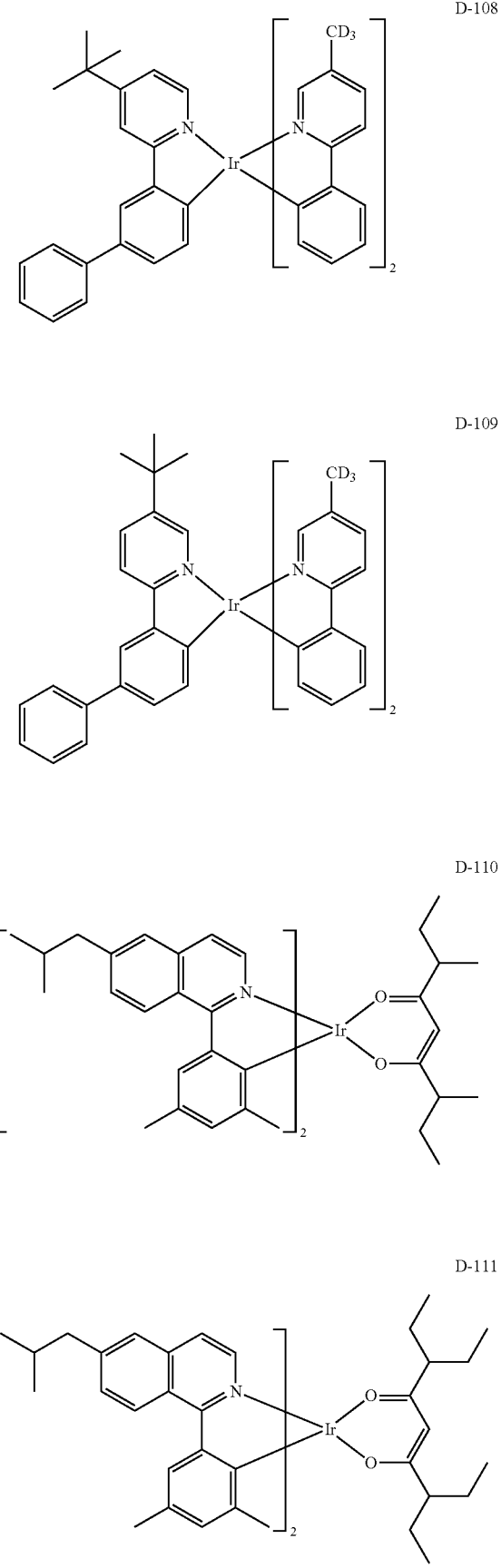

D-112

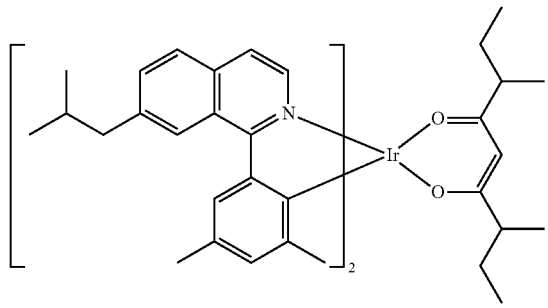

D-113

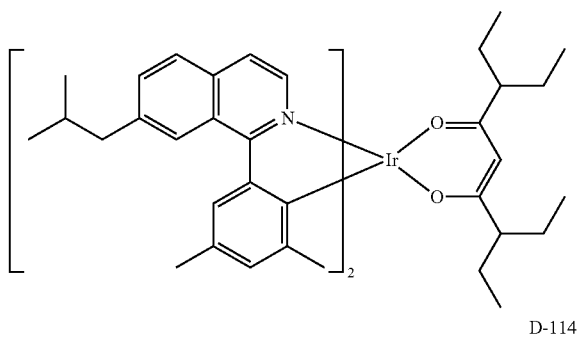

D-114

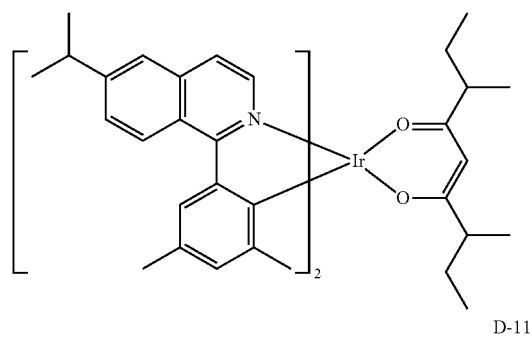

D-115

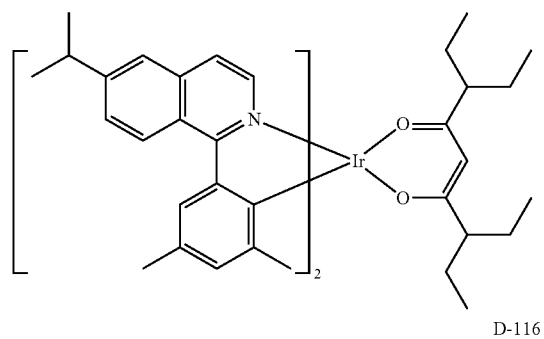

D-116

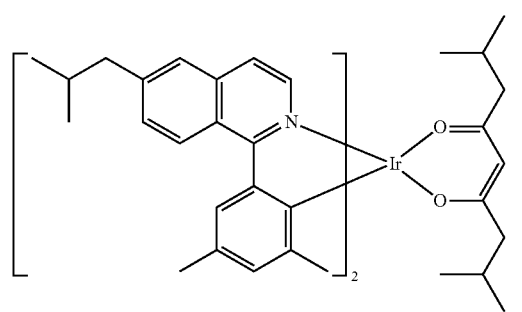

D-117

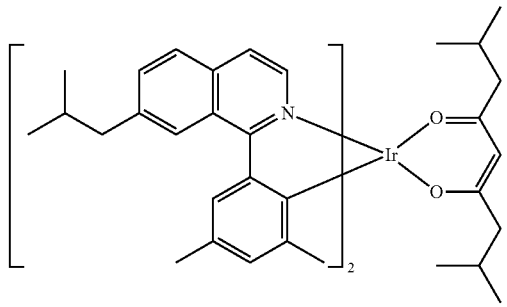

D-118

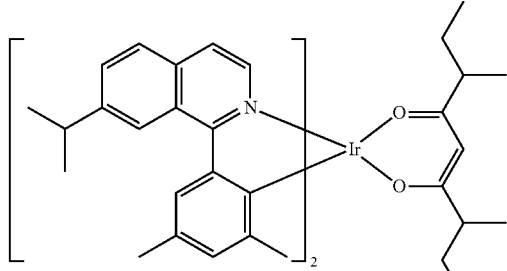

D-119

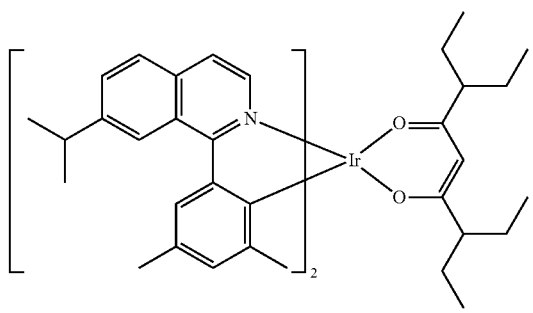

In order to form each layer of the organic electroluminescent device of the present disclosure, dry film-forming methods such as vacuum evaporation, sputtering, plasma and ion plating methods, or wet film-forming methods such as ink jet printing, nozzle printing, slot coating, spin coating, dip coating, and flow coating methods can be used.

When using a solvent in a wet film-forming method, a thin film can be formed by dissolving or diffusing materials forming each layer into any suitable solvent such as ethanol, chloroform, tetrahydrofuran, dioxane, etc. The solvent can be any solvent where the materials forming each layer can be dissolved or diffused, and where there are no problems in film-formation capability.

In addition, the first and the second host compounds of the present disclosure may be film-formed in the above-listed methods, commonly by a co-evaporation process or a mixture-evaporation process. The co-evaporation is a mixed deposition method in which two or more materials are placed in a respective individual crucible source and a current is applied to both cells at the same time to evaporate the materials. The mixture-evaporation is a mixed deposition method in which two or more materials are mixed in one crucible source before evaporating them, and a current is applied to the cell to evaporate the materials. When the first and second host compounds are present in the same layer or another layer in the organic electroluminescent device, the two host compounds can be individually deposited. For example, a first host compound may be deposited, and then a second host compound may be deposited.

The present disclosure may provide a display device by using a plurality of host materials comprising the compound represented by the formula 1 and the compound represented by the formula 2. That is, it is possible to produce a display system or a lighting system by using the plurality of host materials of the present disclosure. Specifically, it is possible to produce a display system, e.g., a display system for smartphones, tablets, notebooks, PCs, TVs, or cars, or a lighting system, e.g., an outdoor or indoor lighting system, by using the plurality of host materials of the present disclosure.

Hereinafter, the preparation method of the compound of the present disclosure, and the properties thereof will be explained in detail with reference to the representative compounds of the present disclosure. However, the present disclosure is not limited to the following examples.

Example 1: Preparation of Compound C-1-127

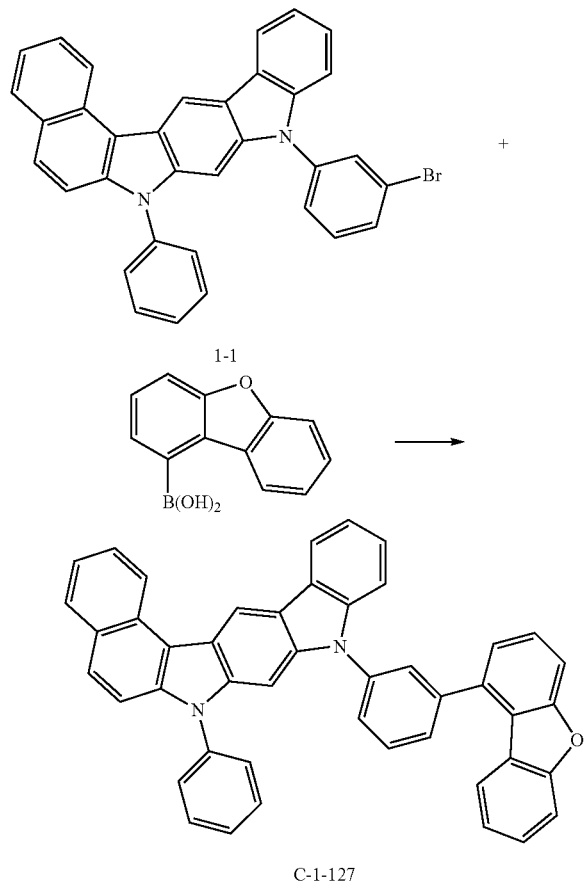

C-1-127

In a flask, 7 g of compound 1-1 (13 mmol), 3 g of dibenzo[b,d]furan-1-yl boronic acid (14.3 mmol), 5.4 g of $K_2CO_3$ (39 mmol), and 0.75 g of $Pd(PPh_3)_4$ (0.65 mmol) were dissolved in 30 mL of $H_2O$, 60 mL of toluene, and 30 mL of EtOH, and the mixture was refluxed at 120° C. for 3 hours. After completion of the reaction, the organic layer was extracted with ethyl acetate (EA), and residual moisture was removed by using magnesium sulfate. The residue was dried and purified by column chromatography to obtain 5.7 g of compound C-1-127 (yield: 70%).

$^1$H NMR (600 MHz, $CDCl_3$, δ) 9.305 (s, 1H), 9.049-9.035 (d, J=8.4 Hz, 1H), 8.379-8.367 (d, J=7.2 Hz, 1H), 8.022-8.008 (d, J=8.4 Hz, 1H) 7.816-7.705 (m, 6H), 7.699-7.392 (m, 16H) 7.195-7.127 (m, 2H)

|  | MW | M.P. |
| --- | --- | --- |
| C-1-127 | 642.73 | 154° C. |

Example 2: Preparation of Compound C-1-128

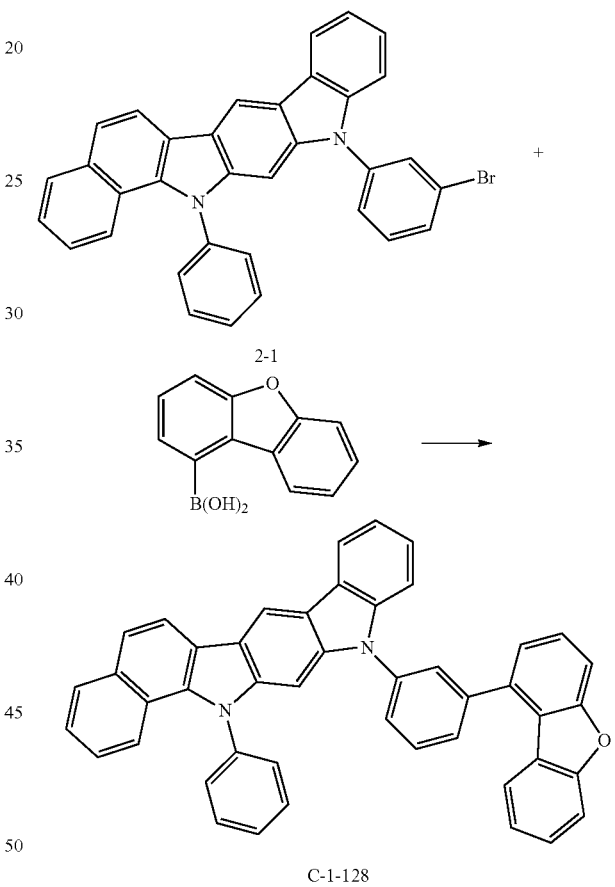

C-1-128

In a flask, 5.7 g of compound 2-1 (10.6 mmol), 2.5 g of dibenzo[b,d]furan-1-yl boronic acid (11.7 mmol), 4.4 g of $K_2CO_3$ (31.8 mmol), and 0.61 g of $Pd(PPh_3)_4$ (0.653 mmol) were dissolved in 30 mL of $H_2O$, 60 mL of toluene, and 30 mL of EtOH, and the mixture was refluxed at 120c for 3 hours. After completion of the reaction, the organic layer was extracted with ethyl acetate (EA), and residual moisture was removed by using magnesium sulfate. The residue was dried and purified by column chromatography to obtain 1.2 g of compound C-1-128 (yield: 18%).

$^1$H NMR (600 MHz, $CDCl_3$, δ) 8.880 (s, 1H), 8.378-8.364 (d, J=8.4 Hz, 1H), 8.297-8.284 (d, J=7.8 Hz, 1H), 8.000-7.987 (d, J=7.8 Hz, 1H), 7.777-7.702 (m, 5H), 7.615-7.332 (m, 15H), 7.189-7.127 (m, 4H)

| | MW | M.P. |
|---|---|---|
| C-1-128 | 624.73 | 239° C. |

Example 3: Preparation of Compound C-1-91

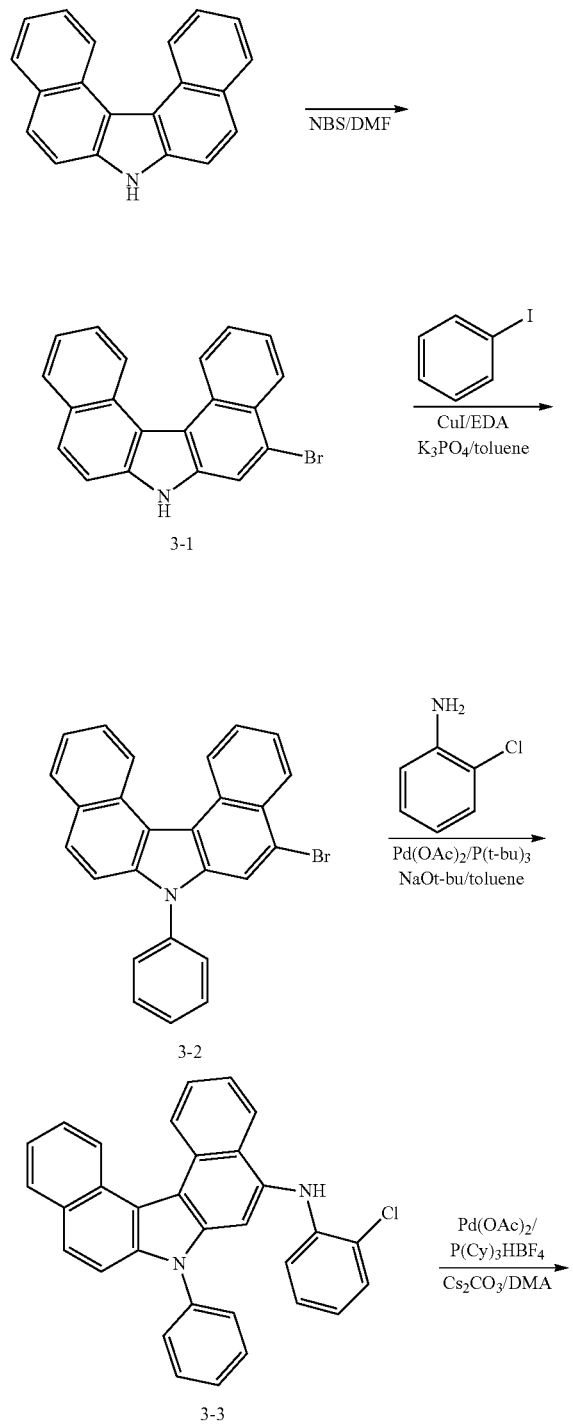

Synthesis of Compound 3-1

In a flask, 60 g of 7H-dibenzo[c,g]carbazole (224 mmol) was dissolved in 900 mL of DMF, and the mixture was cooled and stirred at 0° C. 36 g of NBS (202 mmol) was dissolved in 220 mL of DMF and added dropwise to the cooled mixture for 2.5 hours. The mixture was stirred at room temperature for 2 hours. After completion of the reaction, the reaction product was washed with $Na_2S_2O_3$ aqueous solution and water. The organic layer was extracted with ethyl acetate, and the residual moisture was removed by using $MgSO_4$. The residue was dried and purified by silica filter to obtain 79 g of compound 3-1 (yield: 79%).

Synthesis of Compound 3-2

76 g of compound 3-1 (220 mmol), 90 g of iodobenzene (439 mmol), 20.90 g of CuI (110 mmol), 13 g of ethylenediamine (110 mmol), and 139 g of $K_3PO_4$ (659 mmol) was added to 1.1 L of toluene, and the mixture was stirred under reflux for 2.5 hours. After adding MeOH, the resultant solid was filtered under reduced pressure. Thereafter, the residue was purified by column chromatography to obtain 55.1 g of compound 3-2 (yield: 60%).

Synthesis of Compound 3-3

54.6 g of compound 3-2 (129 mmol), 20 g of 2-chloroaniline (155 mmol), 2.9 g of $Pd(OAc)_2$ (13 mmol), 5.2 g of $P(t-Bu)_3$ (26 mmol), and 31 g of NaOt-Bu (323 mmol) were added to 650 mL of toluene, and the mixture was stirred under reflux for 4 hours. The reaction mixture was cooled to room temperature, and $NH_4Cl(aq)$ was added. The reaction mixture was extracted with EA, and then dried with magnesium sulfate. The extracted organic layer was distilled under reduced pressure, and then purified by column chromatography to obtain 47.9 g of compound 3-3 (yield: 79%).

Synthesis of Compound 3-4

48 g of compound 3-3 (103 mmol), 2.3 g of $Pd(OAc)_2$ (10 mmol), 7.6 g of ligand (tricyclohexylphosphonium tetrafluoroborate) (21 mmol), and 100 g of $Cs_2CO_3$ (308 mmol) were added to 400 mL of DMA, and the mixture was stirred under reflux for 1 hour. The reaction mixture was cooled to room temperature, and NH₄Cl(aq) was added. The reaction mixture was extracted with methylene chloride (MC), and then dried with magnesium sulfate. The extracted organic layer was distilled under reduced pressure, and then purified by column chromatography to obtain 44 g of compound 3-4 (yield: 79%).

Synthesis of Compound C-1-91

5 g of compound 3-4 (12 mmol), 3.5 g of iodobenzene (17 mmol), 1.1 g of CuI (6 mmol), 2.6 g of 1,2-diaminocyclohexane (23 mmol), and 4.9 g of K₃PO₄ (23 mmol) were added to 60 mL of o-xylene, and the mixture was stirred under reflux for one day. The reaction mixture was cooled to room temperature, and filtered through celite with MC. The filtrate was distilled under reduced pressure, and then purified by column chromatography with MC/Hex to obtain 1.3 g of compound C-1-91 (yield: 22%).

¹H NMR (600 MHz, DMSO, δ) 9.16-9.15 (d, 1H), 8.99-8.98 (d, 1H), 8.14-8.13 (d, 1H), 7.94-7.93 (d, 1H), 7.94-7.68 (m, 9H), 7.65-7.61 (m, 3H), 7.60-7.54 (m, 3H), 7.25-7.21 (m, 2H), 7.08-7.07 (d, 1H), 6.78-6.76 (m, 1H), 5.95-5.94 (1H)

|  | MW | UV | PL | M.P. |
|---|---|---|---|---|
| C-1-91 | 508.62 | 342 nm | 427 nm | 184° C. |

Example 4: Preparation of Compound C-1-108

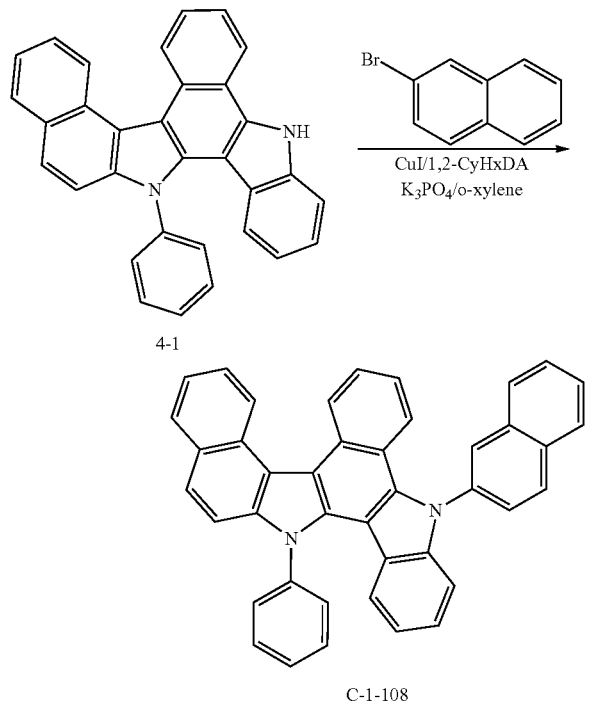

7 g of compound 4-1 (16 mmol), 6.7 g of 2-bromonaphthalene (32 mmol), 1.5 g of CuI (8 mmol), 3.7 g of 1,2-diaminocyclohexane (32 mmol), and 10.3 g of K₃PO₄ (49 mmol) were added to 80 mL of o-xylene, and the mixture was stirred under reflux for one day. The reaction mixture was cooled to room temperature, and filtered through celite with MC. The filtrate was distilled under reduced pressure, and then purified by column chromatography with MC/Hex to obtain 1.3 g of compound C-1-108 (yield: 22%).

¹H NMR (600 MHz, DMSO, δ) 9.17-9.15 (d, 1H), 9.00-8.99 (d, 1H), 8.31-8.30 (m, 2H), 8.20-8.18 (d, 1H), 8.15-8.14 (d, 1H), 8.11-8.10 (d, 1H), 7.95-7.94 (d, 1H), 7.83-7.79 (m, 5H), 7.73-7.69 (m, 4H), 7.60-7.57 (m, 4H), 7.21-7.18 (m, 2H), 7.14-7.13 (d, 1H), 6.78-6.77 (t, 1H) 5.98-5.96 (d, 1H)

|  | MW | UV | PL | M.P. |
|---|---|---|---|---|
| C-1-108 | 558.68 | 340 nm | 431 nm | 263° C. |

Example 5: Preparation of Compound C-1-92

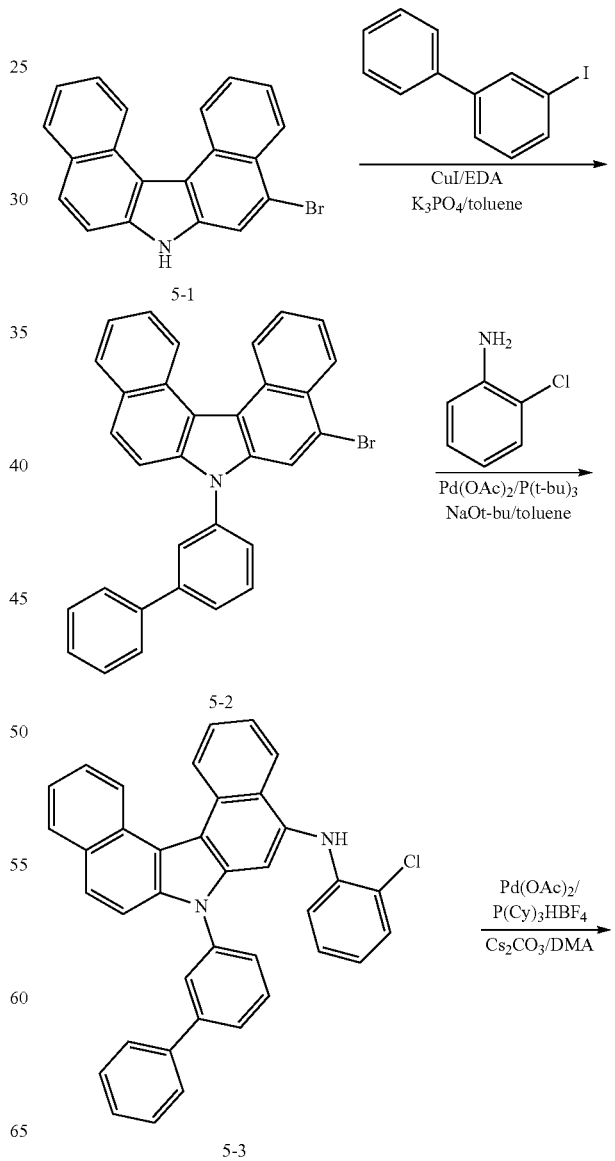

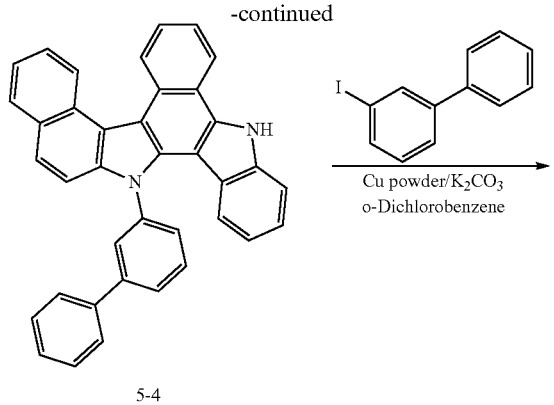

5-4

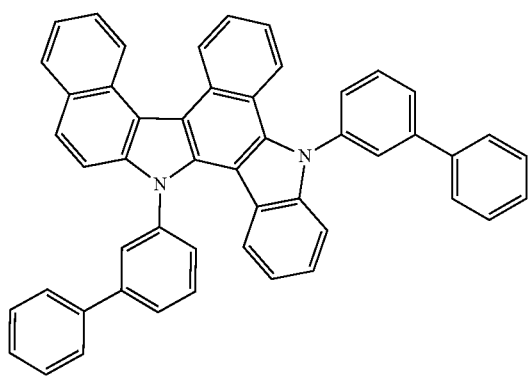

C-1-92

Synthesis of Compound 5-2

15 g of compound 5-1 (220 mmol), 18 g of 3-iodo-1,1'-biphenyl (65 mmol), 4.1 g of CuI (22 mmol), 2.6 g of ethylenediamine (43 mmol), and 23 g of $K_3PO_4$ (108 mmol) were added to 216 mL of toluene, and the mixture was stirred under reflux for 4 hours. After adding MeOH, the resultant solid was filtered under reduced pressure. Thereafter, the residue was purified by column chromatography to obtain 16 g of compound 5-2 (yield: 74%).

Synthesis of Compound 5-3

15 g of compound 5-2 (30 mmol), 7.7 g of 2-chloroaniline (60 mmol), 0.67 g of $Pd(OAc)_2$ (3 mmol), 1.2 g of $P(t-Bu)_3$ (6 mmol), and 7.2 g of NaOt-Bu (75 mmol) were added to 150 mL of toluene, and the mixture was stirred under reflux for 2 hours. The reaction mixture was cooled to room temperature, and $NH_4Cl(aq)$ was added. The reaction mixture was extracted with EA, and then dried with magnesium sulfate. The extracted organic layer was distilled under reduced pressure, and then purified by column chromatography to obtain 10.1 g of compound 5-3 (yield: 62%).

Synthesis of Compound 5-4

10 g of compound 5-3 (18 mmol), 0.41 g of $Pd(OAc)_2$ (1.8 mmol), 1.35 g of ligand (tricyclohexylphosphonium tetrafluoroborate) (3.7 mmol), and 18 g of $Cs_2CO_3$ (55 mmol) were added to 92 mL of DMA, and the mixture was stirred under reflux for 1 hour. The reaction mixture was cooled to room temperature, and $NH_4Cl(aq)$ was added. The reaction mixture was extracted with methylene chloride (MC), and then dried with magnesium sulfate. The extracted organic layer was distilled under reduced pressure, and then purified by column chromatography to obtain 7.1 g of compound 5-4 (yield: 76%).

Synthesis of Compound C-1-92

6.7 g of compound 5-4 (13 mmol), 7.4 g of 3-iodo-1,1'-biphenyl (26 mmol), 0.42 g of Cu powder (7 mmol), and 3.6 g of $K_2CO_3$ (26 mmol) were placed in 70 mL of o-dichlorobenzene, and the mixture was stirred under reflux for one day. The reaction mixture was cooled to room temperature, and filtered through celite with MC. The filtrate was distilled under reduced pressure, and then purified by column chromatography with MC/Hex to obtain 3.1 g of compound C-1-92 (yield: 36%).

$^1$H NMR (600 MHz, DMSO, δ) 9.18-9.17 (d, 1H), 9.01-9.00 (d, 1H), 8.16-8.15 (d, 1H), 8.11-8.09 (d, 1H), 8.06-8.05 (m, 2H), 8.00-7.79 (m, 7H), 7.73-7.57 (m, 8H), 7.48-7.38 (m, 6H), 7.30-7.28 (t, 1H), 7.22-7.18 (m, 2H), 6.80-6.78 (t, 1H), 6.07-6.06 (d, 1H)

|  | MW | M.P. |
| --- | --- | --- |
| C-1-92 | 660.82 | 259° C. |

Example 6: Preparation of Compound C-1-130

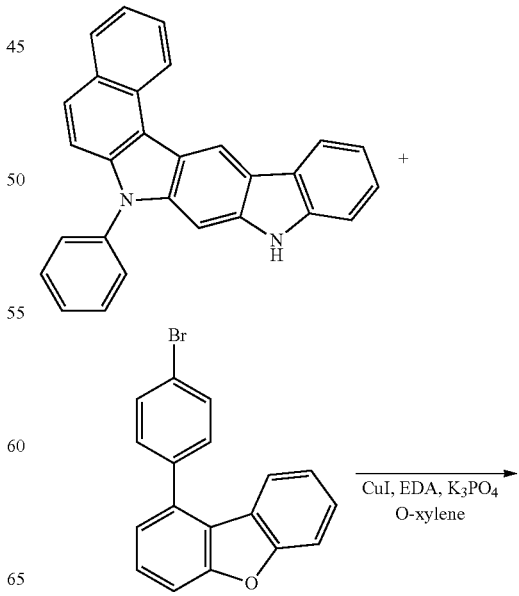

-continued

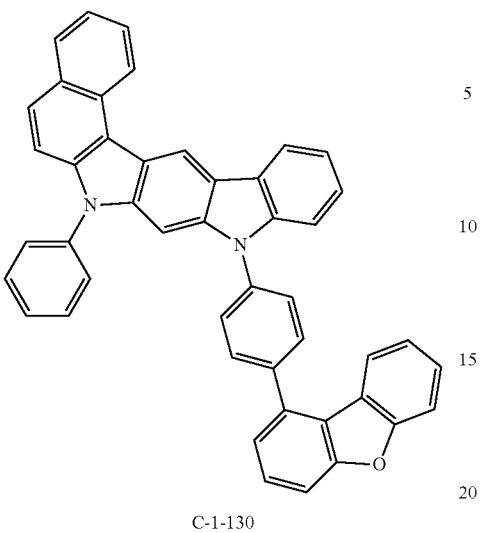

C-1-130

3.6 g of 7-phenyl-7,9-dihydrobenzo[g]indolo[2,3-b]carbazole (9.285 mmol), 3 g of 1-(4-bromophenyl)dibenzo[b,d]furan (9.285 mmol), 0.08 g of CuI (0.464 mmol), 0.5 g of EDA (9.285 mmol), and 4.9 g of $K_3PO_4$ (23.21 mmol) were added to 50 mL of o-xylene, and the mixture was stirred for one day. After completion of the reaction, the reaction mixture was cooled to room temperature and extracted with distilled water and MeOH. Thereafter, the extracted organic layer was purified by column chromatography with MC/Hex to obtain 2.7 g of compound C-1-130 (yield: 47%).

$^1$H NMR (DMSO-$d_6$) δ: 9.69 (s, 1H), 9.26 (d, J=8.3 Hz, 1H), 8.69 (dd, J=7.7, 1.2 Hz, 1H), 8.14 (dd, J=8.0, 1.1 Hz, 1H), 7.97 (d, J=8.8 Hz, 1H), 7.92 (s, 4H), 7.88 (ddd, J=8.2, 6.9, 1.3 Hz, 1H), 7.82-7.76 (m, 4H), 7.73 (t, J=7.8 Hz, 2H), 7.70-7.48 (m, 8H), 7.48-7.44 (m, 2H), 7.42 (td, J=7.3, 1.0 Hz, 1H), 7.26-7.20 (m, 1H)

|  | MW | M.P. |
|---|---|---|
| C-1-130 | 624.7 | 309.7° C. |

Example 7: Preparation of Compound C-1-132

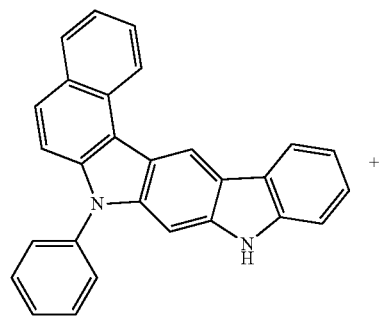

+

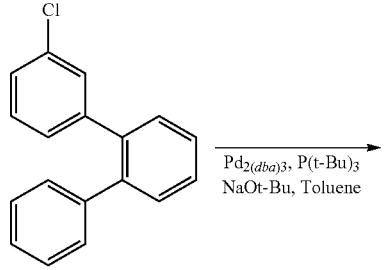

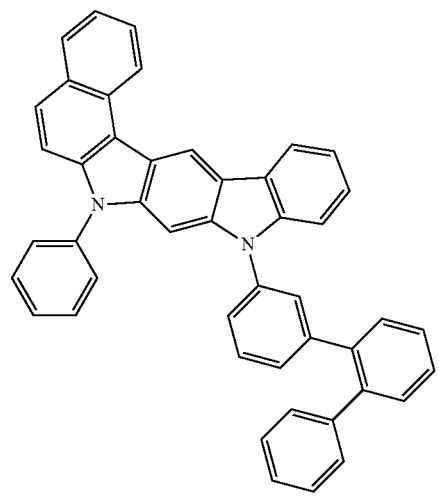

C-1-132

7.6 g of 7-phenyl-7,9-dihydrobenzo[g]indolo[2,3-b]carbazole (18.88 mmol), 5 g of 3-chloro-1,1':2',1''-terphenyl (18.88 mmol), 0.86 g of $Pd_2(dba)_3$ (0.940 mmol), 4.5 g of NaOt-Bu (47.22 mmol), and 0.38 g of $P(t-Bu)_3$ (1.888 mmol) were added to 100 mL of toluene, and the mixture was stirred for one day. After completion of the reaction, the reaction mixture was cooled to room temperature and extracted with distilled water and MeOH. Thereafter, the extracted organic layer was purified by column chromatography with MC/Hex to obtain 0.7 g of compound C-1-132 (yield: 6.2%).

$^1$H NMR (DMSO-$d_6$) δ: 9.58 (s, 1H), 9.20 (d, J=8.4 Hz, 1H), 8.57 (d, J=7.8 Hz, 1H), 8.11 (d, J=8.3 Hz, 1H), 7.94 (d, J=8.9 Hz, 1H), 7.84 (ddd, J=8.3, 6.8, 1.3 Hz, 1H), 7.72 (d, J=6.2 Hz, 4H), 7.64-7.47 (m, 8H), 7.44 (dt, J=6.0, 1.9 Hz, 1H), 7.40-7.17 (m, 10H), 6.50 (d, J=7.9 Hz, 1H)

|  | MW | M.P. |
|---|---|---|
| C-1-132 | 610.7 | 194.6° C. |

Example 8: Preparation of Compound C-1-133

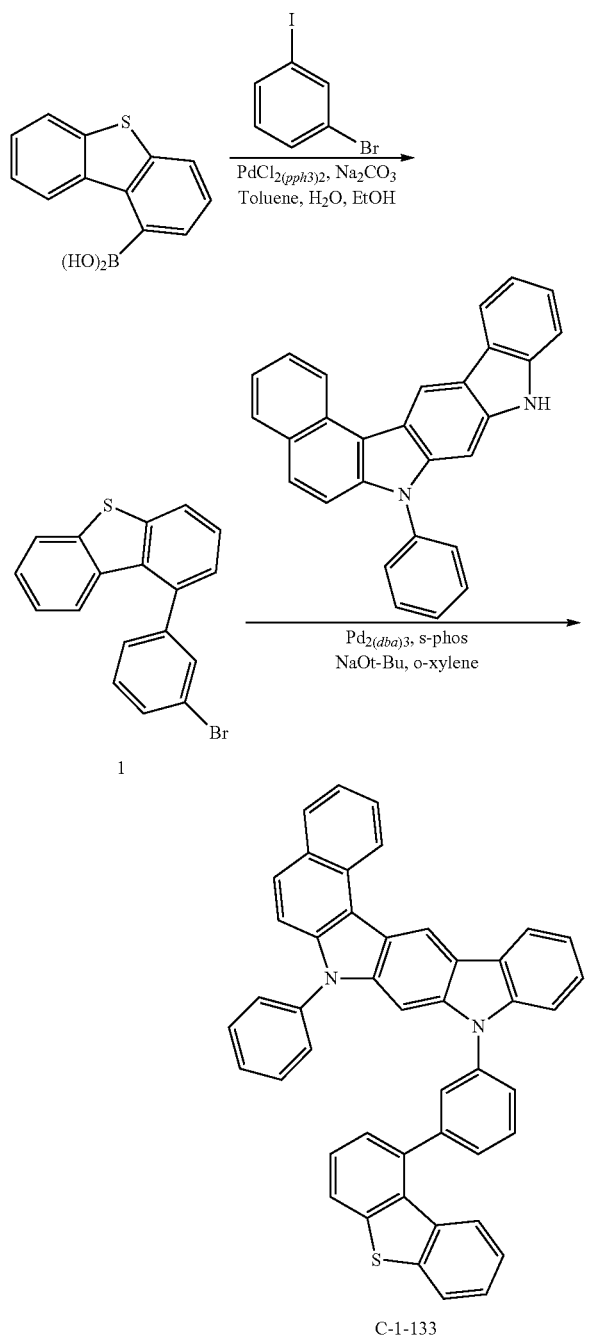

Synthesis of Compound C-1-133

4.4 g of compound 1 (13.07 mmol), 5 g of 7-phenyl-7,9-dihydrobenzo[g]indolo[2,3-b]carbazole (13.07 mmol), 0.6 g of Pd$_2$(dba)$_3$ (0.653 mmol), 0.5 g of s-phos (1.307 mmol), and 3.7 g of NaOt-Bu (39.21 mmol) were added to 70 mL of xylene, and the mixture was stirred under reflux for 2 hours. After completion of the reaction, the reaction mixture was cooled to room temperature and extracted with MeOH. Thereafter, the extracted organic layer was purified by column chromatography with MC/Hex to obtain 5.1 g of compound C-1-133 (yield: 60%).

$^1$H NMR (DMSO-d$_6$) δ: 9.63 (s, 1H), 9.22 (d, J=8.4 Hz, 1H), 8.64 (dd, J=7.5, 1.2 Hz, 1H), 8.14-8.09 (m, 2H), 8.07 (dt, J=8.1, 0.9 Hz, 1H), 7.94 (d, J=8.9 Hz, 1H), 7.91-7.82 (m, 3H), 7.72 (d, J=2.0 Hz, 1H), 7.67 (d, J=7.6 Hz, 2H), 7.63-7.48 (m, 8H), 7.48-7.41 (m, 2H), 7.40 (d, J=6.1 Hz, 1H), 7.36 (td, J=7.4, 1.0 Hz, 1H), 7.33 (d, J=7.3 Hz, 1H), 7.09 (d, J=49.0 Hz, 2H)

|        | MW    | M.P.     |
|--------|-------|----------|
| C-1-133 | 640.7 | 226.7° C. |

Example 9: Preparation of Compound C-1-131

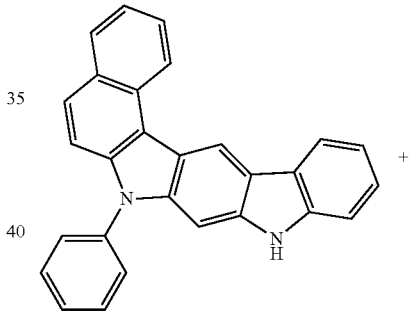

Synthesis of Compound 1

20 g of dibenzo[b,d]thiophene-1-yl boronic acid (87.71 mmol), 50 g of 1-bromo-3-iodobenzene (175.4 mmol), 5 g of Pd(PPh$_3$)$_4$ (4.385 mmol), and 18 g of Na$_2$CO$_3$ (175.4 mmol) were added to 360 mL of toluene, 90 mL of demineralized water, and 90 mL of EtOH, and the mixture was stirred under reflux for 3 hours. After completion of the reaction, the reaction mixture was cooled to room temperature and extracted with distilled water and EA. Thereafter, the extracted organic layer was distilled under reduced pressure, and then purified by column chromatography with MC/Hex to obtain 20 g of compound 1 (yield: 67%).

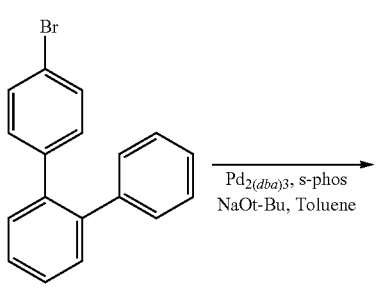

-continued

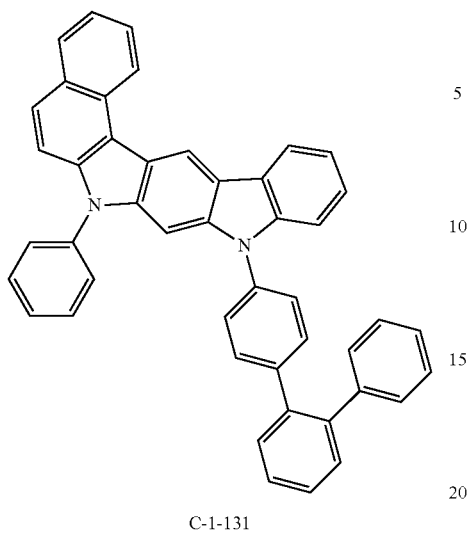

C-1-131

5 g of 7-phenyl-7,9-dihydrobenzo[g]indolo[2,3-b]carbazole (13.07 mmol), 4 g of 4-bromo-1,1':2',1''-terphenyl (13.07 mmol), 0.6 g of $Pd_2(dba)_3$ (0.653 mmol), 3.8 g of NaOt-Bu (39.21 mmol), and 0.5 g of s-phos (1.307 mmol) were added to 70 mL of xylene, and the mixture was stirred for one day. After completion of the reaction, the reaction mixture was cooled to room temperature and extracted with distilled water and MeOH. Thereafter, the extracted organic layer was purified by column chromatography with MC/Hex to obtain 6.3 g of compound C-1-131 (yield: 78%).

$^1$H NMR (DMSO-$d_6$) δ: 9.63 (s, 1H), 9.23 (d, J=8.3 Hz, 1H), 8.63 (dd, J=7.7, 1.1 Hz, 1H), 8.12 (d, J=8.2 Hz, 1H), 7.95 (d, J=8.9 Hz, 1H), 7.85 (ddd, J=8.2, 6.8, 1.4 Hz, 1H), 7.79-7.73 (m, 2H), 7.72-7.66 (m, 3H), 7.60-7.47 (m, 8H), 7.44 (ddd, J=8.2, 7.1, 1.3 Hz, 1H), 7.38-7.33 (m, 3H), 7.32-7.24 (m, 2H), 7.22-7.14 (m, 5H)

|  | MW | M.P. |
|---|---|---|
| C-1-131 | 610.7 | 288° C. |

Example 10: Preparation of Compound C-1-134

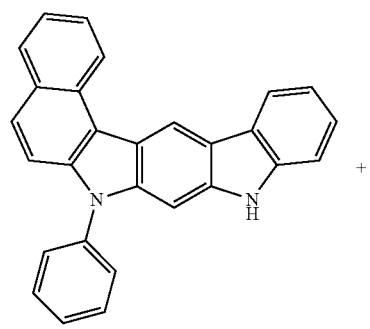

+

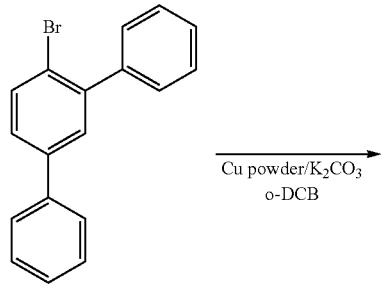

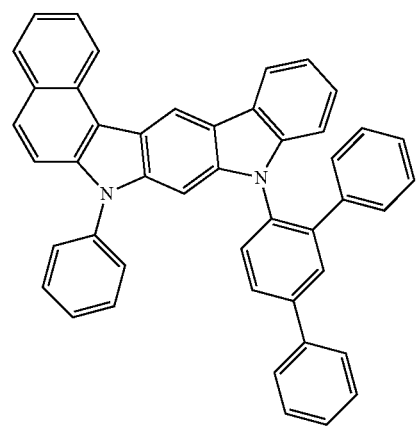

C-1-134

In a flask, 5.0 g of 7-phenyl-7,9-dihydrobenzo[g]indolo[2,3-b]carbazole (13 mmol), 6.06 g of 4'-bromo-1,1':3',1''-terphenyl (20 mmol), 1.307 g of Cu powder (0.65 mmol), and 3.4 g of $K_2CO_3$ (26 mmol) were dissolved in 60 mL of o-DCB, and the mixture was stirred under reflux at 230° C. for 12 hours. After completion of the reaction, the reaction product was extracted with EA, and then dried with $MgSO_4$. The residue was separated by column chromatography, and MeOH was added. The resultant solid was filtered under reduced pressure to obtain 1.3 g of compound C-1-134 (yield: 16.3%).

$^1$H NMR (600 MHz, DMSO-d6, δ) 9.51 (s, 1H), 9.16 (d, J=8.3 Hz, 1H), 8.57 (d, J=7.8 Hz, 1H), 8.10 (d, J=8.0 Hz, 1H), 7.98-7.85 (m, 6H), 7.83 (t, J=7.6 Hz, 1H), 7.76 (s, 1H), 7.70 (d, J=8.1 Hz, 1H), 7.61-7.51 (m, 5H), 7.51-7.42 (m, 3H), 7.38 (t, J=7.8 Hz, 1H), 7.31 (t, J=7.3 Hz, 1H), 7.25 (d, J=8.0 Hz, 1H), 7.13-7.06 (m, 4H), 7.03 (d, J=6.8 Hz, 1H), 6.79 (s, 1H)

|  | MW | M.P. |
|---|---|---|
| C-1-134 | 610.74 | 296° C. |

Example 11: Preparation of Compound C-2-14

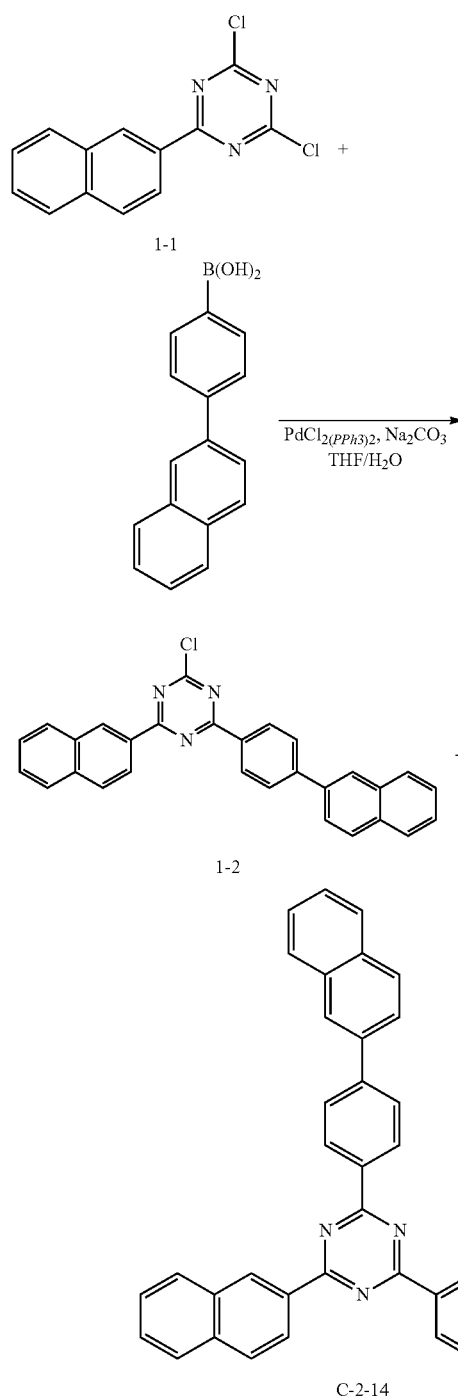

Synthesis of Compound 1-2

In a flask, 15 g of compound 1-1 (54.3 mmol), 10.3 g of (4-(naphthalene-2-yl)phenyl)boronic acid (41.8 mmol), 8.8 g of Na$_2$CO$_3$ (83.8 mmol), and 0.88 g of Pd(PPh$_3$)$_4$ (1.25 mmol) were dissolved in 70 mL of H$_2$O and 210 mL of THF, and the mixture was refluxed at 70'C for 3 hours. After completion of the reaction, the organic layer was extracted with EA, and the residual moisture was removed by using magnesium sulfate. The residue was dried and purified by column chromatography to obtain 10 g of compound 1-2 (yield: 53.9%).

Synthesis of Compound C-2-14

In a flask, 5 g of compound 1-2 (11.3 mmol), 2.3 g of (naphthalene-2-yl) boronic acid (13.5 mmol), 2.4 g of Na$_2$CO$_3$ (22.6 mmol), and 0.24 g of Pd(PPh$_3$)$_4$ (0.335 mmol) were dissolved in 60 mL of toluene, 30 mL of EtOH and 30 mL of H$_2$O, and the mixture was refluxed at 130'C for 3 hours. After completion of the reaction, the organic layer was extracted with EA, and the residual moisture was removed by using magnesium sulfate. The residue was dried and purified by column chromatography to obtain 3.4 g of compound C-2-14 (yield: 56.2%).

$^1$H NMR (600 MHz, CDCl$_3$, δ) 9.305 (s, 1H), 9.049-9.035 (d, J=8.4 Hz, 1H), 8.379-8.367 (d, J=7.2 Hz, 1H), 8.022-8.008 (d, J=8.4 Hz, 1H) 7.816-7.705 (m, 6H), 7.699-7.392 (m, 16H) 7.195-7.127 (m, 2H)

|        | MW     | M.P.      |
|--------|--------|-----------|
| C-2-14 | 535.65 | 248.6° C. |

Example 12: Preparation of Compound C-2-50

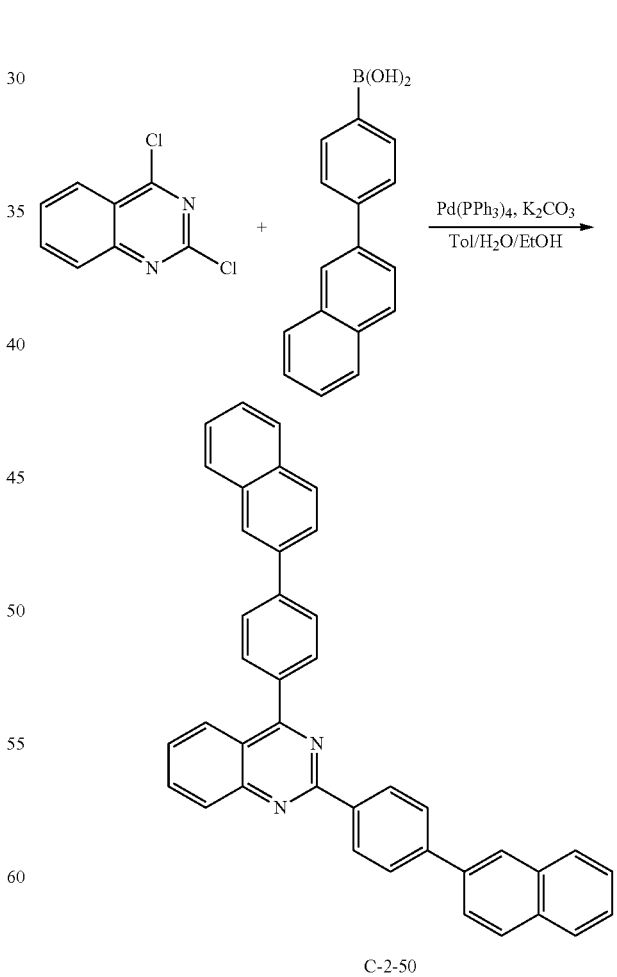

In a flask, 5 g of 2,4-dichloro quinazoline (25.1 mmol), 13.7 g of (4-(naphthalene-2-yl)phenyl) boronic acid (55.3 mmol), 17 g of K₂CO₃ (125.5 mmol), and 2.9 g of Pd(PPh₃)₄ (2.51 mmol) were dissolved in 130 mL of toluene, 65 mL of EtOH and 65 mL of H₂O, and the mixture was refluxed at 70° C. for 3 hours. After completion of the reaction, the organic layer was extracted with EA, and the residual moisture was removed by using magnesium sulfate. The residue was dried and purified by column chromatography to obtain 3.5 g of compound C-2-50 (yield: 26%).

|  | MW | M.P. |
|---|---|---|
| C-2-50 | 534.65 | 290.3° C. |

Example 13: Preparation of Compound C-2-95

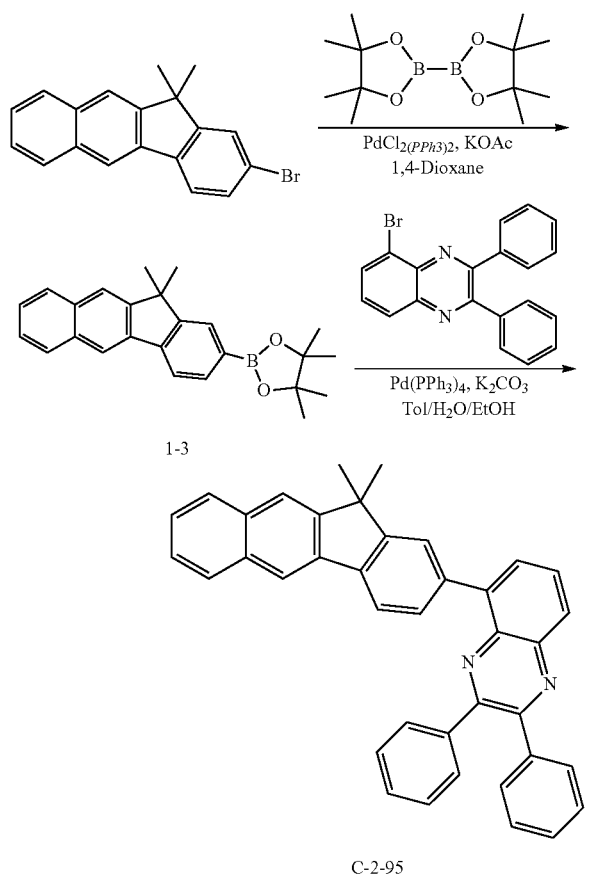

Synthesis of Compound 1-3

In a flask, 10 g of 2-bromo-11,11-dimethyl-11H-benzo[b]fluorene (30.9 mmol), 11.8 g of 4,4,4',4',5,5,5',5'-octamethyl-2,2'-bi(1,3,2-dioxaborolane) (46.4 mmol), 2.2 g of PdCl₂(PPh₃)₄ (3.1 mmol), and 6.7 g of KOAc (68 mmol) were dissolved in 155 mL of 1,4-dioxane, and the mixture was refluxed at 150° C. for 1 hour. After completion of the reaction, the organic layer was extracted with EA, and the residual moisture was removed by using magnesium sulfate. The residue was dried and purified by column chromatography to obtain 11 g of compound 1-3 (yield: 96%).

Synthesis of Compound C-2-95

In a flask, 4.4 g of 5-bromo-2,3-diphenylquinoxaline (12.3 mmol), 5 g of compound 1-3 (13.5 mmol), 5.1 g of K₂CO₃ (36.9 mmol), and 0.71 mg of Pd(PPh₃)₄ (0.619 mmol) were dissolved in 60 mL of toluene, 30 mL of EtOH and 30 mL of H₂O, and the mixture was refluxed at 130° C. for 3 hours. After completion of the reaction, the organic layer was extracted with EA, and the residual moisture was removed by using magnesium sulfate. The residue was dried and purified by column chromatography to obtain 2.9 g of compound C-2-95 (yield: 44.9%).

|  | MW | M.P. |
|---|---|---|
| C-2-95 | 524.67 | 236.1° C. |

Example 14: Preparation of Compound C-2-105

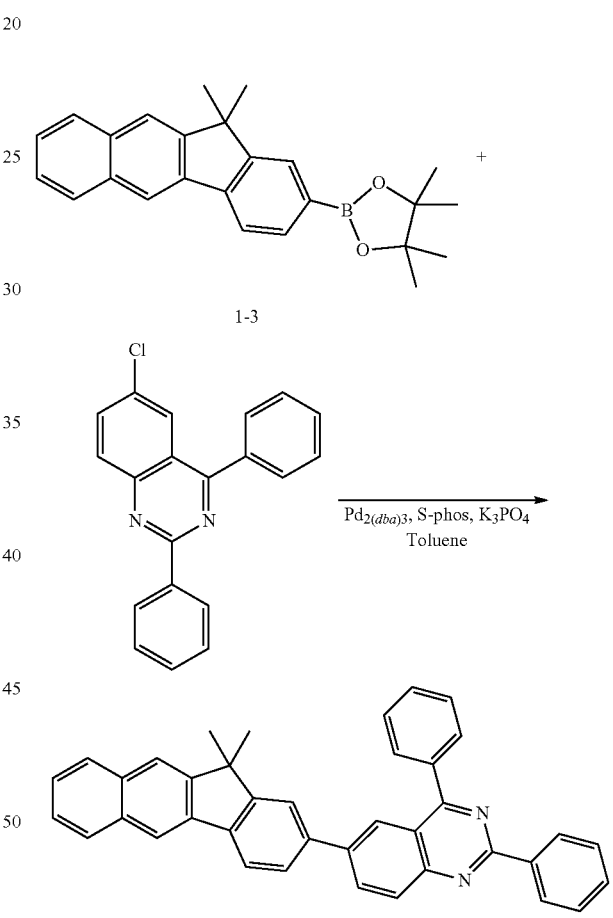

In a flask, 4.3 g of 6-chloro-2,4-diphenylquinazoline (13.5 mmol), 5 g of compound 1-3 (13.5 mmol), 0.49 g of Pd₂(dba)₃ (0.54 mmol), 0.443 mg of S-phos (1.08 mmol), and 14 g of K₃PO₄ (66.15 mmol) were dissolved in 65 mL of toluene, and the mixture was refluxed at 130° C. for 3 hours. After completion of the reaction, the organic layer was extracted with EA, and the residual moisture was removed by using magnesium sulfate. The residue was dried and purified by column chromatography to obtain 2 g of compound C-2-105 (yield: 28%).

| | MW | M.P. |
|---|---|---|
| C-2-105 | 524.67 | 171.7° C. |

Example 15: Preparation of Compound C-2-106

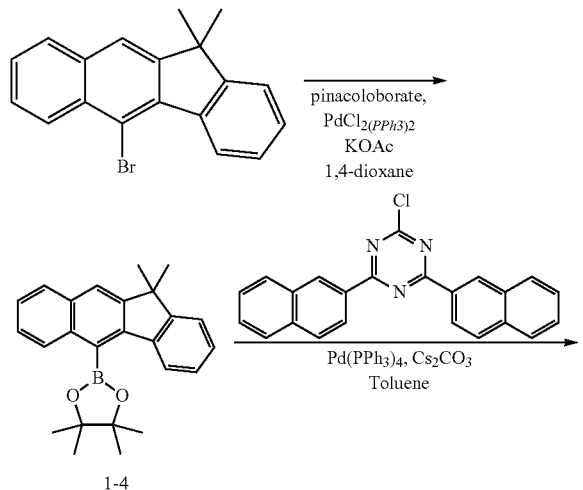

Synthesis of Compound 1-4

In a flask, 20 g of 5-bromo-11,11-dimethyl-11H-benzo[b] fluorene (61.9 mmol), 20.4 g of 4,4,4',4',5,5,5',5'-octamethyl-2,2'-bi(1,3,2-dioxaborolane) (74.28 mmol), 4.34 g of $PdCl_2(PPh_3)_4$ (6.19 mmol), and 12.15 g of KOAc (123.8 mmol) were dissolved in 300 mL of 1,4-dioxane, and the mixture was refluxed at 150° C. for 18 hours. After completion of the reaction, the organic layer was extracted with EA, and the residual moisture was removed by using magnesium sulfate. The residue was dried and purified by column chromatography to obtain 16 g of compound 1-4 (yield: 70%).

Synthesis of Compound C-2-106

In a flask, 6 g of compound 1-4 (16.2 mmol), 7.2 g of 2-chloro-4,6-di(naphthalene-2-yl)-1,3,5-triazine (19.44 mmol), 13.2 g of $Cs_2CO_3$ (40.5 mmol), and 0.936 mg of $Pd(PPh_3)_4$ (0.81 mmol) were dissolved in 81 mL of toluene, and the mixture was refluxed at 130° C. for 18 hours. After completion of the reaction, the organic layer was extracted with EA, and the residual moisture was removed by using magnesium sulfate. The residue was dried and purified by column chromatography to obtain 2 g of compound C-2-106 (yield: 21.4%).

| | MW | M.P. |
|---|---|---|
| C-2-106 | 575.70 | 241.1° C. |

Example 16: Preparation of Compound C-2-107

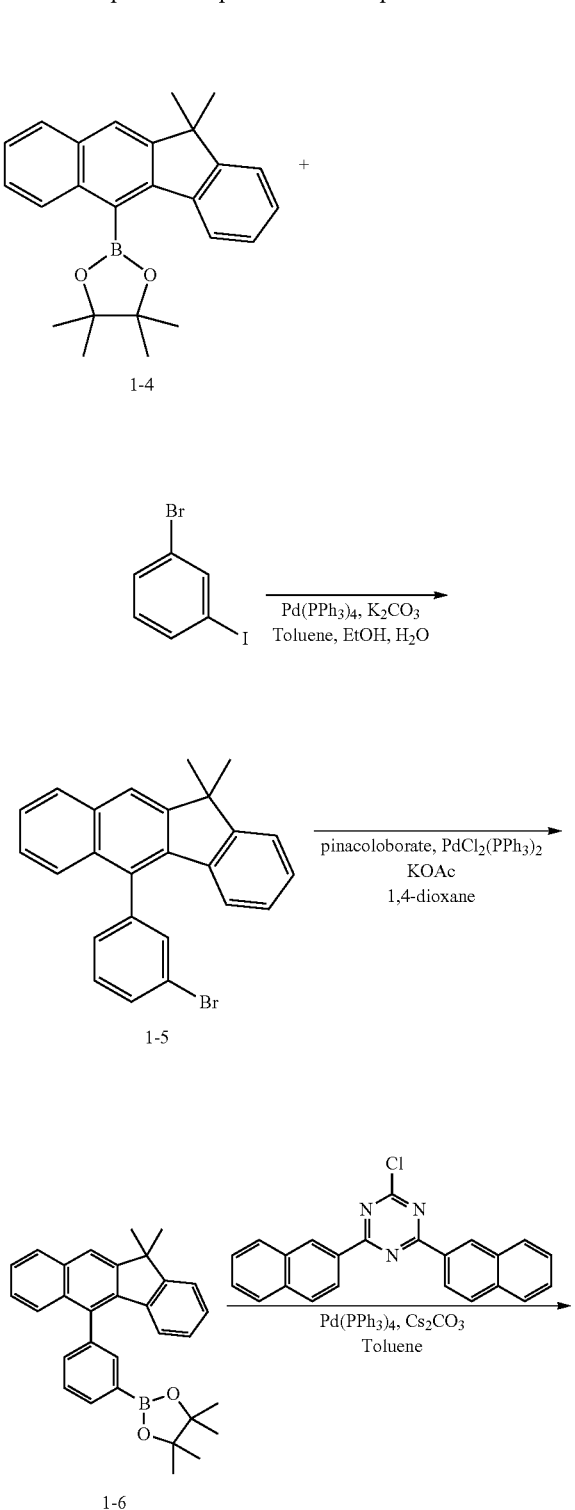

171
-continued

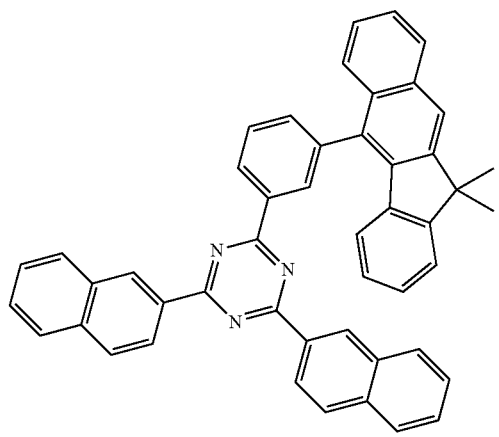

C-2-107

Synthesis of Compound 1-5

In a flask, 10 g of compound 1-4 (27 mmol), 15 g of 1-bromo-3-iodobenzene (54 mmol), 9.3 g of $K_2CO_3$ (67.5 mmol), and 1.56 g of $Pd(PPh_3)_4$ (13.5 mmol) were dissolved in 135 mL of toluene, 67.5 mL of EtOH and 67.5 mL of $H_2O$, and the mixture was refluxed at 130° C. for 18 hours. After completion of the reaction, the organic layer was extracted with EA, and the residual moisture was removed by using magnesium sulfate. The residue was dried and purified by column chromatography to obtain 6.3 g of compound 1-5 (yield: 58.4%).

Synthesis of Compound 1-6

In a flask, 6 g of compound 1-5 (15 mmol), 4.6 g of 4,4,4',4',5,5,5',5'-octamethyl-2,2'-bi(1,3,2-dioxaborolane) (27 mmol), 1 g of $PdCl_2(PPh_3)_4$ (1.5 mmol), and 2.95 g of KOAc (30 mmol) were dissolved in 75 mL of 1,4-dioxane, and the mixture was refluxed at 150° C. for 18 hours. After completion of the reaction, the organic layer was extracted with EA, and the residual moisture was removed by using magnesium sulfate. The residue was dried and purified by column chromatography to obtain 7 g of compound 1-6 (yield: 100%).

Synthesis of Compound C-2-107

In a flask, 7 g of compound 1-6 (15.7 mmol), 6.92 g of 2-chloro-4,6-di(naphthalene-2-yl)-1,3,5-triazine (18.8 mmol), 12.78 g of $Cs_2CO_3$ (39.25 mmol), and 0.907 mg of $Pd(PPh_3)_4$ (0.789 mmol) were dissolved in 78.5 mL of toluene, and the mixture was refluxed at 130° C. for 18 hours. After completion of the reaction, the organic layer was extracted with EA, and the residual moisture was removed by using magnesium sulfate. The residue was dried and purified by column chromatography to obtain 3 g of compound C-2-107 (yield: 29.3%).

|  | MW | M.P. |
|---|---|---|
| C-2-107 | 651.81° C. | 260° C. |

172

Example 17: Preparation of Compound C-2-108

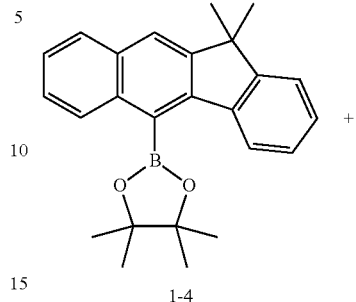

1-4

+

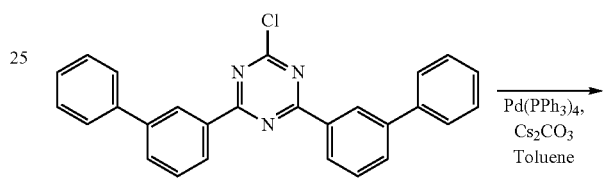

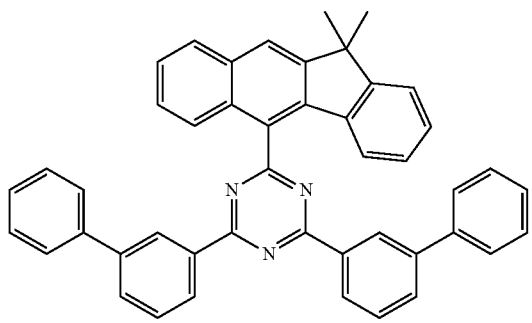

C-2-108

In a flask, 7.3 g of compound 1-4 (19.85 mmol), 10 g of 2,4-di([1,1'-biphenyl]-3-yl)-6-chloro-1,3,5-triazine (23.8 mmol), 16.2 g of $Cs_2CO_3$ (49.62 mmol), and 1.2 g of $Pd(PPh_3)_4$ (0.99 mmol) were dissolved in 100 mL of toluene, and the mixture was refluxed at 130° C. for 18 hours. After completion of the reaction, the organic layer was extracted with EA, and the residual moisture was removed by using magnesium sulfate. The residue was dried and purified by column chromatography to obtain 3 g of compound C-2-108 (yield: 24%).

|  | MW | M.P. |
|---|---|---|
| C-2-108 | 627.79 | 257° C. |

Example 18: Preparation of Compound C-2-100

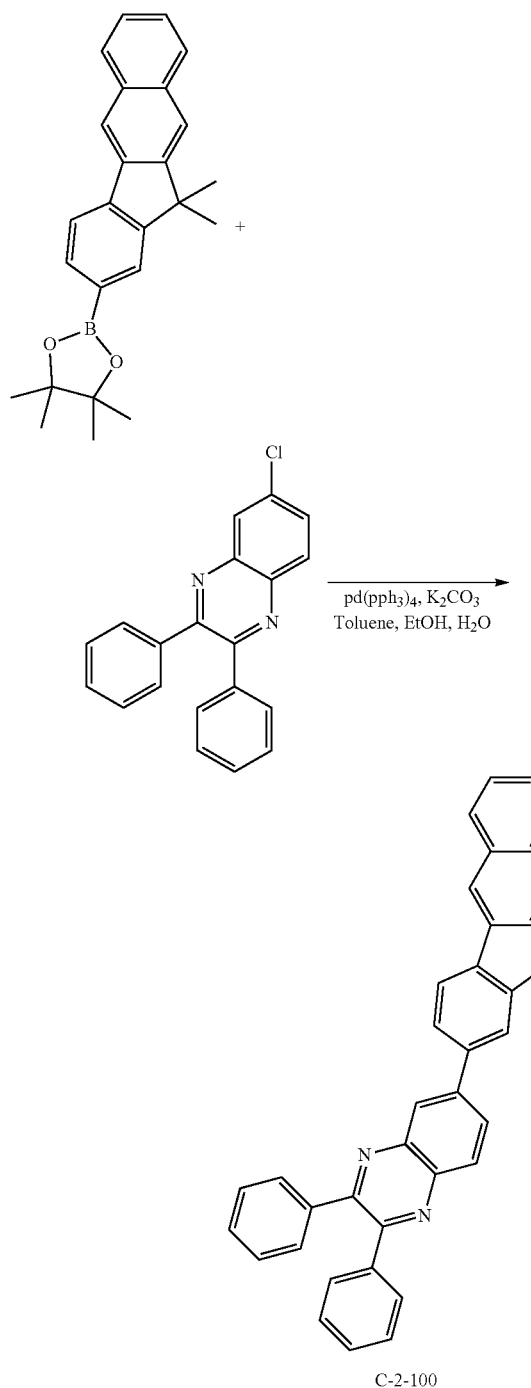

C-2-100

5 g of 2-(11,11-dimethyl-11H-benzo[b]fluorene-2-yl)-4,4,5,5-tetramethyl-1,3,2-dioxaborolane (13.50 mmol), 5.1 g of 6-chloro-2,3-diphenylquinoxaline (16.20 mmol), 1.5 g of Pd(pph$_3$)$_4$ (1.350 mmol), and 3.7 g of K$_2$CO$_3$ (27 mmol) were added to 13.5 mL of EtOH, 54 mL of toluene, and 13.5 mL of distilled water, and the mixture was stirred under reflux for 30 hours. After completion of the reaction, the reaction mixture was cooled to room temperature and stirred. After adding MeOH, the resultant solid was filtered under reduced pressure. Thereafter, the residue was purified by column chromatography with MC/Hex to obtain 1 g of compound C-2-100 (yield: 12%).

|  | MW | M.P. |
|---|---|---|
| C-2-100 | 524.6 | 260.5° C. |

Example 19: Preparation of Compound C-2-109

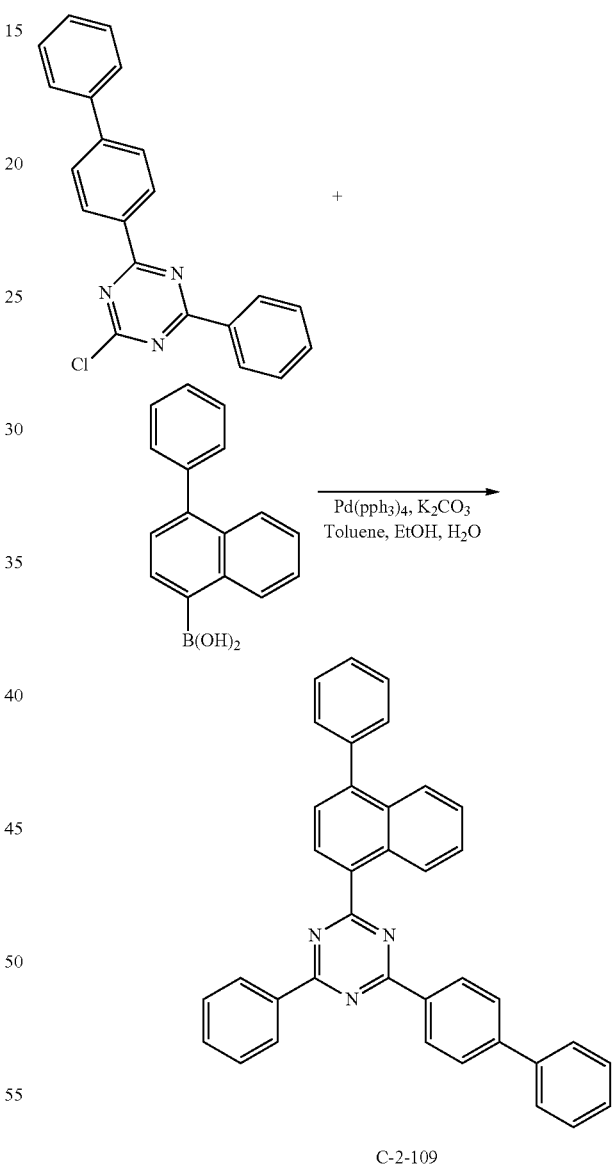

C-2-109

7 g of 2-([1,1'-biphenyl]-4-yl)-4-chloro-6-phenyl-1,3,5-triazine (20.3 mmol), 6 g of 4-phenylnaphthalene-1-yl) boronic acid (24.4 mmol), 1.2 g of Pd(pph$_3$)$_4$ (1.01 mmol), and 7 g of K$_2$CO$_3$ (50.9 mmol) were added to 25.4 mL of EtOH, 101.6 mL of toluene, and 25.4 mL of distilled water, and the mixture was stirred under reflux for 1 hour. After completion of the reaction, the reaction mixture was cooled to room temperature. The organic layer was extracted with ethyl acetate, and purified by column chromatography with MC/Hex to obtain 4.2 g of compound C-2-109 (yield: 40%).

|         | MW     | M.P.     |
|---------|--------|----------|
| C-2-109 | 511.61 | 197.8° C. |

Example 20: Preparation of Compound C-3-29

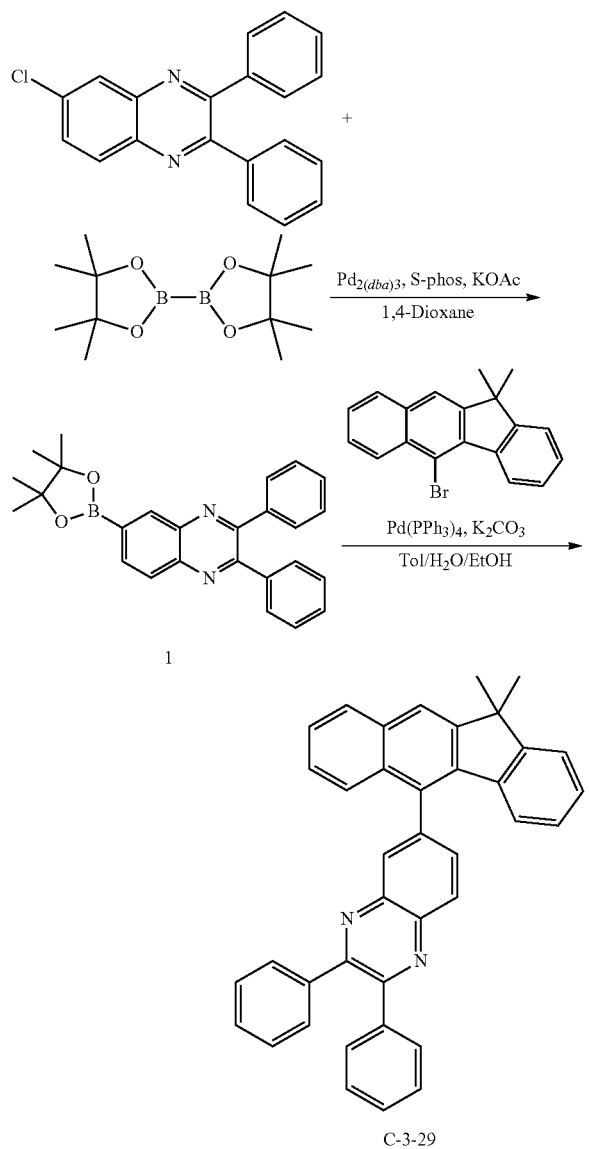

In a flask, 20 g of 6-chloro-2,4-diphenylquinazoline (63.13 mmol), 19.2 g of 4,4,4',4',5,5,5',5'-octamethyl-2,2'-bi (1,3,2-dioxaborolane) (75.7 mmol), 2.3 g of $Pd_2(dba)_3$ (3.1 mmol), 2.1 g of S-phos (5 mmol), and 18.5 g of KOAc (189.3 mmol) were dissolved in 315 mL of 1,4-dioxane, and the mixture was refluxed at 150° C. for 18 hours. After completion of the reaction, the organic layer was extracted with EA, and the residual moisture was removed by using magnesium sulfate. The residue was dried and purified by column chromatography to obtain 19 g of compound 1 (yield: 73.7%).

Synthesis of Compound C-3-29

In a flask, 7 g of 2,3-diphenyl-6-(4,4,5,5-tetramethyl-1,3,2-dioxaborane-2-yl) (17 mmol), 5 g of 5-bromo-11,11-dimethyl-11H-benzo[b]fluorene (15 mmol), 5.2 g of $K_2CO_3$ (37.5 mmol), and 0.87 mg of $Pd(PPh_3)_4$ (0.75 mmol) were dissolved in 100 mL of toluene, 50 mL of EtOH, and 50 mL of $H_2O$, and the mixture was refluxed at 130° C. for 4 hours. After completion of the reaction, the organic layer was extracted with EA, and the residual moisture was removed by using magnesium sulfate. The residue was dried and purified by column chromatography to obtain 5.4 g of compound C-3-29 (yield: 68%).

|        | MW     | M.P.   |
|--------|--------|--------|
| C-3-29 | 524.67 | 261° C. |

Hereinafter, the driving voltage, the luminous efficiency and the lifespan properties of an OLED comprising the compound of the present disclosure will be explained. However, the following examples merely illustrate the properties of an OLED according to the present disclosure in detail, but the present disclosure is not limited to the following examples.

Device Examples 1 to 23: Producing an OLED According to the Present Disclosure

An OLED according to the present disclosure was produced as follows: A transparent electrode indium tin oxide (ITO) thin film (10 Ω/sq) on a glass substrate for an OLED (GEOMATEC CO., LTD., Japan) was subjected to an ultrasonic washing with acetone, ethanol and distilled water, sequentially, and then was stored in isopropanol. The ITO substrate was mounted on a substrate holder of a vacuum vapor deposition apparatus. Compound HI-1 was introduced into a cell of the vacuum vapor deposition apparatus, and then the pressure in the chamber of the apparatus was then controlled to $10^{-6}$ torr. Thereafter, an electric current was applied to the cell to evaporate the above-introduced material, thereby forming a first hole injection layer having a thickness of 80 nm on the ITO substrate. Next, compound HI-2 was introduced into another cell of the vacuum vapor deposition apparatus and was evaporated by applying an electric current to the cell, thereby forming a second hole injection layer having a thickness of 5 nm on the first hole injection layer. Compound HT-1 was then introduced into another cell of the vacuum vapor deposition apparatus and was evaporated by applying an electric current to the cell, thereby forming a first hole transport layer having a thickness of 10 nm on the second hole injection layer. Compound HT-2 was then introduced into another cell of the vacuum vapor deposition apparatus and was evaporated by applying an electric current to the cell, thereby forming a second hole transport layer having a thickness of 60 nm on the first hole transport layer. After forming the hole injection layers and the hole transport layers, a light-emitting layer was formed thereon as follows: The first host and the second host shown in Tables 1 to 3 were introduced into one cell of the vacuum vapor depositing apparatus at a ratio of 50:50, and compound D-39 was introduced into another cell as a dopant. The three materials were evaporated and the dopant was deposited in a doping amount of 3 wt % based on the total amount of the hosts and dopant to form a light-emitting layer having a thickness of 40 nm on the second hole transport layer. Next, compound ET-1 and compound EI-1 were evaporated at a rate of 1:1 in two other cells to deposit an electron transport layer having a thickness of 35 nm on the light-emitting layer. After depositing compound EI-1 as an electron injection layer having a thickness of 2 nm on the electron transport layer, an Al cathode having a thickness of 80 nm was deposited on the electron injection layer by another vacuum vapor deposition apparatus. Thus, an OLED was produced.

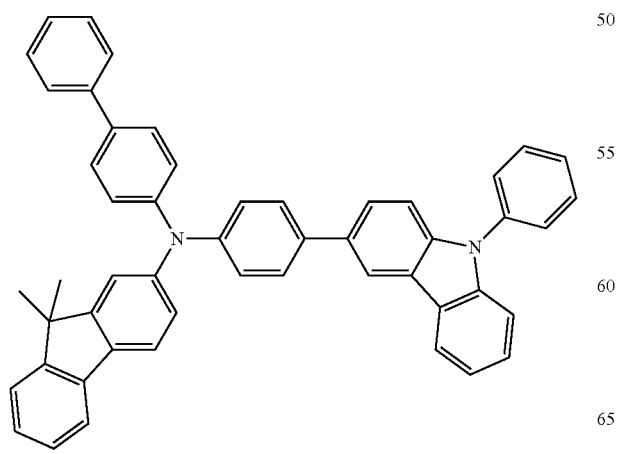

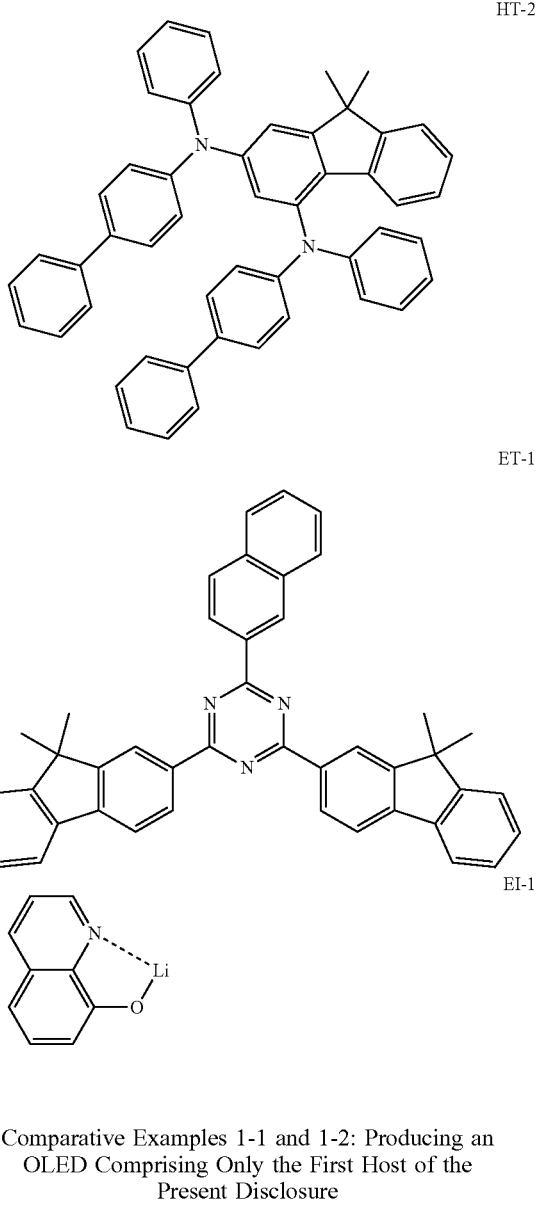

Comparative Examples 1-1 and 1-2: Producing an OLED Comprising Only the First Host of the Present Disclosure OLEDs were produced in the same manner as in Device Example 1, except that only the first host of the present disclosure is used as a host.

Comparative Examples 2-1 to 2-7: Producing an OLED Comprising Only the Second Host of the Present Disclosure OLEDs were produced in the same manner as in Device Example 1, except that only the second host of the present disclosure is used as a host.

Comparative Examples 3-1 and 3-2: Producing an OLED Comprising a Conventional Compound OLEDs were produced in the same manner as in Device Example 1, except that the conventional compounds A and B are used as a host.

A

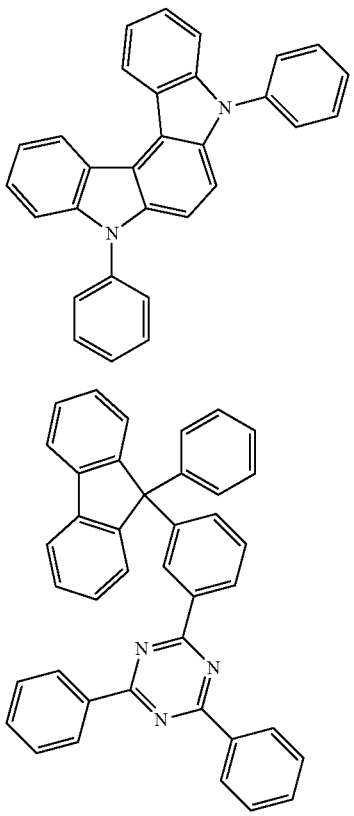

B

The driving voltage and power efficiency based on a luminance of 5,000 nits, and the time taken to be reduced from 100% to 99% of the luminance (lifespan; T99) at 5,000 nits and a constant current of the produced OLEDs are provided in Table 1 below.

TABLE 1

|  | First Host | Second Host | Driving Voltage (V) | Power Efficiency (lm/W) | Lifespan (T99, hr) |
|---|---|---|---|---|---|
| Device Example 1 | C-1-4 | C-2-13 | 4.1 | 18.5 | 126 |
| Device Example 2 | C-1-6 | C-2-13 | 4.2 | 16.1 | 93 |
| Device Example 3 | C-1-103 | C-2-14 | 4.0 | 20.7 | 116 |
| Device Example 4 | C-1-66 | C-2-14 | 4.0 | 19.4 | 37 |
| Device Example 5 | C-1-36 | C-2-14 | 4.0 | 20.1 | 63 |
| Device Example 6 | C-1-32 | C-2-14 | 3.6 | 18.4 | 42 |
| Device Example 7 | C-1-76 | C-2-14 | 4.0 | 19.0 | 29 |
| Device Example 8 | C-1-79 | C-2-14 | 4.1 | 18.4 | 16 |
| Device Example 9 | C-1-74 | C-2-14 | 4.4 | 18.1 | 22 |
| Device Example 10 | C-1-127 | C-2-14 | 4.1 | 19.8 | 58 |
| Device Example 11 | C-1-39 | C-2-7 | 4.0 | 20.0 | 61 |
| Device Example 12 | C-1-46 | C-2-7 | 4.0 | 20.2 | 85 |
| Device Example 13 | C-1-53 | C-2-7 | 3.8 | 18.7 | 43 |
| Device Example 14 | C-1-57 | C-2-7 | 3.8 | 18.8 | 52 |
| Device Example 15 | C-1-92 | C-2-7 | 3.8 | 21.1 | 3.7 |
| Comparative Example 1-1 | C-1-6 | — | 6.6 | 1.9 | 0.6 |
| Comparative Example 2-1 | — | C-2-13 | 5.0 | 13.0 | 0.8 |
| Comparative Example 2-2 | — | C-2-14 | 5.2 | 13.2 | 0.8 |
| Comparative Example 2-3 | — | C-2-7 | 5.0 | 12.3 | 0.8 |
| Comparative Example 3-1 | A | B | 4.7 | 17.2 | 0.3 |

The driving voltage and power efficiency based on a luminance of 8,000 nits, and the time taken to be reduced from 100% to 98% of the luminance (lifespan; T98) at 5,000 nits and a constant current of the produced OLEDs are provided in Table 2 below.

TABLE 2

|  | First Host | Second Host | Driving Voltage (V) | Power Efficiency (lm/W) | Lifespan (T98, hr) |
|---|---|---|---|---|---|
| Device Example 16 | C-1-6 | C-2-87 | 5.0 | 13.3 | 57 |
| Device Example 17 | C-1-6 | C-2-88 | 4.8 | 13.6 | 80 |
| Comparative Example 1-2 | C-1-6 | — | 7.1 | 2.1 | 2.8 |
| Comparative Example 2-4 | — | C-2-87 | 6.7 | 8.3 | 0.3 |
| Comparative Example 2-5 | — | C-2-88 | 5.4 | 10.2 | 0.7 |
| Comparative Example 3-2 | A | B | 5.6 | 13.2 | 0.8 |

The driving voltage and power efficiency based on a luminance of 1,000 nits, and the time taken to be reduced from 100% to 97% of the luminance (lifespan; T97) at 5,000 nits and a constant current of the produced OLEDs are provided in Table 3 below.

TABLE 3

|  | First Host | Second Host | Driving Voltage (V) | Power Efficiency (lm/W) | Lifespan (T97, hr) |
|---|---|---|---|---|---|
| Device Example 18 | C-1-44 | C-2-14 | 2.8 | 28.7 | 50 |
| Device Example 19 | C-1-128 | C-2-14 | 2.8 | 29.9 | 50 |
| Device Example 20 | C-1-113 | C-2-14 | 2.8 | 31.6 | 52 |
| Device Example 21 | C-1-136 | C-2-110 | 3.1 | 28.4 | 147 |
| Device Example 22 | C-1-137 | C-2-14 | 3.4 | 26.0 | 225 |
| Device Example 23 | C-1-91 | C-2-106 | 2.8 | 33.7 | 119 |
| Comparative Example 2-6 | — | C-2-14 | 3.9 | 21.2 | 9.7 |
| Comparative Example 2-7 | — | C-2-106 | 3.2 | 23.0 | 6.8 |

From the Device Examples and the Comparative Examples above, it is confirmed that an OLED having lower driving voltage, higher power efficiency and/or longer lifespan may be produced by comprising a plurality of host materials having a compound represented by formula 1 and a compound represented by formula 2.

In addition, the present disclosure uses the combination of the compound represented by formula 1, which is responsible for hole properties, and the compound represented by formula 2, which is responsible for electron properties, separately. It makes it possible to deposit at a lower deposition temperature by having a lower molecular weight than one light-emitting material having both a hole part responsible for the hole properties and an electron part responsible for the electron properties. Thus, the combination of the present disclosure is excellent in the stability of the material against heat.

Device Example 24: Producing an OLED According to the Present Disclosure

An OLED was produced in the same manner as in Device Example 1, except that compound C-3-29 of the present disclosure was used as a sole host.

Comparative Example 4: Producing an OLED Comprising a Conventional Compound

An OLED was produced in the same manner as in Device Example 1, except that the conventional compound C was used as a sole host.

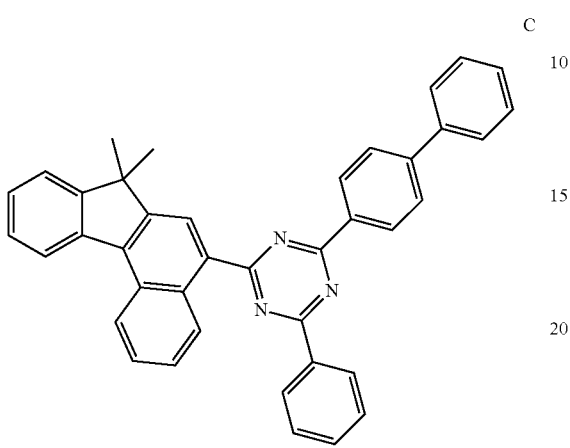

The driving voltage, current efficiency, and power efficiency at 5,000 nits of the produced OLEDs are provided in Table 4 below.

TABLE 4

| | Host | Driving Voltage (V) | Current Efficiency (cd/A) | Power Efficiency (lm/W) |
|---|---|---|---|---|
| Device Example 24 | C-3-29 | 4.6 | 22.6 | 15.5 |
| Comparative Example 4 | C | 6.1 | 5.3 | 2.8 |

From Device Example 24 and Comparative Example 4, it is confirmed that an OLED comprising the compound represented by formula 11 has lower driving voltage, higher current efficiency and/or higher power efficiency compared to an OLED comprising a conventional compound.

The invention claimed is:

1. An organic electroluminescent device comprising an anode, a cathode, and at least one light-emitting layer between the anode and the cathode, wherein at least one layer of the light-emitting layer comprises a plurality of host materials,
wherein
the plurality of host materials comprising a first host material and a second host material, wherein the first host material comprises a compound represented by the following formula 1:

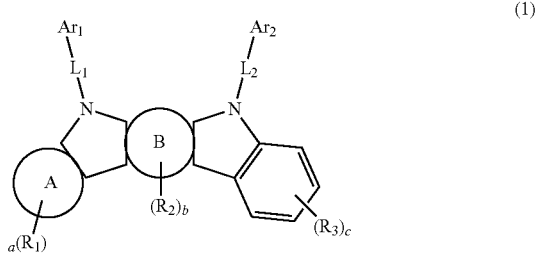

(1)

wherein $L_1$ and $L_2$, each independently, represent a single bond, a substituted or unsubstituted (C6-C30)arylene, or a substituted or unsubstituted (3- to 30-membered)heteroarylene;

$Ar_1$ and $Ar_2$, each independently, represent a substituted or unsubstituted (C6-C30)aryl, a substituted or unsubstituted (3- to 30-membered)heteroaryl, an amino, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino;

A represents a naphthalene ring;

B represents a benzene ring, $R_1$ to $R_3$, each independently, represent hydrogen, deuterium, a halogen, a cyano, a substituted or unsubstituted (C1-C30)alkyl, a substituted or unsubstituted (C2-C30)alkenyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or each of $R_1$ to $R_3$ may be linked to each other to form a substituted or unsubstituted (3- to 30-membered) mono- or polycyclic ring;

a represents an integer of 1 to 6;

b represents 1 or 2;

c represents an integer of 1 to 4; and where if a to c, each independently, are an integer of 2 or more, each of $R_1$ to $R_3$ may be the same or different; and the second host material comprises a compound represented by the following formula 2:

$$HAr\text{-}(L_3\text{-}Ar_3)_d \qquad (2)$$

wherein

HAr represents a substituted or unsubstituted triazine, a substituted or unsubstituted pyrimidine, or a substituted or unsubstituted pyridine;

$L_3$ represents a single bond, or a substituted or unsubstituted (C6-C30)arylene;

$Ar_3$ represents a substituted or unsubstituted (C6-C30)aryl; and d represents an integer of 1 to 3, where if d is an integer of 2 or more, each ($L_3$-$Ar_3$) may be the same or different.

2. The organic electroluminescent device according to claim 1, wherein the compound represented by formula 1 is represented by the following formula 3:

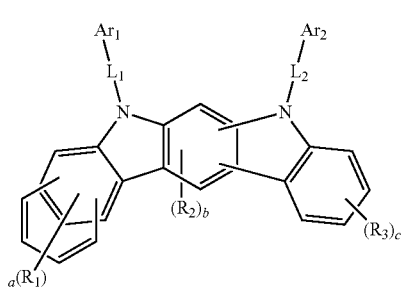

(3)

wherein, $L_1$, $L_2$, $Ar_1$, $Ar_2$, $R_1$ to $R_3$, and a to c are as defined in claim 1.

3. The organic electroluminescent device according to claim 1, wherein the compound represented by formula 2 is represented by at least one of the following formula 5:

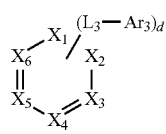

(5)

wherein $X_1$ to $X_6$, each independently, represent $CR_4$ or N, with the proviso that at least one of $X_1$ to $X_4$ represent N;

$R_4$ represents hydrogen, a substituted or unsubstituted (C6-C30)aryl, a substituted or unsubstituted (C2-C30) alkenyl, or a substituted or unsubstituted (C1-C30) alkyl; or two adjacent $R_4$'s may be linked to each other to form a substituted or unsubstituted (3- to 30-membered) mono- or polycyclic ring; and $L_3$, $Ar_3$ and d are as defined in claim 1.

4. The organic electroluminescent device according to claim 1, wherein the substituents of the substituted aryl(ene), the substituted heteroaryl(ene), the substituted mono- or di-alkylamino, the substituted mono- or di-arylamino, the substituted alkylarylamino, the substituted alkyl, the substituted alkenyl, the substituted cycloalkyl, the substituted alkoxy, the substituted trialkylsilyl, the substituted dialkylarylsilyl, the substituted alkyldiarylsilyl, the substituted triarylsilyl, or the substituted mono- or polycyclic ring in $L_1$ to $L_3$, $Ar_1$ to $Ar_3$, HAr, and $R_1$ to $R_3$, each independently, are at least one selected from the group consisting of deuterium, a halogen, a cyano, a carboxyl, a nitro, a hydroxyl, a (C1-C30)alkyl, a halo(C1-C30)alkyl, a (C2-C30)alkenyl, a (C2-C30)alkynyl, a (C1-C30)alkoxy, a (C1-C30)alkylthio, a (C3-C30)cycloalkyl, a (C3-C30)cycloalkenyl, a (3- to 7-membered)heterocycloalkyl, a (C6-C30)aryloxy, a (C6-C30)arylthio, a (5- to 30-membered)heteroaryl, a (C6-C30) aryl, a tri(C1-C30)alkylsilyl, a tri(C6-C30)arylsilyl, a di(C1-C30)alkyl(C6-C30)arylsilyl, a (C1-C30)alkyldi(C6-C30) arylsilyl, an amino, a mono- or di-(C1-C30)alkylamino, a mono- or di-(C6-C30)arylamino, a (C1-C30)alkyl(C6-C30) arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl, and a (C1-C30)alkyl (C6-C30)aryl.

5. The organic electroluminescent device according to claim 1, wherein the compound represented by formula 1 is selected from the group consisting of the following compounds:

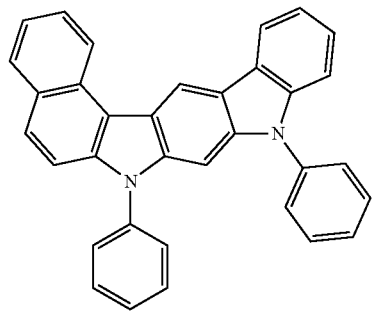

C-1-1

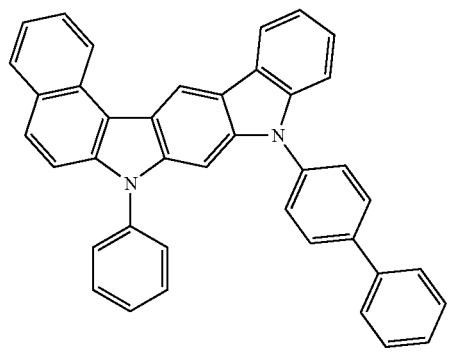

C-1-2

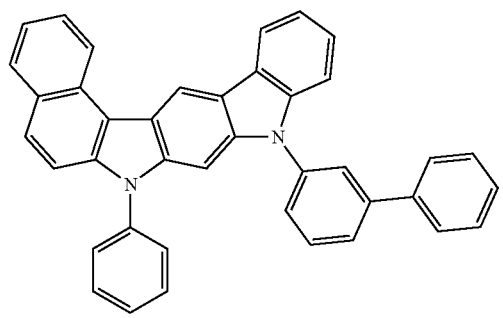

C-1-3

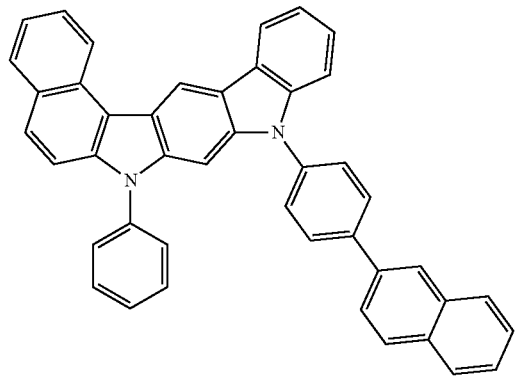

C-1-4

C-1-5
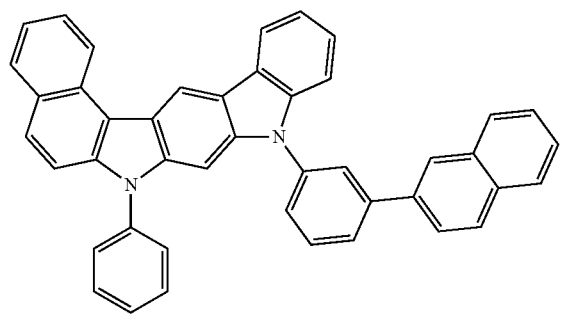
C-1-6
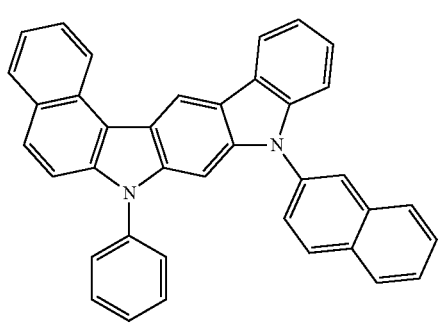
C-1-7
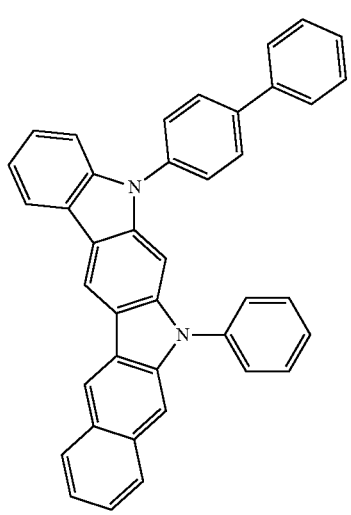
C-1-8
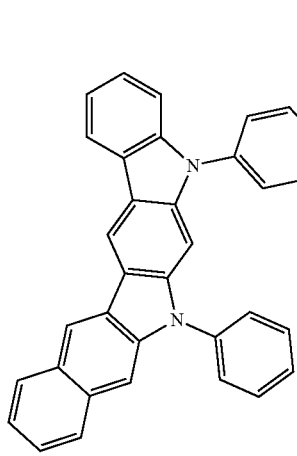
C-1-9
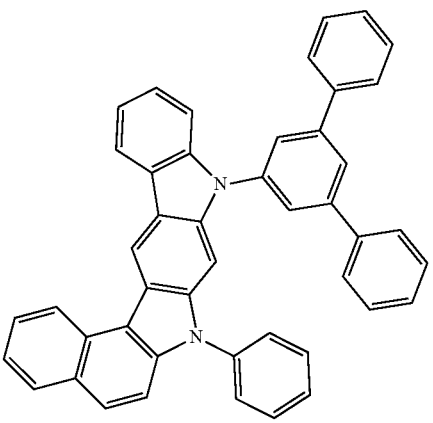
C-1-10
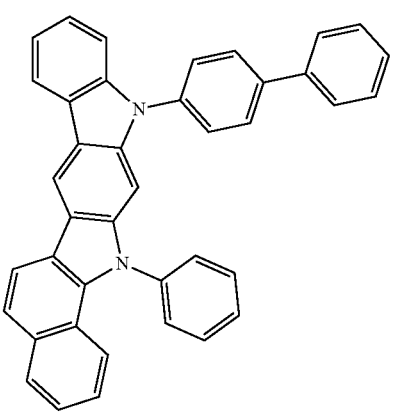
C-1-11
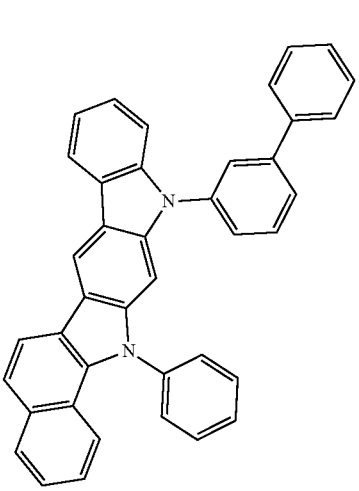

C-1-12
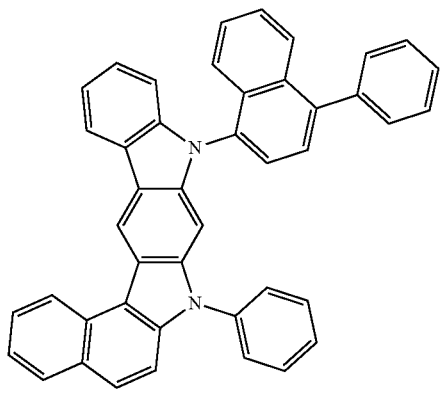
C-1-13
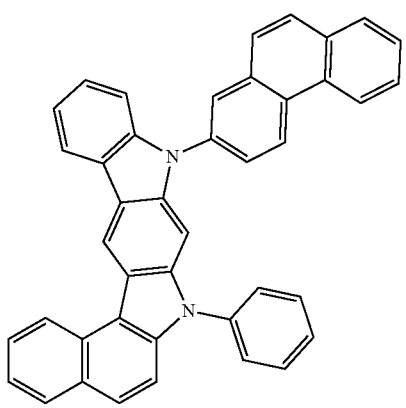
C-1-14
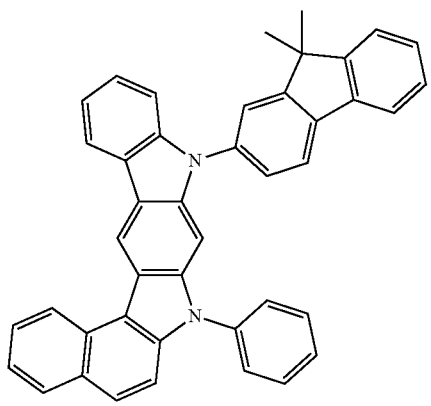
C-1-15
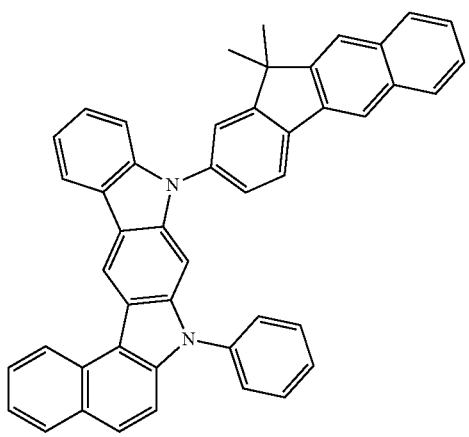
C-1-16
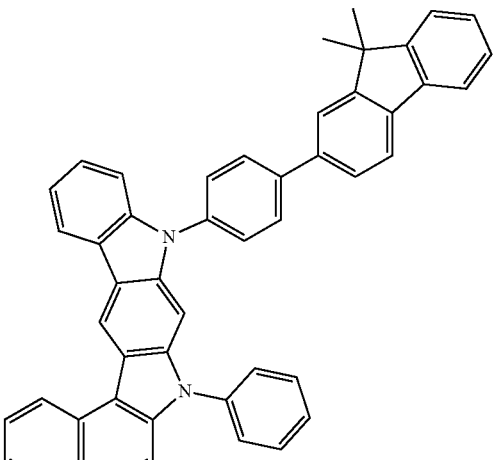
C-1-17
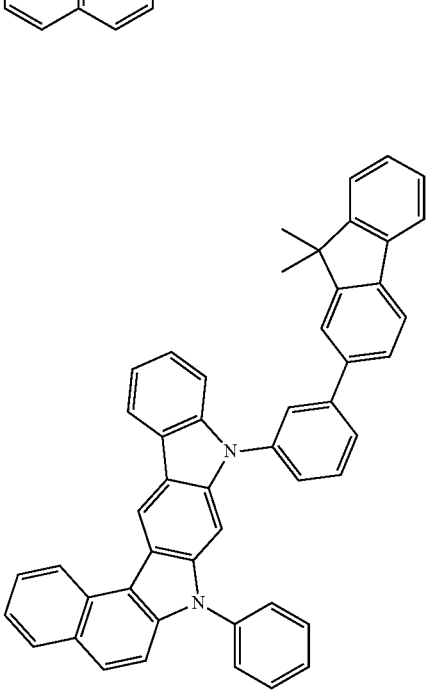
C-1-18
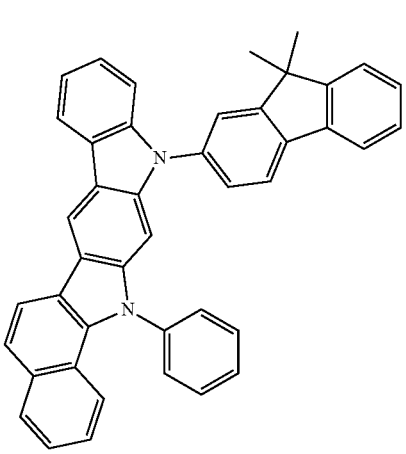

C-1-19
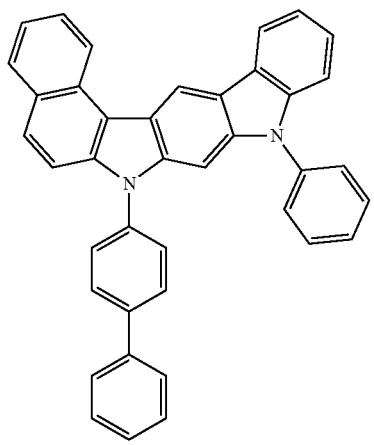
C-1-20
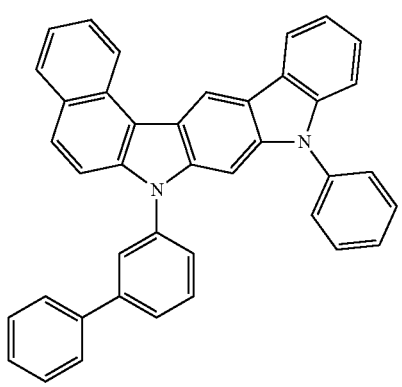
C-1-21
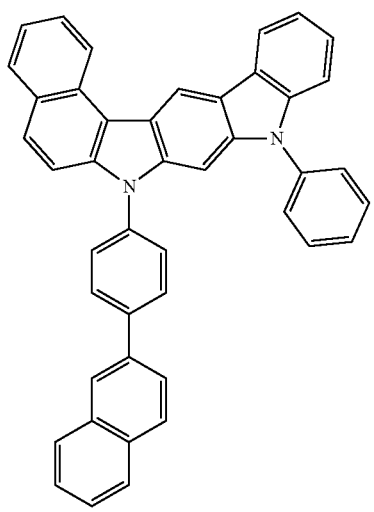
C-1-22
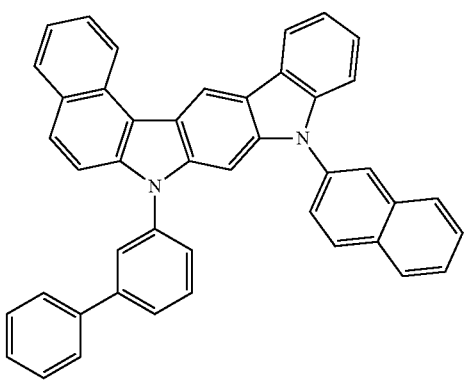
C-1-23
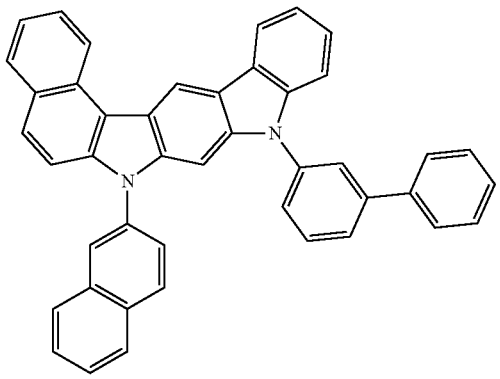
C-1-24
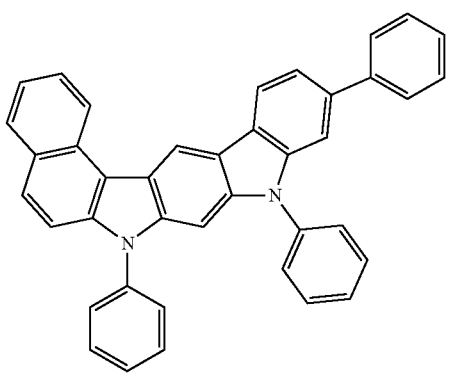
C-1-25
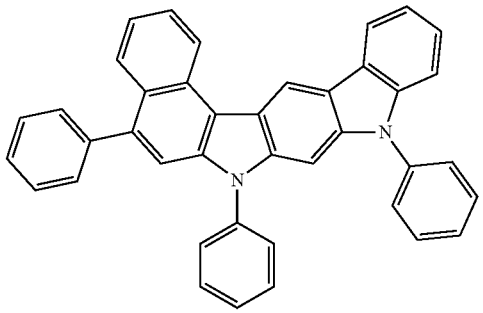

C-1-26
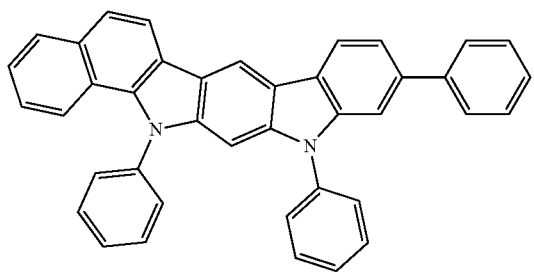
C-1-31
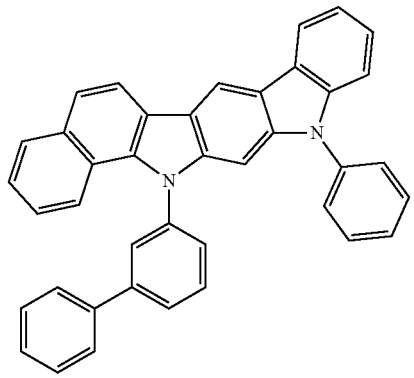
C-1-27
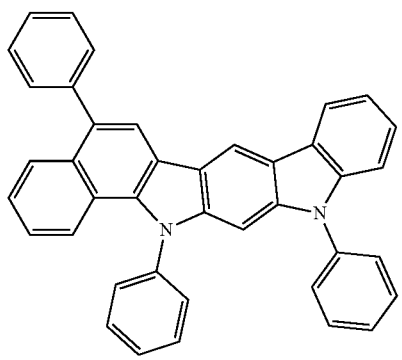
C-1-29
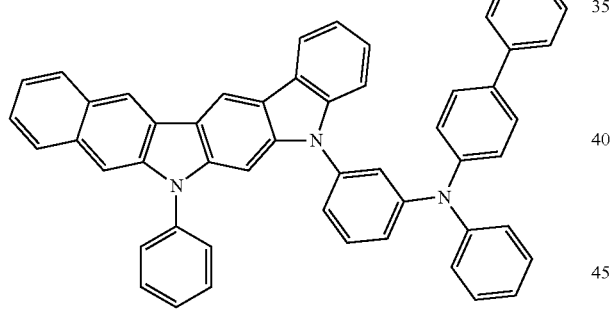
C-1-32
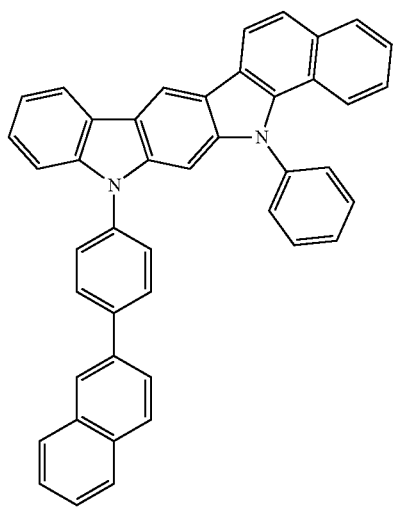
C-1-30
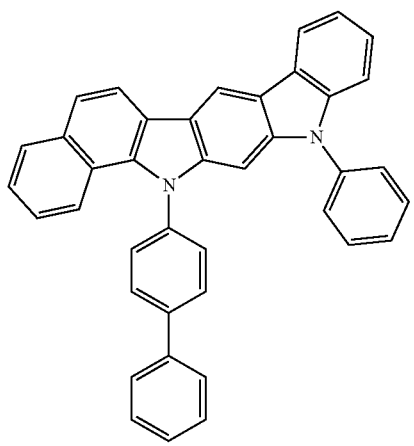
C-1-33
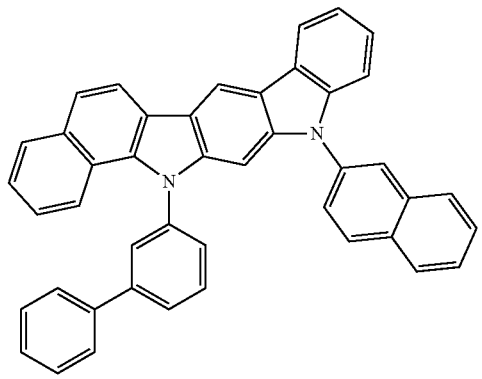

-continued
C-1-34
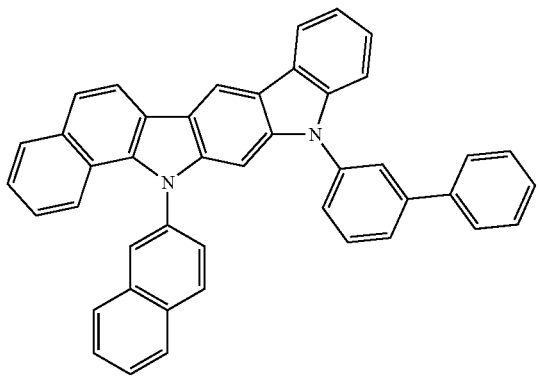
C-1-35
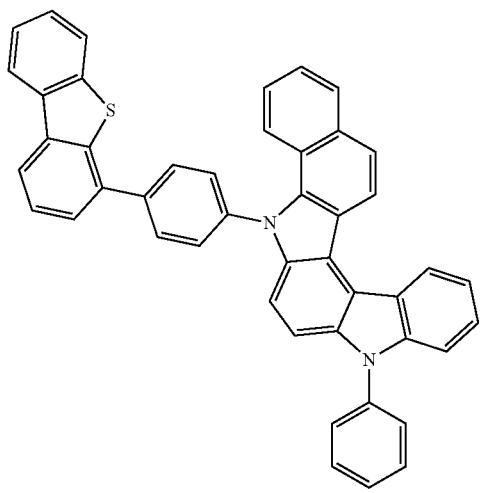
C-1-36
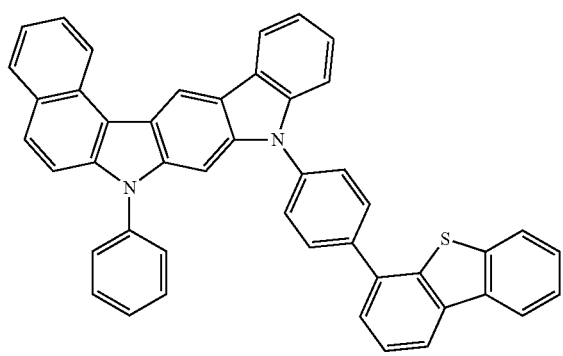
-continued
C-1-37
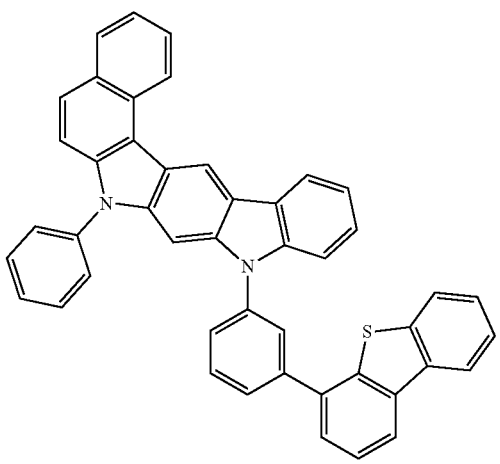
C-1-38
C-1-39
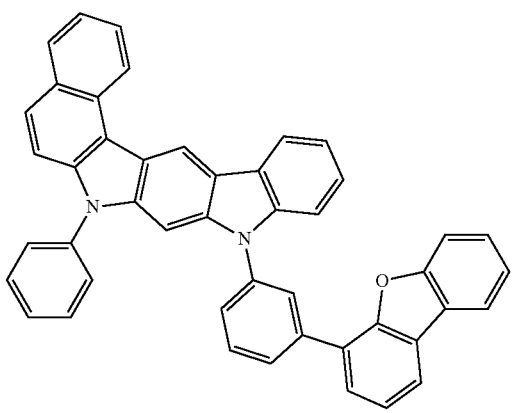

C-1-40
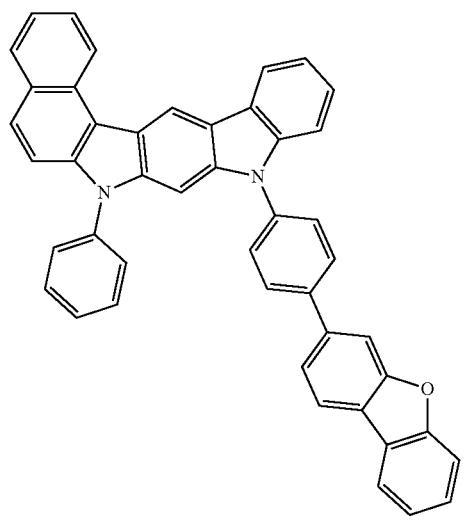
C-1-43
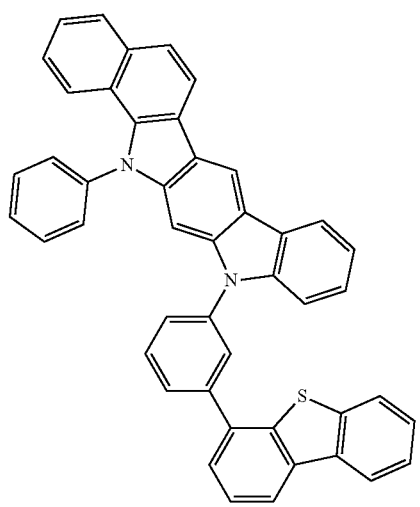
C-1-41
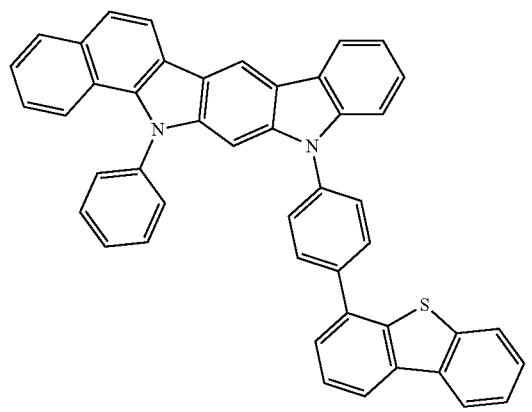
C-1-44
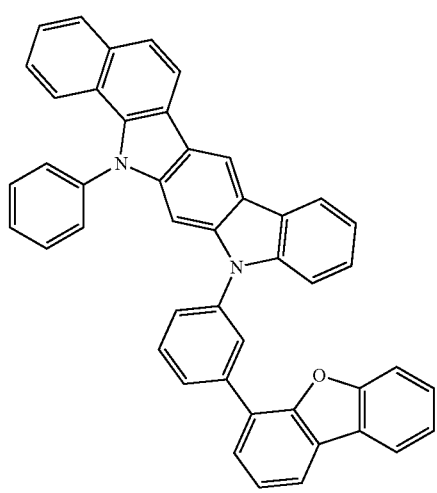
C-1-42
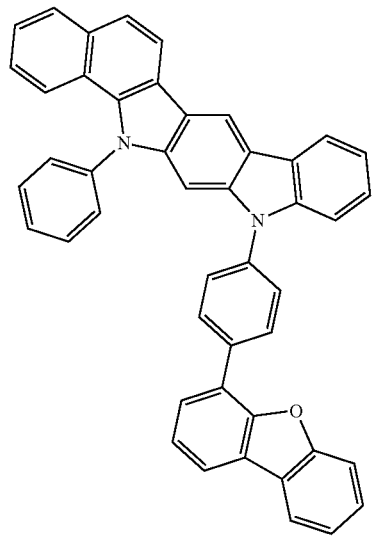
C-1-45
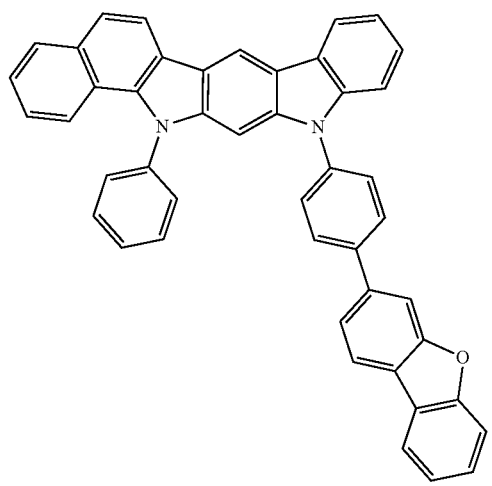

C-1-46
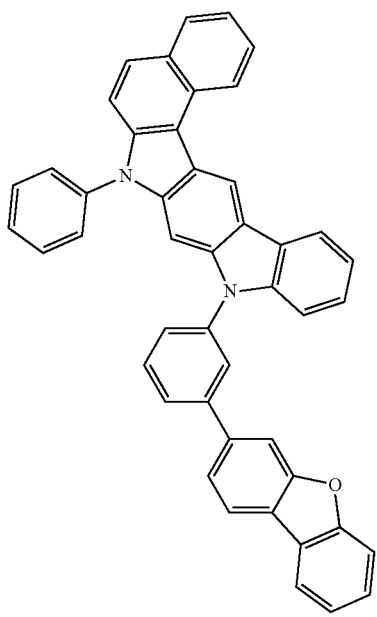
C-1-47
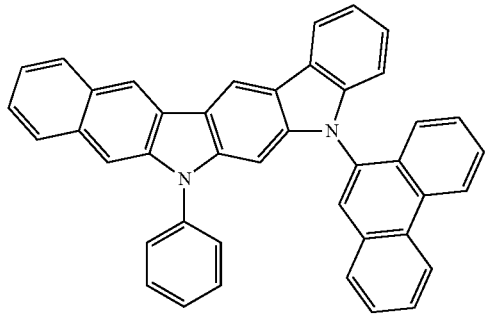
C-1-48
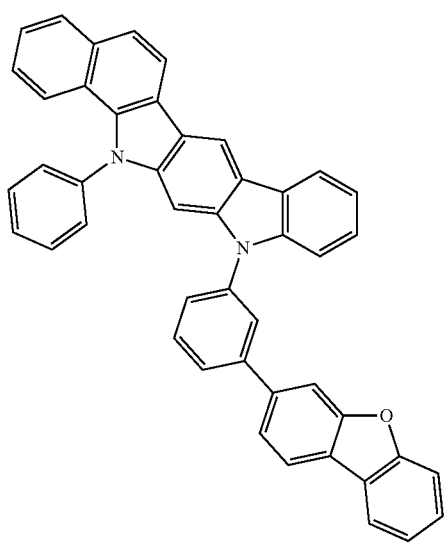
C-1-49
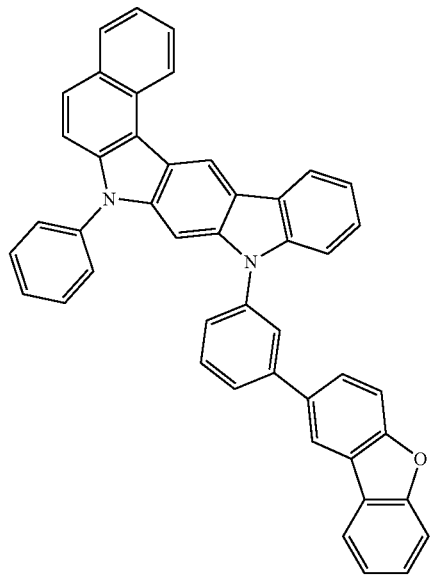
C-1-50
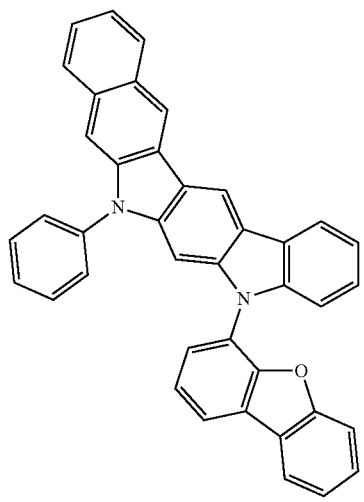
C-1-51
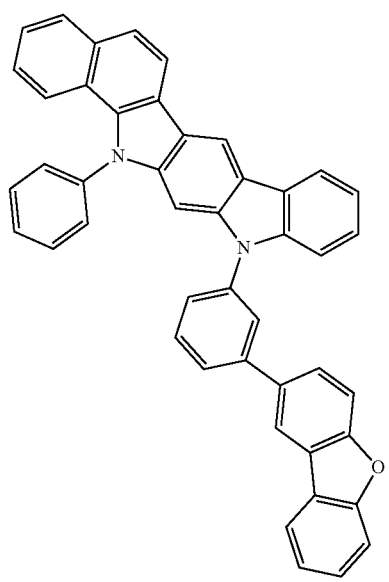

-continued
C-1-52
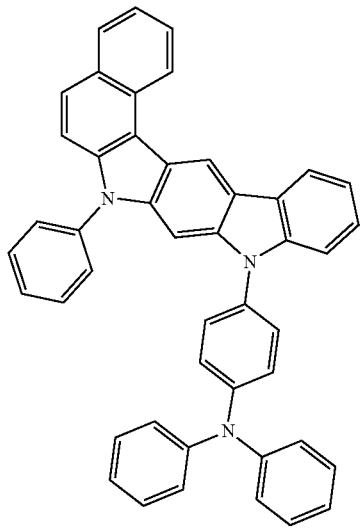
C-1-53
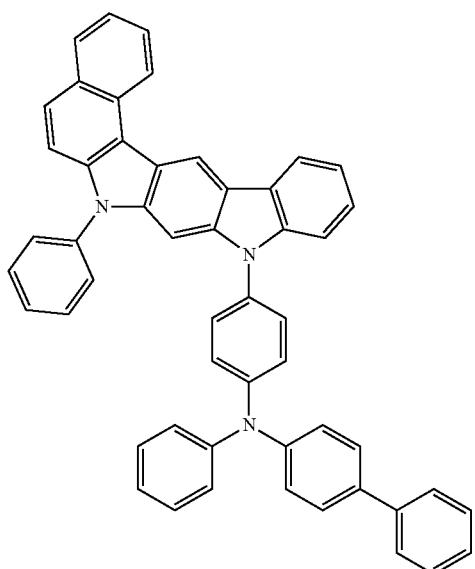
C-1-54
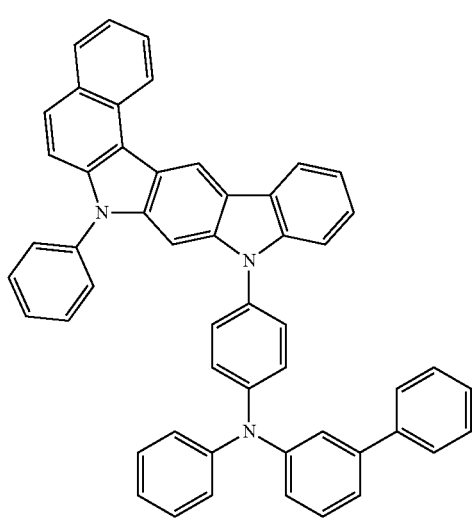
-continued
C-1-55
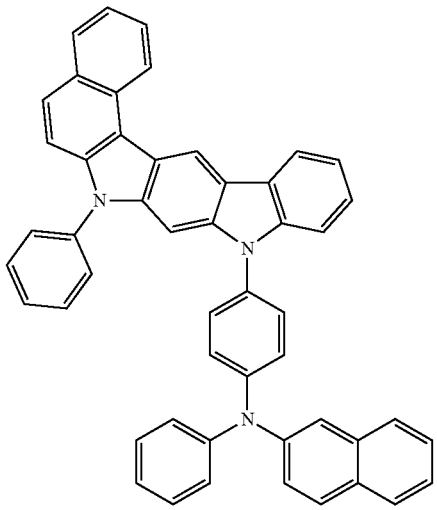
C-1-56
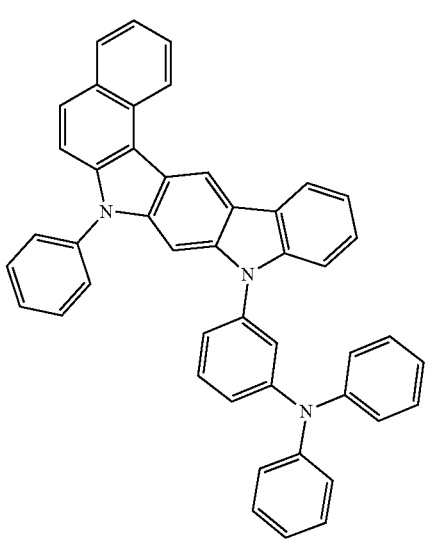
C-1-57
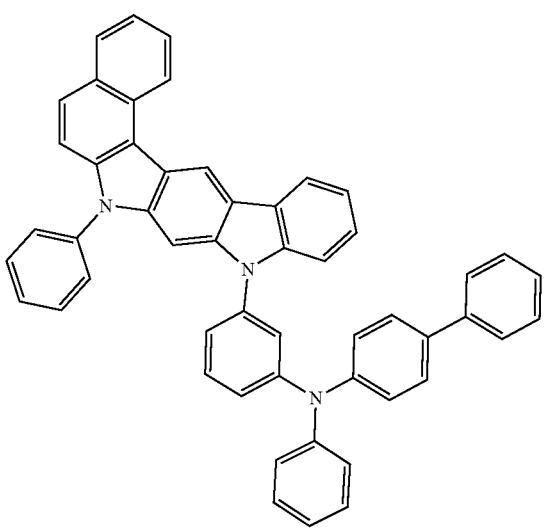

C-1-58
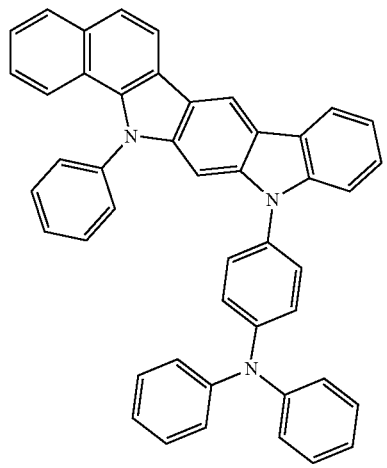
C-1-59
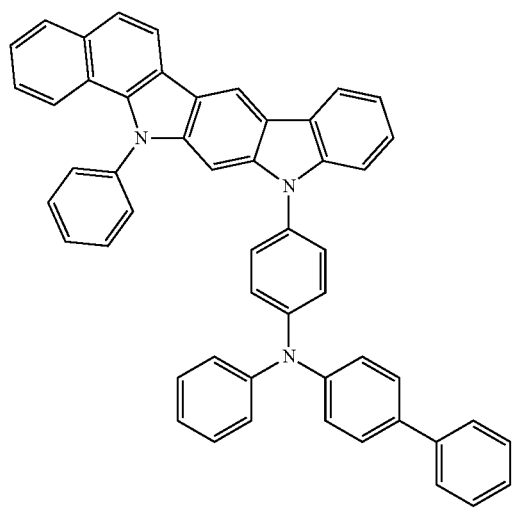
C-1-60
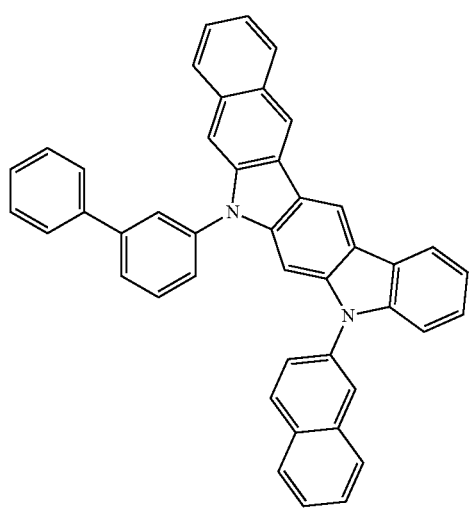
C-1-61
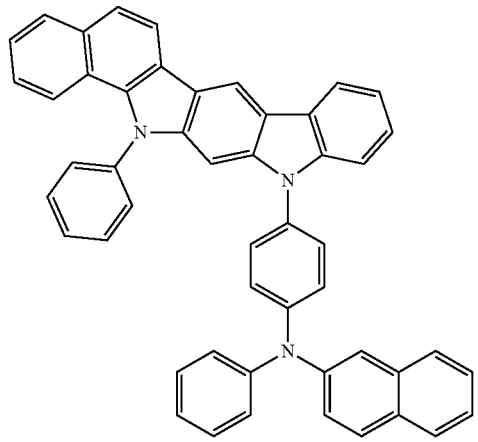
C-1-62
C-1-63
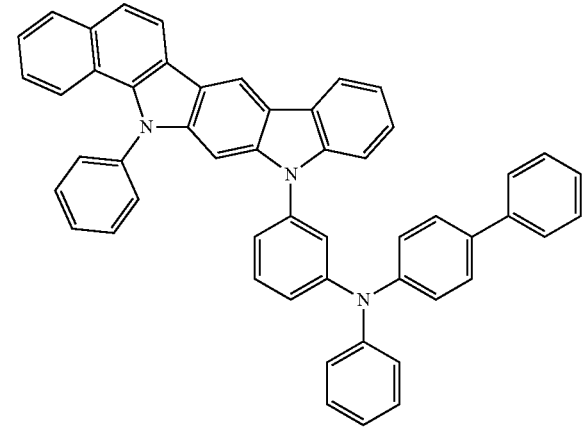

C-1-64
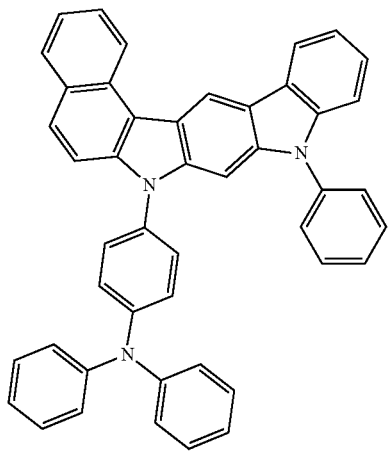
C-1-65
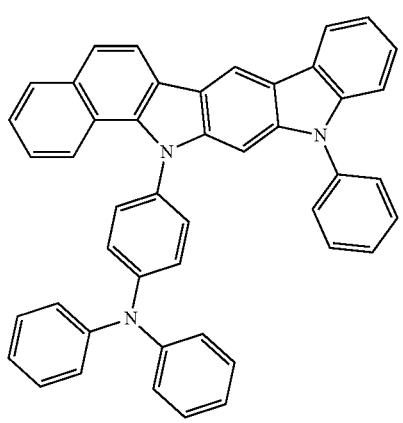
C-1-66
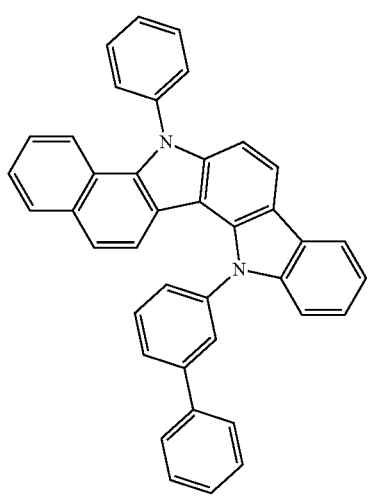
C-1-67
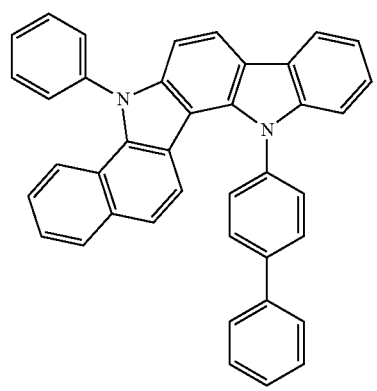
C-1-68
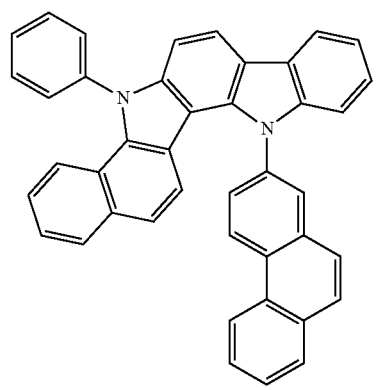
C-1-69
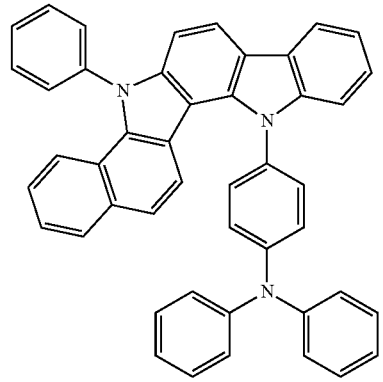
C-1-70
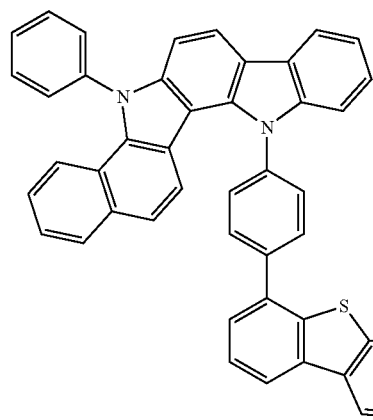

-continued
C-1-71
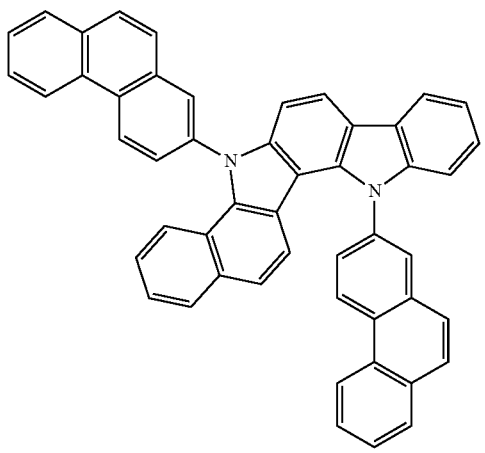
C-1-72
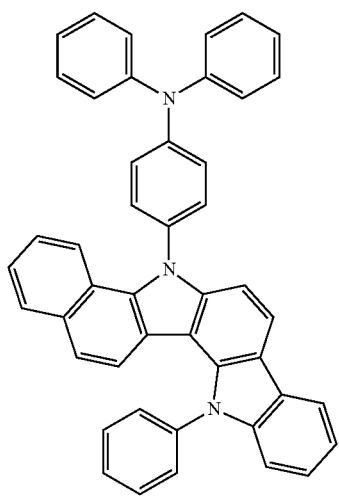
C-1-73
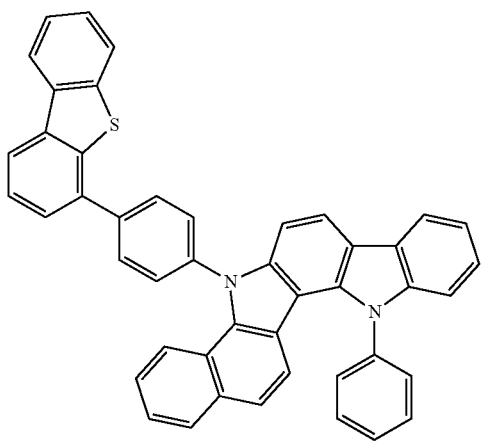
-continued
C-1-74
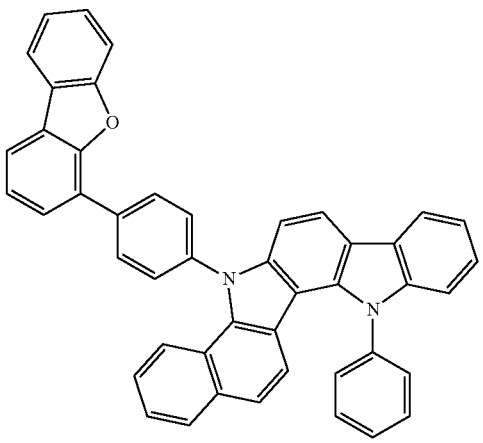
C-1-75
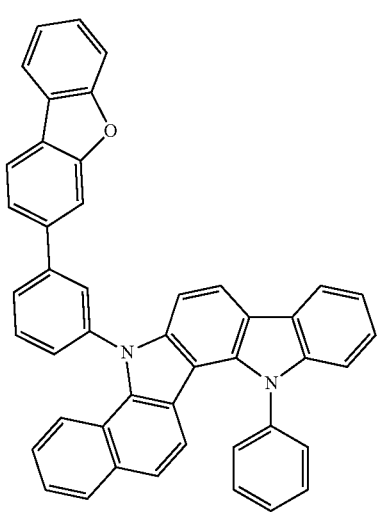
C-1-76
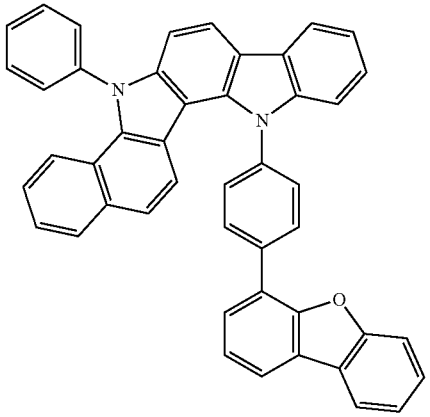

C-1-77
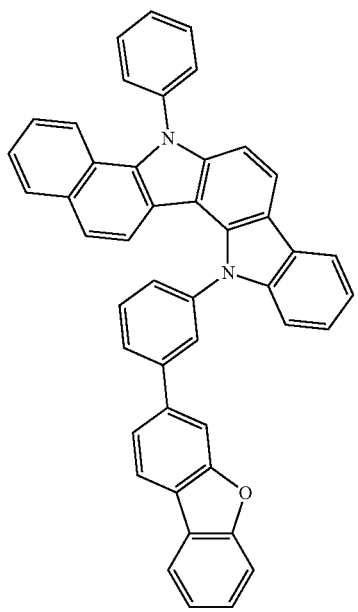
C-1-78
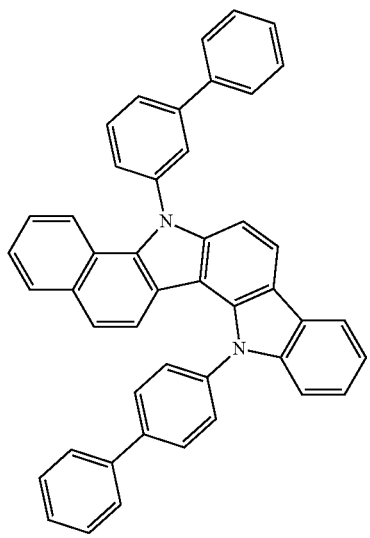
C-1-79
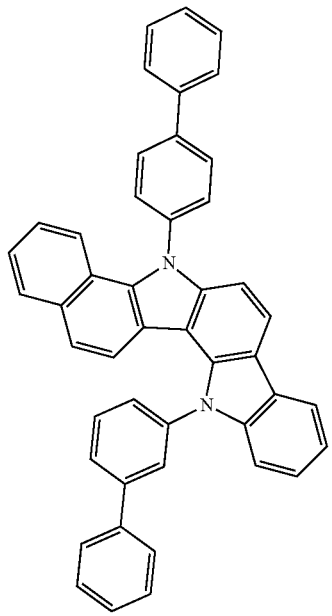
C-1-80
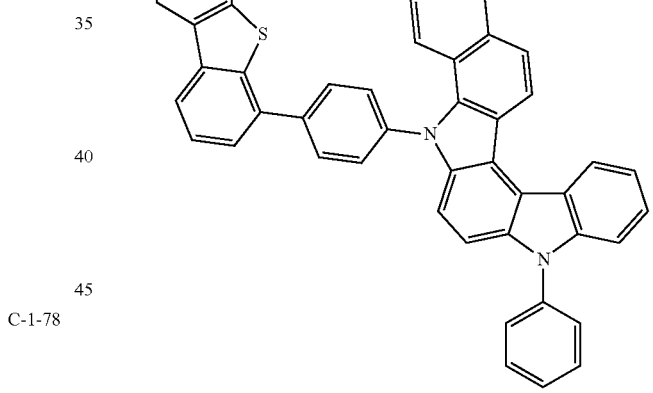
C-1-81
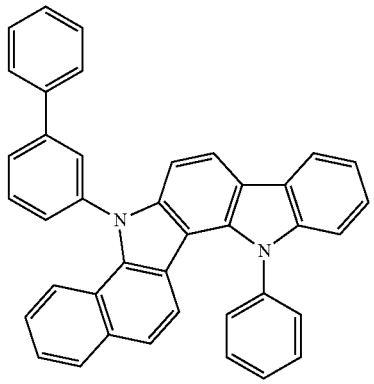

C-1-82
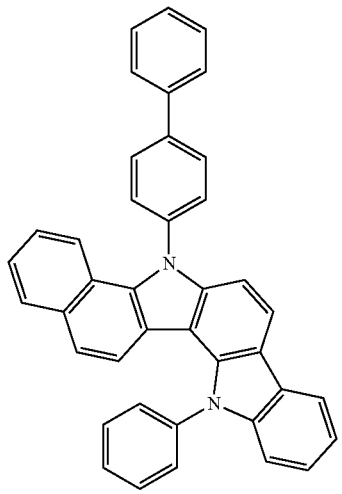
C-1-83
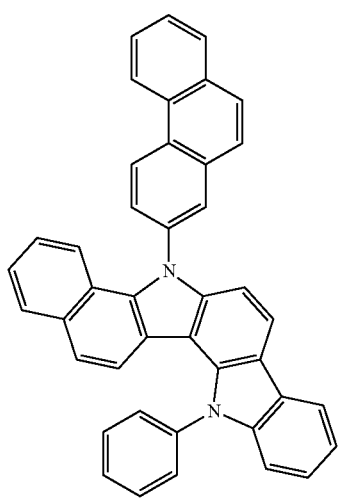
C-1-84
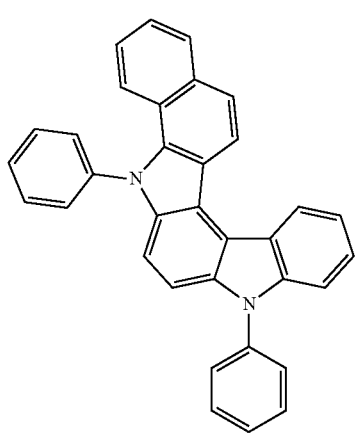
C-1-85
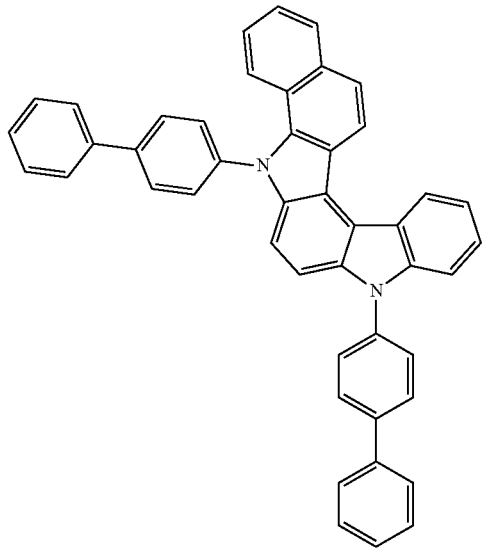
C-1-86
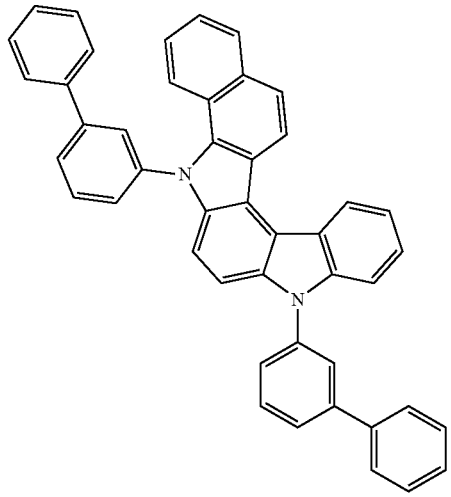
C-1-87
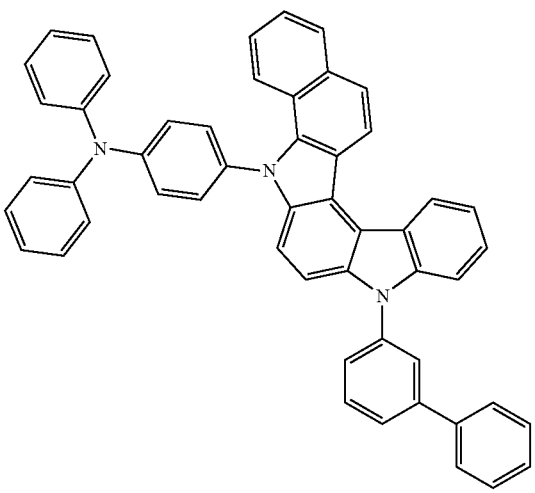

C-1-88
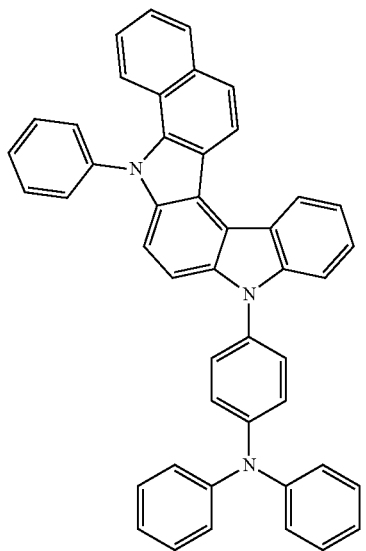
C-1-89
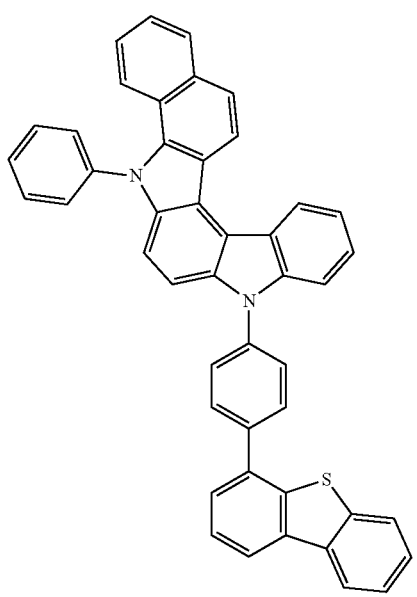
C-1-90
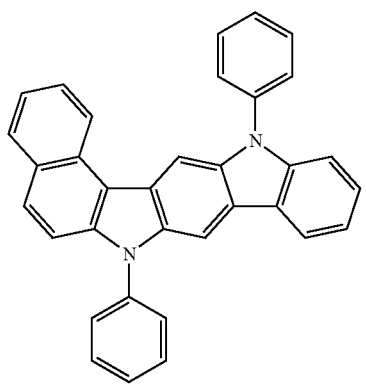
C-1-118
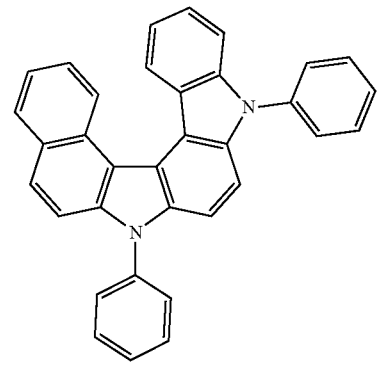
C-1-123
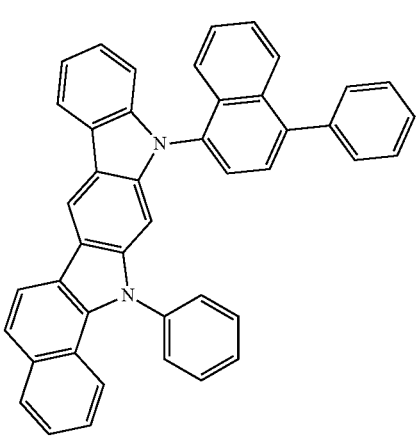
C-1-124
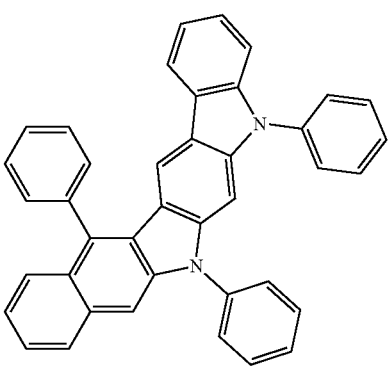
C-1-125
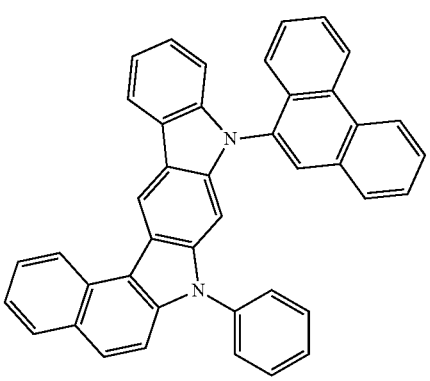

-continued
C-1-126
C-1-127
C-1-128
C-1-129
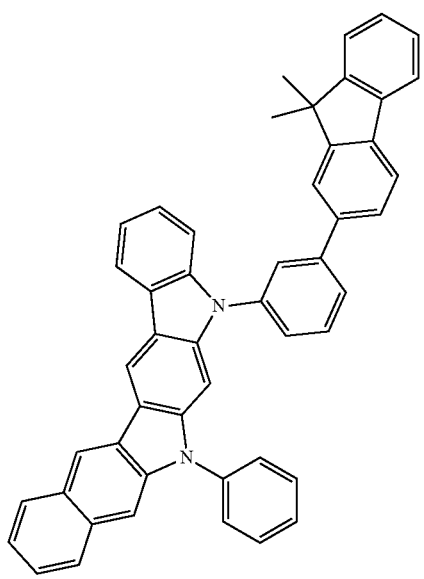
-continued
C-1-130
C-1-131
C-1-132
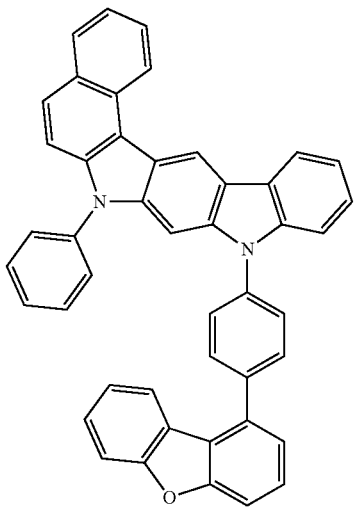
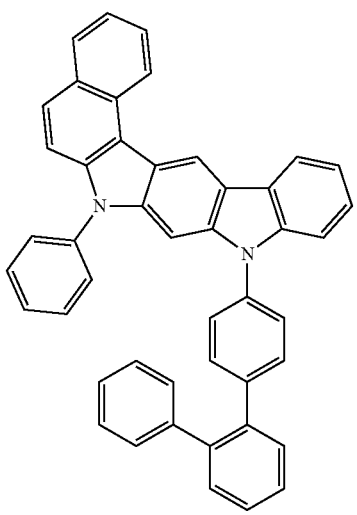
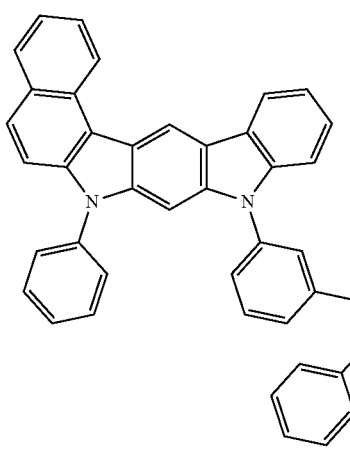

C-1-133
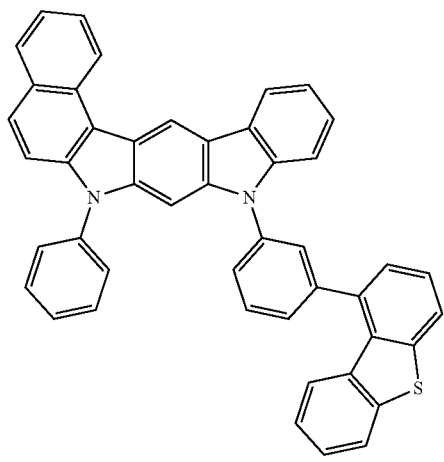
C-1-134
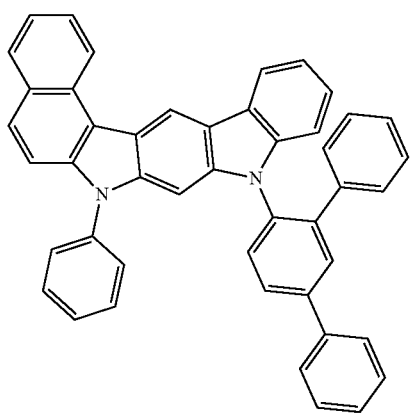
C-1-135
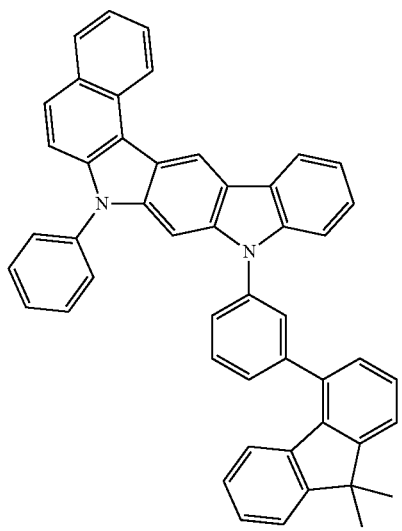
C-1-136
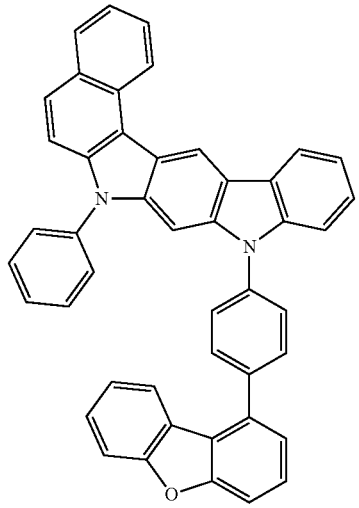
C-1-137
C-1-138
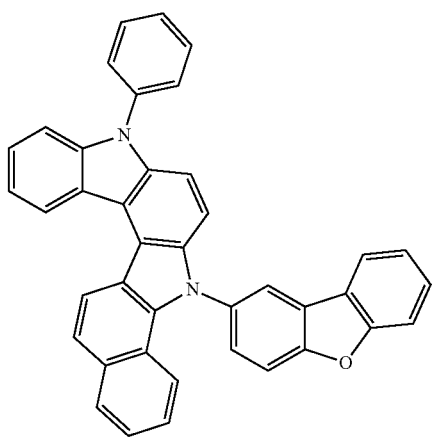

C-1-139
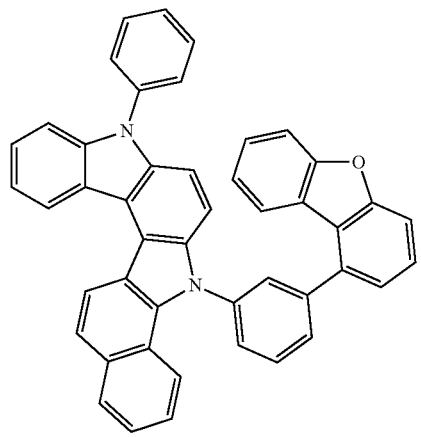
and
C-1-140
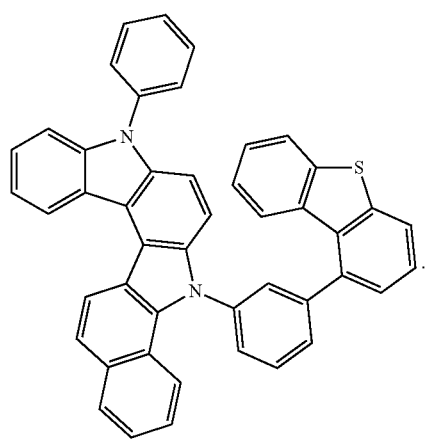
6. The organic electroluminescent device according to claim 1, wherein the compound represented by formula 2 is selected from the group consisting of the following compounds:
C-2-1
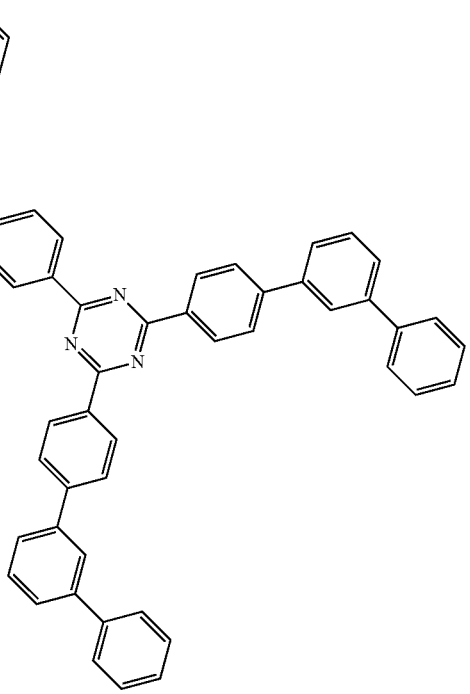
C-2-2
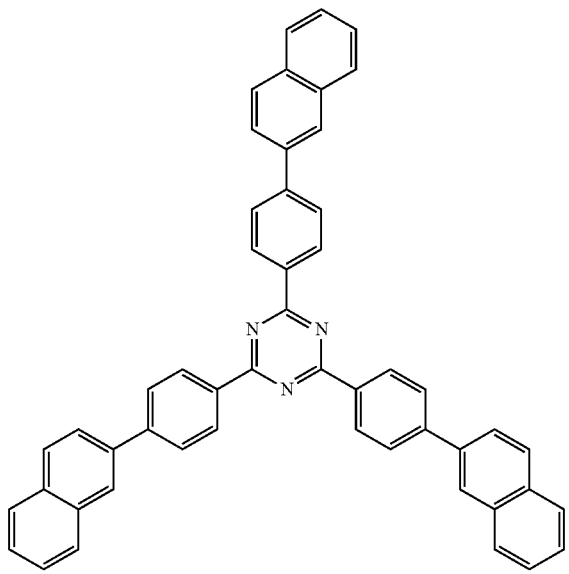

C-2-3
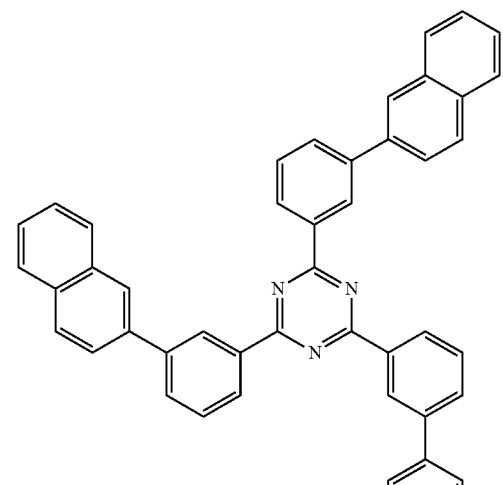
C-2-4
C-2-5
C-2-6
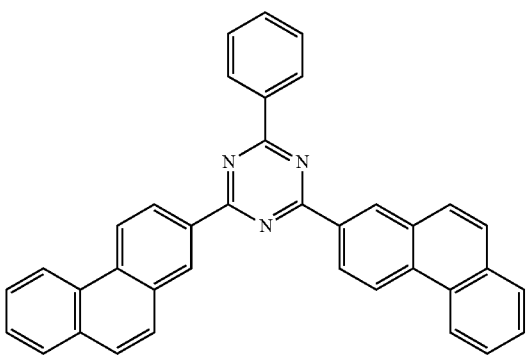
C-2-7
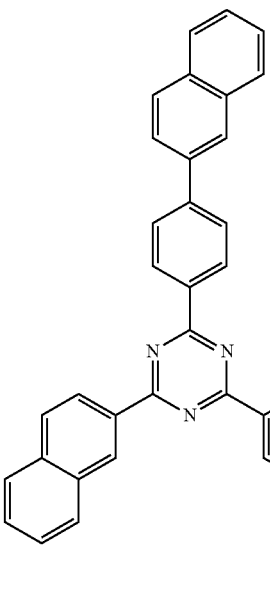
C-2-8
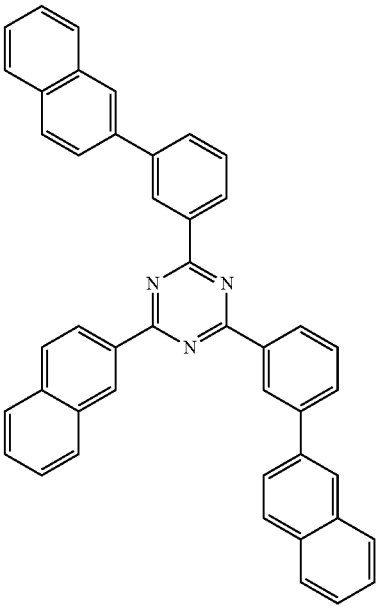

-continued
C-2-9
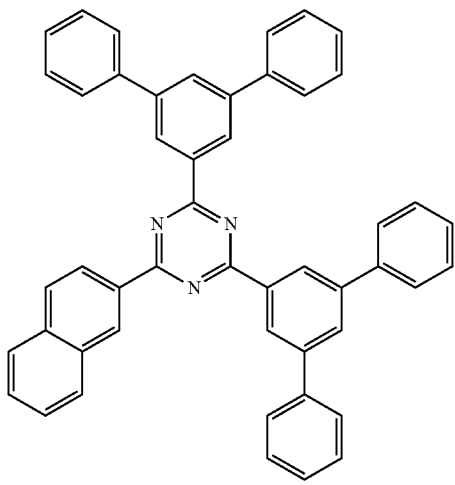
C-2-10
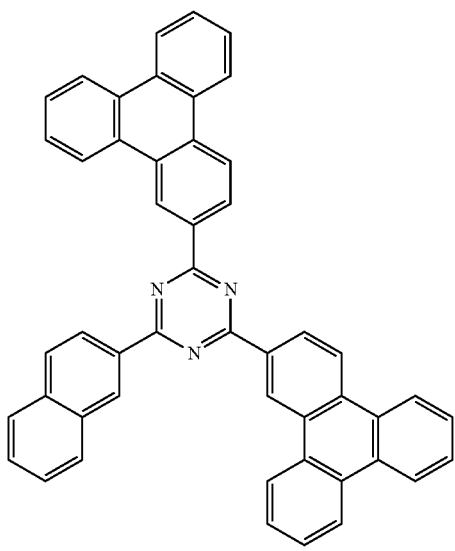
C-2-11
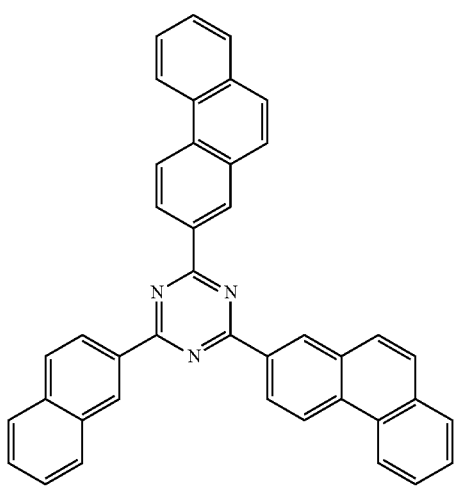
-continued
C-2-12
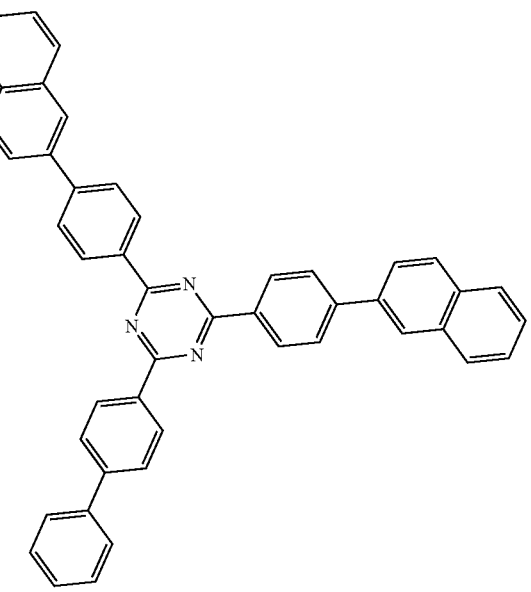
C-2-13
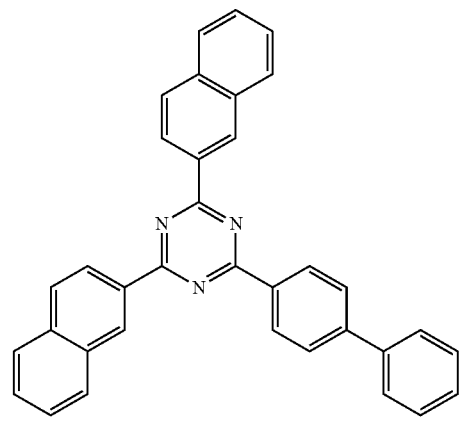
C-2-14
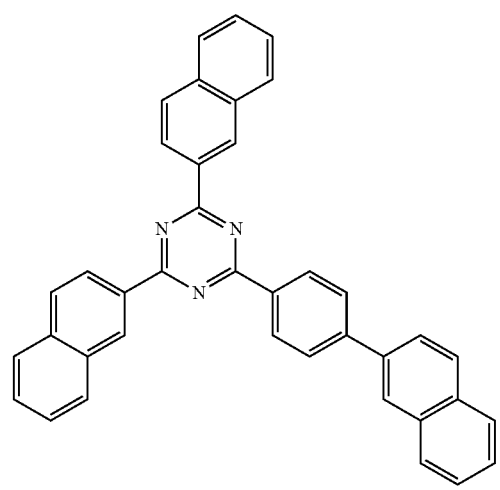

C-2-15
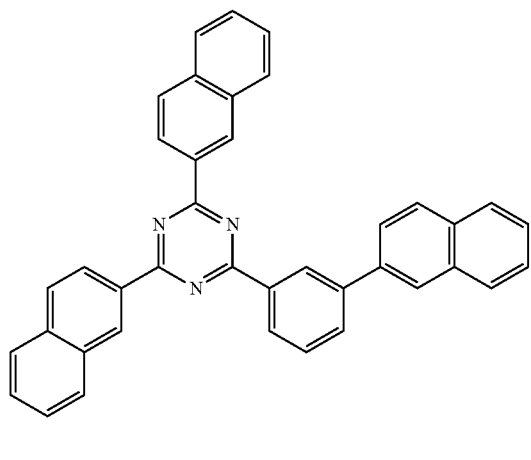
C-2-18
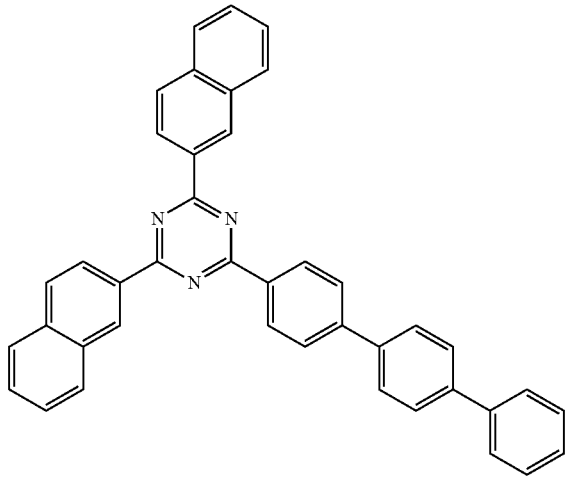
C-2-16
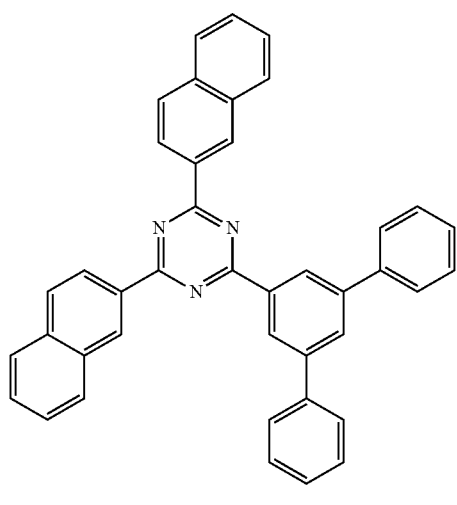
C-2-19
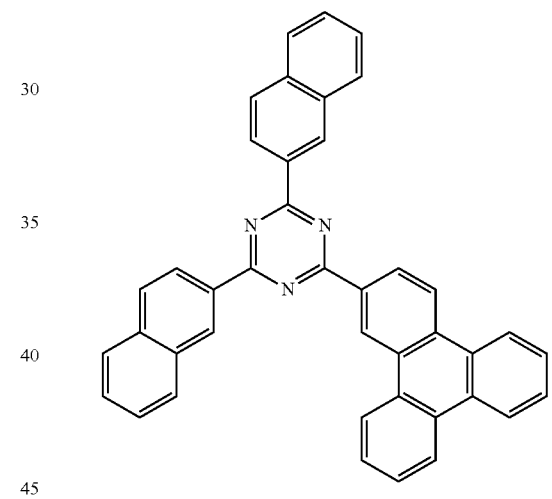
C-2-17
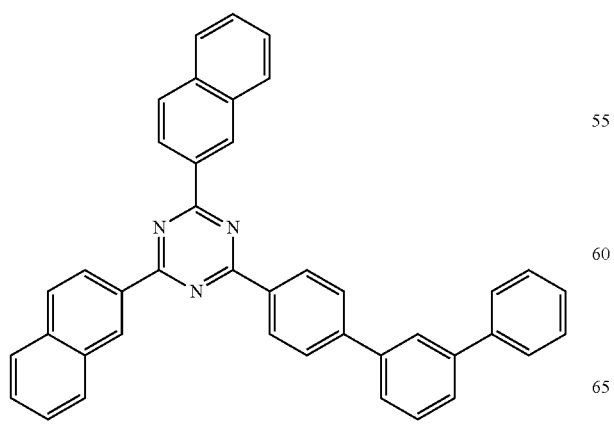
C-2-20
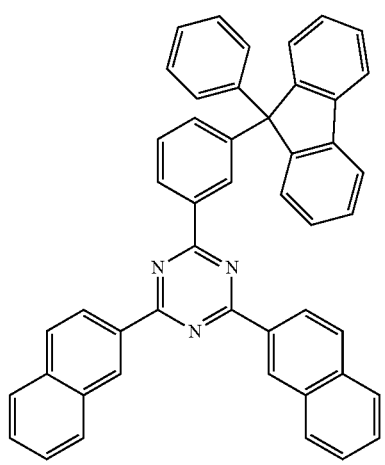

C-2-21
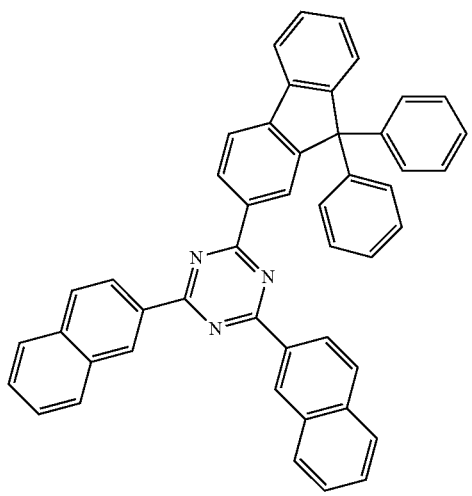
C-2-22
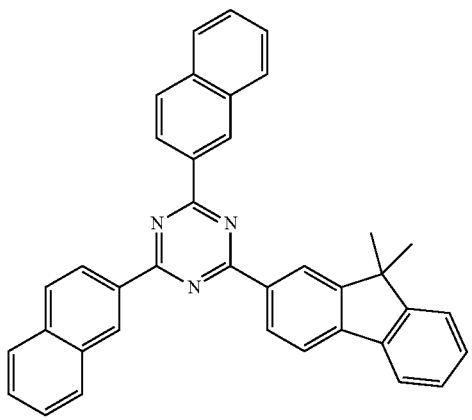
C-2-23
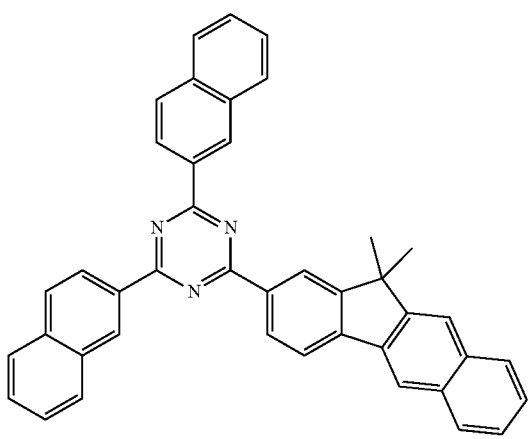
C-2-24
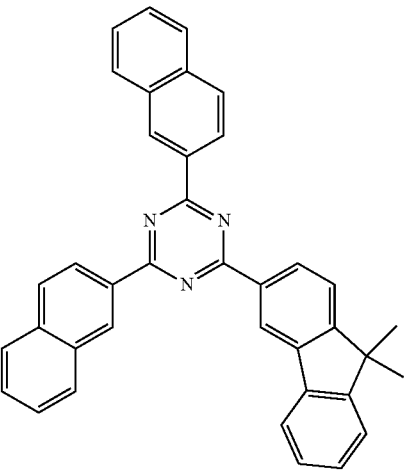
C-2-25
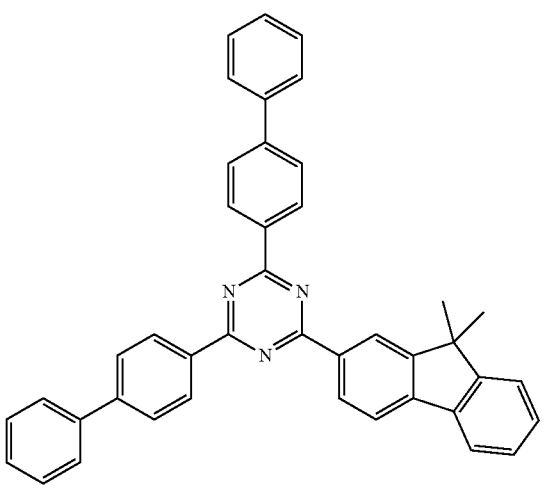
C-2-26
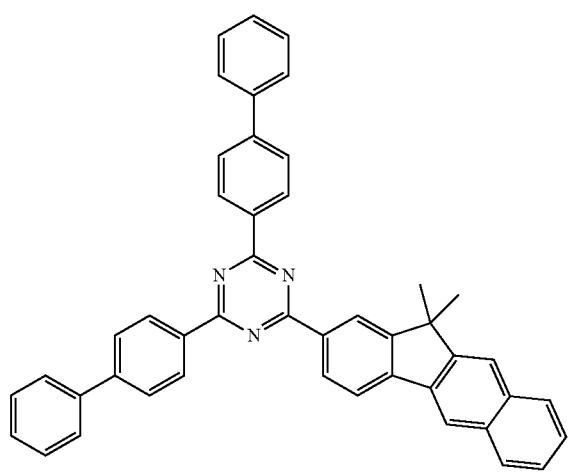

C-2-27
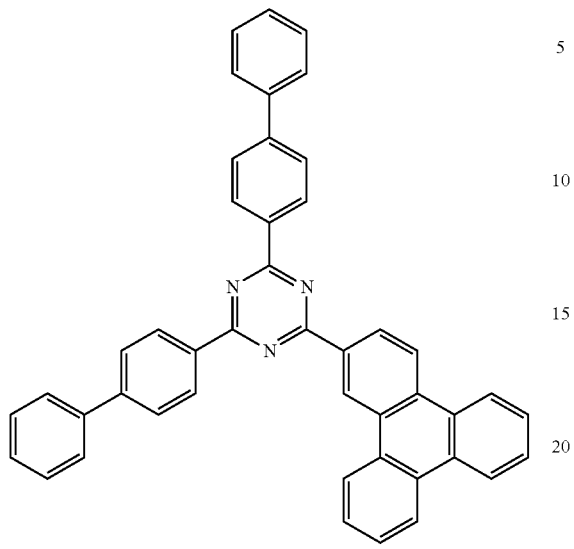
C-2-28
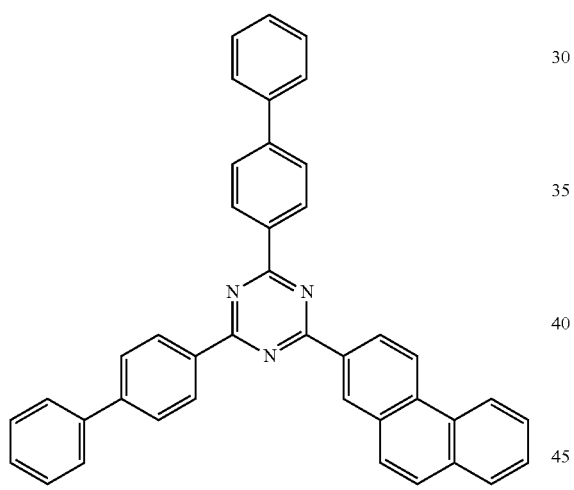
C-2-29
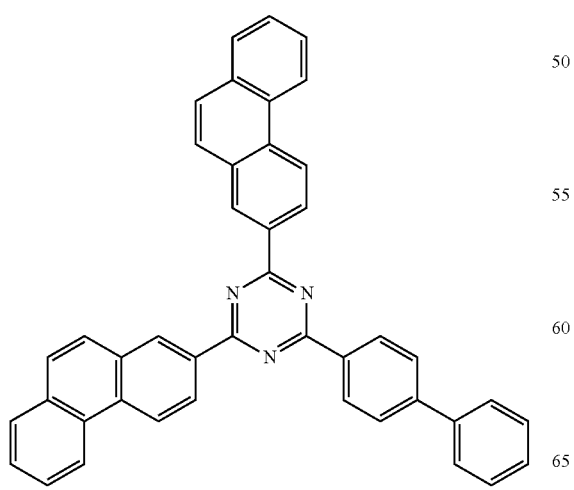
C-2-30
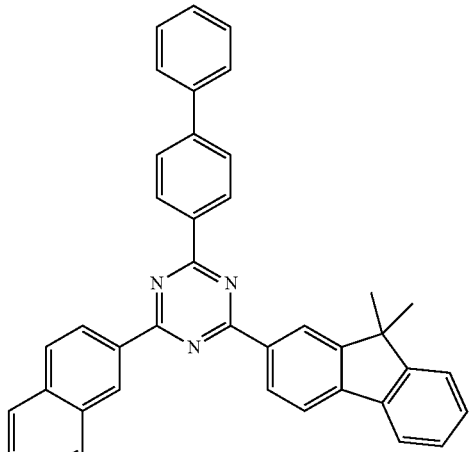
C-2-31
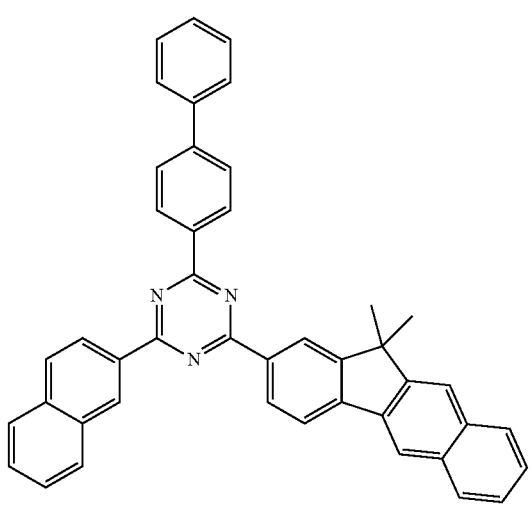
C-2-32
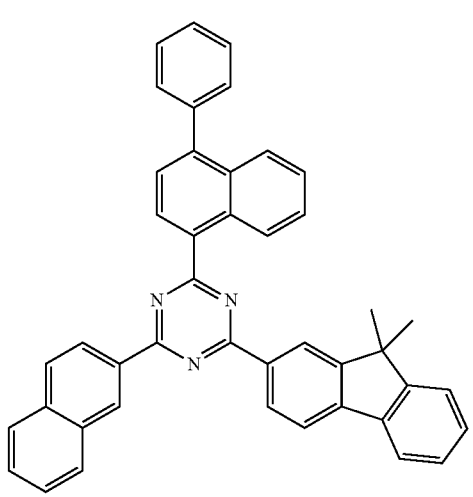

C-2-33
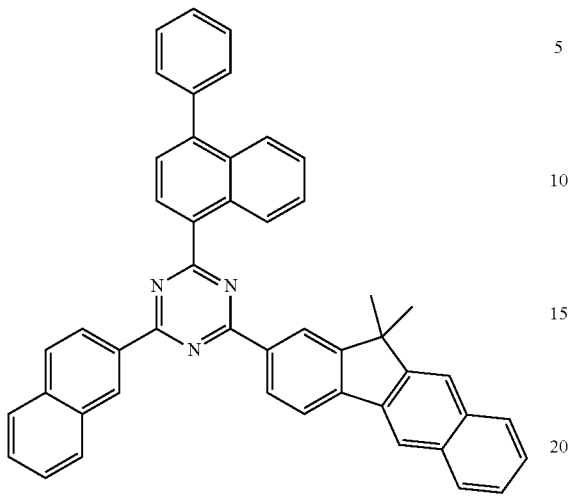
C-2-34
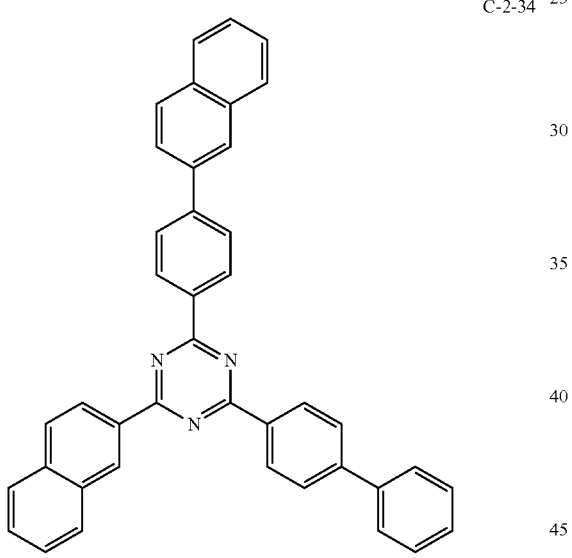
C-2-35
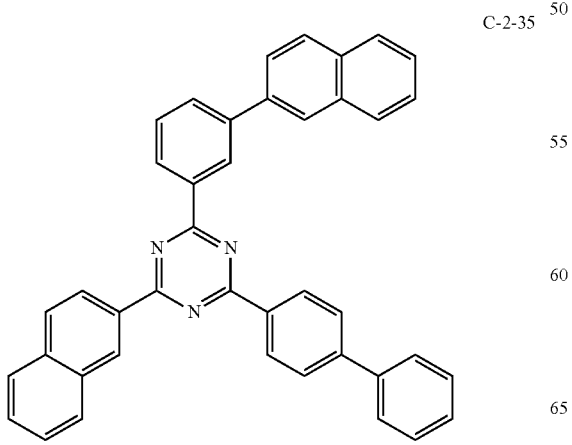
C-2-36
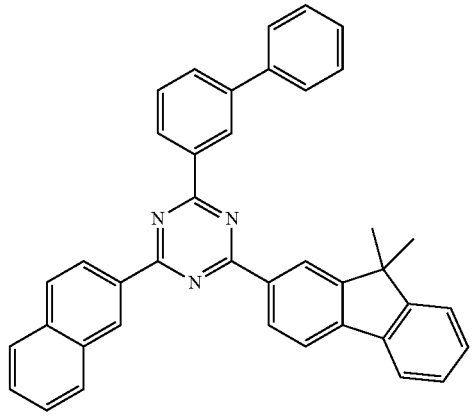
C-2-37
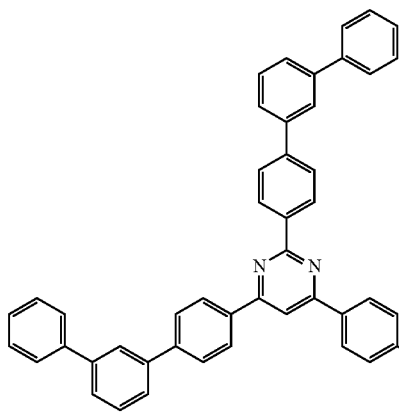
C-2-38
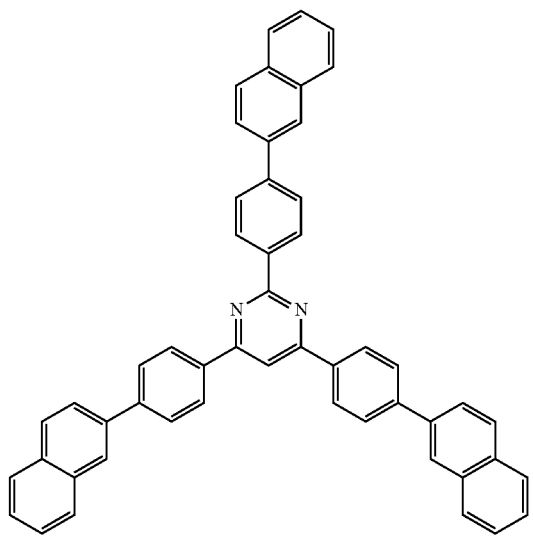

C-2-39
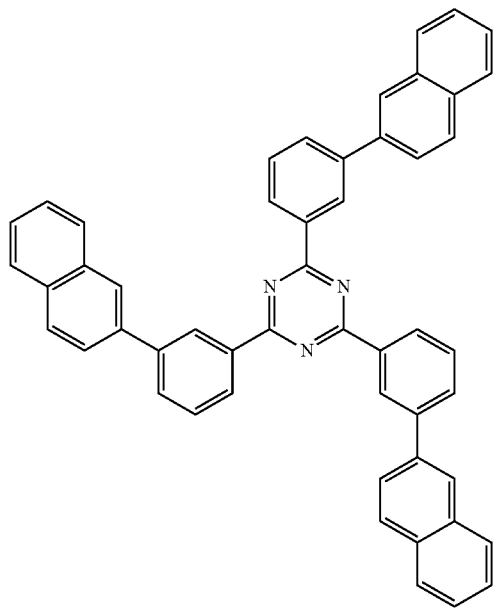
C-2-40
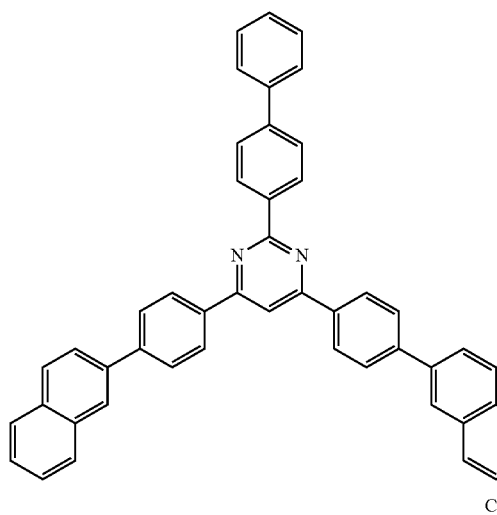
C-2-41
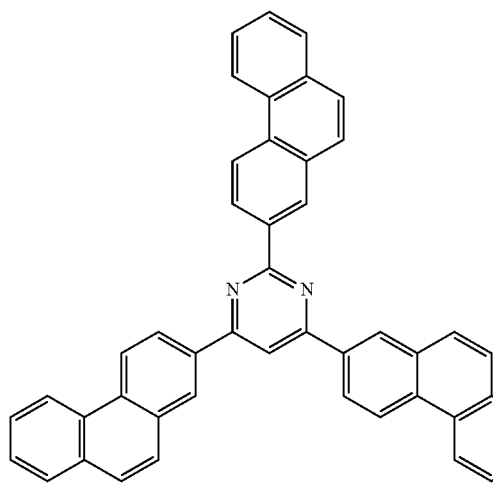
C-2-42
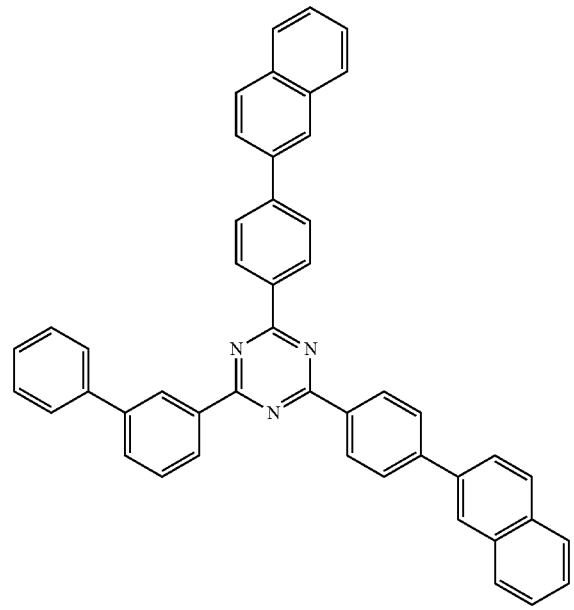
C-2-43
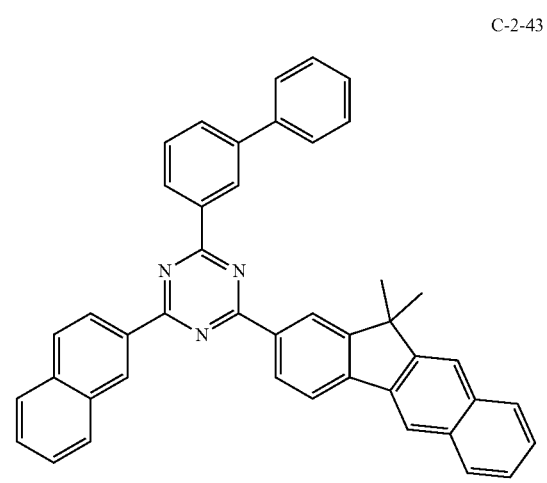
C-2-106
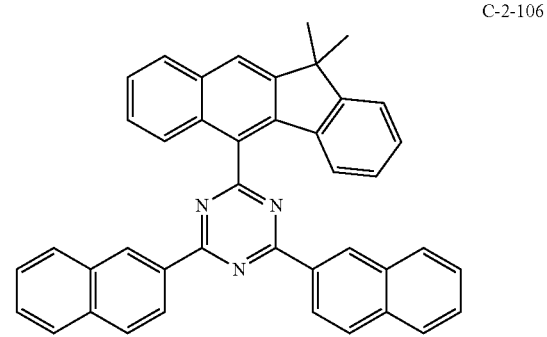

C-2-107
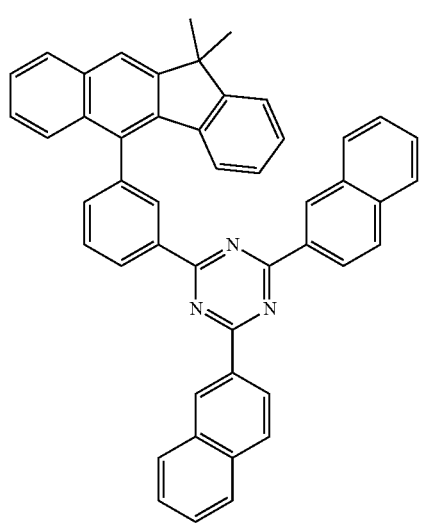
C-2-108
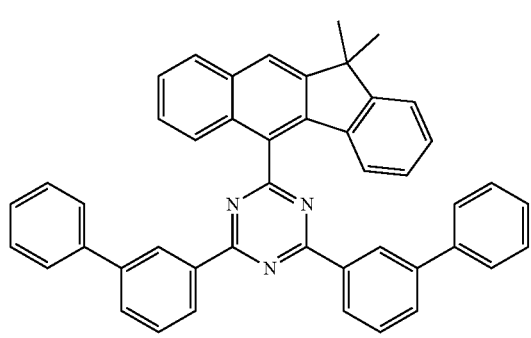
C-2-109
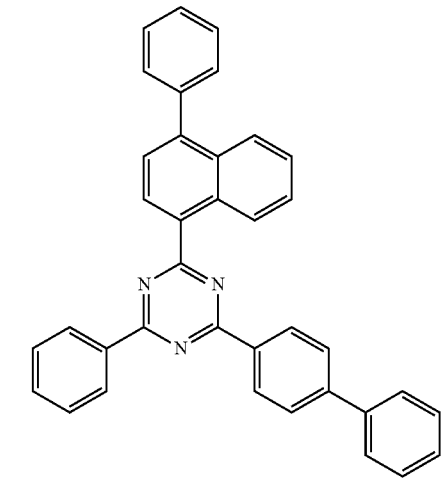
and
C-2-110
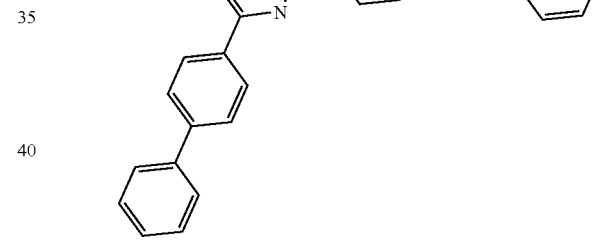
* * * * *